United States Patent
Fu et al.

(10) Patent No.: US 11,634,708 B2
(45) Date of Patent: *Apr. 25, 2023

(54) COMPOSITIONS AND KITS FOR MOLECULAR COUNTING

(71) Applicant: Becton, Dickinson and Company, Franklin Lakes, NJ (US)

(72) Inventors: Glenn K. Fu, Dublin, CA (US); Stephen P. A. Fodor, Palo Alto, CA (US); Julie Wilhelmy, Santa Cruz, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 274 days.

This patent is subject to a terminal disclaimer.

(21) Appl. No.: 17/183,840

(22) Filed: Feb. 24, 2021

(65) Prior Publication Data

US 2021/0238588 A1  Aug. 5, 2021

Related U.S. Application Data

(63) Continuation of application No. 14/381,488, filed as application No. PCT/US2013/028103 on Feb. 27, 2013, now Pat. No. 10,941,396.

(Continued)

(51) Int. Cl.
*C12Q 1/68* (2018.01)
*C12N 15/10* (2006.01)
(Continued)

(52) U.S. Cl.
CPC ....... *C12N 15/1065* (2013.01); *C12Q 1/6806* (2013.01); *C12Q 1/6874* (2013.01); *C12N 2310/141* (2013.01); *C12N 2320/10* (2013.01)

(58) Field of Classification Search
CPC ........................................................ C12Q 1/68
(Continued)

(56) References Cited

U.S. PATENT DOCUMENTS

| 4,510,244 A | 4/1985 | Parks et al. |
| 4,725,536 A | 2/1988 | Fritsch et al. |

(Continued)

FOREIGN PATENT DOCUMENTS

| CA | 2474509 A1 | 2/2003 |
| DE | 102008025656 | 12/2009 |

(Continued)

OTHER PUBLICATIONS

10X Genomics, Inc., 2019, User Guide: Visium Spatial Gene Expression Reagent Kits, www.10xGenomics.com, 76 pp.

(Continued)

*Primary Examiner* — Aaron A Priest
(74) *Attorney, Agent, or Firm* — Sheppard, Mullin, Richter & Hampton LLP

(57) ABSTRACT

Methods, kits and systems are disclosed for analyzing one or more molecules in a sample. Analyzing the one or more molecules may comprise quantitation of the one or more molecules. Individual molecules may quantitated by PCR, arrays, beads, emulsions, droplets, or sequencing. Quantitation of individual molecules may further comprise stochastic labeling of the one or more molecules with a plurality of oligonucleotide tags to produce one or more stochastically labeled molecules. The methods may further comprise amplifying, sequencing, detecting, and/or quantifying the stochastically labeled molecules. The molecules may be DNA, RNA and/or proteins.

20 Claims, 53 Drawing Sheets

Specification includes a Sequence Listing.

Related U.S. Application Data

(60) Provisional application No. 61/745,385, filed on Dec. 21, 2012, provisional application No. 61/603,921, filed on Feb. 27, 2012.

(51) Int. Cl.
  *C12Q 1/6806* (2018.01)
  *C12Q 1/6874* (2018.01)

(58) Field of Classification Search
  USPC ...................................................... 435/6.12
  See application file for complete search history.

(56) References Cited

U.S. PATENT DOCUMENTS

| | | | |
|---|---|---|---|
| 5,124,246 A | 6/1992 | Urdea et al. |
| 5,149,625 A | 9/1992 | Church et al. |
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Wilis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |

(56) References Cited

U.S. PATENT DOCUMENTS

| | | |
|---|---|---|
| 9,188,586 B2 | 11/2015 | Fan et al. |
| 9,228,229 B2 | 1/2016 | Olson et al. |
| 9,262,376 B2 | 2/2016 | Tsuto |
| 9,297,047 B2 | 3/2016 | Furchak et al. |
| 9,371,598 B2 | 6/2016 | Chee |
| 9,582,877 B2 | 2/2017 | Fu et al. |
| 9,593,365 B2 | 3/2017 | Frisen et al. |
| 9,644,204 B2 | 5/2017 | Hindson et al. |
| 9,689,024 B2 | 6/2017 | Hindson et al. |
| 9,695,468 B2 | 7/2017 | Hindson et al. |
| 9,787,810 B1 | 10/2017 | Chiang |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,138,518 B2 | 11/2018 | Chun |
| 10,151,003 B2 | 12/2018 | Fan et al. |
| 10,208,343 B2 | 2/2019 | Hindson et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,266,874 B2 | 4/2019 | Weissleder et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,344,329 B2 | 7/2019 | Hindson et al. |
| 10,450,607 B2 | 10/2019 | Hindson et al. |
| 10,550,429 B2 | 2/2020 | Harada et al. |
| RE47,983 E | 5/2020 | Gao et al. |
| 11,092,607 B2 | 8/2021 | Gaublomme et al. |
| 11,535,882 B2 | 12/2022 | Fu et al. |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0209298 A1 | 10/2004 | Kamberov et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0257902 A1 | 11/2006 | Mendoza et al. |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wille et al. |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |

(56) References Cited

U.S. PATENT DOCUMENTS

| | | |
|---|---|---|
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0072873 A1 | 3/2015 | Heinz et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0355879 A1 | 12/2016 | Kamberov et al. |
| 2017/0044525 A1 | 2/2017 | Kaper et al. |

(56) References Cited

U.S. PATENT DOCUMENTS

| | | |
|---|---|---|
| 2017/0136458 A1 | 5/2017 | Dunne et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0276332 A1 | 9/2018 | Fan et al. |
| 2018/0282803 A1 | 10/2018 | Belgrader et al. |
| 2018/0002738 A1 | 11/2018 | Wang et al. |
| 2018/0320241 A1 | 11/2018 | Nolan et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0095578 A1 | 3/2019 | Shum et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0102598 A1 | 4/2020 | Xie et al. |
| 2020/0109437 A1 | 4/2020 | Chang et al. |
| 2020/0115753 A1 | 4/2020 | Shalek et al. |
| 2020/0149037 A1 | 5/2020 | Shum |
| 2021/0039582 A1 | 2/2021 | Patton et al. |
| 2021/0123044 A1 | 4/2021 | Zhang et al. |
| 2021/0132078 A1 | 5/2021 | Peikon et al. |
| 2021/0198754 A1 | 7/2021 | Fan et al. |
| 2021/0213413 A1 | 7/2021 | Saligrama et al. |
| 2021/0222163 A1 | 7/2021 | Wu et al. |
| 2021/0371914 A1 | 12/2021 | Stoeckius et al. |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162695 A1 | 5/2022 | Sakofsky et al. |
| 2022/0162773 A1 | 5/2022 | Sakofsky et al. |
| 2022/0178909 A1 | 6/2022 | Huang et al. |
| 2022/0214356 A1 | 7/2022 | Henikoff et al. |
| 2022/0219170 A1 | 7/2022 | Khurana et al. |
| 2022/0220549 A1 | 7/2022 | Shum et al. |
| 2022/0267759 A1 | 8/2022 | Sanjana et al. |
| 2022/0333185 A1 | 10/2022 | Fu et al. |
| 2022/0348904 A1 | 11/2022 | Shum et al. |

FOREIGN PATENT DOCUMENTS

| | | |
|---|---|---|
| EP | 1473080 A2 | 11/2004 |
| EP | 1647600 A2 | 4/2006 |
| EP | 1845160 A1 | 10/2007 |
| EP | 2036989 A1 | 3/2009 |
| EP | 1379693 B1 | 5/2009 |
| EP | 2204456 A1 | 7/2010 |
| EP | 2431465 A1 | 3/2012 |
| EP | 2203749 B1 | 8/2012 |
| EP | 2511708 A1 | 10/2012 |
| EP | 2538220 A1 | 12/2012 |
| EP | 2623613 A1 | 8/2013 |
| EP | 1745155 B1 | 10/2014 |
| EP | 2805769 A1 | 11/2014 |
| EP | 2556171 B1 | 9/2015 |
| EP | 2970958 B1 | 12/2017 |
| EP | 3263715 A1 | 1/2018 |
| EP | 2670863 B1 | 6/2018 |
| EP | 3136103 B1 | 8/2018 |
| EP | 2954102 B1 | 12/2018 |
| EP | 3428290 A1 | 1/2019 |
| EP | 2970957 B1 | 4/2019 |
| EP | 3058092 B1 | 5/2019 |
| EP | 3256606 B1 | 5/2019 |
| EP | 3327123 B1 | 8/2019 |
| GB | 2293238 A | 3/1996 |
| JP | H04108385 | 4/1992 |
| JP | 2001078768 A | 3/2001 |
| JP | 2005233974 A | 9/2005 |
| JP | 2007504831 A | 3/2007 |
| JP | 2008256428 A | 10/2008 |
| JP | 2013039275 A | 2/2013 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003031591 | 4/2003 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |

(56) References Cited

FOREIGN PATENT DOCUMENTS

| | | |
|---|---|---|
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010059820 | 5/2010 |
| WO | WO2010117620 | 10/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013137737 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |

(56) References Cited

FOREIGN PATENT DOCUMENTS

| | | |
|---|---|---|
| WO | WO2019157529 | 8/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020159757 | 8/2020 |
| WO | WO2020167920 | 8/2020 |
| WO | WO2020214642 | 10/2020 |
| WO | WO2020242377 | 12/2020 |
| WO | WO2021092386 | 5/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021168015 | 8/2021 |
| WO | WO2021168261 | 8/2021 |
| WO | WO20210178199 | 9/2021 |
| WO | WO2021247593 | 12/2021 |
| WO | WO2022015667 | 1/2022 |
| WO | WO2022026909 | 2/2022 |
| WO | WO2022040453 | 2/2022 |
| WO | WO2022143221 | 7/2022 |

OTHER PUBLICATIONS

2018 Top 10 Innovations, The Scientist Magazine® (2018). Available at: https://www.thescientist.com/features/2018-top-10-innovations-65140, 16 pp.

Achim et al., "High-throughput spatial mapping of single-cell RNA-seq data to tissue of origin," Nature Biotechnology 2015, 33(5), 503-511.

Advisory Action dated Nov. 29, 2019 in U.S. Appl. No. 15/084,307.

Advisory Action dated Dec. 2, 2019 in U.S. Appl. No. 15/055,407.

Advisory Action dated Aug. 25, 2020 in U.S. Appl. No. 15/084,307.

Agasti et al., "Photocleavable DNA barcode-antibody conjugates allow sensitive and multiplexed protein analysis in single cell," J Am Chem Soc. 2012, 134(45), 18499-18502.

Alexandra M. Ewing of Richards, Layton and Finger, P.A., Entry of Appearance dated Jan. 18, 2019 in the USDC District of Delaware, C.A. No. 18-1800-RGA, 1 pp.

Alkan et al., "Personalized copy number and segmental duplication maps using next-generation sequencing," Nat Genet. 2009, 41(10):1061-1067.

Anderson, "Study Describes RNA Sequencing Applications for Molecular Indexing Methods," GenomeWeb 2014, 5 pp.

Ansorge, "Next-generation DNA sequencing techniques," New Biotechnology 2009, 25(4), 195-203.

Applied Biosystems, Apr. 2008, Solid™ System Barcoding, Application Note, 4 pp.

Argrawal et al., "Counting Single Native Biomolecules and Intact Viruses with Color-Coded Nanoparticles," Analytical Chemistry 2006, 78, 1061-1070.

Arslan et al., "An efficient algorithm for the stochastic simulation of the hybridization of DNA to microarrays," BMC Bioinformatics 2009, 10(411), 1-17.

Atanur et al., "The genome sequence ofthe spontaneously hypertensive rat: Analysis and functional significance." Genome Res. 2010, 20(6), 791-803.

Audic et al., "The Significance of Digital Gene Expression Profiles," Genome Res. 1997, 7, 986-995.

Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.

BD Life Sciences, 2018, BD AbSeq antibody-oligo conjugates, www.bd.com/genomics, 2 pp.

BD Life Sciences, 2018, BD AbSeq on the BD Rhapsody system: Exploration of single-cell gene regulation by simultaneous digital mRNA and protein quantification, www.bd.com/genomics, 7 pp.

Bendall et al., "Single-Cell Mass Cytometry of Differential Immune and Drug Responses Across a Human Hematopoietic Continuum," Science 2011, 332(6030), 687-696.

Bionumbers, Aug. 21, 2010, "Useful fundamental numbers in molecular biology," http://bionumbers.hms.harvard.edu/KeyNumbers/aspx, 1-4.

Biosciences Product Catalogue, Dynal® Catalog 1999, Oslo, Norway, 49-51.

Bioscribe "Massively parallel sequencing technology for single-cell gene expression published" (press release), PhysOrg 2015, 1-2.

Blainey, "The future is now: single-cell genomics of bacteria and archaea," FEMS Microbiol Rev. 2013, 37(3), 407-427.

Bogdanova et al., "Normalization of full-length enriched cDNA," Molecular Biosystems 2008, 4(3), 205-212.

Bonaldo et al., "Normalization and Subtraction: Two Approaches to facilitate Gene Discovery," Genome Res. 1996, 6, 791-806.

Bontoux et al., "Integrating whole transcriptome assays on a lab-on-a-chip for single cell gene profiling", Lab on a Chip 2008, 8(3), 443-450.

Bose et al., "Scalable microfluidics for single-cell RNA printing and sequencing," Genome Biology 2015, 16(120), 1-16.

Brady et al., "Construction of cDNA libraries form single cells", Methods in Enzymology 1993, (225), 611-623.

Braha et al., "Simultaneous stochastic sensing of divalent metal ions," Nature Biotechnology 2000, 18, 1005-1007.

Bratke et al., "Differential expression of human granzymes A, B, and K in natural killer cells and during CD8+ T cell differentiation in peripheral blood," Eur J Immunol. 2005, 35, 2608-2616.

Brenner et al., "Gene expression analysis by massively parallel signature sequencing (MPSS) on microbead arrays," Nature Biotechnology 2000, 18, 630-634.

Brenner et al., "In vitro cloning of complex mixtures of DNA on microbeads: Physical separation of differentially expressed cDNAs," PNAS 2000, 97(4), 1665-1670.

Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.

Brisco et al., "Quantification of RNA integrity and its use for measurement of transcript number," Nucleic Acids Research 2012, 40(18), e144, 1-9.

Brodin et al., "Challenges with Using Primer IDs to Improve Accuracy of Next Generation Sequencing," PLoS One 2015, 19(3), 1-12.

Buggenum et al., "A covalent and cleavable antibody DNA conjugation strategy for sensitive protein detection via immunoPCR," Scientific Reports 2016, 6(22675), 1-12.

Buschmann et al., Enhancing the detection of barcoded reads in high throughput DNA sequencing DNA by controlling the false discovery rate, BMC Bioinformatics, 15(1), 264, 1-16.

Bustin, "Absolute quantification of mRNA using real-time reverse transcription polymerase chain reaction assays," Journal of Molecular Endocrinology 2000, 25, 169-193.

Butkus, "Cellular research set to launch first gene expression platform using 'molecular indexing' technology," GenomeWeb 2014, 1-5.

Cai, "Turning single cells in microarrays by super-resolution barcoding," Briefings in Functional Genomics 2012, 12(2), 75-80.

Cao et al., "Comprehensive single-cell transcriptional profiling of a multicellular organism," Science 2017, 357, 661-667.

(56) References Cited

OTHER PUBLICATIONS

Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition," EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number including telomeres and mitochondria, assayed using nextgeneration sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "Smart™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Complaint filed in Becton, *Dickinson and Company and Cellular Research Inc. v. 10X Genomics, Inc.* dated Nov. 15, 2018 in the USDC for the District of Delaware, C.A. 18-1800-RGA, 141 pp.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomics Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomics Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomics Request for Oral Argument Under D. Del. LR 7.1.4, dated Apr. 18, 2019 in the USDC for the District of Delaware, C.A. 18-1800-RGA 2 pp.
Defendant 10X Genomics Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 p. 1.
Delley et al., "Combined aptamer and transcriptome sequencing of single cells," bioRxiv 2017, 1-10.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.

(56) References Cited

OTHER PUBLICATIONS

Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Jul. 6, 2020 in European Patent Application No. 17781265.8.
Examination Report dated Sep. 21, 2020 in European Patent Application No. 18703156.2.
Examination Report dated Nov. 12, 2020 in European Patent Application No. 18716877.8.
Examination Report dated Dec. 3, 2020 in European Patent Application No. 16719706.0.
Examination Report dated Mar. 25, 2021 in European Patent Application No. 17781265.8.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.

(56) References Cited

OTHER PUBLICATIONS

Final Office Action dated Mar. 25, 2021 in U.S. Appl. No. 16/374,626.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
GenBank Accession No. NM_000518.5 for *Homo sapiens* hemoglobin subunit beta (HBB), mRNA. Mar. 22, 2021 [online], [retrieved on Apr. 27, 2021], retrieved from the Internet: <URL: www.ncbi.nlm.nih.gov/nuccore/NM_000518.5?report=Genbank (Year: 2021).
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Grounds for Opposition dated Jul. 21, 2016 and filed in European Patent 2414548B1.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21 (12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Mar. 26, 2019 in PCT Application No. PCT/US2017/053331.
International Preliminary Report on Patentability dated Aug. 6, 2019 in PCT Application No. PCT/US2018/014385.
International Preliminary Report on Patentability dated Nov. 3, 2020 in PCT Application No. PCT/US2019/030175.
International Preliminary Report on Patentability dated Nov. 3, 2020 in PCT Application No. PCT/US2019/030245.
International Preliminary Report on Patentability dated Feb. 9, 2021 in PCT Application No. PCT/US2019/043949.
International Preliminary Report on Patentability dated Feb. 23, 2021 in PCT Application No. PCT/US2019/046549.
International Preliminary Report on Patentability dated Mar. 2, 2021 in PCT Application No. PCT/US2019/048179.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.

(56) References Cited

OTHER PUBLICATIONS

International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated May 18, 2020 in PCT Application No. PCT/US2020/014339.
International Search Report and Written Opinion dated Jun. 30, 2020 in PCT Application No. PCT/US2020/017890.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Additional Search Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute numbers of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., The Technology and Biology of Single-Cell RNA Sequencing, Molecular Cell 2015, 58, 610-620.
Konig et al., "iCLIP reveals the function of hnRNAP particles in splicing at individual nucleotide resolution," Nature Structural & Molecular Biology 2010, 17(7), 909-916.
Kooiker & Xue, "cDNA Library Preparation," Cereal Genomics 2013, 1099, 29-40.

(56) References Cited

OTHER PUBLICATIONS

Kotake et al., "A simple nested RT-PCR method for quantitation of the relative amounts of multiple cytokine mRNAs in small tissue samples," Journal of Immunological Methods 1996, 199, 193-203.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343, 1360-1363.
Lee et al., "Universal process-inert encoding architecture for polymer microparticles," Nature Materials 2014, 13(5), 524-529.
Letter regarding the opposition procedure dated Jul. 22, 2015 for European Patent Application No. 11810645.9.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Lin et al., "Self-Assembled Combinatorial Encoding Nanoarrays for Multiplexed Biosensin," Nano Lett. 2007, 7 (2), 507-512.
Liu et al., "Single-cell transcriptome sequencing: recent advances and remaining challenges," F1000Research 2016, 5(F1000 Faculty Rev)(182), 1-9.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," ThermoFisher Scientific, Oct. 2, 2018, 1 p.
Lucito et al., "Representational Oligonucleotide Microarray Analysis: A High-Resolution Method to Detect Genome Copy Number Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Maamar et al., "Noise in Gene Expression Determines Cell Fate in Bacillus subtilis," Science 2007, 317, 526-529.
MacAulay et al., "Single Cell Genomics: Advances and Future Perspectives," PLoS Genetics 2014, 10(1), 1-9.
MacAulay et al., "G&T-seq: parallel sequencing of single-cell genomes and transcriptomes," Nature Methods 2015, 1-7.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Makrigiorgos et al., "A PCR-Based amplification method retaining quantities difference between two complex genomes," Nature Biotech 2002, 20(9), 936-939.
Marcus et al., "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
McCloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Merriam-Webster, definition of associate: http://www.merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., Protocol for nearly full-length sequencing of HIV-1 RNA from plasma, PLoS One 2008, 3(1), e1420, 1-6.
Nagai et al., "Development of a microchamber array for picoleter PCR," Anal. Chem. 2001, 73, 1043-1047.
Navin et al., "The first five years of single-cell cancer genomics and beyond," Genome Research 2015, 25, 1499-1507.
New COVID-19 Variants, Centers for Disease Control and Prevention 2021, accessed Jan. 21, 2021, 3 pp.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Oct. 3, 2013 in U.S. Appl. No. 12/969,581.
Non-Final Office Action dated Feb. 18, 2015 for U.S. Appl. No. 14/540,007.
Non-Final Office Action dated Feb. 26, 2015 for U.S. Appl. No. 14/540,029.
Non-Final Office Action dated Mar. 19, 2015 in U.S. Appl. No. 14/540,018.
Non-Final Office Action dated May 7, 2015 for U.S. Appl. No. 13/327,526.
Non-Final Office Action dated Dec. 3, 2015 for U.S. Appl. No. 14/281,706.

(56) References Cited

OTHER PUBLICATIONS

Non-Final Office Action dated Dec. 31, 2015 for U.S. Appl. No. 14/800,526.
Non-Final Office Action dated Apr. 11, 2016 in U.S. Appl. No. 14/472,363.
Non-Final Office Action dated May 10, 2016 in U.S. Appl. No. 14/381,488.
Non-Final Office Action dated May 13, 2016 in U.S. Appl. No. 14/508,911.
Non-Final Office Action dated Aug. 17, 2016 for U.S. Appl. No. 14/800,526.
Non-Final Office Action dated Sep. 26, 2016 in U.S. Appl. No. 15/167,807.
Non-Final Office Action dated Oct. 11, 2016 in U.S. Appl. No. 15/224,460.
Non-Final Office Action dated Jan. 19, 2017 in U.S. Appl. No. 15/055,445.
Non-Final Office Action dated Mar. 24, 2017 in U.S. Appl. No. 15/409,355.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Jul. 28, 2017 in U.S. Appl. No. 14/975,441.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Nov. 1, 2017 in U.S. Appl. No. 15/667,125.
Non-Final Office Action dated Nov. 9, 2017 in U.S. Appl. No. 15/004,618.
Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Non-Final Office Action dated Dec. 4, 2020 in U.S. Appl. No. 16/677,012.
Non-Final Office Action dated Dec. 9, 2020 in U.S. Appl. No. 16/788,743.
Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.

(56) References Cited

OTHER PUBLICATIONS

Notice of Allowance dated Apr. 15, 2020 in U.S. Appl. No. 16/012,635.
Notice of Allowance dated Sep. 23, 2020 in Korean Patent Application No. 10-2016-7008144.
Notice of Allowance dated Oct. 29, 2020 in U.S. Appl. No. 15/987,851.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Office Action dated Oct. 29, 2020 in Chinese Patent Application No. 2018800377201.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
Ozkumur et al., "Inertial Focusing for Tumor Antigen-Dependent and—Independent Sorting of Rare Circulating Tumor Cells," Science Translational Medicine 2013, 5(179), 1 -20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes and sample integrity: BestKeeper—Excel-based tool using pair-wise correlations," Biotechnology Letters, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.

(56) References Cited

OTHER PUBLICATIONS

Pinkel et al., "Comparative Genomic Hybridization," Annual Review of Genomics and Human Genetics 2005, 6, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiffs First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Qiu et al., "DNA Sequence-Based "BarCodes" for Tracking the Origins of Expressed Sequence Tags from a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Rhee et al., "Simultaneous detection of mRNA and protein stem cell markers in live cells," BMC Biotechnology 2009, 9(30), 1-10.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody- DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Search Report and Written Opinion dated Aug. 26, 2020 in Singapore Patent Application No. 10201806890V.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
S.H.KO, "An 'equalized cDNA library' by the reassociation of short double-stranded cDNAs," Nucleic Acids Res. 1990, 18(19), 5705-5711.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy Number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.

(56) References Cited

OTHER PUBLICATIONS

Stoeckius et al., "Large-scale simultaneous measurement of epitopes and transcriptomes in single cells," Nature Methods 2017, 14(9), 865-868.
Stoeckius et al., "Cell Hashing with barcoded antibodies enables multiplexing and doublet detection for single cell genomics," Genome Biology 2018, 19(224), 1-12.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Summons to Attend Oral Proceedings dated Nov. 16, 2020 in European Patent Application No. 17202409.3.
Sun et al., "Ultra-deep profiling of alternatively spliced *Drosophila* Dscam isoforms by circularization-assisted multi-segment sequencing," EMBO J. 2013, 32(14), 2029-2038.
Takahashi et al., "Novel technique of quantitative nested real-time PCR assay for *Mycobacterium tuberculosis* DNA," Journal of Clinical Microbiology 2006, 44, 1029-1039.
Tan et al., "Genome-wide comparison of DNA hydroxymethylation in mouse embryonic stem cells and neural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation ofthe highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
TotalSeq™—A0251 anti-human Hashtag 1 Antibody, BioLegend®, Jul. 2018, 1-10.
Treutlein et al., Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization ofthe Yeast Transcriptome," Cell 1997, 88, 243-251.
Vestheim et al., "Application of Blocking Oligonucleotides to Improve Signal-to-Noise Ratio in a PCR," Methods in Molecular Biology 2011, 687, 265-274.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.

Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91 (5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Ye et al., "Fluorescent microsphere-based readout technology for multiplexed human single nucleotide polymorphism analysis and bacterial identification," Human Mutation 2001, 17(4), 305-316.
Yoon et al., "Sensitive and accurate detection of copy number variants using read depth of coverage," Genome Res. 2009, 19, 1586-1592.
Zeberg et al., "The major genetic risk factor for severe COVID-19 is inherited from Neanderthals," Nature 2020, 587(7835), 1-13.
Zagordi et al., "Error correction of next-generation sequencing data and reliable estimation of HIV quasispecies," Nucleic Acids Research 2010, 38(21), 7400-7409.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A Smart Approach for Full-Length cDNA Library Construction," BioTechniques 2001, 30(4), 892-897.

(56) References Cited

OTHER PUBLICATIONS

Adey et al., "Rapid, low-input, low-bias construction of shotgun fragment libraries by high-density in vitro transposition," Genome Biology 2010, 11 (R19), in 17 pages.
Ahern, "Biochemical, Reagent Kits Offer Scientists Good Return on Investment," The Scientist 1995, 9(15), in 5 pages.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Buenrosto et al., "Transposition of native chromatin for multimodal regulatory analysis and personal epigenomics," Nat Methods 2013, 10(12), 1213-1218.
Buenrosto et al., "ATAC-seq: A Method for Assaying Chromatin Accessibility Genome-Wide," Curr Protoc Mol Biol 2016, 109, 1-21.
Chang et al., "Single-cell protein and gene expression profiling of stem memory T cells by BD Ab-seq," Annual Joint Meeting of the American Society for Cell Biology and the European Molecular Biology Organization 2017, 28(26), p. 1896.
Chen et al., "High-throughput sequencing of the transcriptome and chromatin accessibility in the same cell," Nature Biotechnology 2019, 37, 1452-1457.
De Simone et al., "Single Cell T Cell Receptor Sequencing: Techniques and Future Challenges," Frontiers in Immunology 2018, 9(1638), 1-7.
Dengl et al., "Engineered hapten-binding antibody derivatives for modulation of pharmacokinetic properties of small molecules and targeted payload delivery," Immunol Rev. 2016, 270, 165-177.
Dovgan et al., "Antibody- Oligonucleotide Conjugates as Therapeutic, Imaging, and Detection Agents," Bioconjugate Chem. 2019, 30, 2483-2501.
Erickson et al., "AbSeq Protocol Using the Nano-Well Cartridge-Based Rhapsody Platform to Generate Protein and Transcript Expression Data on the Single-Cell Level," Star Protocols 2020, in 31 pages.
Examination Report dated Oct. 8, 2021 in European Patent Application No. 18716877.8.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Apr. 7, 2022 in Singapore Patent Application No. 10201806890V.
Examination Report dated Apr. 8, 2022 in Australian Patent Application No. 2018281745.
Extended European Search Report dated May 6, 2021 in European Patent Application No. 20207621.2.
Extended European Search Report dated May 28, 2021 in European Patent Application No. 20209777.0.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Final Office Action dated Nov. 15, 2022 in U.S. Appl. No. 16/525,054.
Final Office Action dated Nov. 16, 2022 in U.S. Appl. No. 16/588,405.
Fitzgerald and Grivel, "A Universal Nanoparticle Cell Secretion Capture Assay," Cytometry Part A 2012, 83A(2), 205-211.
Gertz et al., "Transposase mediated construction of RNA-seq libraries," Genome Research 2012, 22, 134-141.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
Gratton et al., "Cell-permeable peptides improve cellular uptake and therapeutic gene delivery of replication-deficient viruses in cells and in vivo," Nature Medicine 2003, 9(3), 357-362.
International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
Invitation to Pay Fees dated May 25, 2021 in PCT Application No. PCT/US2021/01598.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Jacobsen et al., "33rd Annual Meeting & Pre-Conference Programs of the Society for Immunotherapy of Cancer," Journal for Immunotherapy of Cancer 2018, 6(S1), 7-11.
Janeway et al., "Structural variation in immunoglobulin constant regions," Immunology: The Immune System in Health and Disease 1999, 101-103.

(56) References Cited

OTHER PUBLICATIONS

Lake et al., "Integrative single-cell analysis of transcriptional and epigenetic states in the human adult brain," Nature Biotechnology 2018, 36(1), 70-80.
Lan et al., "Droplet barcoding for massively parallel single-molecule deep sequencing," Nature Communications 2016, 7(11784), in 10 pages.
Livingstone, "rRNA depletion, poly(A) enrichment, or exonuclease treatment?" Tebu-Bio Blog 2015, in 1 page.
Lutz et al., "Isolation and analysis of high quality nuclear DNA with reduced organellar DNA for plant genome sequencing and resequencing," BMC Biotechnology 2011, 11(54), in 9 pages.
Mair et al., "A Targeted Multi-omic Analysis Approach Measures Protein Expression and Low-Abundance Transcripts on the Single-Cell Level", Cell Reports 2020, 31(1), 107499, in 20 pages.
Minnoye et al., "Chromatin accessibility profiling methods," Nature Reviews Method Primers 2021, 1-24.
Monneron, "One-step Isolation and Characterization of Nuclear Membranes, 1974 Electron Microscopy and Composition of Biological Membranes and Envelops," The Royal Publishing Society 1974, 268, 101-108.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Notice of Allowance dated Aug. 16, 2021 in Japanese Patent Application No. 2018-512152.
Notice of Allowance dated Nov. 16, 2021 in U.S. Appl. No. 16/836,750.
Notice of Allowance dated Jan. 24, 2022 in Korean U.S. Appl. No. 16/836,750.
Notice of Allowance dated Feb. 9, 2022 in U.S. Appl. No. 16/781,814.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 26, 2022 in Chinese Patent Application No. 201780058799.1.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Notice of Allowance dated Jan. 10, 2023 in U.S. Appl. No. 16/588,405.
Novus Biologicals, "Fixation and Permeability in ICC IF," Novus Biologicals 2021, 1-3.
Nowak et al., "Does the KIR2DS5 gene protect from some human diseases?," PLoS One 2010, 5(8), in 6 pages.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.

(56) References Cited

OTHER PUBLICATIONS

Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794.
Office Action dated Sep. 14, 2021, in Chinese Patent Application No. 2016800523302.
Office Action dated Oct. 21, 2021, in Chinese Patent Application No. 2016800073512.
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application No. 201780058799.1.
Office Action dated Feb. 9, 2022 in Japanese Patent Application No. 2019-540515.
Office Action dated Mar. 7, 2022 in Korean Patent Application No. 10-2022-7004715.
Office Action dated May 5, 2022 in European Patent Application No. 19787547.9.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated Jun. 4, 2021 in U.S. Appl. No. 16/551,620.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Restriction Requirement dated Nov. 8, 2022 in U.S. Appl. No. 17/157,872.
Restriction Requirement dated Dec. 23, 2022 in U.S. Appl. No. 17/531,618.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Takara Bio, "SMARTer Human BCR IgG IgM H/K/L Profiling Kit User Manual," Takara Bio USA Inc. 2019, 1-22.
Trzupek et al., "Discovery of CD8O and CD86 as recent activation markers on regulatory T cells by protein-RNA single-cell analysis", Genome Medicine 2020, 12(1), in 22 pages.
Wang et al., "Tagmentation-based whole-genome bisulfite sequencing," Nature Protocols 2013, 8(10), 2022-2032.
Yang & Zhao, "Quantitative Analysis of Nonoxynol-9 in Blood," Contraception 1991, 43(2), 161-166.
Zhang et al., "Immunoaffinity Purification of Plasma Membrane with Secondary Antibody Superparamagnetic Beads," Journal of Proteome 2006, 6, 34-43.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.

Input=120 molecules+1x10^10 background poly A molecules k=122
n=130

Input=120 molecules+1x10^9 background poly A molecules k=116
n=124

Input=120 molecules+1x10^6 background poly A molecules k=109
n=114

Input=120 molecules+0 background poly A molecules k=115
n=122 k is a count of the number of labels detected (as bright spots), and n is the number of RNA molecules measured based on k step a)
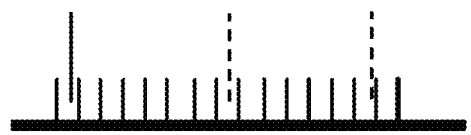
Array detector
step b)
Array detector
*FIG. 7*
step a) 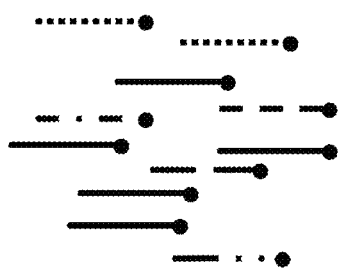 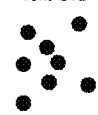
Stochastic labels
step b) 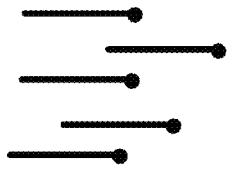
*FIG. 8*

5' CGACTACGACGACTACGCGACATCGACTACGAATGATACGACTAGCGGAT 3'      901 (SEQ ID NO. 3)
    902                  903                904

3' GTTGGTGTACTACGTAG 5'      905 (SEQ ID NO. 4)

FIG. 9

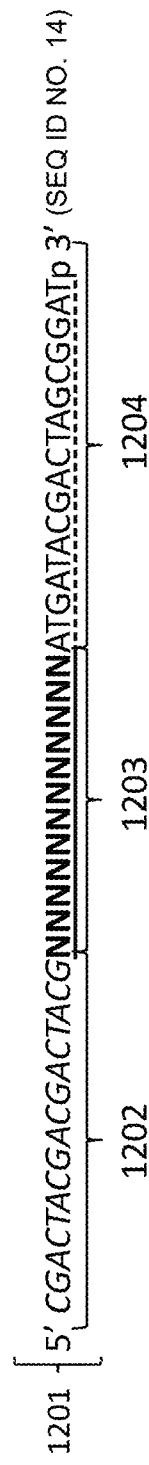
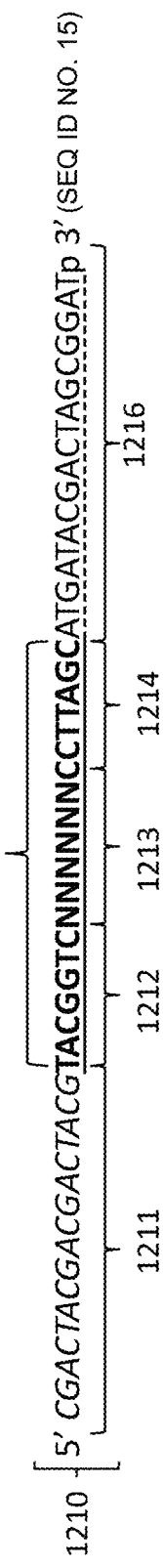
FIG. 12A
FIG. 12B

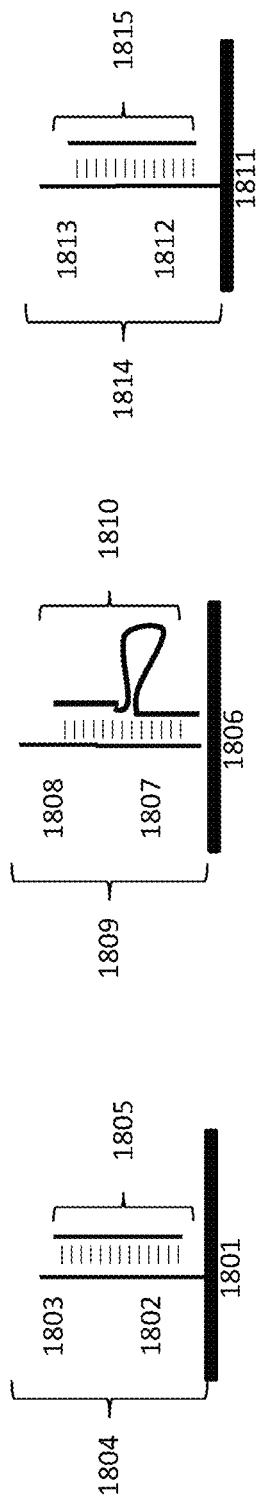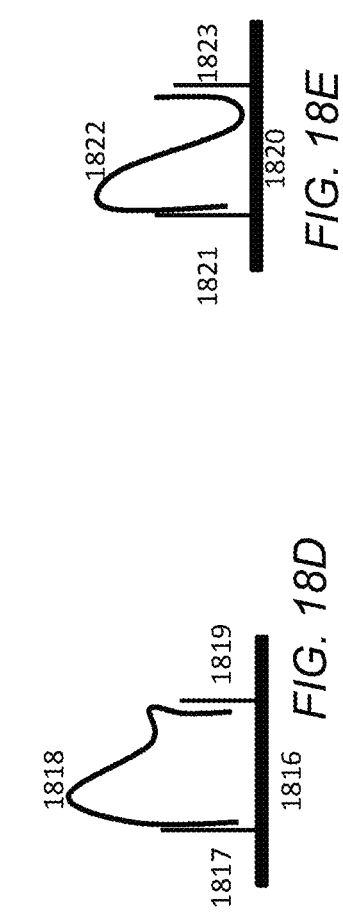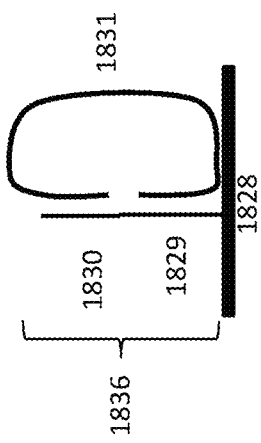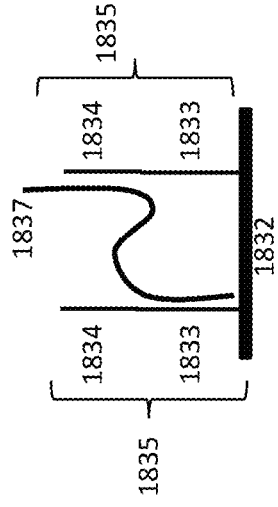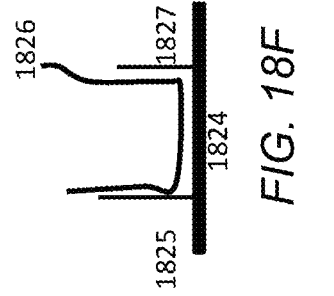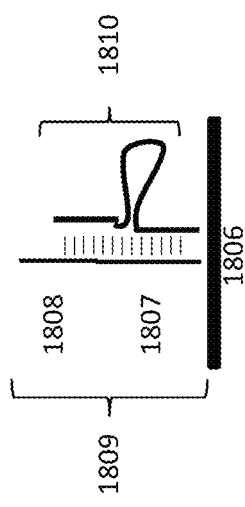
FIG. 18A FIG. 18B FIG. 18C FIG. 18D FIG. 18E FIG. 18F FIG. 18G FIG. 18H

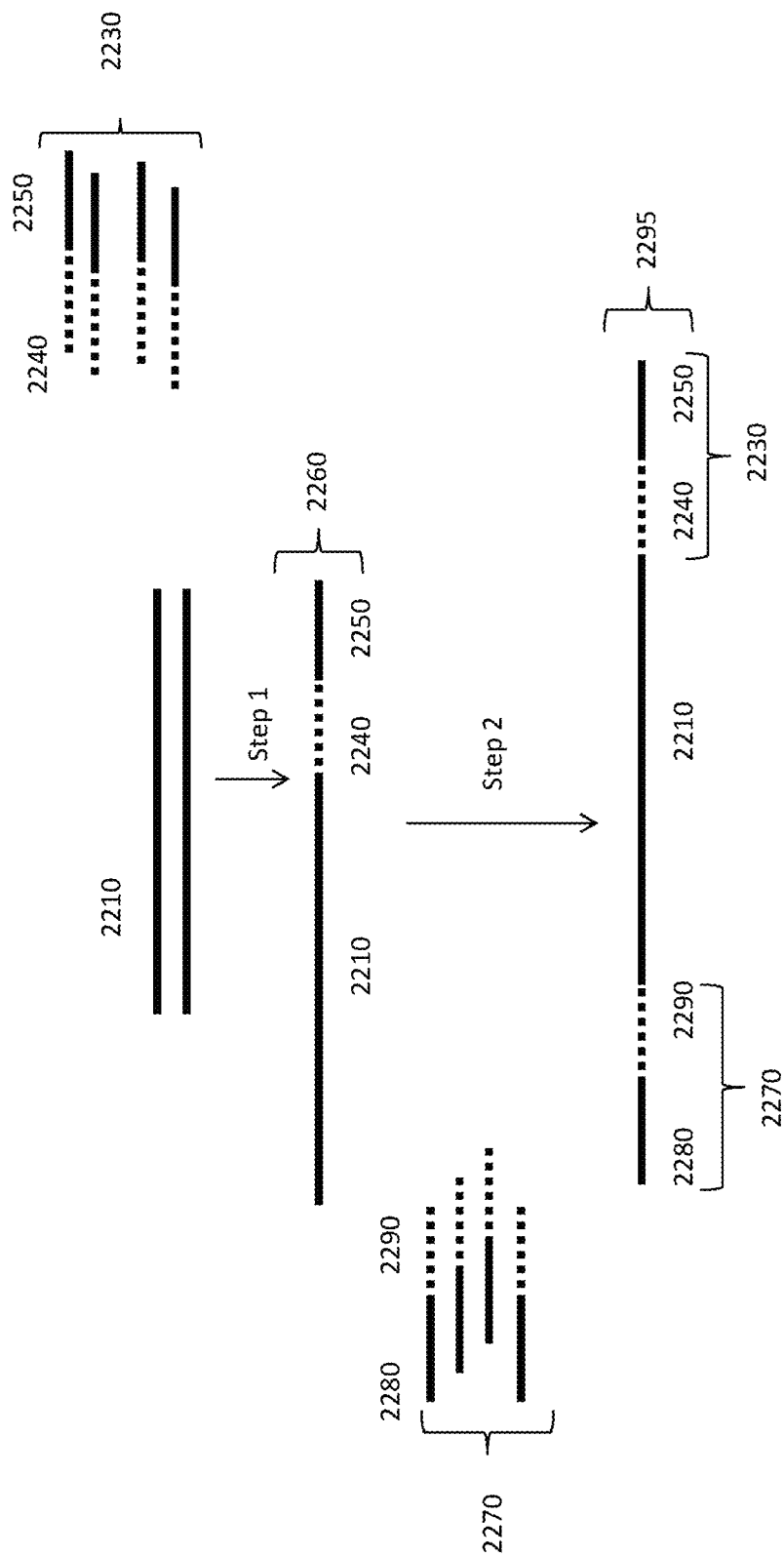

Step 1.

Step 2. Detection of the labeled cDNA molecules

Step 1. 1st strand synthesis

AAAAAAAAAAAAAAAAAAAAAAAAA 3' (SEQ ID NO. 23) } 2610

..UUUUUUUUUUUU 5' (dU15) (SEQ ID NO. 24) } 2620

Step 2. Exo I, UDG, RNA removal, poly A tailing

..TTTTTTTTTTTXXXXXXXXXX 5' (SEQ ID NO. 25) } 2630

Step 3. Labeling (extension with proofreader)

aaaaaaaaaaaaaaaaa.......
(SEQ ID NO. 18)

2660    2670

5' AGCACGAGACGCTGATgcggccgNNNNNNNUUUUUUUUUU*u*u-3' p (term_s6_label) } 2640
(SEQ ID NO. 26)

aaaaaaaaaaaaaaaaa.......TTTTTTTTTTTTTTTT 5'
(SEQ ID NO. 18)                           (SEQ ID NO. 27) } 2630

2650

Step 4. Strand extension

3' TCGTGCTGTCTGCGGACTACgccggccgNNNNNNNaaaaaaaa.......TTTTTTTTTTTTTTTT 5'
(SEQ ID NO. 28)                                      (SEQ ID NO. 27)

5' AGCACGACAGACGCCTGATgcggccgNNNNNNNtttttttt.......aaaaaaaaaaaaaaaa 3'
(SEQ ID NO. 29)                                    (SEQ ID NO. 30) } 2680

Step 5. Labeling again

5' AGCACGACAGACGCCTGATgcggccgNNNNNNNtttttttt.......aaaaaaaaaaaaaaaa 3'
(SEQ ID NO. 29)                                    (SEQ ID NO. 18)

3' p-u*u*UUUUUUUUUUUUUUUUUUNNNNNNNcgccggcgTAGTCCGCAGACAGCACGA
                                                    (SEQ ID NO. 33)

Step 6. UDG treat and PCR

PCR004  5' ATTATGAGCACGACAGACGCCTGAT
            (SEQ ID NO. 31)

*FIG. 26*

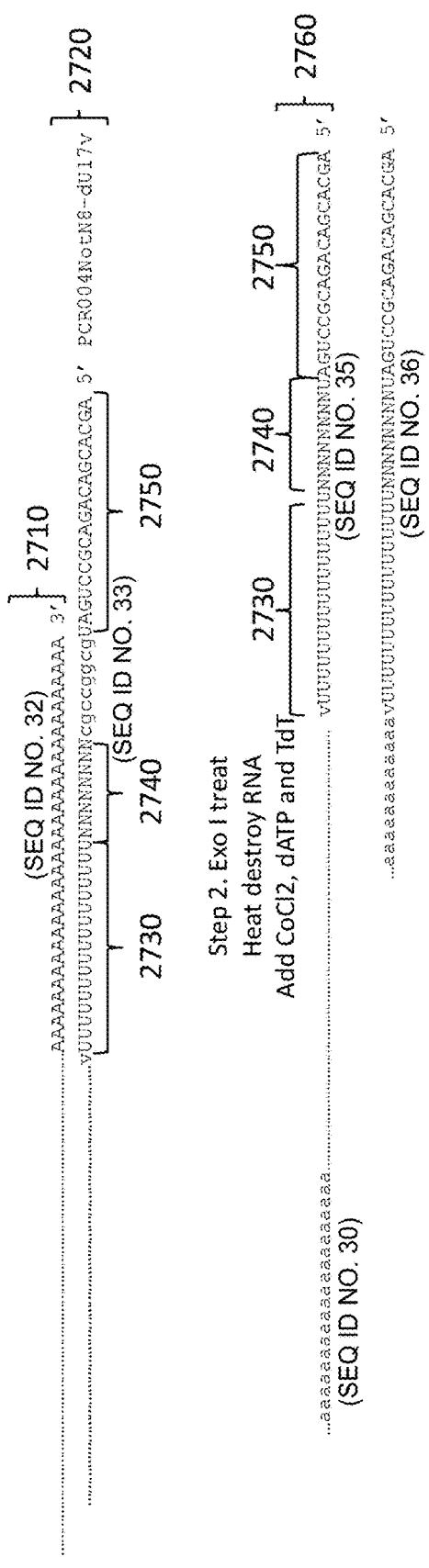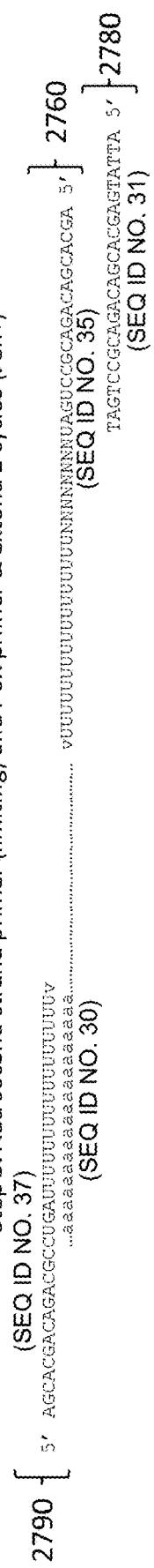
FIG. 27

*Reaction carried out on bead surface* mRNA
..................AAAAAAAAAAAAAAAA
(SEQ ID NO. 30)

1st strand cDNA with SS II (will add a few C's)

................AAAAAAAAAAAAAAAAAA (SEQ ID NO. 30)
CC..............TTTTTTTTTTTTTTTT-Bead
(SEQ ID NO. 27)

RNase H digestion

CC..............TTTTTTTTTTTTTTTTT
(SEQ ID NO. 27)

Oligonucleotide tag

3'Phosphate prevents extension

```
       stem    3P
      cttcgtcggnnn
     N ggaagcag  5P (SEQ ID NO. 38)
    N              N
   N                N
  N                  G
  N                  G
  N                  C
  G                  C
  G                  G
  C                  T
  C                  G
  G                  T
SNP6 PCR prime  G   C
           CGTGTCTGCGCCGGG TAATACTCG
```
Not I    N8 label

*Can also be a double-stranded adaptor* ligation →

Drive reaction to endpoint with excess ligase and excess oligonucleotide tags (72 hrs)

←TTTTTTTTTTTTTTTTT 5'
(SEQ ID NO. 27)
..............TTTTTTTTTTTTTTTTT 5'
(SEQ ID NO. 27)

3' nnnggctgcttcTAATACTCGTGTCTGCGCCGGGCNNNNNNNNgaagcagCC..........
(SEQ ID NO. 39)
S6-PCR ATTATGAGCACGACAGACGC→
(SEQ ID NO. 40)

Cut with Not I and ligate Illumina sequencing primers

*FIG. 28*

SEQUENCE LISTING

<160> NUMBER OF SEQ ID NOS: 61

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aaaaaaaaaa aaaaaaaaaa a                                              21

<210> SEQ ID NO 2
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(24)
<223> OTHER INFORMATION: a, c, t, g, unknown or other

<400> SEQUENCE: 2
nnnnnnnnnn nnnnnnnnnn nnnnttttt ttttttttttt ttttt                    45

<210> SEQ ID NO 3
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
cgactacgac gactacgcga catcgactac gaatgatacg actagcggat               50

<210> SEQ ID NO 4
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gatgcatcat gtggttg                                                   17

<210> SEQ ID NO 5
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
cgactacgac gactacg                                                   17

<210> SEQ ID NO 6
<211> LENGTH: 18

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
atgatacgac tagcggat                                                    18

<210> SEQ ID NO 7
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
cgactacgac gactacgcga catcgactac gagtcggt                              38

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
aatgctatga tacgactagc ggat                                             24

<210> SEQ ID NO 9
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
cgactacgac gactacgcga catcgactac gagtcggtaa tgctatgata cgactagcgg      60
at                                                                     62

<210> SEQ ID NO 10
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
agcattaccg ac                                                          12

<210> SEQ ID NO 11
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 11
atccgctagt cgtatcatac cgac                                            24

<210> SEQ ID NO 12
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
cgactacgac gactacgcga catcgactac gagtcggtat gatacgacta gcggat         56

<210> SEQ ID NO 13
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
auccgcuagu cguaucauac cgac                                            24

<210> SEQ ID NO 14
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (18)..(29)
<223> OTHER INFORMATION: a, c, t, g, unknown or other

<400> SEQUENCE: 14
cgactacgac gactacgnnn nnnnnnnna tgatacgact agcggat                    47

<210> SEQ ID NO 15
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (25)..(30)
<223> OTHER INFORMATION: a, c, t, g, unknown or other

<400> SEQUENCE: 15
cgactacgac gactacgtac ggtcnnnnnn ccttagcatg atacgactag cggat          55

<210> SEQ ID NO 16
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (53)..(55)
<223> OTHER INFORMATION: a, c, t, g, unknown or other

<400> SEQUENCE: 16
gatagcatcg actacgacta gcgcgctagg tacgactacg tacgcctagc gcnnn      55

<210> SEQ ID NO 17
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
cgactacgac gactacgcga catcgactac gatttttttt tttttttttt tt         52

<210> SEQ ID NO 18
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
aaaaaaaaaa aaaaaaaaaa aaaa                                        24

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
tttttttttt tttttttv                                               18

<210> SEQ ID NO 20
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
aaaaaaaaaa aaaaaaaaaa aaaaaa                                      26

<210> SEQ ID NO 21
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
tttttttttt tttttttttt ttttt                                       25

<210> SEQ ID NO 22
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
aaaaaaaaaa aaaaaaaaaa aa                                            22

<210> SEQ ID NO 23
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
aaaaaaaaaa aaaaaaaaaa aaaaaaaaa                                     29

<210> SEQ ID NO 24
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
uuuuuuuuuu uuuuu                                                    15

<210> SEQ ID NO 25
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t, g, unknown or other

<400> SEQUENCE: 25
nnnnnnnnnn nntttttttt tttt                                          24

<210> SEQ ID NO 26
<211> LENGTH: 54
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (28)..(35)
<223> OTHER INFORMATION: a, c, u, g, unknown or other

<400> SEQUENCE: 26
agcacgacag acgccugaug cggccgcnnn nnnnuuuuu uuuuuuuuu uuuu            54

<210> SEQ ID NO 27
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
tttttttttt tttttttttt                                              20

<210> SEQ ID NO 28
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(17)
<223> OTHER INFORMATION: a, c, t, g, unknown or other

<400> SEQUENCE: 28
aaaaaaaaan nnnnnnngcg gccgcatcag gcgtctgtcg tgct                   44

<210> SEQ ID NO 29
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (28)..(35)
<223> OTHER INFORMATION: a, c, t, g, unknown or other

<400> SEQUENCE: 29
agcacgacag acgcctgatg cggccgcnnn nnnnttttt tttt                    44

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
aaaaaaaaaa aaaaaaaaaa                                              20

<210> SEQ ID NO 31
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
attatgagca cgacagacgc ctgat                                        25

<210> SEQ ID NO 32
<211> LENGTH: 33
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
aaaaaaaaaa aaaaaaaaaa aaaaaaaaaa aaa                                    33

<210> SEQ ID NO 33
<211> LENGTH: 53
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (28)..(35)
<223> OTHER INFORMATION: a, c, u, g, unknown or other

<400> SEQUENCE: 33
agcacgacag acgccugaug cggccgcnnn nnnnnuuuu uuuuuuuuuu uuv              53

<210> SEQ ID NO 34
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
uuuuuuuuuu uuuuuuuv                                                     18

<210> SEQ ID NO 35
<211> LENGTH: 45
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(27)
<223> OTHER INFORMATION: a, c, u, g, unknown or other

<400> SEQUENCE: 35
agcacgacag acgccugaun nnnnnnnuuu uuuuuuuuu uuuuv                        45

<210> SEQ ID NO 36
<211> LENGTH: 57
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(27)
<223> OTHER INFORMATION: a, c, u, g, unknown or other

<400> SEQUENCE: 36
agcacgacag acgccugaun nnnnnnnuuu uuuuuuuuu uuuvaaaaa aaaaaaa            57
```

```
<210> SEQ ID NO 37
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
agcacgacag acgccugauu uuuuuuuuu uuuuuv                              36

<210> SEQ ID NO 38
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(10)
<223> OTHER INFORMATION: a, c, t, g, unknown or other
<220> FEATURE:
<221> NAME/KEY: modified_base
<222> LOCATION: (46)..(48)
<223> OTHER INFORMATION: a, c, t, g, unknown or other

<400> SEQUENCE: 38
gacgaagnnn gcggccgcgt ctgtcgtgct cataatcttc gtcggnnn               48

<210> SEQ ID NO 39
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(17)
<223> OTHER INFORMATION: a, c, t, g, unknown or other
<220> FEATURE:
<221> NAME/KEY: modified_base
<222> LOCATION: (53)..(55)
<223> OTHER INFORMATION: a, c, t, g, unknown or other

<400> SEQUENCE: 39
ccgacgaagn nnnnnnngcg gccgcgtctg tcgtgctcat aatcttcgtc ggnnn        55

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
attatgagca cgacagacgc                                               20

<210> SEQ ID NO 41
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 41
aaaaaaaaaa aaaa                                                14

<210> SEQ ID NO 42
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(8)
<223> OTHER INFORMATION: a, c, t, g, unknown or other

<400> SEQUENCE: 42
nnnnnnnntt tttttttttt ttttttt                                  27

<210> SEQ ID NO 43
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (22)..(22)
<223> OTHER INFORMATION: a, c, t, g, unknown or other

<400> SEQUENCE: 43
tttttttttt tttttttttt vn                                       22

<210> SEQ ID NO 44
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
aaaaaaaaaa aaaaaaaaaa aaaaaaaaaa a                             31

<210> SEQ ID NO 45
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (64)..(64)
<223> OTHER INFORMATION: a, c, t, g, unknown or other

<400> SEQUENCE: 45
tgtgttgggt gtgtttggcg gccgcbbbbb bbbbbbbttt tttttttttt tttttttttt   60 ttvn                                                           64

<210> SEQ ID NO 46
<211> LENGTH: 64

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (64)..(64)
<223> OTHER INFORMATION: a, c, u, g, unknown or other

<400> SEQUENCE: 46
uguguugggu guguuuggcg gccgcbbbbb bbbbbbbuuu uuuuuuuuuu uuuuuuuuuu      60 uuvn                                                                  64

<210> SEQ ID NO 47
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
uuuuuuuuuu uuuuuuuuuu uuuuu                                           25

<210> SEQ ID NO 48
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
tgtgttgggt gtgtttggcg cgccbbbbbb bbbbbbtt                             38

<210> SEQ ID NO 49
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (37)..(38)
<223> OTHER INFORMATION: a, c, t, g, unknown or other

<400> SEQUENCE: 49
tgtgttgggt gtgtttggcg cgccbbbbbb bbbbbbnn                             38

<210> SEQ ID NO 50
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
tgtgttgggt gtgtttggcg cgcckkkkkk kkkkkktt                             38

<210> SEQ ID NO 51
```

-continued

```
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (37)..(38)
<223> OTHER INFORMATION: a, c, t, g, unknown or other

<400> SEQUENCE: 51
tgtgttgggt gtgtttggcg cgcckkkkkk kkkkkknn                              38

<210> SEQ ID NO 52
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
tgtgttgggt gtgtttgg                                                   18

<210> SEQ ID NO 53
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ggccagatcg gaagagcggt tcagcaggaa tgccgag                              37

<210> SEQ ID NO 54
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
caagcagaag acggcatacg agatcggtct cggcattcct gctgaaccgc tcttccgatc     60
t                                                                     61

<210> SEQ ID NO 55
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
aatgatacgg cgaccaccga gatctacact ctttccctac acgacgctct tccgatct       58

<210> SEQ ID NO 56
<211> LENGTH: 37
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 56
cgcgagatcg gaagagcgtc gtgtagggaa agagtgt                              37

<210> SEQ ID NO 57
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
aatgatacgg cgaccaccga ga                                              22

<210> SEQ ID NO 58
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
caagcagaag acggcatacg aga                                             23

<210> SEQ ID NO 59
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
aaaaaaaaaa aaaaaa                                                     16

<210> SEQ ID NO 60
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
tttttttttt tttttttttt tttt                                            24

<210> SEQ ID NO 61
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
tttttttttt tttttttttt tttttttttt tttttttttt                           40
```

COMPOSITIONS AND KITS FOR MOLECULAR COUNTING

CROSS-REFERENCE TO RELATED APPLICATIONS

This application is a continuation of U.S. patent application Ser. No. 14/381,488, filed on Aug. 27, 2014, now U.S. Pat. No. 10,941,396, which is a U.S. national phase under 35 U.S.C. § 371 of International Application No. PCT/US2013/028103, entitled "COMPOSITIONS AND KITS FOR MOLECULAR COUNTING," filed on Feb. 27, 2013, and published on Sep. 6, 2013 as WO/2013/130674, which claims the benefit of U.S. Provisional Application No. 61/603,921 filed Feb. 27, 2012, and U.S. Provisional Application No. 61/745,385, filed Dec. 21, 2012. These related applications are incorporated by reference herein in their entirety.

FIELD OF THE INVENTION

Methods and uses of molecular counting are disclosed. Molecules can be counted by sequencing and tracking the number of occurrences of a target molecule. Molecules can also be counted by hybridization of the molecule to a solid support and detection of the hybridized molecules. In some instances, the molecules to be counted are labeled. The molecules to be counted may also be amplified.

BACKGROUND OF THE INVENTION

Accurate determination of the quantity of nucleic acids is necessary in a wide variety of clinical and research measurements. When dissolved in solution, the average concentration of nucleic acids (RNA or DNA) can be determined by UV light absorbance spectrophotometry or by fluorescent DNA-binding stains. However, the measurement required is often not just for the total amount of nucleic acids present, but specifically for one or more species of interest contained and mixed with all of the other nucleic acids within the sample. In these cases, the nucleic acid molecule of interest is usually distinguished from all of the other nucleic acids through a defined sequence of nucleotides that is unique to the species of interest. A short synthetic ribo- or deoxyribo-oligonucleotide with a complementary sequence to the nucleic acid of interest can be used for its detection and identification. For instance, the Polymerase Chain Reaction (PCR) uses a pair of these oligonucleotides to serve as annealing primers for repeated cycles of DNA polymerization mediated by DNA polymerase enzymes. DNA microarrays are another common detection method where oligonucleotides are immobilized on solid supports to hybridize to DNA molecules bearing complementary sequences. Although both PCR and microarray methods are capable of specific detection, accurate determination of the quantity of the detected molecules is difficult (especially when it is present in low abundance or when contained within a large background of other nucleic acids). In the case of PCR (also sometimes referred to as quantitative-PCR, qPCR, TaqMan, or real-time PCR), the amount of amplified DNA molecules represents an estimate of its concentration in the starting solution. In the case of microarrays, the amount of DNA hybridized is an estimate of its concentration in solution. In both cases, only relative measurements of concentration can be made, and the absolute number of copies of nucleic acid in the sample cannot be precisely determined. However, when reference nucleic acids of pre-determined concentrations are included in the test, relative comparisons can be made to this standard reference to estimate the absolute number of copies of nucleic acids being detected.

Digital PCR is one method that can be used to determine the absolute number of DNA molecules of a particular nucleotide sequence (Sykes et al. Biotechniques 13: 444-449 (1992), Vogelstein et al. Digital PCR. Proc Natl Acad Sci USA 96: 9236-9241 (1999)). In this method, the nucleic acid solution is diluted and stochastically partitioned into individual containers so that there is on average less than one molecule in every two containers. PCR is then used to detect the presence of the nucleic acid molecule of interest in each container. If quantitative partitioning is assumed, the dynamic range is governed by the number of containers available for stochastic separation. Micro fabrication and picoliter-sized emulsion droplets can be used to increase the number of containers available thereby extending the measurement dynamic range (Fan et al. Am J Obstet Gynecol 200: 543 e541-547 (2009), Kalinina et al. Nucleic Acids Res 25: 1999-2004 (1997)). Due to the physical constraints of manufacturing large numbers of separate containers and in carrying out these larger numbers of reactions, in practice the digital PCR method is limited to investigations on only a small number of different DNA molecules at a time.

Recently, a new method to determine the absolute quantity of DNA molecules has been demonstrated where identical copies of individual DNA molecules can be counted after the stochastic attachment of a set of diverse nucleic acid labels (Fu et al. Proc Natl Acad Sci USA 108: 9026-9031 (2011)). Unlike digital PCR, this is a highly parallel method capable of counting many different DNA molecules simultaneously. In this method, each copy of a molecule randomly attaches to a short nucleic acid label by choosing from a large, non-depleting reservoir of diverse labels. The subsequent diversity of the labeled molecules is governed by the statistics of random choice, and depends on the number of copies of identical molecules in the collection compared to the number of kinds of labels. Once the molecules are labeled, they can be amplified so that simple present/absent threshold detection methods can be used for each. Counting the number of distinctly labeled targets reveals the original number of molecules of each species. Unlike digital PCR, which stochastically expands identical molecules into physical space, the method of stochastic labeling expands identical molecules into chemical space. An important distinction from digital PCR is that the stochastic labeling method does not require the challenging physical separation of identical molecules into individual physical containers. The approach is practical, and after labeling, a simple detector device such as a microarray with complementary probe sequences to the labels can be used to identify and count the number of labels present. In addition, when stochastic labels are attached to DNA molecules that are prepared for DNA sequencing readouts, the labeling sequence can serve as discreet counting tags for absolute quantitation, or as unique identifiers to distinguish each originally tagged template from its amplified daughter molecules (Kinde et al. Proc Natl Acad Sci USA 108: 9530-9535 (2011)).

SUMMARY OF THE INVENTION

In some embodiments is a digital reverse transcription method comprising: a) contacting a sample comprising a plurality of RNA molecules with a plurality of oligonucleotide tags to produce a labeled-RNA molecule, wherein: the plurality of RNA molecules comprise at least 2 mRNA molecules of different sequences; the plurality of oligonucleotide tags comprises at least 2 oligonucleotide tags of different sequences; and the plurality of oligonucleotide tags comprises an oligodT sequence; b) conducting a first strand synthesis reaction by contacting the labeled-RNA molecules with a reverse transcriptase enzyme to produce a labeled-cDNA molecule; and c) detecting the labeled-cDNA molecule by hybridizing the labeled-cDNA molecule to a solid support.

In some embodiments is a stochastic label-based hybridization chain reaction method comprising stochastically labeling one or more nucleic acid molecules with a plurality of hairpin oligonucleotide tags, wherein the hairpin oligonucleotide tag comprises an overhang; and the one or more nucleic acid molecules act as initiators for a hybridization chain reaction.

At least a portion of the hairpin oligonucleotide tag may hybridize to at least a portion of the one or more nucleic acid molecules. The hairpin oligonucleotide tag may comprise an oligodT sequence. The one or more nucleic acid molecules may comprise one or more adapters. At least a portion of the hairpin oligonucleotide tag may hybridize to at least a portion of the one or more adapters. At least one hairpin oligonucleotide tag of the plurality of hairpin oligonucleotide tags may comprise one or more labels. At least one hairpin oligonucleotide tag of the plurality of hairpin oligonucleotide tags may comprise two or more labels.

Each hairpin oligonucleotide tag of the plurality of hairpin oligonucleotide tags may comprise one or more labels. Each hairpin oligonucleotide tag of the plurality of hairpin oligonucleotide tags may comprise two or more labels. In some instances, the hairpin oligonucleotide tag does not comprise a label.

The plurality of hairpin oligonucleotide tags may comprise one or more hairpin oligonucleotide tags with a 5' overhang, hairpin oligonucleotide tags with a 3' overhang, or a combination thereof.

The stem portion of the hairpin oligonucleotide tag can be one or more nucleotides in length. The stem portion of the hairpin oligonucleotide tag can be two or more nucleotides in length. The stem portion of the hairpin oligonucleotide tag can be three or more nucleotides in length. The stem portion of the hairpin oligonucleotide tag can be four or more nucleotides in length. The stem portion of the hairpin oligonucleotide tag can be five or more nucleotides in length. The stem portion of the hairpin oligonucleotide tag can be six or more nucleotides in length. The stem portion of the hairpin oligonucleotide tag can be seven or more nucleotides in length. The stem portion of the hairpin oligonucleotide tag can be eight or more nucleotides in length. The stem portion of the hairpin oligonucleotide tag can be nine or more nucleotides in length. The stem portion of the hairpin oligonucleotide tag can be ten or more nucleotides in length. The stem portion of the hairpin oligonucleotide tag can be 15, 20, 25, 30, 35, 40, 45, 50, 60, 70, 80, 90, 100 or more nucleotides in length.

The loop portion of the hairpin oligonucleotide tag can be one or more nucleotides in length. The loop portion of the hairpin oligonucleotide tag can be two or more nucleotides in length. The loop portion of the hairpin oligonucleotide tag can be three or more nucleotides in length. The loop portion of the hairpin oligonucleotide tag can be four or more nucleotides in length. The loop portion of the hairpin oligonucleotide tag can be five or more nucleotides in length. The loop portion of the hairpin oligonucleotide tag can be six or more nucleotides in length. The loop portion of the hairpin oligonucleotide tag can be seven or more nucleotides in length. The loop portion of the hairpin oligonucleotide tag can be eight or more nucleotides in length. The loop portion of the hairpin oligonucleotide tag can be nine or more nucleotides in length. The loop portion of the hairpin oligonucleotide tag can be ten or more nucleotides in length. The loop portion of the hairpin oligonucleotide tag can be 15, 20, 25, 30, 35, 40, 45, 50, 60, 70, 80, 90, 100 or more nucleotides in length.

The hairpin oligonucleotide tag may comprise a unique identifier region. The unique identifier region can be in the loop portion of the hairpin oligonucleotide tag. The unique identifier region can be in the stem portion of the hairpin oligonucleotide tag. The unique identifier region can be in the overhang portion of the hairpin oligonucleotide tag.

The label may comprise a unique identifier region.

In some embodiments the oligonucleotide tag further comprises a unique identifier region. In some embodiments the unique identifier region is at least one nucleotide in length. In some embodiments the oligonucleotide tag further comprises a universal primer binding site. In some embodiments the oligonucleotide tag is at least one nucleotide in length.

In some embodiments the solid support is an array. In some embodiments the solid support is an addressable array. In some embodiments the solid support is an Affymetrix 3K tag array, Arrayjet non-contact printed array, or Applied Microarrays Inc (AMI) array. In some embodiments the solid support is a bead.

Further disclosed herein is cell analysis method comprising: a) contacting a sample comprising a plurality of molecules with a plurality of oligonucleotide tags to produce a labeled-molecule, wherein: the plurality of molecules comprise at least 2 molecules of different sequences; the plurality of oligonucleotide tags comprises at least 2 oligonucleotide tags of different sequences; and the sample is from at least one cell; and b) detecting the labeled-molecule by hybridizing the labeled-molecule to a solid support.

In some embodiments is a clonal amplification method comprising: a) stochastically labeling a plurality of molecules with a plurality of oligonucleotide tags to produce a labeled-molecule, wherein: the plurality of molecules comprise at least 2 molecules of different sequences; and the plurality of oligonucleotide tags comprises at least 2 oligonucleotide tags of different sequences; b) amplifying the labeled-molecules to produce a labeled-amplicon; and c) detecting the labeled-amplicon.

Further disclosed herein is a kit comprising: a) a plurality of oligonucleotide tags, wherein the oligonucleotide tag of the plurality of oligonucleotide tags comprises: a target specific region; and a unique identifier region; and b) an enzyme.

In some embodiments the enzyme is a reverse transcriptase enzyme. In some embodiments the enzyme is a ligase. In some embodiments the enzyme is a polymerase. In some embodiments the enzyme is an RNase. In some embodiments the enzyme is a DNase. In some embodiments the enzyme is an endonuclease.

In some embodiments the oligonucleotide tag is at least 25 nucleotides in length. In some embodiments the unique identifier region is at least 10 nucleotides in length. In some embodiments the target specific region is at least 10 nucleotides in length. In some embodiments the target specific region comprises an oligodT sequence. In some embodiments the oligonucleotide tag further comprises a universal primer binding site.

In some embodiments the kit further comprises a support. In some embodiments the support is a semi-solid support. In some embodiments the support is a solid support. In some embodiments the solid support is an array. In some embodiments the support is an addressable array. In some embodiments the support is an Affymetrix 3K tag array, Arrayjet non-contact printed array, or Applied Microarrays Inc (AMI) array. In some embodiments the support is a bead.

In some embodiments the kit further comprises a primer. In some embodiments the primer is a universal primer. In some embodiments the primer binds to the oligonucleotide tag. In some embodiments the primer binds to the universal primer binding site of the oligonucleotide tag.

In some embodiments the kit further comprises a control oligo. In some embodiments the control oligo comprises at least 15 nucleotides. In some embodiments the control oligo is a bright hybridization control oligo. In some embodiments the control oligo is a spike-in template control. In some embodiments the oligonucleotide tag further comprises a label.

In some embodiments the primer further comprises a label. In some embodiments the control oligo further comprises a label. In some embodiments the label is a dye label. In some embodiments the label is a Cy3 dye. In some embodiments the label is a Tye563 dye.

In some embodiments the kit further comprises a buffer.
In some embodiments the kit further comprises a carrier.
In some embodiments the kit further comprises a detergent.

Further disclosed herein is a system for determining the absolute quantity of a plurality of nucleic acid molecules. The system may comprise a) a plurality of oligonucleotide tags; and b) a detector for detecting at least a portion of the oligonucleotide tags.

The detector may comprise an array detector, fluorescent reader, non-fluorescent detector, CR reader, or scanner. In some embodiments the method further comprises the fluorescent reader is a Sensovation or AG fluorescent reader. In some embodiments the method further comprises the scanner is a flatbed scanner.

The system may further comprise a thermal cycler. In some embodiments the system further comprises a sequencer. In some embodiments the system further comprises a hybridization chamber.

The system may further comprise a computer. In some embodiments the computer comprises a memory device. In some embodiments the memory device is capable of storing data. In some embodiments the system further comprises a software program. In some embodiments the system further comprises a computer-readable program.

In some embodiments the oligonucleotide tag further comprises a unique identifier region. In some embodiments the unique identifier region is at least 10 nucleotides in length. In some embodiments the unique identifier region cannot hybridize to the molecule. In some embodiments the oligonucleotide tag further comprises a universal primer binding site. In some embodiments the oligonucleotide tag is at least 20 nucleotides in length. In some embodiments the oligonucleotide tag further comprises a target specific region. In some embodiments the target specific region comprises an oligodT sequence. In some embodiments the target specific region is at least 10 nucleotides in length. In some embodiments the method further comprises conducting a first strand synthesis reaction to produce a labeled-cDNA molecule.

In some embodiments the amplifying the labeled-molecule comprises conducting a polymerase chain reaction. Alternatively, amplifying the labeled-molecule may comprise conducting a non-PCR based amplification reaction. Amplifying the labeled-molecule may comprise exponential amplification of the labeled-molecule. Amplifying the labeled-molecule may comprise linear amplification of the labeled molecule. Amplifying the labeled-molecule may comprise hybridization chain reaction (HCR) based amplification method.

Amplifying the labeled-molecule may comprise amplifying at least the label portion of the labeled molecule, the molecule portion of the labeled molecule, or a combination thereof.

In some embodiments the method further comprises conducting a polymerase chain reaction on the labeled-molecule or any product thereof to produce a double-stranded labeled-molecule. In some embodiments conducting the polymerase chain reaction comprises annealing a first target specific primer to the labeled-molecule or any product thereof. In some embodiments conducting the polymerase chain reaction further comprises annealing a universal primer to the universal primer binding site of the oligonucleotide tag. In some embodiments the polymerase chain reaction comprises absolute PCR, HD-PCR, Next Gen PCR, digital RTA, or any combination thereof. In some embodiments the method comprises conducting a nested PCR reaction on the double-stranded labeled-cDNA molecule. In some embodiments conducting the nested PCR reaction comprises denaturing the labeled-molecule or any product thereof to produce a denatured single-stranded labeled-molecule or any product thereof. In some embodiments conducting the nested PCR reaction further comprises annealing a second target specific primer to the denatured single-stranded labeled-molecule or any product thereof. In some embodiments conducting the nested PCR reaction further comprises annealing a universal primer to the universal primer binding site of the oligonucleotide tag.

In some embodiments the method further comprises conducting a sequencing reaction to determine the sequence of at least a portion of the oligonucleotide tag, at least a portion of the labeled-molecule, a product thereof, a complement thereof, a reverse complement thereof, or any combination thereof.

In some embodiments detecting the labeled-molecules or any products thereof comprises an array detector, fluorescent reader, non-fluorescent detector, CR reader, or scanner. In some embodiments the molecule is a nucleic acid molecule.

In some embodiments the nucleic acid molecule is a DNA molecule. In some embodiments the nucleic acid molecule is an RNA molecule. In some embodiments the molecule is a peptide. In some embodiments the peptide is a polypeptide.

In some embodiments the plurality of molecules is from a cell. In some embodiments the sample is from a single cell. In some embodiments the sample is from less than about 100 cells. In some embodiments the sample is from less than about 50 cells. In some embodiments the sample is from less than about 20 cells. In some embodiments the sample is from less than about 10 cells. In some embodiments the sample is from less than about 5 cells. In some embodiments the cell is a mammalian cell. In some embodiments the cell is a human cell. In some embodiments the cell is from a subject suffering from a disease or condition. In some embodiments the disease or condition is cancer. In some embodiments the disease or condition is a pathogenic infection. In some embodiments the disease or condition is a genetic disorder. In some embodiments the cell is from a healthy subject. In some embodiments the cell is a diseased cell. In some embodiments the diseased cell is a cancerous cell. In some embodiments the cell is a healthy cell. In some embodiments the cell is not a diseased or infected cell. In some embodiments the labeled-molecules are produced by stochastic labeling.

BRIEF DESCRIPTION OF THE DRAWINGS

The skilled artisan will understand that the drawings described below are for illustration purposes only. The drawings are not intended to limit the scope of the present teachings in any way.

FIG. 7 shows a schematic of detection of a labeled molecule by an array detector FIG. 8 shows a schematic of stochastic labeling of a plurality of molecules FIG. 9 Exemplary PCR primer consisting of a universal PCR sequence, a short label sequence and a target or gene-specific sequence.

FIG. 12A-FIG. 12B depict degerate oligonucleotide tags FIG. 13A-FIG. 13B Additional Examples of Labeled Primers.

DETAILED DESCRIPTION OF THE INVENTION

Figure 1:
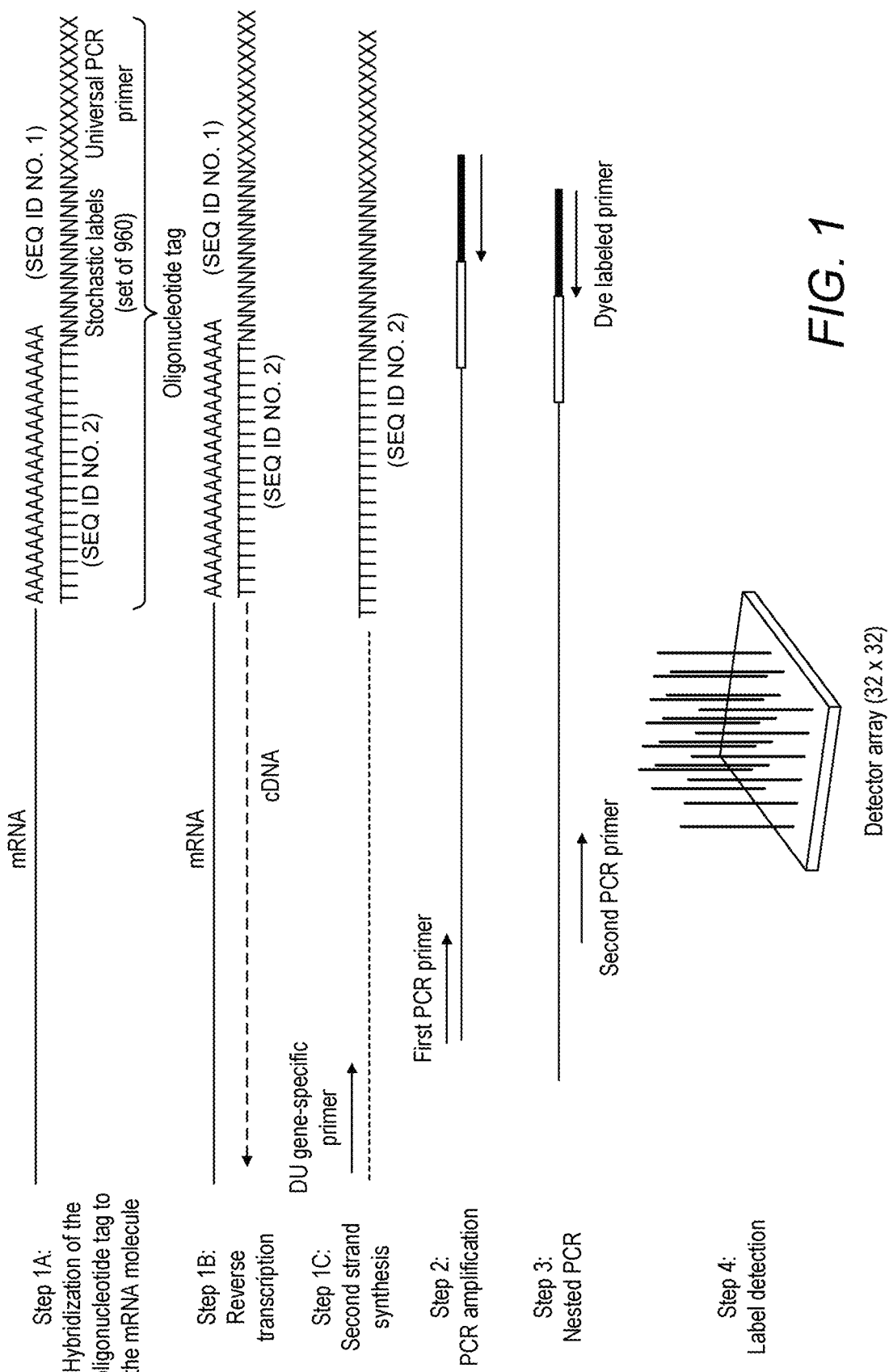
FIG. 1 shows a schematic of labeling and detection of a target molecule
Figure 2A:
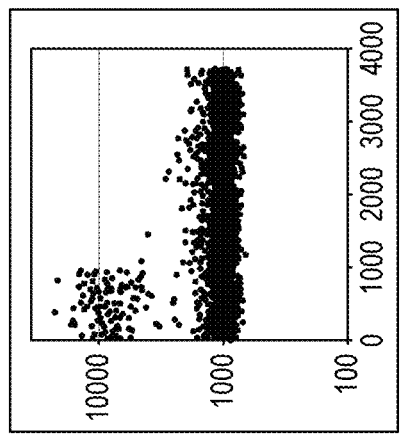
FIG. 2A-FIG. 2D show signals for the detection of labels in hybridized molecules
Figure 2B:
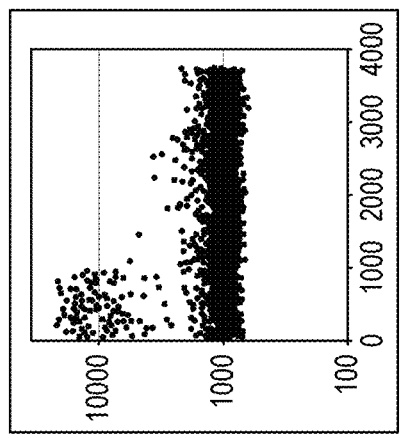
Figure 2C:
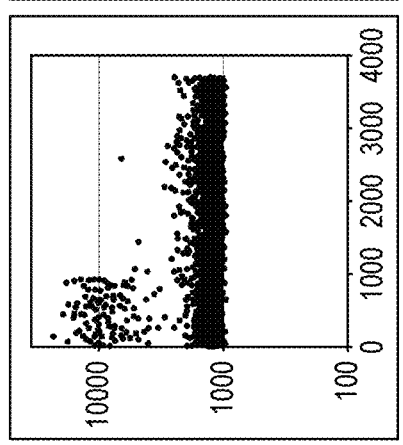
Figure 2D:
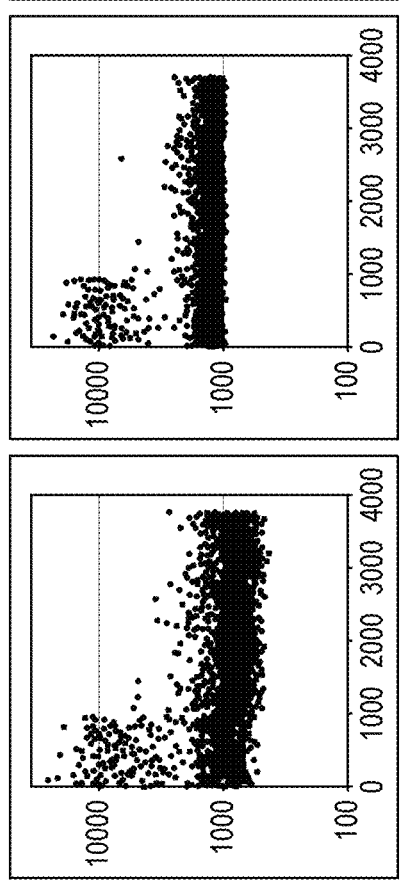

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention has many preferred embodiments and relies on many patents, applications and other references for details known to those of the art. Therefore, when a patent, application, or other reference, such as a printed publication, is cited or repeated below, it should be understood that it is incorporated by reference in its entirety for all purposes and particularly for the proposition that is recited.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, 2 to 6, from 3 to 6 etc., as well as individual numbers within that range, for example, 1, 2, 3, 4, 5, and 6. This applies regardless of the breadth of the range.

Disclosed herein are methods, kits, and systems for detecting and/or quantifying molecules in a sample. In some instances, methods, kits, and systems for individually counting molecules in a sample are provided. Alternatively, methods, kits, and systems for determining the expression level of a gene or gene produce are provided. In some instances, the methods comprise the attachment of an oligonucleotide tag to a molecule (e.g., RNA, DNA, protein) to form a labeled molecule. The oligonucleotide tag can comprise a target specific region, unique identifier region, universal primer binding region, detectable label region, or any combination thereof. In some instances, the attachment of the oligonucleotide tag to the molecule results in the formation of a unique junction comprising at least a portion of the oligonucleotide tag and at least a portion of the molecule. An expression level of a gene or gene product can be determined by detecting and/or quantifying at least a portion of the labeled molecule (e.g., unique junction, oligonucleotide tag, molecule). The absolute quantity of a target molecule can also be determined by detecting the number of unique oligonucleotide tags of the labeled molecules and/or the number of unique junctions in the labeled molecules.

Figure 14:
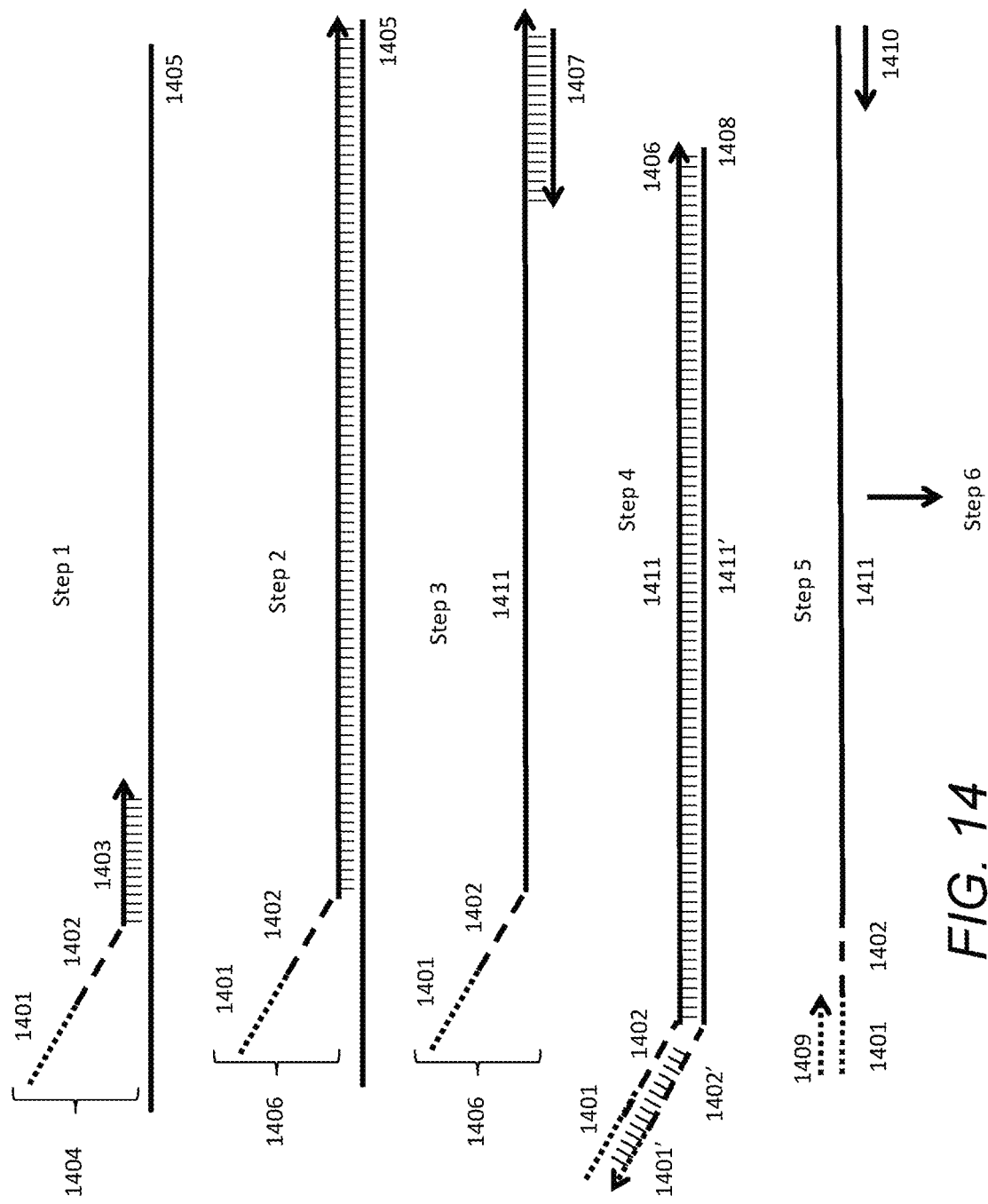

Further disclosed herein are absolute PCR methods for amplifying and/or quantifying one or more molecules. A schematic of the absolute PCR protocol is depicted in FIG. 14. As shown in Step 1 of FIG. 14, an oligonucleotide tag (1404) comprising a universal primber binding site (1401), unique identifier region (1402) and a target specific region (1403) is hybridized to a target molecule (1405). As shown in Step 2 of FIG. 14, the oligonucleotide tag (1404) may act as a primer and a copy of the target molecule (1405) can be synthesized by primer extension by a polymerase (e.g., DNA polymerase) to produce an amplicon (1406). The amplicon (1406) may comprise a universal primber binding site (1401), unique identifier region (1402) and a complement of target molecule (1411). As shown in Step 3 of FIG. 14, a reverse primer (1407) can anneal to the amplicon (1406). As shown in Step 4 of FIG. 14, the amplicon (1406) can act as a template for synthesizing second amplicon (1408). The second amplicon (1408) can comprise a copy of the target molecule (1411') and a complement of the universal primer binding site (1401') and a complement of the unique identifier region (1402'). As shown in Step 5 of FIG. 14, the amplicons (1406, 1408) can act as templates for subsequent amplification with a forward primer (1409) comprising the universal primer binding site and a reverse primer (1410) comprising a target specific sequence. Each subsequent amplicon comprises the unique identifier region (1402). By incorporating the unique identifier region into each amplicon, the amplification efficiency and/or amplification bias can be determined. In addition, the quantity of the target molecules can be determined by counting the number of different unique identifier regions that are associated with each target molecule. The absolute PCR method can be used for subsequent analysis of the target molecules (Step 6 of FIG. 14). For example, the amplicons produced by the absolute PCR method can be used to detect and/or quantify one or more target molecules. Unincorporated oligonucleotide tags can be removed by purification of the amplicons.

I. Labeling of Molecules with Oligonucleotide Tags

A. Stochastic Labeling of Molecules

The methods disclosed herein comprise the attachment of oligonucleotide tags to molecules in a sample. In some instances, attachment of the oligonucleotide tags to the molecules comprises stochastic labeling of the molecules. Methods for stochastically labeling molecules can be found, for example, in U.S. Ser. Nos. 12/969,581 and 13/327,526. Generally, the stochastic labeling method comprises the random attachment of a plurality of oligonucleotide tags to one or more molecules. The plurality oligonucleotide tags are provided in excess of the one or more molecules to be labeled. In stochastic labeling, each individual molecule to be labeled has an individual probability of attaching to the plurality of oligonucleotide tags. The probability of each individual molecule to be labeled attaching to a particular tag can be about the same as any other individual molecule to be labeled. Accordingly, in some instances, the probability of any of the molecules in a sample finding any of the tags is assumed to be equal, an assumption that can be used in mathematical calculations to estimate the number of molecules in the sample. In some circumstances the probability of attaching can be manipulated by, for example electing tags with different properties that would increase or decrease the binding efficiency of that tag with a individual molecule. The oligonucleotide tags can also be varied in numbers to alter the probability that a particular tag will find a binding partner during the stochastic labeling. For example one tag may be overrepresented in a pool of tags, thereby increasing the chances that the overrepresented tag finds at least one binding partner.

B. Methods for Attaching an Oligonucleotide Tag to a Molecule

Attachment of an oligonucleotide tag to a molecule can occur by a variety of methods, including, but not limited to, hybridization of the oligonucleotide tag to the molecule. In some instances, the oligonucleotide tag comprises a target specific region. The target specific region can comprise a sequence that is complementary to at least a portion of the molecule to be labeled. The target specific region can hybridize to the molecule, thereby producing a labeled molecule.

Attachment of the oligonucleotide tag to a molecule can occur by ligation. Ligation techniques comprise blunt-end ligation and sticky-end ligation. Ligation reactions can include DNA ligases such as DNA ligase I, DNA ligase III, DNA ligase IV, and T4 DNA ligase. Ligation reactions can include RNA ligases such as T4 RNA ligase I and T4 RNA ligase II.

Methods of ligation are described, for example in Sambrook et al. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'→5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of adaptors to one or both ends to facilitate ligation by generating ends that are compatible with ligation.

In some instances, both ends of the oligonucleotide tag are attached to the molecule. For example, both ends of the oligonucleotide tag can be hybridized and/or ligated to one or more ends of the molecule. In some instances, attachment of both ends of the oligonucleotide tag to both ends of the molecule results in the formation of a circularized labeled-molecule. Both ends of the oligonucleotide tag can also be attached to the same end of the molecule. For example, the 5' end of the oligonucleotide tag is ligated to the 3' end of the molecule and the 3' end of the oligonucleotide tag is hybridized to the 3'end of the molecule, resulting in a labeled-molecule with a hairpin structure at one end. In some instances the oligonucleotide tag is attached to the middle of the molecule.

In some instances, attachment of the oligonucleotide tag to the molecule comprises the use of one or more adaptors. Adaptors can comprise a target specific region on one end, which allows the attachment of the adaptor to the molecule, and an oligonucleotide tag specific region on the other end, which allows attachment of the oligonucleotide tag to the adaptor. Adaptors can be attached to the molecule and/or oligonucleotide by methods including, but not limited to, hybridization and/or ligation.

Methods for ligating adaptors to fragments of nucleic acid are well known. Adaptors may be double-stranded, single-stranded or partially single-stranded. In preferred aspects adaptors are formed from two oligonucleotides that have a region of complementarity, for example, about 10 to 30, or about 15 to 40 bases of perfect complementarity, so that when the two oligonucleotides are hybridized together they form a double stranded region. Optionally, either or both of the oligonucleotides may have a region that is not complementary to the other oligonucleotide and forms a single stranded overhang at one or both ends of the adaptor. Single-stranded overhangs may preferably by about 1 to about 8 bases, and most preferably about 2 to about 4. The overhang may be complementary to the overhang created by cleavage with a restriction enzyme to facilitate "sticky-end" ligation. Adaptors may include other features, such as primer binding sites and restriction sites. In some aspects the restriction site may be for a Type IIS restriction enzyme or another enzyme that cuts outside of its recognition sequence, such as EcoP151 (see, Mucke et al. *J Mol Biol* 2001, 312(4):687-698 and U.S. Pat. No. 5,710,000 which is incorporated herein by reference in its entirety).

The oligonucleotide tag can be attached to any region of a molecule. For example, the oligonucleotide can be attached to the 5' or 3' end of a polynucleotide (e.g., DNA, RNA). For example, the target-specific region of the oligonucleotide tag comprises a sequence that is complementary to a sequence in the 5' region of the molecule. The target-specific region of the oligonucleotide tag can also comprise a sequence that is complementary to a sequence in the 3' region of the molecule. In some instances, the oligonucleotide tag is attached a region within a gene or gene product. For example, genomic DNA is fragmented and an oligonucleotide tag is attached to the fragmented DNA. In other instances, an RNA molecule is alternatively spliced and the oligonucleotide tag is attached to the alternatively spliced variants. In another example, the polynucleotide is digested and the oligonucleotide tag is attached to the digested polynucleotide. In another example, the target-specific region of the oligonucleotide tag comprises a sequence that is complementary to a sequence within the molecule.

II. Reverse Transcription

In some instances, the methods disclosed herein comprise attachment of an oligonucleotide tag to an RNA molecule to produce a labeled-RNA molecule. The methods disclosed herein can further comprise reverse transcription of the labeled-RNA molecule to produce a labeled-cDNA molecule. In some instances, at least a portion of the oligonucleotide tag acts as a primer for the reverse transcription reaction. For example, as shown in FIG. 1, Steps 1A-B, an oligonucleotide tag comprising an oligodT sequence hybridizes to the polyA tail of an mRNA molecule. The oligodT portion of the oligonucleotide tag acts as a primer for first strand synthesis of the cDNA molecule.

In some instances the labeled cDNA molecule can be used as a molecule for a new stochastic labeling reaction. The labeled cDNA can have a first tag or set of tags from attachment to the RNA prior to reverse transcription and a second tag or set of tags attached to the cDNA molecule. These multiple labeling reactions can, for example, be used to determine the efficiency of events that occur between the attachment of the first and second tags, e.g. an optional amplification reaction or the reverse transcription reaction.

In another example, an oligonucleotide tag is attached to the 5' end of an RNA molecule to produce a labeled-RNA molecule. Reverse transcription of the labeled-RNA molecule can occur by the addition of a reverse transcription primer. In some instances, the reverse transcription primer is an oligodT primer, random hexanucleotide primer, or a target-specific oligonucleotide primer. Generally, oligo(dT) primers are 12-18 nucleotides in length and bind to the endogenous poly(A)+tail at the 3' end of mammalian mRNA. Random hexanucleotide primers can bind to mRNA at a variety of complementary sites. Target-specific oligonucleotide primers typically selectively prime the mRNA of interest.

In some instances, the method comprises repeatedly reverse transcribing the labeled-RNA molecule to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

III. Amplification of Labeled Molecules

The methods disclosed herein may comprise amplification of the labeled molecules to produce labeled amplicons. Amplification of the labeled molecules can comprise PCR-based methods or non-PCR based methods. Amplification of the labeled molecules may comprise exponential amplification of the labeled molecules. Amplification of the labeled molecules may comprise linear amplification of the labeled molecules.

In some instances, amplification of the labeled molecules comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification.

Amplification of the labeled molecules may comprise hybridization chain reaction (HCR) based methods (Dirks and Pierce, PNAS, 2004; Zhang et al., *Anal Chem,* 2012). HCR based methods may comprise DNA-based HCR. HCR based methods may comprise one or more labeled probes. The one or more labeled probes may comprise one or more oligonucleotide tags disclosed herein.

In some instances, the methods disclosed herein further comprise conducting a polymerase chain reaction on the labeled-molecule (e.g., labeled-RNA, labeled-DNA, labeled-cDNA) to produce a labeled-amplicon. The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise the oligonucleotide tag. Alternatively, the labeled-amplicon is a single-stranded molecule. The single-stranded molecule can comprise DNA, RNA, or a combination thereof. The nucleic acids of the present invention can comprise synthetic or altered nucleic acids.

The polymerase chain reaction can be performed by methods such as PCR, HD-PCR, Next Gen PCR, digital RTA, or any combination thereof. Additional PCR methods include, but are not limited to, allele-specific PCR, Alu PCR, assembly PCR, asymmetric PCR, droplet PCR, emulsion PCR, helicase dependent amplification HDA, hot start PCR, inverse PCR, linear-after-the-exponential (LATE)-PCR, long PCR, multiplex PCR, nested PCR, hemi-nested PCR, quantitative PCR, RT-PCR, real time PCR, single cell PCR, and touchdown PCR.

In some instances, conducting a polymerase chain reaction comprises annealing a first target specific primer to the labeled-molecule. Alternatively or additionally, conducting a polymerase chain reaction further comprises annealing a universal primer to a universal primer binding site region of the oligonucleotide tag, wherein the oligonucleotide tag is on a labeled-molecule or labeled-amplicon. The methods disclosed herein can further comprise annealing a second target specific primer to the labeled-molecule and/or labeled-amplicon.

In some instances, the method comprises repeatedly amplifying the labeled-molecule to produce multiple labeled-amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, PNAS 92:4641 (1995) and Liu et al., J. Am. Chem. Soc. 118:1587 (1996)) and U.S. Pat. No. 5,648,245, strand displacement amplification (see Lasken and Egholm, *Trends Biotechnol.* 2003 21(12):531-5; Barker et al. *Genome Res.* 2004 May; 14(5):901-7; Dean et al. *Proc Natl Acad Sci USA.* 2002; 99(8):5261-6; Walker et al. 1992, Nucleic Acids Res. 20(7):1691-6, 1992 and Paez, et al. *Nucleic Acids Res.* 2004; 32(9):e71), Qbeta Replicase, described in PCT Patent Application No. PCT/US87/00880 and nucleic acid based sequence amplification (NABSA). (See, U.S. Pat. Nos. 5,409,818, 5,554,517, and 6,063,603, each of which is incorporated herein by reference), Other amplification methods that may be used are described in, U.S. Pat. Nos. 6,582,938, 5,242,794, 5,494,810, 4,988,617, and US Pub. No. 20030143599 each of which is incorporated herein by reference. DNA may also be amplified by multiplex locus-specific PCR or using adaptor-ligation and single primer PCR (See Kinzler and Vogelstein, NAR (1989) 17:3645-53. Other available methods of amplification, such as balanced PCR (Makrigiorgos, et al. (2002), *Nat Biotechnol*, Vol. 20, pp. 936-9), may also be used.

Molecular inversion probes ("MIPs") may also be used for amplification of selected targets. MIPs may be generated so that the ends of the pre-circle probe are complementary to regions that flank the region to be amplified. The gap can be closed by extension of the end of the probe so that the complement of the target is incorporated into the MIP prior to ligation of the ends to form a closed circle. The closed circle can be amplified and detected by sequencing or hybridization as previously disclosed in Hardenbol et al., *Genome Res.* 15:269-275 (2005) and in U.S. Pat. No. 6,858,412.

Amplification of the labeled molecule may comprise the use of one or more primers. FIG. 9 shows an examplary forward and reverse primers. The forward primer (901) may comprise a a universal PCR sequence (902), unique identifier sequence (903) and target sequence (904). The reverse primer (905) may comprise a target sequence.

Primers used in the method can be designed with the use of the Primer 3, a computer program which suggests primer sequences based on a user defined input sequence. Other primer designs may also be used, or primers may be selected by eye without the aid of computer programs. There are many options available with the program to tailor the primer design to most applications. Primer3 can consider many factors, including, but not limited to, oligo melting temperature, length, GC content, 3' stability, estimated secondary structure, the likelihood of annealing to or amplifying undesirable sequences (for example interspersed repeats) and the likelihood of primer-dimer formation between two copies of the same primer. In the design of primer pairs, Primer3 can consider product size and melting temperature, the likelihood of primer-dimer formation between the two primers in the pair, the difference between primer melting temperatures, and primer location relative to particular regions of interest to be avoided.

IV. Sequencing

In some aspects, the methods disclosed herein further comprise determining the sequence of the labeled-molecule or any product thereof (e.g., labeled-amplicons, labeled-cDNA molecules). Determining the sequence of the labeled-molecule or any product thereof can comprise conducting a sequencing reaction to determine the sequence of at least a portion of the oligonucleotide tag, at least a portion of the labeled-cDNA molecule, a complement thereof, a reverse complement thereof, or any combination thereof. In some instances only the tag or a portion of the tag is sequenced. Determining the sequence of the labeled-molecule or any product thereof can be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, and VisiGen Biotechnologies approach. Alternatively, determining the sequence of the labeled-molecule or any product thereof can use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.).

In some instances, determining the sequence of the labeled-molecule or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the labeled-molecule or any product thereof can be determined by electron microscopy or a chemical-sensitive field effect transistor (chemFET) array.

In another example, determining the sequence of labeled-molecules or any product thereof comprises RNA-Seq or microRNA sequencing. Alternatively, determining the sequence of labeled-molecules or any products thereof comprises protein sequencing techniques such as Edman degradation, peptide mass fingerprinting, mass spectrometry, or protease digestion.

The sequencing reaction can, in certain embodiments, occur on a solid or semi-solid support, in a gel, in an emulsion, on a surface, on a bead, in a drop, in a continuous follow, in a dilution, or in one or more physically separate volumes.

Sequencing may comprise sequencing at least about 10, 20, 30, 40, 50, 60, 70, 80, 90, 100 or more nucleotides or base pairs of the labeled molecule. In some instances, sequencing comprises sequencing at least about 200, 300, 400, 500, 600, 700, 800, 900, 1000 or more nucleotides or base pairs of the labeled molecule. In other instances, sequencing comprises sequencing at least about 1500; 2,000; 3,000; 4,000; 5,000; 6,000; 7,000; 8,000; 9,000; or 10,000 or more nucleotides or base pairs of the labeled molecule.

Sequencing may comprise at least about 200, 300, 400, 500, 600, 700, 800, 900, 1000 or more sequencing reads per run. In some instances, sequencing comprises sequencing at least about 1500; 2,000; 3,000; 4,000; 5,000; 6,000; 7,000; 8,000; 9,000; or 10,000 or more sequencing reads per run.

V. Detection Methods

The methods disclosed herein can further comprise detection of the labeled-molecules and/or labeled-amplicons. Detection of the labeled-molecules and/or labeled-amplicons can comprise hybridization of the labeled-molecules to surface, e.g. a solid support. Alternatively, or additionally, detection of the labeled-molecules comprises contacting the labeled-molecules and/or labeled-amplicons with surface, e.g. a solid support. In some instances, the method further comprises contacting the labeled-molecules and/or labeled-amplicons with a detectable label to produce a detectable-label conjugated labeled-molecule. The methods disclosed herein can further comprise detecting the detectable-label conjugated labeled-molecule. Detection of the labeled-molecules or any products thereof (e.g., labeled-amplicons, detectable-label conjugated labeled-molecule) can comprise detection of at least a portion of the oligonucleotide tag, molecule, detectable label, a complement of the oligonucleotide tag, a complement of the molecule, or any combination thereof.

Detection of the labeled-molecules or any products thereof can comprise an emulsion. For example, the labeled-molecules or any products thereof can be in an emulsion. Alternatively, detection of the labeled-molecules or any products thereof comprises one or more solutions. In other instances, detection of the labeled-molecules comprises one or more containers.

Detection of the labeled-molecules or any products thereof (e.g., labeled-amplicons, detectable-label conjugated labeled-molecule) can comprise detecting each labeled-molecule or products thereof. For example, the methods disclosed herein comprise sequencing at least a portion of each labeled-molecule, thereby detecting each labeled-molecule.

In some instances, detection of the labeled-molecules and/or labeled-amplicons comprises electrophoresis, spectroscopy, microscopy, chemiluminescence, luminescence, fluorescence, immunofluorescence, colorimetry, or electrochemiluminescence methods. For example, the method comprises detection of a fluorescent dye. Detection of the labeled-molecule or any products thereof can comprise colorimetric methods. For example, the colorimetric method comprises the use of a colorimeter or a colorimetric reader. A non-limiting list of colorimeters and colorimetric readers include Sensovation's Colorimetric Array Imaging Reader (CLAIR), ESEQuant Lateral Flow Immunoassay Reader, SpectraMax 340PC 38, SpectraMax Plus 384, SpectraMax 190, VersaMax, VMax, and EMax.

Additional methods used alone or in combination with other methods to detect the labeled-molecules and/or amplicons can comprise the use of an array detector, fluorescence reader, non-fluorescent detector, CR reader, luminometer, or scanner. In some instances, detecting the labeled-molecules and/or labeled-amplicons comprises the use of an array detector. Examples of array detectors include, but are not limited to, diode-array detectors, photodiode array detectors, HLPC photodiode array detectors, pixel array detectors, Germanium array detectors, CMOS and CCD array detectors, Gated linear CCD array detectors, InGaAs photodiode array systems, and TE cooled CCD systems. The array detector can be a microarray detector. Non-limiting examples of microarray detectors include microelectrode array detectors, optical DNA microarray detection platforms, DNA microarray detectors, RNA microarray detectors, and protein microarray detectors.

In some instances, a fluorescence reader is used to detect the labeled-molecule and/or labeled-amplicons. The fluorescence reader can read 1, 2, 3, 4, 5, or more color fluorescence microarrays or other structures on biochips, on slides, or in microplates. In some instances, the fluorescence reader is a Sensovation Fluorescence Array imaging Reader (FLAIR). Alternatively, the fluorescence reader is a fluorescence microplate reader such as the Gemini XPS Fluorescence microplate reader, Gemini EM Fluorescence microplate reader, Finstruments® Fluoroskan filter based fluorescence microplate reader, PHERAstar microplate reader, FlUOstar microplate reader, POLARstar Omega microplate reader, FLUOstar OPTIMA multi-mode microplate reader and POLARstar OPTIMA multi-mode microplate reader. Additional examples of fluorescence readers include PharosFX™ and PharosFX Plus systems.

In some instances, detection of the labeled-molecule and/or labeled-amplicon comprises the use of a microplate reader. In some instances, the microplate reader is an xMark™ microplate absorbance spectrophotometer, iMark microplate absorbance reader, EnSpire® Multimode plate reader, EnVision Multilabel plate reader, VICTOR X Multilabel plate reader, FlexStation, SpectraMax Paradigm, SpectraMax M5e, SpectraMax M5, SpectraMax M4, SpectraMax M3, SpectraMax M2-M2e, FilterMax F series, Fluoroskan Ascent FL Microplate Fluorometer and Luminometer, Fluoroskan Ascent Microplate Fluorometer, Luminoskan Ascent Microplate Luminometer, Multiskan EX Microplate Photometer, Muliskan FC Microplate Photometer, and Muliskan GO Microplate Photometer. In some instances, the microplate reader detects absorbance, fluorescence, luminescence, time-resolved fluorescence, light scattering, or any combination thereof. In some embodiments, the microplate reader detects dynamic light scattering. The microplate reader, can in some instances, detect static light scattering. In some instances, detection of the labeled-molecules and/or labeled-amplicons comprises the use of a microplate imager. In some instances, the microplate imager comprises ViewLux uHTS microplate imager and BioRad microplate imaging system.

Detection of labeled-molecules and/or products thereof can comprise the use of a luminometer. Examples of luminometers include, but are not limited to, SpectraMax L, GloMax®-96 microplate luminometer, GloMax®-20/20 single-tube luminometer, GloMax®-Multi⁺ with Instinct™ software, GloMax®-Multi Jr single tube multimode reader, LUMIstar OPTIMA, LEADER HC⁺ luminometer, LEADER 450i luminometer, and LEADER 50i luminometer.

In some instances, detection of the labeled-molecules and/or labeled-amplicons comprises the use of a scanner. Scanners include flatbed scanners such as those provided by Cannon, Epson, HP, Fujitsu, and Xerox. Additional examples of flatbed scanners include the FMBIO® fluorescence imaging scanners (e.g., FMBIO® II, III, and III Plus systems). Scanners can include microplate scanners such as the Arrayit ArrayPix™ microarray microplate scanner. In some instances, the scanner is a Personal Molecular Imager™ (PMI) system provided by Bio-rad.

Detection of the labeled-molecule can comprise the use of an analytical technique that measures the mass-to-charge ratio of charged particles, e.g. mass spectrometry. In some embodiments the mass-to-charge ratio of charged particles is measured in combination with chromatographic separation techniques. In some embodiments sequencing reactions are used in combination with mass-to-charge ratio of charged particle measurements. In some embodiments the tags comprise isotopes. In some embodiments the isotope type or ratio is controlled or manipulated in the tag library.

Detection of the labeled-molecule or any products thereof comprises the use of small particles and/or light scattering. For example, the amplified molecules (e.g., labeled-amplicons) are attached to haptens or directly to small particles and hybridized to the array. The small particles can be in the nanometer to micrometer range in size. The particles can be detected when light is scattered off of its surface.

A colorimetric assay can be used where the small particles are colored, or haptens can be stained with colorimetric detection systems. In some instances, a flatbed scanner can be used to detect the light scattered from particles, or the development of colored materials. The methods disclosed herein can further comprise the use of a light absorbing material. The light absorbing material can be used to block undesirable light scatter or reflection. The light absorbing material can be a food coloring or other material. In some instances, detection of the labeled-molecule or any products thereof comprises contacting the labeled-molecule with an off-axis white light.

Figure 33:
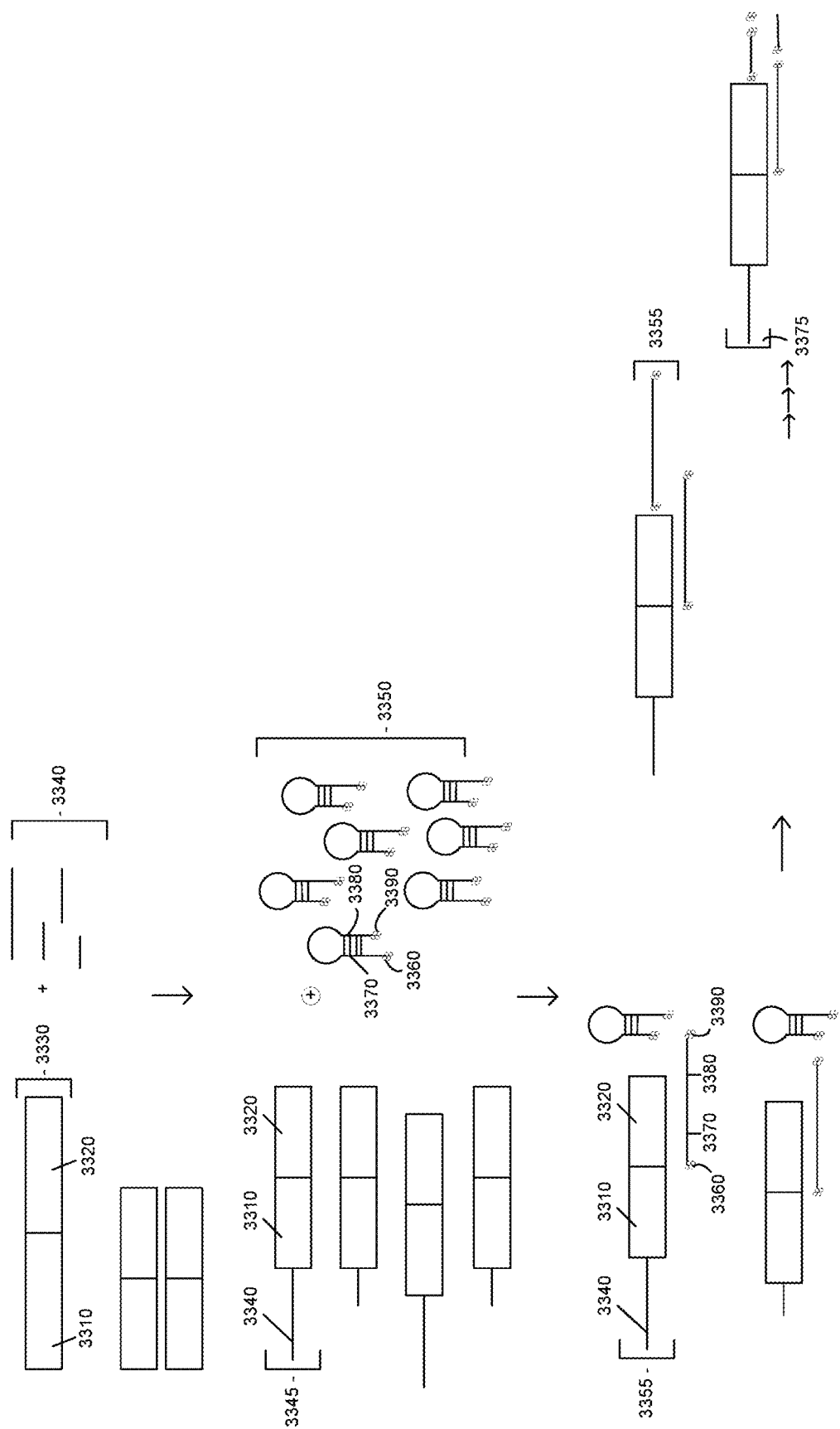

Detection of the labeled-molecule may comprise hybridization chain reaction (HCR). As depicted in FIG. 33, a sample comprising a plurality of nucleic acid molecules (3340) is stochastically labeled with a plurality of oligonucleotide tags (3330). The oligonucleotide tags (3330) comprise a unique identifier region (3310) and an adapter region (3320). Stochastically labeling the nucleic acid molecules can comprise attachment of one or more oligonucleotide tags (3330) to one or more ends of the nucleic acid molecule (3340) to produce one or more labeled-molecules (3345). The one or more labeled molecules can be contacted with a plurality of HCR probes (3350). The plurality of HCR probes (3350) may comprise a hairpin molecules with an overhang and one or more labels (3360, 3390). The plurality of HCR probes (3350) may comprise a mixture of hairpin molecules with 5' overhangs and hairpin molecules with 3' overhangs. The plurality of HCR probes may comprise a stem (3370, 3380). The sequence of the stem (3370, 3380) may be complementary to at least a portion of the oligonucleotide tag. The sequence of the stem (3370, 3380) may be complementary to the adapter region (3320) of the oligonucleotide tag. The adapter region (3320) of the oligonucleotide may act as an initiator for a hybridization chain reaction. As shown in FIG. 33, the stem (3370) of the HCR probe (3350) can hybridize to the adapter region (3320) of the labeled molecule (3345). Hybridization of the stem (3370) of the HCR probe (3350) to the adapter region (3320) of the labeled molecule (3345) can result in opening of the stem (e.g., 3370 and 3380 of the stem are no longer annealed) and linearization of the HCR probe (3350), which results in the formation of a labeled molecule hybridized to a HCR probe (3355). The linearized HCR probe can then act as an initiator for subsequent hybridization of another HCR probe. The stem of a second HCR probe can hybridize to the linearized HCR probe that has hybridized to the labeled molecule, resulting in linearization of the second HCR probe and the formation of a labeled-molecule containing two linearized HCR probes. The linearized second HCR probe can act as an initiator for another hybridization reaction. This process can be repeated multiple times to produce a labeled molecule with multiple linearized HCR probes (3375). The labels (3360, 3390) on the HCR probe can enable detection of the labeled molecule. The labels (3360, 3390) may be any type of label (e.g., fluorphore, chromophore, small molecule, nanoparticle, hapten, enzyme, antibody, magnet). The labels (3360 and 3390) may comprise fragments of a single label. The labels (3360, 3390) may generate a detectable signal when they are in close proximity. When the HCR probe is a hairpin, the labels (3360 and 3390) may be too far away to produce a detectable signal. When the HCR probe is linearized and multiple linearized HCR probes are hybridized together, the labels (3360, 3390) may be in close enough proximity to generate a detectable signal. For example, a HCR probe (3350) may comprise two pyrene moieties as labels (3360, 3390). Alternatively, the labels may be nanoparticles. The HCR can enable attachment of multiple HCR probes to a labeled molecule, which can result in signal amplification. Stoachastic labeling followed by HCR may increase the sensitivity of detection, analysis and/or quantification of the nucleic acid molecules. Stochastic labeling followed by HCR may increase the accuracy of detection, analysis, and/or quantification of one or more nucleic acid molecules.

Additional methods and apparatus for signal detection and processing of intensity data are disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Patent Pub. Nos. 20040012676 and 20050059062 and in PCT Application PCT/US99/06097 (published as WO99/47964), each of which also is hereby incorporated by reference in its entirety for all purposes.

Detection and/or quantification of the labeled molecules may comprise the use of computers or computer software. Computer software products may comprise a computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See also U.S. Pat. No. 6,420,108.

Computer program products and software may be used for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654. Additionally, the present disclosure may have preferred embodiments that include methods for providing genetic information over networks such as the Internet as shown in U.S. Patent Pub. Nos. 20030097222, 20020183936, 20030100995, 20030120432, 20040002818, 20040126840, and 20040049354.

Detection and/or quantification of the labeled-molecules or any products thereof can comprise the use of one or more algorithms. Alternatively, or additionally, the methods, kits and compositions can further comprise a computer, software, printer, and/or electronic data or information.

The methods disclosed herein can further comprise the transmission of data/information. For example, data/information derived from the detection and/or quantification of the labeled-molecule or any products thereof are transmitted to another device and/or instrument. In some instances, the information obtained from an algorithm can also be transmitted to another device and/or instrument. Transmission of the data/information can comprise the transfer of data/information from a first source to a second source. The first and second sources can be in the same approximate location (e.g., within the same room, building, block, campus). Alternatively, first and second sources are in multiple locations (e.g., multiple cities, states, countries, continents, etc). In some embodiments a non-transitory computable readable media is used to store or analyze data generated using methods described herein.

Transmission of the data/information can comprise digital transmission or analog transmission. Digital transmission can comprise the physical transfer of data (a digital bit stream) over a point-to-point or point-to-multipoint communication channel. Examples of such channels are copper wires, optical fibres, wireless communication channels, and storage media. The data can be represented as an electromagnetic signal, such as an electrical voltage, radiowave, microwave, or infrared signal.

Analog transmission can comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

The applications and uses of the systems and methods described herein can produce one or more result useful to diagnose a disease state of an individual, for example, a patient. In one embodiment, a method of diagnosing a disease comprises reviewing or analyzing data relating to the presence and/or the concentration level of a target in a sample. A conclusion based review or analysis of the data can be provided to a patient, a health care provider or a health care manager. In one embodiment the conclusion is based on the review or analysis of data regarding a disease diagnosis. It is envisioned that in another embodiment that providing a conclusion to a patient, a health care provider or a health care manager includes transmission of the data over a network.

Accordingly, business systems and methods using the systems and methods described herein are provided.

One aspect of the invention is a business method comprising screening patient test samples for the presence or absence of a biologically active analyte to produce data regarding the analyte, collecting the analyte data, providing the analyte data to a patient, a health care provider or a health care manager for making a conclusion based on review or analysis of the data regarding a disease diagnosis. In one embodiment the conclusion is provided to a patient, a health care provider or a health care manager includes transmission of the data over a network.

Accordingly FIG. 8 is a block diagram showing a representative example logic device through which reviewing or analyzing data relating to the present invention can be achieved. Such data can be in relation to a disease, disorder or condition in an individual. FIG. 8 shows a computer system (or digital device) 800 connected to an apparatus 820 for use with the scanning sensing system 824 to, for example, produce a result. The computer system 800 may be understood as a logical apparatus that can read instructions from media 811 and/or network port 805, which can optionally be connected to server 809 having fixed media 812. The system shown in FIG. 8 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. The communication medium can comprise a non-transitory computer readable media. For example, the communication medium can be a network connection, a wireless connection or an internet connection. Such a connection can provide for communication over the World Wide Web. It is envisioned that data can be transmitted over such networks or connections for reception and/or review by a party 822. The receiving party 822 can be but is not limited to a patient, a health care provider or a health care manager.

In one embodiment, a computer-readable medium includes a medium suitable for transmission of a result of an analysis of an environmental or biological sample. The medium can include a result regarding a disease condition or state of a subject, wherein such a result is derived using the methods described herein. The computer readable media can be non-transitory.

Data Analysis: In some embodiments the scanner instrument produces the raw intensity values for each position on the array as well as the background intensity. Many methods can be used to calculate the number of molecules in the sample. For example, the values for the control positions on the array are removed from the dataset and a scatter plot is generated to provide an image of the data. This may occur with or without the background intensity subtracted from the raw data. A threshold intensity value can be established in order to classify the positive spots and the negative spots. All of the positive spots are summed to provide a total count of unique stochastic labels. This process can be automated in Microsoft excel or another computer software program.

An alternative to this strategy is the use of clustering algorithms such as k-means clustering. K-means clustering is a method of cluster analysis which aims to partition all of the observations into clusters in which each observation belongs to the cluster with the nearest mean. The data can be split into 2 or 3 clusters (or more, 3 clusters seems to produce the cleanest numbers so far) and the number of data points can be added up to determine the counts.

VI. Target Molecules

The methods, kits, and systems disclosed herein can be used in the stochastic labeling of molecules. Such molecules include, but are not limited to, polynucleotides and polypeptides. As used herein, the terms "polynucleotide" and "nucleic acid molecule" refers to a polymeric form of nucleotides of any length, either ribonucleotides, deoxyribonucleotides, locked nucleic acids (LNA) or peptide nucleic acids (PNAs), that comprise purine and pyrimidine bases, or other natural, chemically or biochemically modified, non-natural, or derivatized nucleotide bases. A "polynucleotide" or "nucleic acid molecule" can consist of a single nucleotide or base pair. Alternatively, the "polynucleotide" or "nucleic acid molecule" comprises two or more nucleotides or base pairs. For example, the "polynucleotide" or "nucleic acid molecule" comprises at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the polynucleotide comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. In some instances, the molecules are DNA, RNA, or DNA-RNA hybrids. The molecules can be single-stranded or double-stranded. In some instances, the molecules are RNA molecules, such as mRNA, rRNA, tRNA, ncRNA, lncRNA, siRNA, or miRNA. The RNA molecules can be polyadenylated. Alternatively, the mRNA molecules are not polyadenylated. Alternatively, the molecules are DNA molecules. The DNA molecules can be genomic DNA. The DNA molecules can comprise exons, introns, untranslated regions, or any combination thereof.

In some instances, the molecules are polypeptides. As used herein, the term "polypeptide" refers to a molecule comprising at least one peptide. In some instances, the polypeptide consists of a single peptide. Alternatively, the polypeptide comprises two or more peptides. For example, the polypeptide comprises at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides. Examples of polypeptides include, but are not limited to, amino acids, proteins, peptides, hormones, oligosaccharides, lipids, glycolipids, phospholipids, antibodies, enzymes, kinases, receptors, transcription factors, and ligands.

The methods, kits, and systems disclosed herein can be used to stochastically label individual occurrences of identical or nearly identical molecules and/or different molecules. In some instances, the methods, kits, and systems disclosed herein can be used to stochastically label identical or nearly identical molecules (e.g., molecules comprise identical or nearly identical sequences). For example, the molecules to be labeled comprise at least about 80%, 85%, 90%, 95%, 96%, 97%, 98%, 99%, or 100% sequence identity. The nearly identical molecules may differ by less than about 100, 90, 80, 70, 60, 50, 40, 30, 25, 20, 25, 10, 9, 8, 7, 6, 5, 4, 3, 2, or 1 nucleotides or base pairs. In some instances, the molecules to be labeled are variants of each other. For example, the molecules to be labeled may contain single nucleotide polymorphisms or other types of mutations. In another example, the molecules to be labeled are splice variants. In some instances, at least one molecule is stochastically labeled. In other instances, at least 2, 3, 4, 5, 6, 7, 8, 9, or 10 identical or nearly identical molecules are stochastically labeled. Alternatively, at least 20, 30, 40, 50, 60, 70, 80, 90, 100, 200, 300, 400, 500, 600, 700, 800, 900, or 1000 identical or nearly identical molecules are stochastically labeled. In other instances, at least 1500; 2,000; 2500; 3,000; 3500; 4,000; 4500; 5,000; 6,000; 7,000; 8,000; 9,000; or 10000 identical or nearly identical molecules are stochastically labeled. In other instances; at least 15,000; 20,000; 25,000; 30,000; 35,000; 40,000; 45,000; 50,000; 60,000; 70,000; 80,000; 90,000; or 100,000 identical or nearly identical molecules are stochastically labeled.

In other instances, the methods, kits, and systems disclosed herein can be used to stochastically label different molecules. For example, the molecules to be labeled comprise less than 75%, 70%, 65%, 60%, 55%, 50%, 45%, 40%, 35%, 30%, 25%, 20%, 15%, 10%, 5%, 4%, 3%, 2%, 1% sequence identity. The different molecules may differ by at least about 1, 2, 3, 4, 5, 6, 7, 8, 9, 10, 15, 20, 25, 30, 40, 50, 60, 70, 80, 90, 100 or more nucleotides or base pairs. In some instances, at least one molecule is stochastically labeled. In other instances, at least 2, 3, 4, 5, 6, 7, 8, 9, or 10 different molecules are stochastically labeled. Alternatively, at least 20, 30, 40, 50, 60, 70, 80, 90, 100, 200, 300, 400, 500, 600, 700, 800, 900, or 1000 different molecules are stochastically labeled. In other instances, at least 1500; 2,000; 2500; 3,000; 3500; 4,000; 4500; 5,000; 6,000; 7,000;

8,000; 9,000; or 10000 different molecules are stochastically labeled. In other instances; at least 15,000; 20,000; 25,000; 30,000; 35,000; 40,000; 45,000; 50,000; 60,000; 70,000; 80,000; 90,000; or 100,000 different molecules are stochastically labeled.

The different molecules to be labeled can be present in the sample at different concentrations or amounts. For example, the concentration or amount of one molecule is greater than the concentration or amount of another molecule in the sample. In some instances, the concentration or amount of at least one molecule in the sample is at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times greater than the concentration or amount of at least one other molecule in the sample. In another example, the concentration or amount of one molecule is less than the concentration or amount of another molecule in the sample. The concentration or amount of at least one molecule in the sample can be at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times less than the concentration or amount of at least one other molecule in the sample.

In some instances, the molecules to be labeled are in one or more samples. The molecules to be labeled can be in two or more samples. The two or more samples can contain different amounts or concentrations of the molecules to be labeled. In some instances, the concentration or amount of one molecule in one sample can be greater than the concentration or amount of the same molecule in a different sample. For example, a blood sample might contain a higher amount of a particular molecule than a urine sample. Alternatively, a single sample is divided into two or more subsamples. The subsamples can contain different amounts or concentrations of the same molecule. The concentration or amount of at least one molecule in one sample can be at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times greater than the concentration or amount of the same molecule in another sample. Alternatively, the concentration or amount of one molecule in one sample can be less than the concentration or amount of the same molecule in a different sample. For example, a heart tissue sample might contain a higher amount of a particular molecule than a lung tissue sample. The concentration or amount of at least one molecule in one sample can be at least about 1.5, 2, 3, 4, 5, 6, 7, 8, 9, 10, 11, 12, 13, 14, 15, 20, 25, 30, 35, 40, 45, 50, 60, 70, 80, 90, or 100 or more times less than the concentration or amount of the same molecule in another sample. In some instances, the different concentrations or amounts of a molecule in two or more different samples is referred to as sample bias.

VII. Oligonucleotide Tags

In some embodiments, the methods, kits, and systems disclosed herein comprise a plurality of oligonucleotide tags. The oligonucleotide tags can comprise a target specific region, a unique identifier region, an adapter region, a universal primer binding site region, or any combination thereof. FIG. 10-13 shows examplary oligonucleotide tags.

Figure 10:
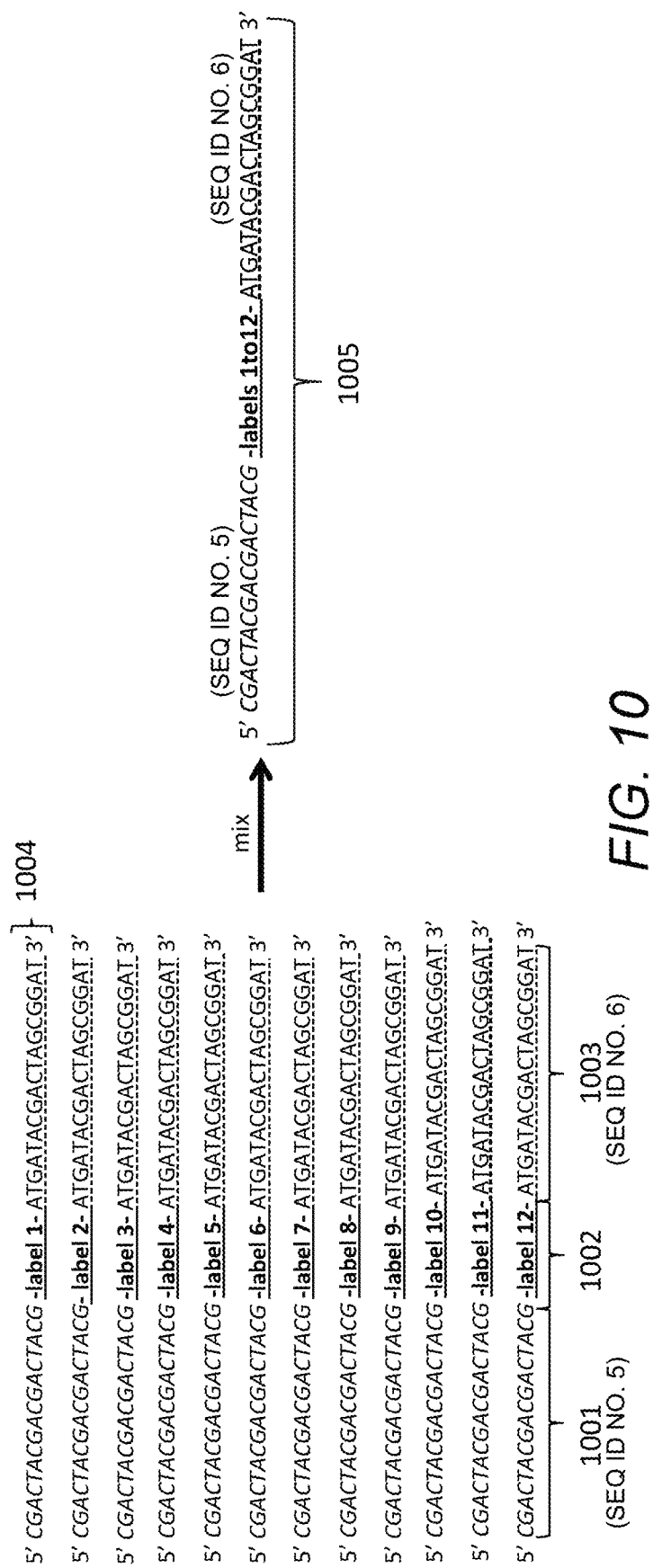
FIG. 10 shows a schematic for the synthesis of oligonucleotide tags

As shown in FIG. 10, the oligonucleotide tag (1004) may comprise a universal primer binding site (1001), unique identifier region (1002) and a target specific region (1003).

Figure 11A:
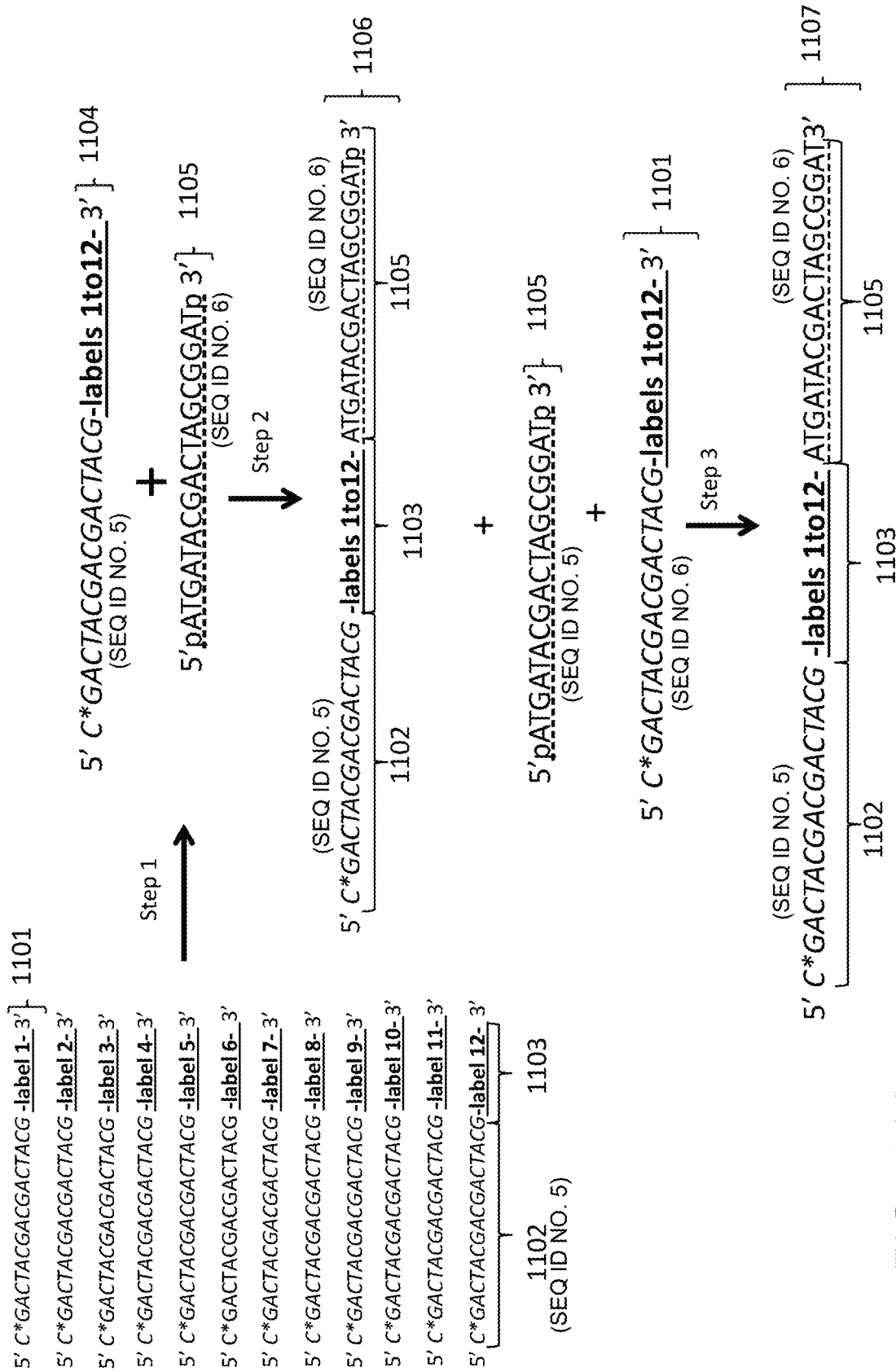
FIG. 11A shows a schematic for the synthesis of oligonucleotide tags without target-specific sequence
Figure 11B:
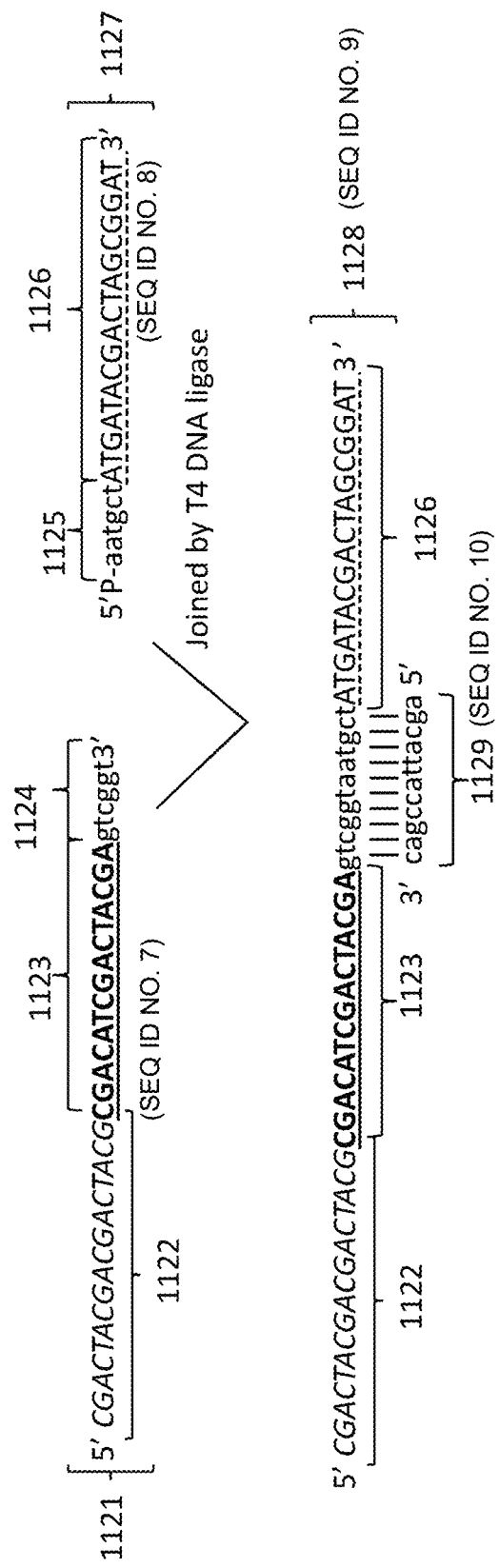
FIG. 11B-FIG. 11D show a schematic for the synthesis of oligonucleotide tags
Figure 11C:
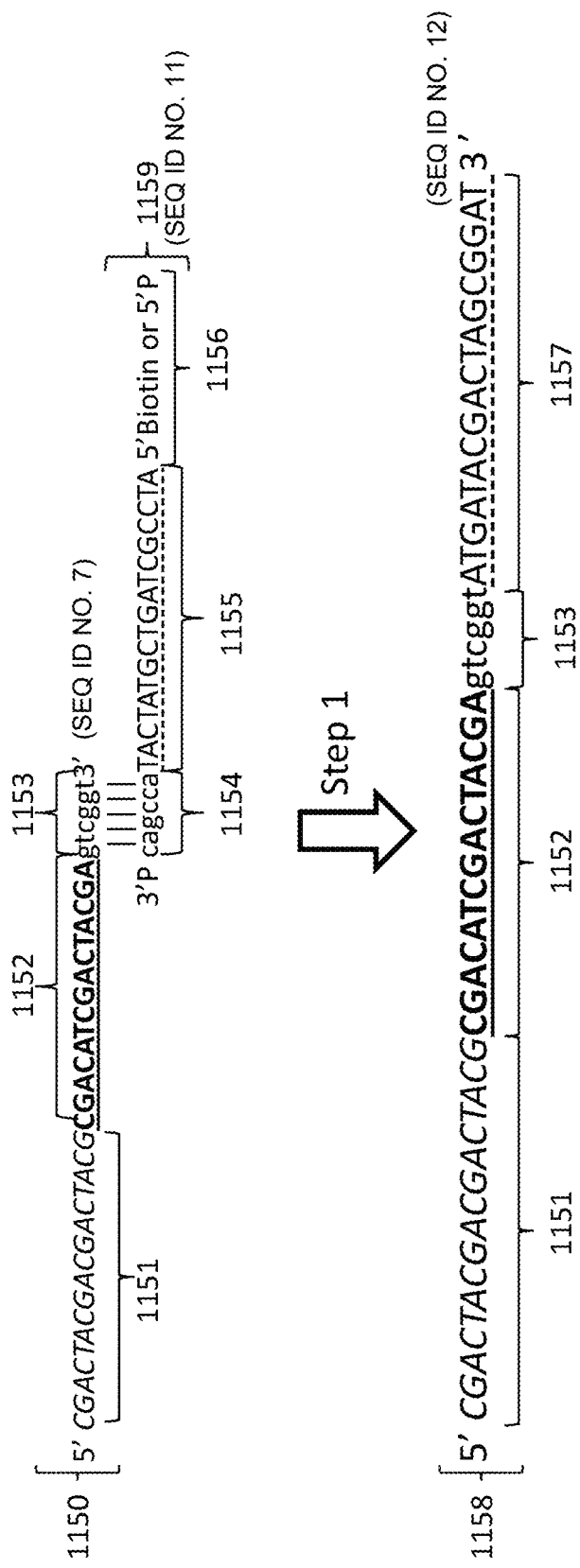
Figure 11D:
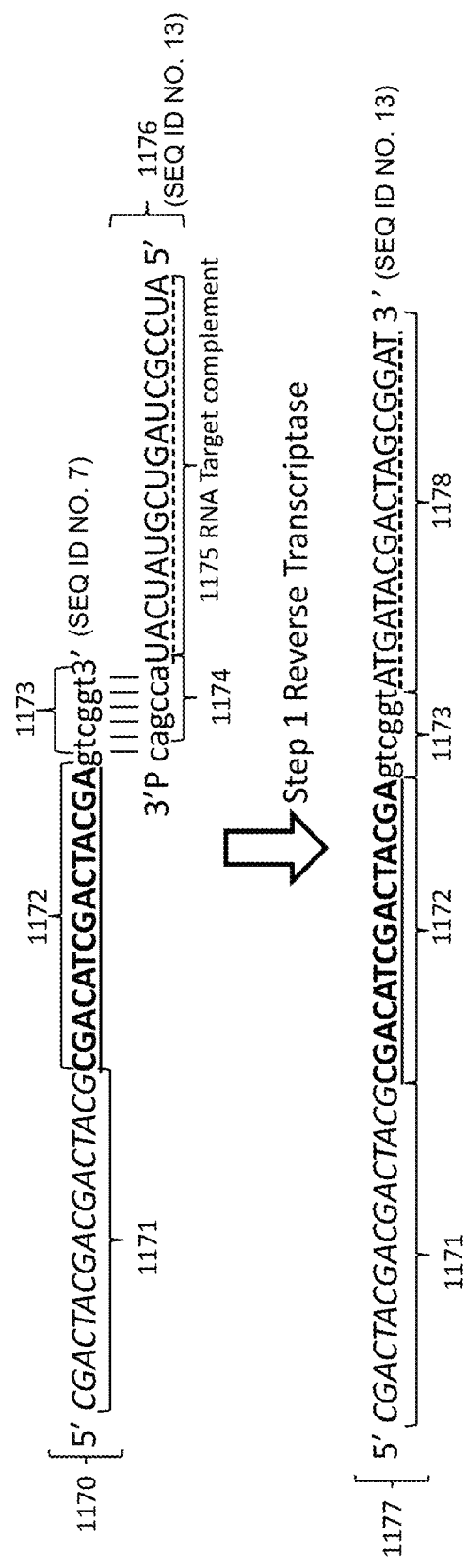

As shown in FIG. 11A, the oligonucleotide tag (1107) can comprise a universal primer binding site (1102), a unique identifier region (1103) and a target specific region (1105). The universal primer binding site (1102) may comprise a phosphorothioate linkage, as depicted by an "*" in FIG. 11A. As shown in FIG. 11B, the oligonucleotide tag (1128) can comprise a universal primer binding site (1122), a unique identifier region (1123), bridge splint (1129), and a target specific region (1126). As shown in FIG. 11C, the oligonucleotide tag (1158) may comprise a universal primer binding site (1151), unique identifier region (1152), ligation sequence (1153), and a target specific sequence (1157). As shown in FIG. 11D, the oligonucleotide tag (1177) may comprise a universal primer binding site (1171), unique identifier region (1172), ligation sequence (1173), and a DNA target specific sequence (1178).

As shown in FIG. 12A, an oligonucleotide tag (1201) may comprise a universal primer binding site (1202), a unique identifier region comprising a degenerate sequence (1203) and a target specific region (1204). As shown in FIG. 12B, an oligonucleotide tag (1210) may comprise a universal primer binding site (1211), a unique identifier region (1215) comprising a degenerate sequence (1213) flanked by two flanking sequences (1212 and 1214) and a target specific region (1216).

Figure 13A:
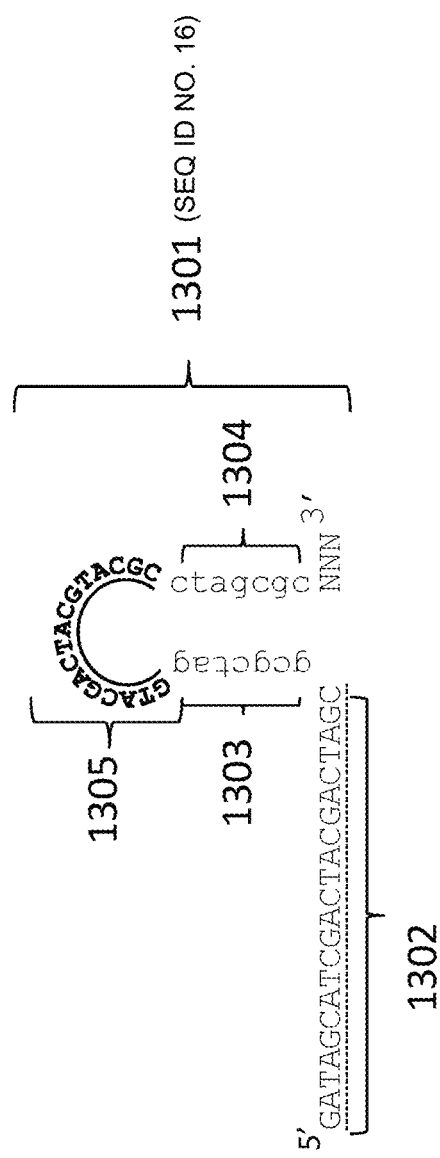
FIG. 13A Labeled Primer without generic primer sequence.

The oligonucleotide tag may be comprise one or more secondary structures. As shown in FIG. 13A, the oligonucleotide tag (1301) comprises a hairpin structure. The oligonucleotide tag (1301) can comprise a target specific region (1302), a cleavable stem (1303, 1304), and a unique identifier region (1305).

Figure 13B:
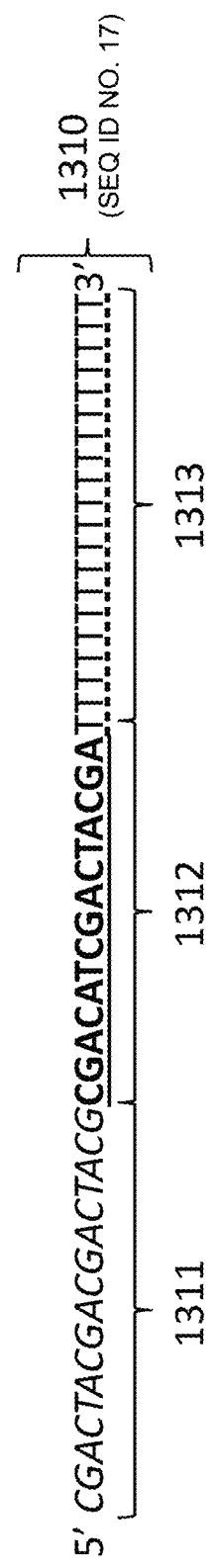
FIG. 13B Labeled Primer with universal target sequence FIG. 14 Absolute PCR Protocol FIG. 15 Formation of Primer Dimers FIG. 16 Method to prevent the formation of primer artifacts FIG. 17 Differences between a standard array and a digital array FIG. 18A-FIG. 18H Digital microarray probes—detection using a combination of gene and label sequences FIG. 19 Absolute quantitation of mRNA molecules by counting individual DNA molecules FIG. 20 Digital microarray for RNA expression FIG. 21 Digital microarray for DNA copy number FIG. 22 Digital microarray for microRNAs FIG. 23A Digital microarray for single cell pre-implantation genetic diagnosis (PGD) (a) cycle 0; (b) cycle 5; (c) cycle 10; (d) cycle 15

The oligonucleotide tag may comprise a target specific region that can hybridize to a plurality of different target molecules. For example, as shown in FIG. 13B, the oligonucleotide tag (1310) comprises a universal primer binding site (1311), unique identifier region (1312), and a universal target specific region (1313). The universal target specific region (1313) may comprise an oligodT sequence that enables hybridization to target molecules comprising a polyA or polyU sequence.

A method for synthesizing a plurality of oligonucleotdie tags is depicted in FIG. 10. As shown in FIG. 10, oligonucleotide tags (1004) can be synthesized separately. The oligonucleotide tags (1004) can comprise a universal primer binding site (1001), a unique identifier region (1002), and a target specific region. The individual oligonucleotide tags can be pooled to produce a plurality of oligonucleotide tags (1005) comprising a plurality of different unique identifier regions.

A method for synthesizing a plurality of oligonucleotdie tags is depicted in FIG. 11A. As shown in FIG. 11A, oligonucleotide fragments (1101) can be synthesized separately. The oligonucleotide fragments (1101) can comprise a universal primer binding site (1102) and a unique identifier region (1103). The universal primer binding site (1102) may comprise a phosphorothioate linkage, as depicted by an "*" in FIG. 11A. As shown in Step 1 of FIG. 11A, the individual oligonucleotide fragments (1101) may be mixed to produce a plurality of oligonucleotide fragments (1104). The plurality of oligonucleotide fragments (1104) can be attached to a target specific region (1105). As shown in Step 2 of FIG. 11A, the target specific region can be ligated to the oligonucleotide tag to produce an oligonucleotide tag comprising a target specific region (1105). 5' and 3' exonucleases may be added to the reaction to remove non-ligated products (1105, 1101). The oligonucleotide tag (1106) comprising the universal primer binding site (1102), unique identifier region (1103) and target specific region (1105) may be resistant to 5' and 3' exonucleases. As shown in Step 3 of FIG. 11A, the 3' phosphate group from the ligated oligonucleotide tag (1106) can be removed to produce an oligonucleotide tag (1107) without a 3' phosphate group. The 3' phosphate group can be removed enzymatically. For example, a T4 polynucleotide kinase can be used to remove the 3' phosphate group.

Another method of synthesizing oligonucleotide tags is depicted in FIG. 11B. As shown in FIG. 11B, an oligonucleotide tag (1128) can be synthesized by ligating two oligonucleotide fragments (1121 and 1127). One oligonucleotide fragment (1121) may comprise a universal primer binding site (1122), unique identifier region (1123) and a left splint (1123). The other oligonucleotide fragment (1128) may comprise a right splint (1125) and a target specific region (1126). A ligase (e.g., T4 DNA ligase) can be used to join the two oligonucleotide fragments (1121 and 1127) to produce an oligonucleotide tag (1128). Double stranded ligation of the left splint (1124) and right splint (1125) can produce an oligonucleotide tag (1128) with a bridge splint (1129).

An alternative method of synthesizing an oligonucleotide tag by ligating two oligonucleotide fragments is depicted in FIG. 11C. As shown in FIG. 11C, an oligonucleotide tag (1158) is synthesized by ligating two oligonucleotide fragments (1150 and 1158). One oligonucleotide fragment (1150) may comprise a universal primer binding site (1151), unique identifier region (1152), and a ligation sequence (1153). The other oligonucleotide fragment (1158) may comprise a ligation sequence (1154) that is complementary to the ligation sequence (1153) of the first oligonucleotide fragment (1150), a complement of a target specific region (1155), and a label (1156). The oligonucleotide fragment (1159) may also comprise a 3' phosphate which prevents extension of the oligonucleotide fragment. As shown in Step 1 of FIG. 11C, the ligation sequences (1153 and 1154) of the two oligonucleotide fragments may anneal and a polymerase can be used to extend the 3' end of the first oligonucleotide fragment (1150) to produce an oligonucleotide tag (1158). The oligonucleotide tag (1158) may comprise a universal primer binding site (1151), unique identifier region (1152), ligation sequence (1153), and a target specific sequence (1157). The target specific sequence (1157) of the oligonucleotide tag (1158) may be the complement of the complement of the target specific region (1155) of the second oligonucleotide fragment (1159). The oligonucleotide fragment comprising the label (1156) can be removed from the oligonucleotide tags (1158). For example, the label (1156) may comprise biotin and oligonucleotide fragments (1159) comprising the biotin label (1156) can be removed via streptavidin capture. In another example, the label (1156) may comprise a 5' phosphate and oligonucleotide fragments (1159) comprising the 5' phosphate (1156) can be removed via an exonuclease (e.g., Lambda exonuclease).

As depicted in FIG. 11D, a first oligonucleotide fragment (1170) comprising a universal primer binding site (1171), unique identifier region (1172), a first ligation sequence (1173) is annealed to a second oligonucleotide fragment (1176) comprising a second ligation sequence (1174) and an RNA complement of the target sequence (1175). Step 1 may comprise annealing the first and second ligation sequences (1173 and 1174) followed by reverse transcription of the RNA complement of the target sequence (1175) to produce an oligonucleotide tag (1177) comprising a universal primer binding site (1171), unique identifier region (1172), a first ligation sequence (1173), and a target specific region (1178). The oligonucleotide fragments comprising the RNA complement of the target sequence can be selectively degraded by RNAse treatment.

The oligonucleotide tag can comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the oligonucleotide tag comprises at least about 1500, 2,000; 2500, 3,000; 3500, 4,000; 4500, 5,000; 5500, 6,000; 6500, 7,000; 7500, 8,000; 8500, 9,000; 9500, or 10,000 nucleotides or base pairs.

The tags can be hexamers, e.g. random hexamers. The tags can be randomly generated from a set of mononucleotides. The tags can be assembled by randomly incorporating mononucleotides.

The tags can also be assembled without randomness, to generate a library of different tags which are not randomly generated but which includes sufficient numbers of different tags to practice the methods.

In some embodiments an oligonucleotide tag can comprise a cutback in a target molecule. The cutback can be, for example, a enzymatic digestion of one or both ends of a target molecule. The cutback can be used in conjunction with the addition of added oligonucleotide tags. The combination of the cutback and the added tags can contain information related to the particular starting molecule. By adding a random cutback to the tag a smaller diversity of the added tags may be necessary for counting the number of target molecules when detection allows a determination of both the random cutback and the added oligonucleotides.

The oligonucleotide tag can comprise a target specific region. The target specific region can comprise a sequence that is complementary to the molecule. In some instances, the molecule is an mRNA molecule and the target specific region comprises an oligodT sequence that is complementary to the polyA tail of the mRNA molecule. The target specific region can also act as a primer for DNA and/or RNA synthesis. For example, the oligodT sequence of the target specific region can act as a primer for first strand synthesis of a cDNA copy of the mRNA molecule. Alternatively, the target specific region comprises a sequence that is complementary to any portion of the molecule. In other instances, the target specific region comprises a random sequence that can be hybridized or ligated to the molecule. The target specific region can enable attachment of the oligonucleotide tag to the molecule. Attachment of the oligonucleotide tag can occur by any of the methods disclosed herein (e.g., hybridization, ligation). In some instances, the target specific region comprises a sequence that is recognized by one or more restriction enzymes. The target specific region can comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. Preferably, the target specific region comprises at least about 5-10, 10-15, 10-20, 10-30, 15-30, or 20-30 nucleotides or base pairs.

In some instances, the target specific region is specific for a particular gene or gene product. For example, the target specific region comprises a sequence complementary to a region of a p53 gene or gene product. Therefore, the oligonucleotide tags can only attach to molecules comprising the p53-specific sequence. Alternatively, the target specific region is specific for a plurality of different genes or gene products. For example, the target specific region comprises an oligodT sequence. Therefore, the oligonucleotide tags can attach to any molecule comprising a polyA sequence. In another example, the target specific region comprises a random sequence that is complementary to a plurality of different genes or gene products. Thus, the oligonucleotide tag can attach to any molecule with a sequence that is complementary to the target specific region. In other instances, the target specific region comprises a restriction site overhang (e.g., EcoRI sticky-end overhang). The oligonucleotide tag can ligate to any molecule comprising a sequence complementary to the restriction site overhang.

The oligonucleotide tag disclosed herein often comprises a unique identifier region. The unique identifier region may be used to uniquely identify occurrences of target species thereby marking each species with an identifier that can be used to distinguish between two otherwise identical or nearly identical targets. The unique identifier region of the plurality of oligonucleotide tags can comprise a collection of different semiconductor nanocrystals, metal compounds, peptides, oligonucleotides, antibodies, small molecules, isotopes, particles or structures having different shapes, colors, barcodes or diffraction patterns associated therewith or embedded therein, strings of numbers, random fragments of proteins or nucleic acids, different isotopes, or any combination thereof. The unique identifier region can comprise a degenerative sequence. The unique identifier region can comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the unique identifier region comprises at least about 1500; 2,000; 2500, 3,000; 3500, 4,000; 4500, 5,000; 5500, 6,000; 6500, 7,000; 7500, 8,000; 8500, 9,000; 9500, or 10,000 nucleotides or base pairs. Preferably, the unique identifier region comprises at least about 10-30, 15-40, or 20-50 nucleotides or base pairs.

In some instances, the oligonucleotide tag comprises a universal primer binding site. The universal primer binding site allows the attachment of a universal primer to the labeled-molecule and/or labeled-amplicon. Universal primers are well known in the art and include, but are not limited to, −47F (M13F), alfaMF, AOX3', AOX5', BGH_r, CMV_-30, CMV_−50, CVM_f, LACrmt, lamgda gt10F, lambda gt 10R, lambda gt11F, lambda gt11R, M13 rev, M13Forward (−20), M13Reverse, male, p10SEQP_pQE, pA_−120, pet_4, pGAP Forward, pGL_RVpr3, pGLpr2_R, pKLAC1_4, pQE_FS, pQE_RS, puc_U1, puc_U2, revers_A, seq_IRES_tam, seq_IRES_zpet, seq_ori, seq_PCR, seq_pIRES−, seq_pIRES+, seq_pSecTag, seq_p-SecTag+, seq_retro+PSI, SP6, T3-prom, T7-prom, and T7-term Inv. Attachment of the universal primer to the universal primer binding site can be used for amplification, detection, and/or sequencing of the labeled-molecule and/or labeled-amplicon. The universal primer binding site can comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500; 2,000; 2500, 3,000; 3500, 4,000; 4500, 5,000; 5500, 6,000; 6500, 7,000; 7500, 8,000; 8500, 9,000; 9500, or 10,000 nucleotides or base pairs. Preferably, the universal primer binding site comprises 10-30 nucleotides or base pairs.

The oligonucleotide tag may comprise an adapter region. The adapter region may enable hybridization of one or more probes. The adapter region may enable hybridization of one or more HCR probes.

The oligonucleotide tag may comprise one or more labels.

The oligonucleotide tag may act as an initiator for a hybridization chain reaction (HCR). The adapter region of the oligonucleotide tag may act as an initiation for HCR. The universal primer binding site may act as an initiator for HCR.

In some instances, the oligonucleotide tag is single-stranded. In other instances, the oligonucleotide tag is double-stranded. The oligonucleotide tag can be linear. Alternatively, the oligonucleotide tag comprises a secondary structure. As used herein, "secondary structure" includes tertiary, quaternary, etc. . . . structures. In some instances, the secondary structure is a hairpin, a stem-loop structure, an internal loop, a bulge loop, a branched structure or a pseudoknot, multiple stem loop structures, cloverleaf type structures or any three dimensional structure. In some instances, the secondary structure is a hairpin. The hairpin can comprise an overhang sequence. The overhang sequence of the hairpin can act as a primer for a polymerase chain reaction and/or reverse transcription reaction. The overhang sequence comprises a sequence that is complementary to the molecule to which the oligonucleotide tag is attached and the overhang sequence hybridizes to the molecule. The overhang sequence can be ligated to the molecule and acts as a template for a polymerase chain reaction and/or reverse transcription reaction. In some embodiments the tag comprises nucleic acids and/or synthetic nucleic acids and/or modified nucleic acides.

Figure 34:
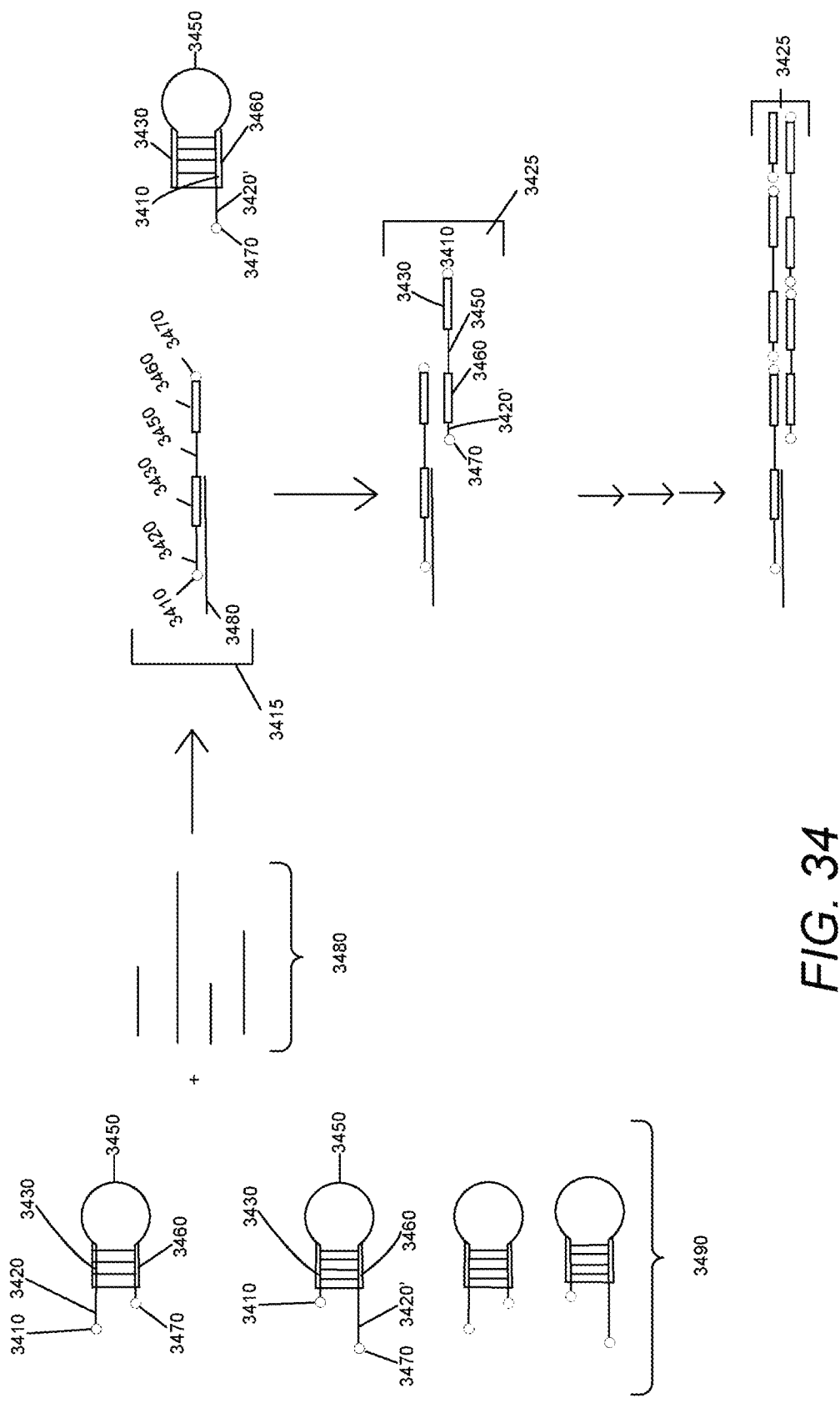

An oligonucleotide tag comprising a hairpin may act as a probe for a hybrization chain reaction. Further disclosed herein is a stochastic label-based hybridization chain reaction (HCR) method comprising stochastically labeling one or more nucleic acid molecules with an oligonucleotide tag, wherein the oligonucleotide tag is a hairpin and the one or more nucleic acid molecules act as initiators for a hybridization chain reaction. A schematic of a stochastic label-based hybridization reaction is depicted in FIG. 34. As shown in FIG. 34, one or more nucleic acid molecules (3480) are stochastically labeled with a plurality of hairpin oligonucleotide tags (3490) by initiating a hybridization chain reaction. The hairpin oligonucleotide tags may comprise one or more labels (3410, 3470), an overhang (3420, 3420'), a stem (3430, 3460), and a loop (3450). The overhang region (3420) of the hairpin oligonucleotide tag (3490) may comprise a target specific region. The overhang region (3420) may comprise an oligodT sequence. The sample comprising the one or more nucleic acid molecules may be treated with one or more restriction nucleases prior to stochastic labeling. The overhang region (3420) may comprise a restriction enzyme recognition sequence. The sample comprising the one or more nucleic acid molecules may be contacted with one or more adapters prior to stochastic labeling to produce an adapter-nucleic acid molecule hybrid. The overhang region (3420) and the stem (3430) may be complementary to the one or more adapters. The loop (3450) of the oligonucleotide tag may comprise a unique identifier region. Hybridization of a first hairpin oligonucleotide tag (3490) to the nucleic acid molecules (3480) may result in the formation of a labeled molecule (3415), wherein the first hairpin oligonucleotide tag is linearized to produce a first linearized oligonucleotide tag. The first linearized oligonucleotide tag of labeled molecule (3415) can act as an initiator for hybrization of a second hairpin oligonucleotide tag to the labeled molecule (3415) to produce a labeled molecule with two linearized oligonucleotide tags (3425). The second linearized oligonucleotide tag can act as an initiator for another hybridization reaction. This process can be repeated multiple times to produce a labeled molecule with multiple linearized HCR probes (3435). The labels (3410, 3470) on the HCR probe can enable detection of the labeled molecule. The labels (3410, 3470) may be any type of label (e.g., fluorphore, chromophore, small molecule, nanoparticle, hapten, enzyme, antibody, magnet). The labels (3360 and 3390) may comprise fragments of a single label. The labels (3410, 3470) may generate a detectable signal when they are in close proximity. When the oligonucleotide tag is a hairpin, the labels (3360 and 3390) may be too far away to produce a detectable signal. When the hairpin oligonucleotide tag is linearized and multiple linearized hairpin oligonucleotide tags are hybridized together, the labels (3410, 3470) may be in close enough proximity to generate a detectable signal. For example, a hairpin oligonucleotide tag (3350) may comprise two pyrene moieties as labels (3410, 3470). Alternatively, the labels may be nanoparticles. The stochastic label-based HCR can enable attachment of multiple hairpin oligonucleotide tags to a labeled molecule, which can result in signal amplification. Stoachastic label-based HCR may increase the sensitivity of detection, analysis and/or quantification of the nucleic acid molecules. Stochastic label-based HCR may increase the accuracy of detection, analysis, and/or quantification of one or more nucleic acid molecules.

In some instances, the plurality of oligonucleotide tags comprises at least about 2, 3, 4, 5, 6, 7, 8, 9, 10, 15, 20, 25, 30, 35, 40, 45, 50, 55, 60, 65, 70, 75, 80, 85, 90, 95, or 100 different oligonucleotide tags. In other instances, the plurality of oligonucleotide tags comprises at least about 200; 300; 400; 500; 600; 700; 800; 900; 1,000; 2,000; 3,000; 4,000; 5,000; 6,000; 7,000; 8,000; 9,000; or 10000 different oligonucleotide tags. Alternatively; the plurality of oligonucleotide tags comprises at least about 20,000; 30,000; 40,000; 50,000; 60,000; 70,000; 80,000; 90,000; or 100,000 different oligonucleotide tags.

The number of oligonucleotide tags in the plurality of oligonucleotide tags is often in excess of the number of molecules to be labeled. In some instances, the number of oligonucleotide tags in the plurality of oligonucleotide tags is at least about 2, 3, 4, 5, 6, 7, 8, 9, 10, 15, 20, 30, 40, 50, 60, 70, 80, 90, or 100 times greater than the number of molecules to be labeled.

The number of different oligonucleotide tags in the plurality of oligonucleotide tags is often in excess of the number of different molecules to be labeled. In some instances, the number of different oligonucleotide tags in the plurality of oligonucleotide tags is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled.

In some instances, stochastic labeling of a molecule comprises a plurality of oligonucleotide tags, wherein the concentration of the different oligonucleotide tags in the plurality of oligonucleotide tags is the same. In such instances, the plurality of oligonucleotide tags comprises equal numbers of each different oligonucleotide tag. Additionally, the relative ratio of the different oligonucleotide tags in the plurality of oligonucleotide is 1:1:1 . . . 1.

In some instances, stochastic labeling of a molecule comprises a plurality of oligonucleotide tags, wherein the concentration of the different oligonucleotide tags in the plurality of oligonucleotide tags is different. In such instances, the plurality of oligonucleotide tags comprises different numbers of each different oligonucleotide tag. Additionally, the relative ratio of the different oligonucleotide tags in the plurality of oligonucleotide is not 1:1:1 . . . 1. In some instances, some oligonucleotide tags are present at higher concentrations than other oligonucleotide tags in the plurality of oligonucleotide tags. In some instances, stochastic labeling with different concentrations of oligonucleotide tags extends the sample measurement dynamic range without increasing the number of different labels used. For example, consider stochastically labeling 3 nucleic acid sample molecules with 10 different oligonucleotide tags all at equal concentration. We expect to observe 3 different labels. Now instead of 3 nucleic acid molecules, consider 30 nucleic acid molecules, and we expect to observe all 10 labels. In contrast, if we still used 10 different stochastic labels and alter the relative ratios of the labels to 1:2:3:4 . . . 10, then with 3 nucleic acid molecules, we would expect to observe between 1-3 labels, but with 30 molecules we would expect to observe only approximately 5 labels thus extending the range of measurement with the same number of stochastic labels.

The relative ratios of the different oligonucleotide tags in the plurality of oligonucleotide tags can be 1:X, where X is at least about 1, 2, 3, 4, 5, 6, 7, 8, 9, 10, 15, 20, 25, 30, 35, 40, 45, 50, 55, 60, 65, 70, 75, 80, 85, 90, 95, or 100. Alternatively, the relative ratios of "n" different oligonucleotide tags in the plurality of oligonucleotide tags is 1:A:B:C: . . . $Z_n$, where A, B, is at least about 1, 2, 3, 4, 5, 6, 7, 8, 9, 10, 15, 20, 25, 30, 35, 40, 45, 50, 55, 60, 65, 70, 75, 80, 85, 90, 95, or 100.

In some instances, the concentration of two or more different oligonucleotide tags in the plurality of oligonucleotide tags is the same. For "n" different oligonucleotide tags, the concentration of at least 2, 3, 4, . . . n different oligonucleotide tags is the same. Alternatively, the concentration of two or more different oligonucleotide tags in the plurality of oligonucleotide tags is different. For "n" different oligonucleotide tags, the concentration of at least 2, 3, 4, . . . n different oligonucleotide tags is different. In some instances, for "n" different oligonucleotide tags, the difference in concentration for at least 2, 3, 4, . . . n different oligonucleotide tags is at least about 0.1, 0.2, 0.3, 0.4, 0.5, 0.6, 0.7, 0.8, 0.9, 1, 1.25, 1.5, 1.75, 2, 2.25, 2.5, 2.75, 3, 4, 5, 6, 7, 8, 9, 10, 15, 20, 30, 40, 50, 60, 70, 80, 90, 100, 200, 300, 400, 500, 600, 700, 800, 900, or 1000-fold.

In some instances, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different oligonucleotide tags in the plurality of oligonucleotide tags have the same concentration. Alternatively, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different oligonucleotide tags in the plurality of oligonucleotide tags have a different concentration.

Figure 15:
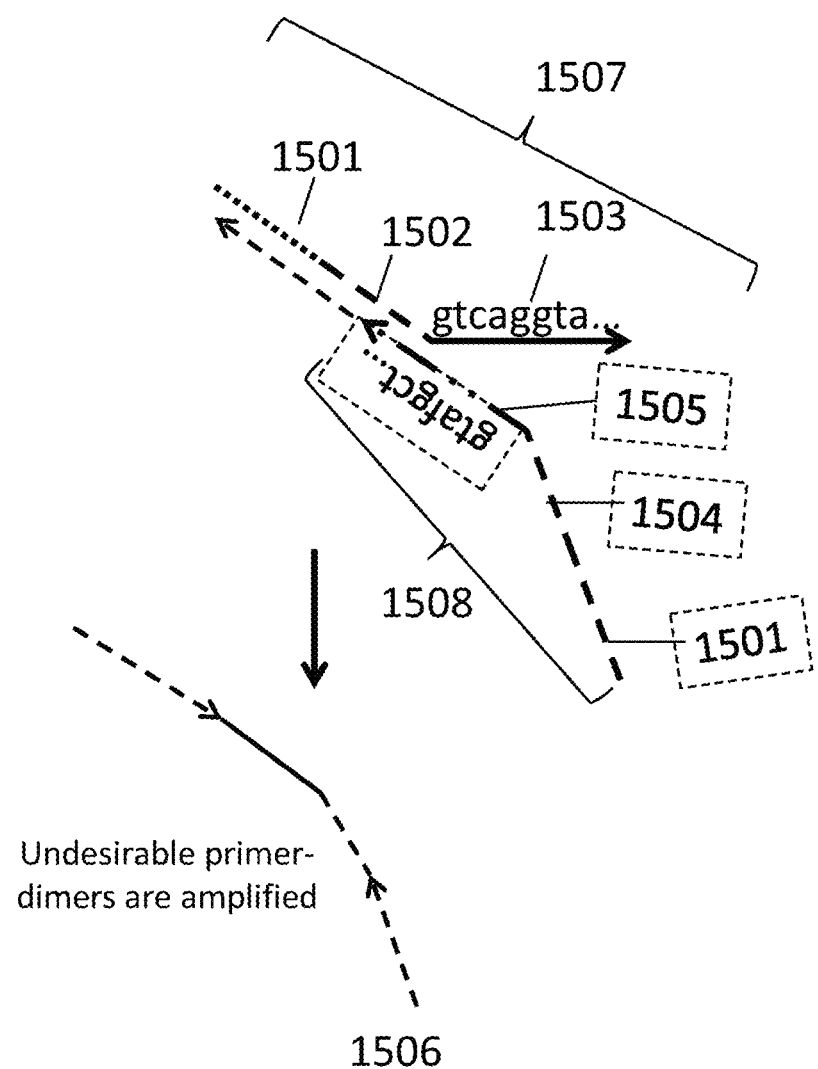

The sequences of the oligonucleotide tags may be optimized to minimize dimerization of oligonucleotide tags. FIG. 15 depicts the formation of oligonucleotide tag dimers when the oligonucleotide tag sequences are not optimized. As shown in FIG. 15, when oligonucleotide tag sequences are not optimized, a first oligonucleotide tag (1507) comprising a universal primer binding site (1501), a first unique identifier region (1502) and a first target specific region (1503) can anneal to a second oligonucleotide tag (1508) comprising a universal primer binding site (1501), a second unique identifier region (1504) and a second target specific region (1505). The oligonucleotide tag dimer can be amplified and result in the formation of an amplicon (1506) comprising two universal primer binding sites on each end of the amplicon and a target specific region and a unique identifier region. Because the concentration of the oligonucleotide tags are far greater that the number of DNA templates, these oligonucleotide tag dimers can outcompete the labeled DNA molecules in an amplification reaction. Unamplified DNAs lead to false negatives, and amplified oligonucleotide tag dimers lead to high false positives. Thus, the oligonucleotide tags can be optimized to minimize oligonucleotide tag dimer formation. Alternatively, oligonucleotide tags that dimerize are discarded, thereby eliminating oligonucleotide tag dimer formation.

Figure 16:
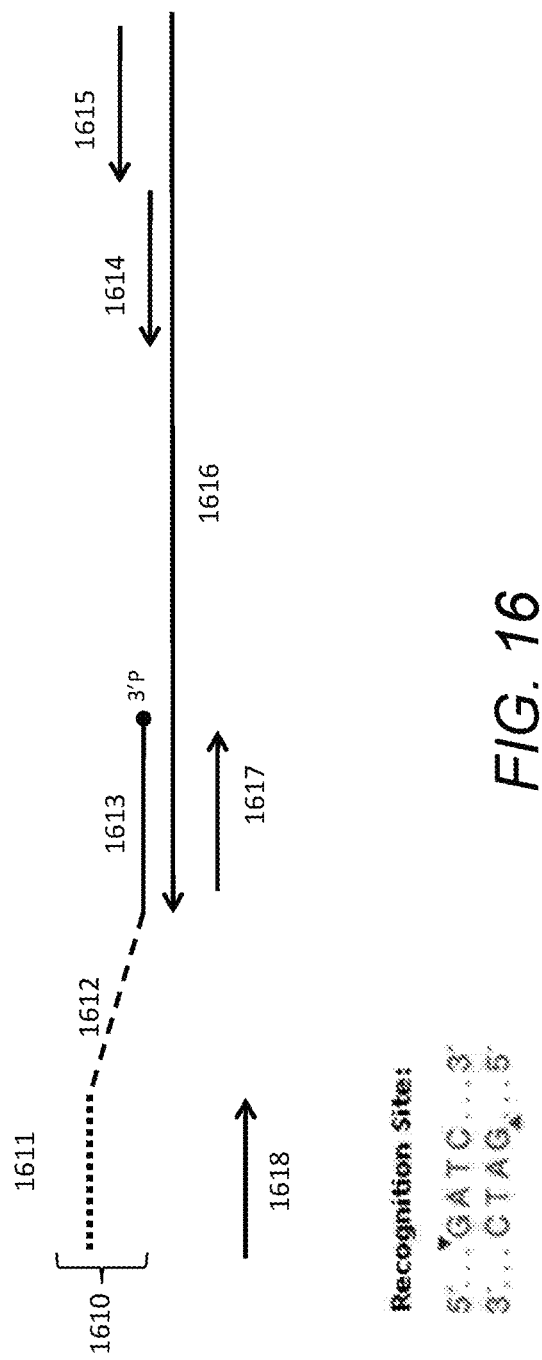

Alternatively, as depicted in FIG. 16, oligonucleotide tag dimer formation can be eliminated or reduced by incorporating one or more modifications into the oligonucleotide tag sequence. As shown in FIG. 16, an oligonucleotide tag (1610) comprising a universal primer binding site (1611), unique identifier region (1612), and target specific region (1613) comprising uracils and a 3' phosphate group is annealed to a target molecule (1616). The target molecule (1616) may be a restriction endonuclease digested fragment. The restriction endonuclease may recognize the recognition site depicted in FIG. 16. PCR amplification may comprise one or more forward primers (1618 and 1618) and one or more reverse primers (1614 and 1615). PCR amplification may comprise nested PCR with a forward primer (1618) specific for the universal primer binding site (1611) of the oligonucleotide tag and a forward primer (1617) specific for the target specific region (1613) of the oligonucleotide tag and reverse primers (1614 and 1615) that are specific for the target molecule. The target molecule can be amplified using a Pfu DNA polymerase, which cannot amplify template comprising one or more uracils. Thus, any dimerized oligonucleotide tags cannot be amplified by Pfu DNA polymerase.

VIII. Detectable Labels

The methods, kits, and systems disclosed herein can further comprise a detectable label. The terms "detectable label" or "label" can be used interchangeabley and refer to any chemical moiety attached to a nucleotide, nucleotide polymer, or nucleic acid binding factor, wherein the attachment may be covalent or non-covalent. Preferably, the label is detectable and renders the nucleotide or nucleotide polymer detectable to the practitioner of the invention. Detectable labels that may be used in combination with the methods disclosed herein include, for example, a fluorescent label, a chemiluminescent label, a quencher, a radioactive label, biotin, pyrene moiety, gold, or combinations thereof. Non-limiting example of detectable labels include luminescent molecules, fluorochromes, fluorescent quenching agents, colored molecules, radioisotopes or scintillants.

In some instances, the methods disclosed herein further comprise attaching one or more detectable labels to the labeled-molecule or any product thereof (e.g., labeled-amplicon). The methods can comprise attaching two or more detectable labels to the labeled-molecule. Alternatively, the method comprises attaching at least about 3, 4, 5, 6, 7, 8, 9, or 10 detectable labels to a labeled-molecule. In some instances, the detectable label is a Cy™ label. The Cy™ label is a Cy3 label. Alternatively, or additionally, the detectable label is biotin. In some embodiments the detectable label is attached to a probe which binds the molecule or labeled molecule. This can occur, for example, after the molecule or labeled molecule has been hybridized to an array. In one example the molecule is bound to partners on an array. After the binding a probe with can bind the molecule is bound to the molecules on the array. This process can be repeated with multiple probes and labeles to decrease the likelihood that a signal is the result of nonspecific binding of a label or nonspecific binding of the molecule to the array.

In some instances a donor acceptor pair can be used as the detectable labels. Either the donor or acceptor can be attached to a probe that binds a nucleic acid. The probe can be, for example, a nucleic acid probe that can bind to a the molecule or the labeled molecule. The corresponding donor or acceptor can be added to cause a signal.

In some instances, the detectable label is a Freedom dye, Alexa Fluor® dye, Cy™ dye, fluorescein dye, or LI-COR IRDyes®. In some instances, the Freedom dye is fluorescein (6-FAM™, 6-carboxyfluoroscein), MAX (NETS Ester), TYE™ 563, TEX 615, TYE™ 665, TYE 705. The detectable label can be an Alexa Fluor dye. Examples of Alexa Fluor® dyes include Alexa Fluor® 488 (NHS Ester), Alexa Fluor® 532 (NHS Ester), Alexa Fluor® 546 (NHS Ester), Alexa Fluor® 594 (NHS Ester), Alexa Fluor® 647 (NHS Ester), Alexa Fluor® 660 (NHS Ester), or Alexa Fluor® 750 (NHS Ester). Alternatively, the detectable label is a Cy™ dye. Examples of Cy™ dyes include, but are not limited to, Cy2, Cy3, Cy3B, Cy3.5, Cy5, Cy5.5, and Cy7. In some instances, the detectable label is a fluorescein dye. Non-limiting examples of fluorescein dyes include 6-FAM™ (Azide), 6-FAM™ (NHS Ester), Fluorescein dT, JOE (NHS Ester), TET™, and HEX™. In some instances, the detectable label is a LI-COR IRDyes®, such as 5' IRDye® 700, 5' IRDye® 800, or IRDye® 800CW (NHS Ester). In some instances, the detectable label is TYE™ 563. Alternatively, the detectable label is Cy3.

The detectable label can be Rhodamine dye. Examples of rhodamine dyes include, but are not limited to, Rhodamine Green™-X (NHS Ester), TAMRA™, TAMRA™ (NHS Ester), Rhodamine Red™-X(NHS Ester), ROX™ (NHS Ester), and 5'TAMRA™ (Azide). In other instances, the detectable label is a WellRED Dye. WellRED Dyes include, but are not limited to, WellRED D4 dye, WellRED D3 dye, and WellRED D2 dye. In some instances, the detectable label is Texas Red®-X (NHS Ester), Lightcycler® 640 (NHS Ester), or Dy 750 (NHS Ester).

In some instances, detectable labels include a linker molecule. Examples of linker molecules include, but are not limited to, biotin, avidin, streptavidin, HRP, protein A, protein G, antibodies or fragments thereof, Grb2, polyhistidine, $Ni^{2+}$, FLAG tags, myc tags. Alternatively, detectable labels include heavy metals, electron donors/acceptors, acridinium esters, dyes and calorimetric substrates. In other instances, detectable labels include enzymes such as alkaline phosphatase, peroxidase and luciferase.

A change in mass can be considered a detectable label, as is the case of surface plasmon resonance detection. The skilled artisan would readily recognize useful detectable labels that are not mentioned herein, which may be employed in the operation of the present invention.

In some instances, detectable labels are used with primers. For example, the universal primer is a labeled with the detectable label (e.g., Cy3 labeled universal primer, fluorophore labeled universal primer). Alternatively, the target specific primer is labeled with the detectable label (e.g., TYE 563-labeled target specific primer). In other instances, detectable labels are used with the oligonucleotide tags. For example, the oligonucleotide tag is labeled with a detectable label (e.g., biotin-labeled oligonucleotide tag). In other instances, detectable labels are used with the nucleic acid template molecule. Detectable labels can be used to detect the labeled-molecules or labeled-amplicons. Alternatively, detectable labels are used to detect the nucleic acid template molecule.

In some instances, the detectable label is attached to the primer, oligonucleotide tag, labeled-molecule, labeled-amplicon, probe, HCR probe, and/or non-labeled molecule. Methods for attaching the detectable label to the primer, oligonucleotide tag, labeled-molecule, labeled-amplicon, and/or non-labeled molecule include, but are not limited to, chemical labeling and enzymatic labeling. In some instances, the detectable label is attached by chemical labeling. In some embodiments, chemical labeling techniques comprise a chemically reactive group. Non-limiting examples of reactive groups include amine-reactive succinimidyl esters such as NHS-fluorescein or NHS-rhodamine, amine-reactive isothiocyanate derivatives including FITC, and sulfhydryl-reactive maleimide-activated fluors such as fluorescein-5-maleimide. In some embodiments, reaction of any of these reactive dyes with another molecule results in a stable covalent bond formed between a fluorophore and the linker and/or agent. In some embodiments, the reactive group is isothiocyanates. In some embodiments, a label is attached to an agent through the primary amines of lysine side chains. In some embodiments, chemical labeling comprises a NHS-ester chemistry method.

Alternatively, the detectable label is attached by enzymatic labeling. Enzymatic labeling methods can include, but are not limited to, a biotin acceptor peptide/biotin ligase (AP/Bir A), acyl carrier protein/phosphopantetheine transferase (ACP/PPTase), human $O^6$-alkylguanine transferase (hAGT), Q-tag/transglutaminase (TGase), aldehyde tag/formylglycine-generating enzyme, mutated prokaryotic dehalogenase (HaloTag™), and farnesylation motif/protein farnesyltransferase (PFTase) methods. Affinity labeling can include, but is not limited to, noncovalent methods utilizing dihydrofolate reductase (DHFR) and Phe36Val mutant of FK506-binding protein 12 (FKBP12(F36V)), and metal-chelation methods.

Crosslinking reagents can be used to attach a detectable label to the primer, oligonucleotide tag, labeled-molecule, labeled-amplicon, and/or non-labeled molecule. In some instances, the crosslinking reagent is glutaraldehyde. Glutaraldehyde can react with amine groups to create crosslinks by several routes. For example, under reducing conditions, the aldehydes on both ends of glutaraldehyde couple with amines to form secondary amine linkages.

In some instances, attachment of the detectable label to the primer, oligonucleotide tag, labeled-molecule, labeled-amplicon, and/or non-labeled molecule comprises periodate-activation followed by reductive amination. In some instances, Sulfo-SMCC or other heterobifunctional crosslinkers are used to conjugate the detectable to the primer, oligonucleotide tag, labeled-molecule, labeled-amplicon, and/or non-labeled molecule. For example, Sulfo-SMCC is used to conjugate an enzyme to a drug. In some embodiments, the enzyme is activated and purified in one step and then conjugated to the drug in a second step. In some embodiments, the directionality of crosslinking is limited to one specific orientation (e.g., amines on the enzyme to sulfhydryl groups on the antibody).

IX. Supports

In some instances, the methods, kits, and systems disclosed herein comprise a support. The term "support" and "substrate" as used herein are used interchangeably and refer to a material or group of materials having a rigid or semi-rigid surface or surfaces. The support or substrate can be a solid support. Alternatively, the support is a non-solid support. The support or substrate can comprise a membrane, paper, plastic, coated surface, flat surface, glass, slide, chip, or any combination thereof. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Alternatively, the solid support(s) comprises silica chips, microparticles, nanoparticles, plates, and arrays. Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Publication No. WO 99/36760 and WO 01/58593, which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but many of the same techniques may be applied to polypeptide arrays. Additional exemplary substrates are disclosed in U.S. Pat. No. 5,744,305 and US Patent Pub. Nos. 20090149340 and 20080038559.

In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluorochrome microbead, and BcMag™ Carboxy-Terminated Magnetic Beads.

The solid support can be an array or microarray. The solid support can comprise discrete regions. The solid support can be an addressable array. In some instances, the array comprises a plurality of probes fixed onto a solid surface. The plurality of probes enables hybridization of the labeled-molecule and/or labeled-amplicon to the solid surface. The plurality of probes comprises a sequence that is complementary to at least a portion of the labeled-molecule and/or labeled-amplicon. In some instances, the plurality of probes comprises a sequence that is complementary to the oligonucleotide tag portion of the labeled-molecule and/or labeled-amplicon. In other instances, the plurality of probes comprises a sequence that is complementary to the junction formed by the attachment of the oligonucleotide tag to the molecule.

The array can comprise one or more probes. The probes can be in a variety of formats as depicted in FIG. 18. As shown in FIGS. 18A-18C, 18G and 18H, the array (1801, 1806, 1811, 1828, 1832) can comprise a probe (1804, 1809, 1814, 1836, 1835) comprising a sequence that is complementary to at least a portion of the target molecule (1802, 1807, 1813, 1829, 1833) and a sequence that is complementary to the unique identifier region of an oligonucleotide tag (1803, 1808, 1812, 1830, 1834). As shown FIGS. 18A-18B, 18G and 18H, the sequence that is complementary to at least a portion of the target molecule (1802, 1807, 1829, 1833) can be attached to the array. As shown in FIG. 18C, the sequence that is complementary to the unique identifier region (1812) can be attached to the array. As shown in FIG. 18D-18F, the array (1816, 1820, 1824) can comprise a first probe (1817, 1821, 1825) comprising a sequence that is complementary to at least a portion of the target molecule and a second probe (1819, 1823, 1827) that is complementary to the unique identifier region. FIG. 18A-18H also depict the various ways in which a stochastically labeled molecule (1805, 1810, 1815, 1818, 1822, 1826, 1831, 1837) can hybridize to the arrays. For example, as shown in FIGS. 18A and 18C, the junction of the unique identifier region and the target molecule of the stochastically labeled molecule (1805, 1815) can hybridize to the probe (1804, 1814) on the array. As shown in FIG. 18B, 18D-18H, there can be a gap in the regions of the stochastically labeled molecule (1810, 1818, 1822, 1826, 1831, 1837) that can hybridize to the probe on the array. As shown in FIGS. 18D-18F and 18H, different regions of the stochastically labeled molecule (1818, 1822, 1826, 1837) can hybridize to two or more probes on the array. Thus, the array probes can be in many different formats. The array probes can comprise a sequence that is complementary to a unique identifier region, a sequence that is complementary to the target molecule, or a combination thereof. Hybridization of the stochastically labeled molecule to the array can occur by a variety of ways. For example, two or more nucleotides of the stochastically labeled molecule can hybridize to one or more probes on the array. The two or more nucleotides of the stochastically labeled molecule that hybridize to the probes may be consecutive nucleotides, non-consecutive nucleotides, or a combination thereof. The stochastically labeled molecule that is hybridized to the probe can be detected by any method known in the art. For example, the stochastically labeled molecules can be directly detected. Directly detecting the stochastically labeled molecule may comprise detection of a fluorophore, hapten, or detectable label. The stochastically labeled molecules can be indirectly detected. Indirect detection of the stochastically labeled molecule may comprise ligation or other enzymatic or non-enzymatic methods.

The array can be in a variety of formats. For example, the array can be in a 16-, 32-, 48-, 64-, 80-, 96-, 112-, 128-, 144-, 160-, 176-, 192-, 208-, 224-, 240-, 256-, 272-, 288-, 304-, 320-, 336-, 352-, 368-, 384-, or 400-format. Alternatively, the array is in an 8×60K, 4×180K, 2×400K, 1×1M format. In other instances, the array is in an 8×15K, 4×44K, 2×105K, 1×244K format.

The array can comprise a single array. The single array can be on a single substrate. Alternatively, the array is on multiple substrates. The array can comprise multiple formats. The array can comprise a plurality of arrays. The plurality of arrays can comprise two or more arrays. For example, the plurality of arrays can comprise at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 arrays. In some instances, at least two arrays of the plurality of arrays are identical. Alternatively, at least two arrays of the plurality of arrays are different.

In some instances, the array comprises symmetrical chambered areas. For example, the array comprises 0.5×0.5 mm, 1×1 mm, 1.5×1.5 mm, 2×2 mm, 2.5×2.5 mm, 3×3 mm, 3.5×3.5 mm, 4×4 mm, 4.5×4.5 mm, 5×5 mm, 5.5×5.5 mm, 6×6 mm, 6.5×6.5 mm, 7×7 mm, 7.5×7.5 mm, 8×8 mm, 8.5×8.5 mm, 9×9 mm, 9.5×9.5 mm, 10×10 mm, 10.5×10.5 mm, 11×11 mm, 11.5×11.5 mm, 12×12 mm, 12.5×12.5 mm, 13×13 mm, 13.5×13.5 mm, 14×14 mm, 14.5×14.5 mm, 15×15 mm, 15.5×15.5 mm, 16×16 mm, 16.5×16.5 mm, 17×17 mm, 17.5×17.5 mm, 18×18 mm, 18.5×18.5 mm, 19×19 mm, 19.5×19.5 mm, or 20×20 mm chambered areas. In some instances, the array comprises 6.5×6.5 mm chambered areas. Alternatively, the array comprises asymmetrical chambered areas. For example, the array comprises 6.5×0.5 mm, 6.5×1 mm, 6.5×1.5 mm, 6.5×2 mm, 6.5×2.5 mm, 6.5×3 mm, 6.5×3.5 mm, 6.5×4 mm, 6.5×4.5 mm, 6.5×5 mm, 6.5×5.5 mm, 6.5×6 mm, 6.5×6.5 mm, 6.5×7 mm, 6.5×7.5 mm, 6.5×8 mm, 6.5×8.5 mm, 6.5×9 mm, 6.5×9.5 mm, 6.5×10 mm, 6.5×10.5 mm, 6.5×11 mm, 6.5×11.5 mm, 6.5×12 mm, 6.5×12.5 mm, 6.5×13 mm, 6.5×13.5 mm, 6.5×14 mm, 6.5×14.5 mm, 6.5×15 mm, 6.5×15.5 mm, 6.5×16 mm, 6.5×16.5 mm, 6.5×17 mm, 6.5×17.5 mm, 6.5×18 mm, 6.5×18.5 mm, 6.5×19 mm, 6.5×19.5 mm, or 6.5×20 mm chambered areas.

The array can comprise at least about 1 µm, 2 µm, 3 µm, 4 µm, 5 µm, 6 µm, 7 µm, 8 µm, 9 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, or 500 µm spots. In some instances, the array comprises 70 µm spots.

The array can comprise at least about 1 µm, 2 µm, 3 µm, 4 µm, 5 µm, 6 µm, 7 µm, 8 µm, 9 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm, 625 µm, 650 µm, 675 µm, 700 µm, 725 µm, 750 µm, 775 µm, 800 µm, 825 µm, 850 µm, 875 µm, 900 µm, 925 µm, 950 µm, 975 µm, 1000 µm feature pitch. In some instances, the array comprises 161 µm feature pitch.

The array can comprise one or more probes. In some instances, the array comprises at least about 5, 10, 15, 20, 25, 30, 40, 50, 60, 70, 80, 90, or 100 probes. Alternatively, the array comprises at least about 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 probes. The array can comprise at least about 3500, 4000, 4500, 5000, 5500, 6000, 6500, 7000, 7500, 8000, 8500, 9000, 9500, or 10000 probes. In some instances, the array comprises at least about 960 probes. Alternatively, the array comprises at least about 2780 probes. The probes can be specific for the plurality of oligonucleotide tags. The probes can be specific for at least a portion of the plurality of oligonucleotide tags. The probes can be specific for at least about 5%, 10%, 20%, 30%, 40%, 50%, 60%, 70%, 80%, 90%, 95%, 97% or 100% of the total number of the plurality of oligonucleotide tags. Alternatively, the probes are specific for at least about 5%, 10%, 20%, 30%, 40%, 50%, 60%, 70%, 80%, 90%, 95%, 97% or 100% of the total number of different oligonucleotide tags of the plurality of oligonucleotide tags. In other instances, the probes are non-specific probes. For example, the probes can be specific for a detectable label that is attached to the labeled-molecule. The probe can be streptavidin.

The array can be a printed array. In some instances, the printed array comprises one or more oligonucleotides attached to a substrate. For example, the printed array comprises 5' amine modified oligonucleotides attached to an epoxy silane substrate.

Alternatively, the array comprises a slide with one or more wells. The slide can comprise at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 wells. Alternatively, the slide comprises at least about 125, 150, 175, 200, 250, 300, 350, 400, 450, 500, 650, 700, 750, 800, 850, 900, 950, or 1000 wells. In some instances, the slide comprises 16 wells. Alternatively, the slide comprises 96 wells. In other instances, the slide comprises at least about 80, 160, 240, 320, 400, 480, 560, 640, 720, 800, 880, or 960 wells.

In some instances, the solid support is an Affymetrix 3K tag array, Arrayjet non-contact printed array, or Applied Microarrays Inc (AMI) array. Alternatively, the support comprises a contact printer, impact printer, dot printer, or pin printer.

The solid support can comprise the use of beads that self assemble in microwells. For example, the solid support comprises Illumina's BeadArray Technology. Alternatively, the solid support comprises Abbott Molecular's Bead Array technology, and Applied Microarray's FlexiPlex™ system.

In other instances, the solid support is a plate. Examples of plates include, but are not limited to, MSD multi-array plates, MSD Multi-Spot® plates, microplate, ProteOn microplate, AlphaPlate, DELFIA plate, IsoPlate, and Luma-Plate.

X. Enzymes

The methods, kits, and systems disclosed herein comprise one or more enzymes. Examples of enzymes include, but are not limited to, ligases, reverse transcriptases, polymerases, and restriction nucleases. In some instances, attachment of the oligonucleotide tag to the molecules comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods, kits, and systems disclosed herein can further comprise the use of one or more reverse transcriptases. In some instances, the reverse transcriptase is a HIV-1 reverse transcriptase, M-MLV reverse transcriptase, AMV reverse transcriptase, and telomerase reverse transcriptase. In some instances, the reverse transcriptase is M-MLV reverse transcriptase.

In some instances, the methods, kits, and systems disclosed herein comprise the use of one or more polymerases. Examples of polymerases include, but are not limited to, DNA polymerases and RNA polymerases. In some instances, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, Sulfolobus DNA Polymerase IV, Taq DNA Polymerase, 9° N™m DNA Polymerase, Deep VentR™ (exo-) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, phi29 DNA Polymerase, T4 DNA Polymerase, T7 DNA Polymerase, and Terminal Transferase. Alternatively, the polymerase is an RNA polymerases such as RNA polymerase I, RNA polymerase II, RNA polymerase III, E. coli Poly(A) polymerase, phi6 RNA polymerase (RdRP), Poly(U) polymerase, SP6 RNA polymerase, and T7 RNA polymerase.

In some instances, the methods, kits, and systems disclosed herein comprise one or more restriction enzymes. Restriction enzymes include type I, type II, type III, and type IV restriction enzymes. In some instances, Type I enzymes are complex, multisubunit, combination restriction-and-modification enzymes that cut DNA at random far from their recognition sequences. Generally, type II enzymes cut DNA at defined positions close to or within their recognition sequences. They can produce discrete restriction fragments and distinct gel banding patterns. Type III enzymes are also large combination restriction-and-modification enzymes. They often cleave outside of their recognition sequences and can require two such sequences in opposite orientations within the same DNA molecule to accomplish cleavage; they rarely give complete digests. In some instances, type IV enzymes recognize modified, typically methylated DNA and can be exemplified by the McrBC and Mrr systems of E. coli.

XI. Miscellaneous Components

The methods, kits, and systems disclosed herein can comprise the use of one or more reagents. Examples of reagents include, but are not limited to, PCR reagents, ligation reagents, reverse transcription reagents, enzyme reagents, hybridization reagents, sample preparation reagents, and reagents for nucleic acid purification and/or isolation.

The methods, kits, and systems disclosed herein can comprise the use of one or more buffers. Examples of buffers include, but are not limited to, wash buffers, ligation buffers, hybridization buffers, amplification buffers, and reverse transcription buffers. In some instances, the hybridization buffer is a commercially available buffer, such as TMAC Hyb solution, SSPE hybridization solution, and ECONO™ hybridization buffer. The buffers disclosed herein can comprise one or more detergents.

The methods, kits, and systems disclosed herein can comprise the use of one or more carriers. Carriers can enhance or improve the efficiency of one or more reactions disclosed herein (e.g., ligation reaction, reverse transcription, amplification, hybridization). Carriers can decrease or prevent non-specific loss of the molecules or any products thereof (e.g., labeled-molecule, labeled-cDNA molecule, labeled-amplicon). For example, the carrier can decrease non-specific loss of a labeled-molecule through absorption to surfaces. The carrier can decrease the affinity of the molecule, labeled-molecule, or any product thereof to a surface or substrate (e.g., container, eppendorf tube, pipet tip). Alternatively, the carrier can increase the affinity of the molecule or any product thereof to a surface or substrate (e.g., bead, array, glass, slide, chip). Carriers can protect the molecule or any product thereof from degradation. For example, carriers can protect an RNA molecule or any product thereof from ribonucleases. Alternatively, carriers can protect a DNA molecule or any product thereof from a DNase. Examples of carriers include, but are not limited to, nucleic acid molecules such as DNA and/or RNA, or polypeptides. Examples of DNA carriers include plasmids, vectors, polyadenylated DNA, and DNA oligonucleotides. Examples of RNA carriers include polyadenylated RNA, phage RNA, phage MS2 RNA, E. coli RNA, yeast RNA, yeast tRNA, mammalian RNA, mammalian tRNA, short polyadenylated synthetic ribonucleotides and RNA oligonucleotides. The RNA carrier can be a polyadenylated RNA. Alternatively, the RNA carrier can be a non-polyadenylated RNA. In some instances, the carrier is from a bacteria, yeast, or virus. For example, the carrier can be a nucleic acid molecule or a polypeptide derived from a bacteria, yeast or virus. For example, the carrier is a protein from Bacillus subtilis. In another example, the carrier is a nucleic acid molecule from Escherichia coli. Alternatively, the carrier is a nucleic acid molecule or peptide from a mammal (e.g., human, mouse, goat, rat, cow, sheep, pig, dog, or rabbit), avian, amphibian, or reptile.

The methods, kits, and systems disclosed herein can comprise the use of one or more control agents. Control agents can include control oligos, inactive enzymes, non-specific competitors. Alternatively, the control agents comprise bright hybridization, bright probe controls, nucleic acid templates, spike-in templates, PCR amplification controls. The PCR amplification controls can be positive controls. In other instances, the PCR amplification controls are negative controls. The nucleic acid template controls can be of known concentrations. The control agents can comprise one or more labels.

Spike-in templates can be templates that are added to a reaction or sample. For example, a spike-in template can be added to an amplification reaction. The spike-in template can be added to the amplification reaction any time after the first amplification cycle. In some instances, the spike-in template is added to the amplification reaction after the $2^{nd}$, $3^{rd}$, $4^{th}$, $5^{th}$, $6^{th}$, $7^{th}$ $8^{th}$, $9^{th}$, $10^{th}$, $11^{th}$, $12^{th}$, $13^{th}$, $14^{th}$, $15^{th}$, $20^{th}$, $25^{th}$, $30^{th}$, $35^{th}$, $40^{th}$, $45^{th}$ or $50^{th}$ amplification cycle. The spike-in template can be added to the amplification reaction any time before the last amplification cycle. The spike-in template can comprise one or more nucleotides or nucleic acid base pairs. The spike-in template can comprise DNA, RNA, or any combination thereof. The spike-in template can comprise one or more labels.

The methods, kits, and systems disclosed herein can comprise the use of one or more pipet tips and/or containers (e.g., tubes, vials, multiwell plates). In some instances, the pipet tips are low binding pipet tips. Alternatively, or additionally, the containers can be low binding containers. Low binding pipet tips and low binding containers can have reduced leaching and/or subsequent sample degradation associated with silicone-based tips and non-low binding containers. Low binding pipet tips and low binding containers can have reduced sample binding as compared to non-low binding pipet tips and containers. Examples of low binding tips include, but are not limited to, Corning® DeckWorks™ low binding tips and Avant Premium low binding graduated tips. A non-limiting list of low-binding containers include Corning® Costar® low binding micro-centrifuge tubes and Cosmobrand low binding PCR tubes and microcentrifuge tubes.

XIII. Indications

The methods disclosed herein may be used in gene expression monitoring, transcript profiling, library screening, genotyping, epigenetic analysis, methylation pattern analysis, tumor typing, pharmacogenomics, agrigenetics, pathogen profiling and detection and diagnostics. Gene expression monitoring and profiling methods have been shown in U.S. Pat. Nos. 5,800,992, 6,013,449, 6,020,135, 6,033,860, 6,040,138, 6,177,248 and 6,309,822. Genotyping and uses therefore are shown in U.S. Patent Publication Nos. 20030036069 and 20070065816 and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

Disclosed herein are methods, kits and compositions for detection, monitoring, and/or prognosis of a disease or condition in a subject. Generally, the method comprises (a) stochastically labeling a molecule to produce a stochastically-labeled molecule; and (b) detecting and/or quantifying the stochastically-labeled molecule, thereby detecting, monitoring, and/or prognosing a disease or condition in a subject. Detecting a disease or condition can comprise diagnosing a disease or condition.

Monitoring a disease or condition in a subject can further comprise monitoring a therapeutic regimen. Monitoring a therapeutic regimen can comprise determining the efficacy of a therapeutic regimen. In some instances, monitoring a therapeutic regimen comprises administrating, terminating, adding, or altering a therapeutic regimen. Altering a therapeutic regimen can comprise increasing or reducing the dosage, dosing frequency, or mode of administration of a therapeutic regimen. A therapeutic regimen can comprise one or more therapeutic drugs. The therapeutic drugs can be an anticancer drug, antiviral drug, antibacterial drug, antipathogenic drug, or any combination thereof.

A. Cancer

In some instances, the disease or condition is a cancer. The molecules to be stochastically labeled can be from a cancerous cell or tissue. In some instances, the cancer is a sarcoma, carcinoma, lymphoma or leukemia. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

B. Pathogenic Infection

In some instances, the disease or condition is a pathogenic infection. The molecules to be stochastically labeled can be from a pathogen. The pathogen can be a virus, bacterium, fungi, or protozoan. In some instances, the pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belh*), *Microsporidium* (e.g., *M. africanum, M. ceylonensis*), *Naegleria* (e.g., *N. fowlen*), *Nosema* (e.g., *N. algerae, N. ocularum*), *Pleistophora, Trachipleistophora* (e.g., *T. anthropophthera, T. hominis*), and *Vittaforma* (e.g., *V. corneae*). The pathogen may be a fungus, such as, *Candida, Aspergillus, Cryptococcus, Histoplasma, Pneumocystis,* and *Stachybotrys.*

The pathogen can be a bacterium. Exemplary bacteria include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia.*

The virus can be a reverse transcribing virus. Examples of reverse transcribing viruses include, but are not limited to, single stranded RNA-RT (ssRNA-RT) virus and double-stranded DNA-RT (dsDNA-RT) virus. Non-limiting examples of ssRNA-RT viruses include retroviruses, alpharetrovirus, betaretrovirus, gammaretrovirus, deltaretrovirus, epsilonretrovirus, lentivirus, spuma virus, metavirirus, and pseudoviruses. Non-limiting examples of dsDNA-RT viruses include hepadenovirus and caulimovirus. Alternatively, the virus is a DNA virus or RNA virus. The DNA virus can be a double-stranded DNA (dsDNA) virus. In some instances, the dsDNA virus is an adenovirus, herpes virus, or pox virus. Examples of adenoviruses include, but are not limited to, adenovirus and infectious canine hepatitis virus. Examples of herpes viruses include, but are not limited to, herpes simplex virus, varicella-zoster virus, cytomegalovirus, and Epstein-Barr virus. A non-limiting list of pox viruses includes smallpox virus, cow pox virus, sheep pox virus, monkey pox virus, and vaccinia virus. The DNA virus can be a single-stranded DNA (ssDNA) virus. The ssDNA virus can be a parvovirus. Examples of parvoviruses include, but are not limited to, parvovirus B19, canine parvovirus, mouse parvovirus, porcine parvovirus, feline panleukopenia, and Mink enteritis virus.

Alternatively, the virus is a RNA virus. The RNA virus can be a double-stranded RNA (dsRNA) virus, (+) sense single-stranded RNA virus ((+)ssRNA) virus, or (−) sense single-stranded ((−)ssRNA) virus. A non-limiting list of dsRNA viruses include reovirus, orthoreovirus, cypovirus, rotavirus, bluetongue virus, and phytoreovirus. Examples of (+) ssRNA viruses include, but are not limited to, picornavirus and togavirus. Examples of picornaviruses include, but are not limited to, enterovirus, rhinovirus, hepatovirus, cardiovirus, aphthovirus, poliovirus, parechovirus, erbovirus, kobuvirus, teschovirus, and coxsackie. In some instances, the togavirus is a rubella virus, Sindbis virus, Eastern equine encephalitis virus, Western equine encephalitis virus, Venezuelan equine encephalitis virus, Ross River virus, O'nyong'nyong virus, Chikungunya, or Semliki Forest virus. A non-limiting list of (−) ssRNA viruses include orthomyxovirus and rhabdovirus. Examples of orthomyxoviruses include, but are not limited to, influenzavirus a, influenzavirus B, influenzavirus C, isavirus, and thogotovirus. Examples of rhabdoviruses include, but are not limited to, cytorhabdovirus, dichorhabdovirus, ephemerovirus, lyssavirus, novirhabdovirus, and vesiculovirus.

C. Fetal Disorders

In some instances, the disease or condition is pregnancy. The methods disclosed herein can comprise diagnosing a fetal condition in a pregnant subject. The methods disclosed herein can comprise identifying fetal mutations or genetic abnormalities. The molecules to be stochastically labeled can be from a fetal cell or tissue. Alternatively, or additionally, the molecules to be labeled can be from the pregnant subject.

The methods, kits, and systems disclosed herein can be used in the diagnosis, prediction or monitoring of autosomal trisomies (e.g., Trisomy 13, 15, 16, 18, 21, or 22). In some cases the trisomy may be associated with an increased chance of miscarriage (e.g., Trisomy 15, 16, or 22). In other cases, the trisomy that is detected is a liveborn trisomy that may indicate that an infant will be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The molecule(s) to be labeled can be on one or more of the following chromosomes: 13, 18, 21, X, or Y. For example, the molecule is on chromosome 21 and/or on chromosome 18, and/or on chromosome 13.

Further fetal conditions that can be determined based on the methods, kits, and systems disclosed herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g. XXXX, XXYY, XXXY, XYYY, XXXXX, XXXXY, XXXYY, XYYYY and XXYYY), monoploidy, triploidy (three of every chromosome, e.g. 69 chromosomes in humans), tetraploidy (four of every chromosome, e.g. 92 chromosomes in humans), pentaploidy and multiploidy.

Exemplary Embodiments

Disclosed herein, in some embodiments, are methods, kits, and systems for digital reverse transcription of an RNA molecule. In some instances, the method comprises (a) producing a labeled-RNA molecule by contacting a sample comprising a plurality of RNA molecules with a plurality of oligonucleotide tags, wherein (i) the plurality of RNA molecules comprises two or more RNA molecules comprising at least two different sequences; and (ii) the plurality of oligonucleotide tags comprises oligonucleotide tags comprising two or more different unique identifier sequences; (b) conducting a first strand synthesis reaction by contacting the labeled-RNA molecules with a reverse transcriptase enzyme to produce a labeled-cDNA molecule; and (c) detecting the labeled-cDNA molecule by hybridizing the labeled-cDNA molecule to a solid support.

Producing a labeled-RNA molecule can comprise attaching the oligonucleotide tag to the RNA molecule. In some instances, the oligonucleotide tag is attached to the RNA molecule by hybridization. In other instances, the oligonucleotide tag is attached to the RNA molecule by ligation. The attachment of the oligonucleotide tag can comprise the use of a ligase enzyme. The oligonucleotide tag can be attached to any portion of the RNA molecule. For example, the oligonucleotide tag can be attached to the 5' end of the RNA molecule. Alternatively, the oligonucleotide tag is attached to the 3' end of the RNA molecule. In other instances, the oligonucleotide tag is attached to an internal region of the RNA molecule. Attachment of the oligonucleotide tag to the RNA molecule can comprise the use of one or more adaptor molecules.

In some instances, the oligonucleotide tag comprises a target specific region. The target specific region can enable attachment of the plurality of oligonucleotide tags to at least one RNA molecule. The target specific region can enable attachment of the plurality of oligonucleotide tags to two more different RNA molecules. In some instances, the target specific region enables attachment of the plurality of oligonucleotide tags to at least about 3, 4, or 5 different RNA molecules. Alternatively, the target specific region enables attachment of the plurality of oligonucleotide tags to at least about 6, 7, 8, 9, or 10 different RNA molecules. In other instances, the target specific region enables attachment of the plurality of oligonucleotide tags to at least about 11, 12, 13, 14, or 15 different RNA molecules. The target specific region can comprise an oligodT sequence. Alternatively, the target specific region comprises a random sequence that can attach to any portion of the RNA molecule.

In some instances, the oligonucleotide tag further comprises a universal primer region. The unique identifier region can be placed between the universal primer region and the target specific region. The oligonucleotide tag can be at least one nucleotide in length. The unique identifier region can be at least one nucleotides in length. The target specific region can be at least one nucleotide in length. The universal primer region can be at least one nucleotide in length. The oligonucleotide tag can comprise one or more nucleotide moieties. Alternatively, or additionally, the nucleotide tag comprises one or more non-nucleotide moieties.

In some instances, producing the labeled-RNA molecule further comprises a dNTP mix, annealing buffer, ligase, ligation buffer, or any combination thereof. Conducting the first strand synthesis reaction can further comprise a first strand buffer, dithiothreitol (DTT), RNase inhibitor, DNA polymerase, or any combination thereof.

The first strand synthesis reaction can further comprise a thermal cycler. The first strand synthesis reaction can further comprise a thermal cycler program comprising 1 cycle of 50° C. for 60 minutes, followed by 3 cycles of 94° C. for 2 minutes, 58° C. for 2 minutes, and 68° C. for 2 minutes, followed by 1 cycle of 4° C. for at least 2 minutes. The methods disclosed herein can further comprise contacting the labeled-cDNA molecule with a target specific primer. The target specific primer can be a uracil-containing DNA primer. The target specific primer can hybridize to the labeled-cDNA molecule and a polymerase chain reaction can be conducted to produce a double-stranded labeled-cDNA molecule.

The sample can be further treated with one or more enzymes to remove or degrade RNA molecules, labeled-RNA molecules, unbound oligonucleotide tags, and/or unbound target specific primers. For example, the sample can be treated with an RNase enzyme to remove the RNA molecules (labeled and/or unbound RNA molecules) from the sample. Alternatively, the sample can be treated with a uracil DNA glycosylase (UDG) to hydrolyze the uracil from the DNA.

The method can further comprise conducting a polymerase chain reaction (PCR) to produce labeled-amplicons. In some instances, the polymerase chain reaction is a nested PCR. The nested PCR can comprise conducting a first PCR comprising mixing the double-stranded labeled-cDNA molecule with a first PCR mixture comprising a first target specific PCR primer, universal PCR primer, polymerase buffer, DNA polymerase, dNTP mix, or any combination thereof. The first PCR can be conducted in thermal cycler. The first PCR can comprise a thermal cycler program comprising 1 cycle of 94° C. for 2 minutes, followed by 30 cycles of 94° C. for 20 seconds, 58° C. for 20 seconds, and 68° C. for 20 seconds, followed by 1 cycle of 68° C. for 4 minutes and 1 cycle of 4° C. for at least 2 minutes. The nested PCR can comprise conducting a second PCR comprising mixing at least a portion of the amplicons produced in the first PCR reaction with a second PCR mixture comprising a second target specific PCR primer, labeled-universal PCR primer, polymerase buffer, DNA polymerase, dNTP mix, or any combination thereof. The second target specific primer can hybridize to a region in the labeled molecule that is downstream of the first target specific primer. The labeled-universal PCR primer is labeled with a detectable label. In some instances, the labeled-universal PCR primer is a Cy3-labeled universal PCR primer. Alternatively, the labeled-universal PCR primer is a TYE 563-labeled universal PCR primer. The second PCR can be conducted in thermal cycler. The second PCR can comprise a thermal cycler program comprising 1 cycle of 94° C. for 2 minutes, followed by 30 cycles of 94° C. for 20 seconds, 58° C. for 20 seconds, and 68° C. for 20 seconds, followed by 1 cycle of 68° C. for 4 minutes and 1 cycle of 4° C. for at least 2 minutes. The second PCR of the nested PCR can produce a labeled-amplicon comprising the cDNA molecule, oligonucleotide tag and the detectable label. In some instances, the labeled-cDNA molecule of step 1c is the labeled-amplicon produced by the second PCR of the nested PCR.

In some instances, detecting the labeled-cDNA molecule comprises hybridizing at least a portion of the sample comprising the labeled-amplicons comprising the cDNA molecule, oligonucleotide tag and the detectable label to a solid support. Hybridizing at least a portion of the sample comprising the labeled-amplicons can comprise a hybridization mixture comprising at least a portion of the sample comprising the labeled-amplicons produced in the second PCR of nested PCR, control oligo, hybridization buffer, or any combination thereof. The control oligo can comprise the detectable label conjugated to an oligonucleotide. The detectable label is the same as the detectable label in the labeled-amplicon. For example, the labeled-amplicon comprises a Cy3 label and the control oligo comprises a Cy3-labeled oligonucleotide. The labeled-amplicons in the hybridrization mixture are denatured. In some instances, denaturing the labeled-amplicons comprises incubating the hybridization mixture at 95° C. In some instances, the hybridization mixture is incubated at 95° C. for at least about 1, 2, 3, 4, or 5 minutes. After denaturation of the labeled-amplicons, the hybridization mixture is incubated at 4° C. for at least 2 minutes. Hybridization of the labeled-amplicon to the support can comprise adding at least a portion of the hybridization mixture to the solid support. In some instances, hybridization of the labeled-amplicon to the solid support comprises adding at least a portion of the hybridization mixture to a well of an AMI array slide. The labeled-amplicon can be hybridized to the support for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours. The labeled-amplicon can be hybridized to the support for at least about 4 hours. The labeled-amplicon can be hybridized to the support overnight. Alternatively, the labeled-amplicon is hybridized to the support for about 12-14 hours. In other instances, the labeled-amplicon is hybridized to the support for about 3-5 hours, 4-6 hours, 6-8 hours, 8-10 hours, 9-11 hours, 13-15 hours, 14-16 hours, 17-19 hours, or 18-20 hours. Hybridization of the labeled-amplicon to the support can comprise contacting the support with the labeled-amplicon and incubating the labeled-amplicon and support at a hybridization temperature. In some instances, the hybridization temperature is at least about 20° C., 21° C., 22° C., 23° C., 24° C., 25° C., 26° C., 27° C., 28° C., 29° C., 30° C., 32° C., 34° C., 36° C., 38° C., 40° C., 45° C., 50° C., 55° C., 60° C., or 65° C.

The solid support can comprise a plurality of probes. The plurality of probes can comprise a sequence that is complementary to at least a portion of the labeled-cDNA molecule or labeled-amplicon. The plurality of probes can be arranged on the solid support in discrete regions, wherein a discrete region on the solid support comprises probes of identical or near-identical sequences. In some instances, two or more discrete regions on the solid support comprise two different probes comprising sequences complementary to the sequence of two different unique identifier regions of the oligonucleotide tag.

The method further comprise covering the array slide with an adhesive to produce a sealed array slide. The sealed array slide can be incubated at 37° C. The sealed array slide can be incubated at 37° C. overnight. In some instances, the sealed array is incubated at 37° C. for at least about 12-14 hours. After incubating the sealed array at 37° C., the method can further comprise removing the sealed array from 37° C. The hybridization mixture can be removed from each well. The hybridization mixture can be stored at −20° C. Alternatively, the hybridization mixture is discarded.

The method can further comprise washing the wells with a first wash buffer. Washing the wells comprises adding a wash buffer to the well and then aspirating the wash buffer. Additionally, a second wash can be performed with the same or a second wash buffer. Once the wash buffers have been aspirated from the wells, the array slide can be scanned. In some instances, the array slide is scanned dry (e.g., fluid is removed from the wells). Alternatively, the array slide is scanned wet (e.g., fluid is in the wells). The array slide can be scanned by a scanner.

The method can comprise fragmentation of the amplification products (e.g., labeled amplicons) to produce fragmented labeled-amplicons. The fragmented labeled-amplicons can be attached to the solid support. The methods disclosed herein can further comprise attaching a detectable label to the labeled-molecules, labeled-amplicons, or fragmented-labeled amplicons. The detectable label can be attached to the labeled-molecules, labeled-amplicons, or fragmented-labeled amplicons prior to attachment of the labeled-molecules, labeled-amplicons, or fragmented-labeled amplicons to the solid support. Alternatively, the detectable label is attached to the labeled-molecules, labeled-amplicons, or fragmented-labeled amplicons after attachment of the labeled-molecules, labeled-amplicons, or fragmented-labeled amplicons to the solid support. The methods disclosed herein can comprise attaching two or more detectable labels to the labeled-molecules, labeled-amplicons, or fragmented-labeled amplicons. In some instances, a detectable label is the labeled-cDNA molecule and the detectable label is incorporated into the labeled-amplicon. For example, a Cy3 universal PCR primer is annealed to the labeled-cDNA molecule. Amplication of the labeled-cDNA molecule with Cy3 universal PCR primer can produce a Cy3-labeled amplicons. The methods disclosed herein can further comprise attaching a second detectable label to the first-detectable labeled-molecule. For example, The methods disclosed herein can comprise attaching biotin to the Cy3-labeled amplicons to produce biotin/Cy3-labeled amplicons.

In some instances, detecting the labeled-cDNA molecule comprises a fluorescent reader. The fluorescent reader can be a Sensovation FLAIR instrument.

In some instances, the data from the scanner is stored on a computer. Alternatively, or additionally, the data from the scanner is exported. In some instances, the data from the scanner is transmitted electronically. Exportation and/or transmission of the data can comprise one or more computer networks.

Further disclosed herein are methods, kits, and systems for stochastically labeling a molecule. Generally, the method comprises contacting a sample comprising a plurality of molecules with a plurality of oligonucleotide tags and randomly attaching one or more oligonucleotide tags from the plurality of oligonucleotide tags to one or more molecules in the sample. The plurality of oligonucleotide tags comprises oligonucleotide tags comprising two or more different unique identifier regions.

In some instances, the methods, kits, and systems comprise concentrations of the different oligonucleotide tags in the plurality of oligonucleotide tags. For example, the different oligonucleotide tags are present in the plurality of oligonucleotide tags in the same concentration. Alternatively, the concentration of at least one oligonucleotide tag in the plurality of oligonucleotide tags is greater than the concentration of at least one other oligonucleotide tag in the plurality of oligonucleotide tags. The concentration of the at least one oligonucleotide tag in the plurality of oligonucleotide tags is at least about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, or 100 times greater than the concentration of the at least one other oligonucleotide tag in the plurality of oligonucleotide tags. In some instances, the concentration of at least one oligonucleotide tag in the plurality of oligonucleotide tags is less than the concentration of at least one other oligonucleotide tag in the plurality of oligonucleotide tags. The concentration of the at least one oligonucleotide tag in the plurality of oligonucleotide tags is at least about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, or 100 times less than the concentration of the at least one other oligonucleotide tag in the plurality of oligonucleotide tags. In some instances, at least about 1%, 2%, 3%, 4%, 5%, 10%, 15%, 20%, 25%, 30%, 40%, 50%, 60%, 70%, 80%, 90%, 95%, 97%, or 100% of the different oligonucleotide tags in the plurality of oligonucleotide tags are present in the plurality of oligonucleotide tags in the same or similar concentration. Alternatively, at least about 1%, 2%, 3%, 4%, 5%, 10%, 15%, 20%, 25%, 30%, 40%, 50%, 60%, 70%, 80%, 90%, 95%, 97%, or 100% of the different oligonucleotide tags in the plurality of oligonucleotide tags are present in the plurality of oligonucleotide tags in different concentrations.

The oligonucleotide tags can further comprise a target specific region, universal primer binding site, or any combination thereof. In some instances, the unique identifier region is between the target specific region and the universal primer binding site. The oligonucleotide tags can be attached to the molecules by hybridization, ligation, or any combination thereof. In some instances, one or more oligonucleotide tags are attached to a molecule. The oligonucleotide tag can be attached to the 5' end of the molecule, 3' end of the molecule, an internal site within the molecule, or any combination thereof. One or both ends of the oligonucleotide tag can be attached to the molecule.

The molecule can be a polynucleotide. The polynucleotide can comprise RNA, DNA, or any combination thereof. The molecule can be an RNA molecule. The RNA molecule can be an mRNA. The molecule can be polyadenylated. Alternatively, the molecule is not polyadenylated.

Further disclosed herein are digital pre-amplification methods for increasing the quantity of a nucleic acid molecule in a sample. Generally, the method comprises (a) stochastically labeling a nucleic acid molecule in a sample by any of the methods disclosed herein to produce a labeled-nucleic acid molecule, wherein the labeled-nucleic acid molecule comprises an oligonucleotide tag attached to the nucleic acid molecule; and (b) amplifying the labeled-nucleic acid molecule to produce a plurality of labeled-amplicons, wherein a labeled-amplicon in the plurality of labeled-amplicons is a copy of the labeled-nucleic acid molecule. The labeled-nucleic acid molecule of step (a) can be repeatedly amplified to increase the quantity of the nucleic acid molecule in the sample. The oligonucleotide tag comprises a unique identifier region that can be used to distinguish identical or nearly identical nucleic acid molecules.

Stochastic labeling of the nucleic acid molecule prior to amplification can enable the identification of clonally replicated molecules originating from the sample template parent molecule. Stochastic labeling of the nucleic acid molecule prior to amplification can allow for controlled amplification of the nucleic acid molecule, wherein the amplification of an individual nucleic acid molecule can be tracked and monitored by the oligonucleotide label. The digital pre-amplification method can account for the true abundance levels of nucleic acid molecules in a sample. This method can be particularly useful for samples comprising limited quantities of a nucleic acid molecule. For example, this method can be used to increase the quantity of a nucleic acid molecule from a single cell. Stochastic labeling of the nucleic acid molecule sin the cell followed by amplification of the labeled-nucleic acid molecules can allow for more precise quantitative measurements of the nucleic acid molecules.

In some instances, the labeled-nucleic acid molecules in the sample are amplified at least about 1, 2, 3, 4, 5, 6, 7, 8, 9, or 10 times. Alternatively, the labeled-nucleic acid molecules in the sample are amplified at least about 11, 12, 13, 14, 15, 20, 25, 30, 35, 40, 45, 50, 60, 70, 80, 90, or 100 times.

Digital pre-amplification of the nucleic acid molecules can enable repeated sampling of the nucleic acid molecules in the sample without depletion of the original sample. Repeated sampling of the nucleic acid molecules in the sample can comprise conducting one or more measurements and/or experiments on the labeled-amplicons produced from the amplification or repeated amplification reactions conducted on the labeled-nucleic acid molecules. Repeated sampling of the nucleic acid molecules in the sample can comprise measurements for detecting and/or quantifying a nucleic acid molecule. Repeated sampling of the nucleic acid molecule in the sample can comprise conducting additional experimentation on the nucleic acid molecules in the sample.

In some embodiments, methods, kits, and systems for gene-specific detection of labeled molecules are disclosed. The methods, kits, and systems can be used to increase the detection specificity for one or more genes of interest. A schematic of the method is depicted in FIG. 7. Generally, the method comprises: a) hybridizing at least one target molecule to a solid support; and b) hybridizing a labeled gene-specific oligo to the target molecule to produce a labeled-target molecule.

Figure 17:
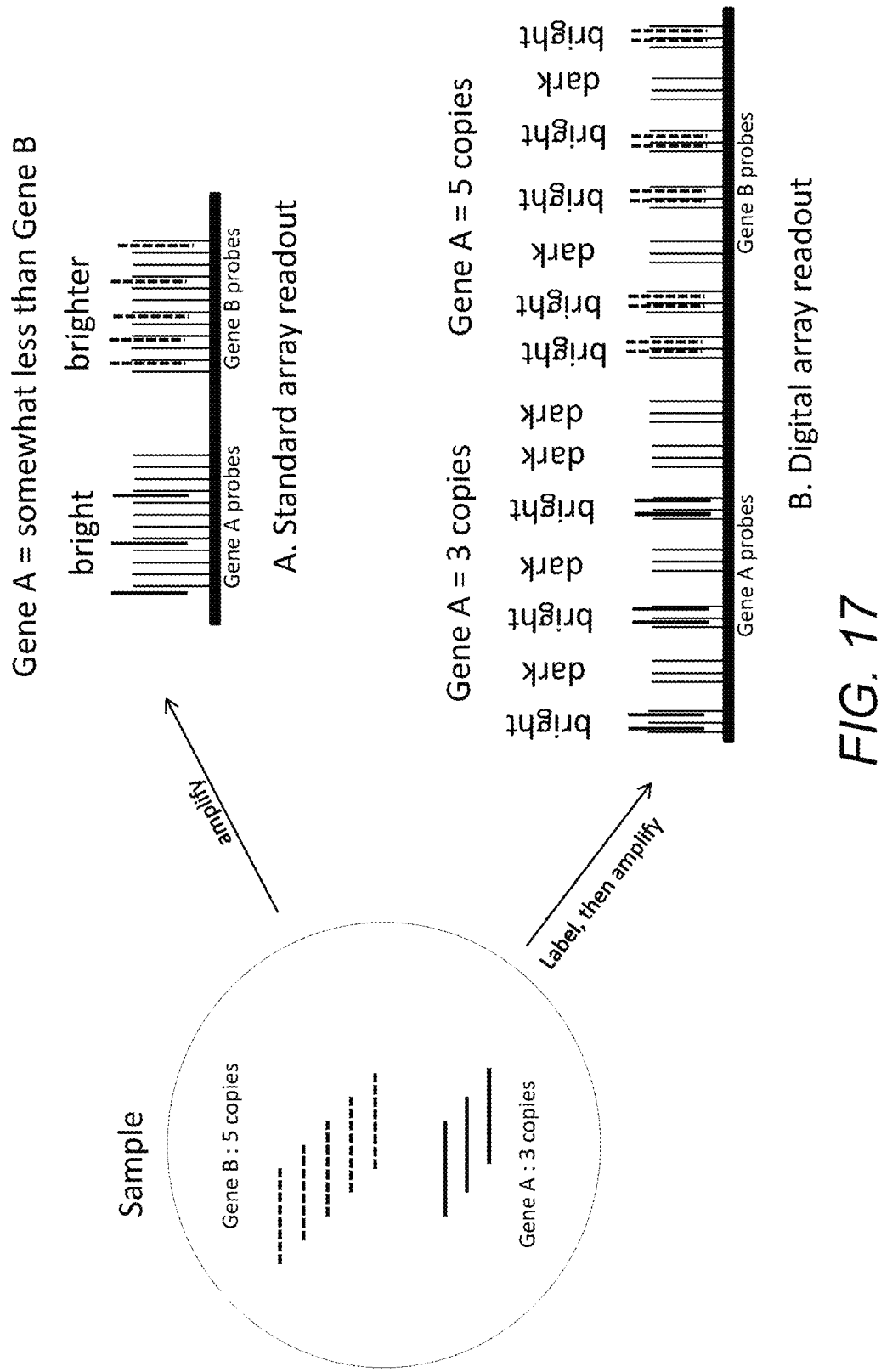

Further disclosed herein are methods, kits and systems for the absolute quantification of one or more molecules. FIG. 17 depicts a comparison of the quantification of two genes (gene A and gene B). Quantification of the two genes by a standard array readout can provide a relative quantification of genes A and B. In the standard array readout, the genes are amplified and the amplicons are hybridized to an array. The relative amounts of genes A and B can be detected by fluorescence and the intensity (e.g., brightness) of the signal can be used to determine that the quantity of gene B is greater than the quantity of gene A. The digital amplification method disclosed herein can be used to provide an absolute quantification of genes A and B. The absolute quantification method can comprise (a) stochastically labeling two or more genes with a plurality of oligonucleotide tags to produce a stochastically labeled molecule, wherein the plurality of oligonucleotide tags comprises two or more different unique identifier region; (b) amplifying the stochastically labeled molecule to produce one or more stochastically labeled amplicons; and (c) detecting the number of different unique identifier regions associated with each stochastically labeled amplicons, thereby determining the absolute quantity of two or more molecules. As shown in FIG. 17B, detecting the unique identifier regions comprises hybridizing the stochastically labeled amplicons to a solid support (e.g., array). The stochastically labeled amplicons can hybridize to discrete locations on the solid support and the number of different unique identifier regions can be determined by counting the number of discrete locations as detected by fluorescence.

Figure 19:
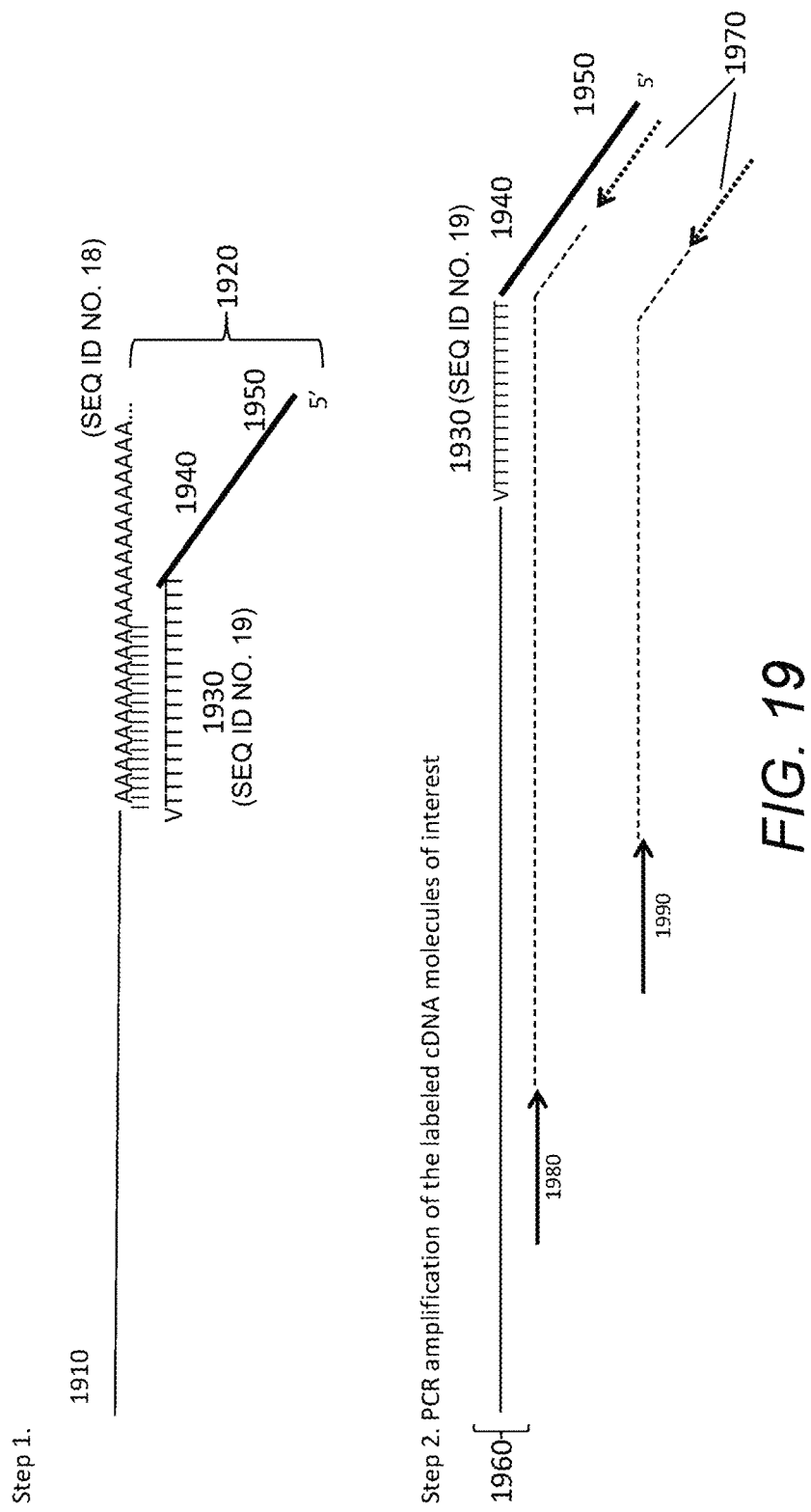

FIG. 19 depicts a schematic of an absolute quantification method of one or more RNA molecules. As shown in Step 1 of FIG. 19, cDNA synthesis of one or more target RNA molecules comprises annealing the oligodT sequence (e.g., target specific region, 1920) of an oligonucleotide tag (1920) to the polyA tail of a mRNA molecule (1910). The oligonucleotide tag (1920) further comprises a unique identifier region (1940) and a universal primer binding site (1950). The unique identifier region (1940) may comprise a predetermined sequence. Alternatively, the unique identifier region (1940) comprises a random sequence. The resulting cDNA molecule (1960) comprises a copy of the mRNA molecule, the unique identifier region (1940) and the universal primer binding site (1950). As shown in Step 2, the cDNA molecule (1960) can be amplified by nested PCR comprising a first forward primer (1980), a second forward primer (1990) and a reverse primer comprising universal primer (1970) to produce one or more labeled amplicons (e.g., amplicons comprising the unique identifier region). The forward primers (1980, 1990) may be gene-specific primers. The labeled amplicons can be detected by any method known in the art. Absolute quantitation of mRNA molecules can occur by the detection and counting of different unique identifier regions.

Figure 20:
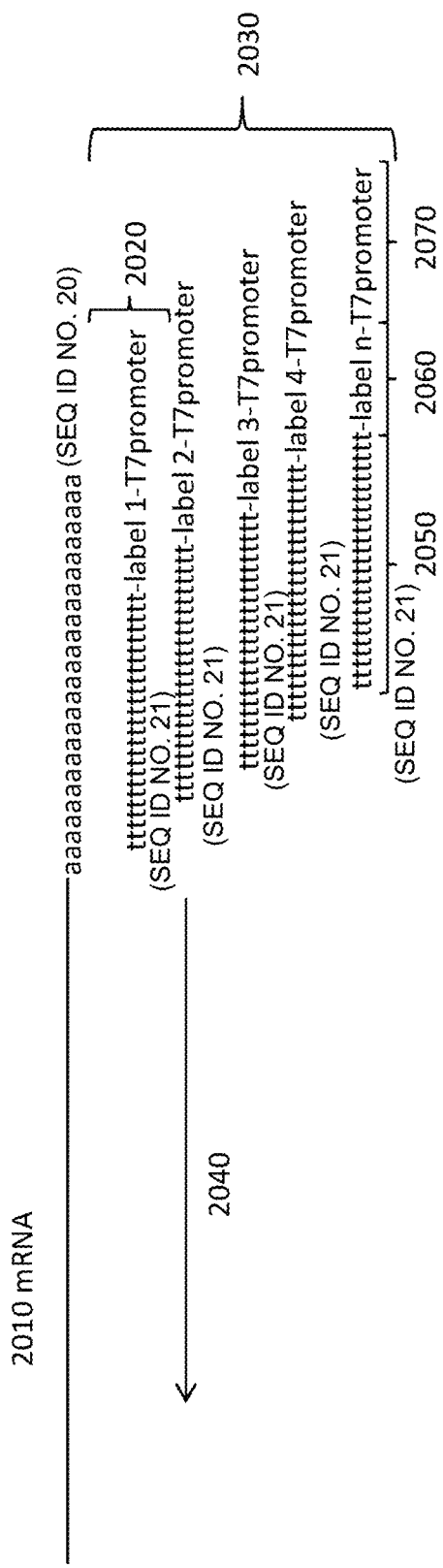

FIG. 20 depicts another method for quantifying one or more molecules. The method may comprise (a) reverse transcribing one or more RNA molecules using a plurality of oligonucleotide tags (2030) comprising two or more oligonucleotide tags (2020) comprising a target specific region (2050), a unique identifier region (2060) and a universal primer binding site (2070) to produce one or more stochastically labeled cDNA copies, wherein the stochastically labeled cDNA copies comprise the unique identifier region. The unique identifier region may comprise a random sequence. The method may further comprising amplifying the stochastically labeled cDNA copies to produce one or more stochastically labeled amplicons. Amplifying may comprise PCR and T7 amplification. The stochastically labeled amplicons may comprise the unique identifier region. The method may further comprise detecting the stochastically labeled cDNA copies or stochastically labeled amplicons. Detecting the stochastically labeled molecules can comprise hybridizing the stochastically labeled molecules to one or more digital arrays to determine the number of distinct labels for each gene of interest. Hybridization may require both the presence of the mRNA sequence, most likely a segment on the 3'exon of the gene, and the unique identifier region. The array may comprise 7 million features. The one or more molecules may be in a sample. The sample may comprise 20,000 different mRNA sequences. The method may comprise determining the number of copies of each mRNA present in the sample. The plurality of oligonucleotide tags may comprise 350 or more oligonucleotide tags. In some instances, a subset of the 350 oligonucleotide tags may be applied at a lower concentration to increase the effective dynamic range of measurement.

Figure 25:
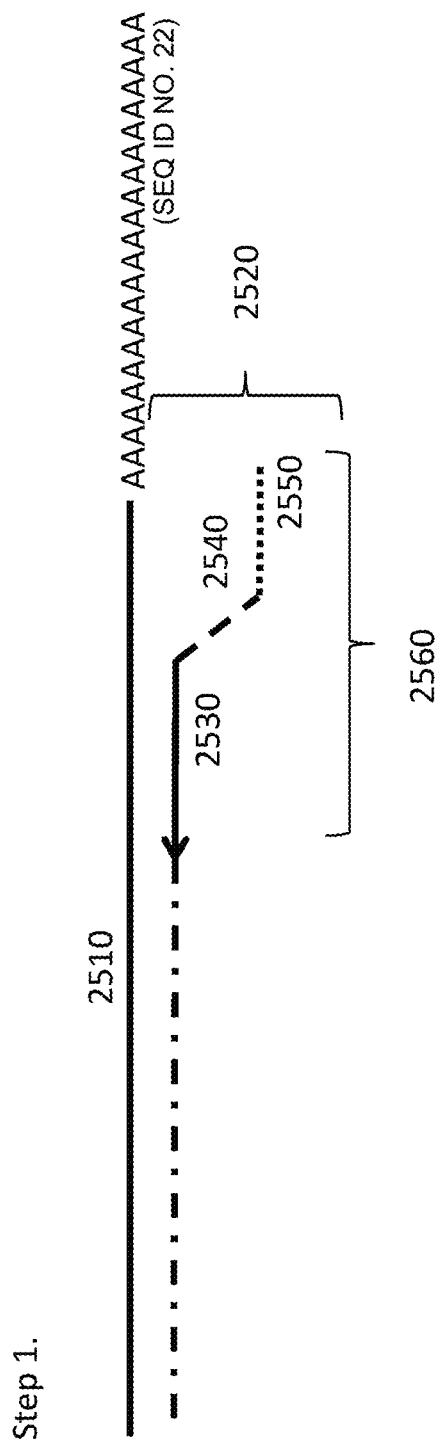
FIG. 25 Absolute quantitation of mRNA molecules by counting individual DNA molecules FIG. 26 Labeling with an "inert" primer FIG. 27 Emulsion PCR to prevent artifacts from outcompeting cDNAs during amplification FIG. 28 A method that does not rely on homopolymer tailing FIG. 29 Linear amplification methods FIG. 30 Labeling with strand switching FIG. 31 Labeling by random priming

FIG. 25 depicts another method of absolute quantitation of mRNA molecules. As shown in FIG. 25, the method comprises (a) conducting a reverse transcription reaction with an oligonucleotide tag (2560) to produce a stochastically labeled cDNA molecule (2520), wherein the stochastically labeled cDNA molecule comprises a cDNA copy of an mRNA molecule (2510), a unique identifier region (2540) and a universal primer binding site (2550); and (b) detecting the stochastically labeled cDNA molecule. The oligonucleotide tag (2560) can serve as a primer for the reverse transcription reaction. The oligonucleotide tag (2560) may comprise a target specific region (2530), unique identifier region (2540) and a universal primer binding site (2550). The method may further comprise absolutely quantifying the mRNA molecules based on the detection of the stochastically labeled cDNA molecules. Detection of the stochastically labeled cDNA molecules may comprise counting the number of different unique identifier regions that are associated with each type of cDNA molecule. The method may further comprise amplifying the stochastically labeled cDNA molecule prior to said detecting to produce one or more stochastically labeled amplicons.

Figure 21:
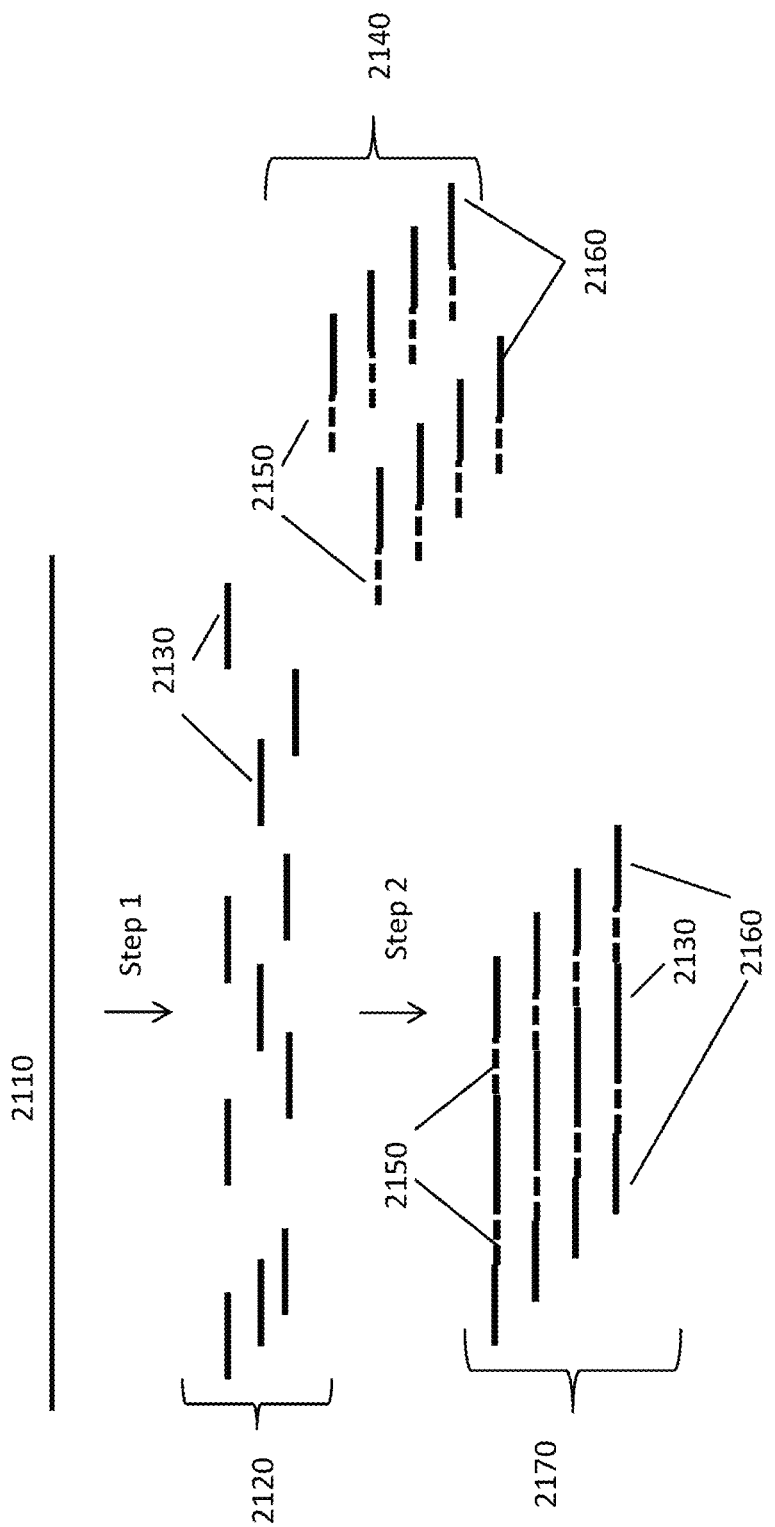

Further disclosed herein are methods, kits and systems for determining the DNA copy number. A general schematic of the method is depicted in FIG. 21. As shown in step 1 of FIG. 21, a genomic DNA (2110) can be fragmented to produce a DNA fragment (2130). Fragmentation of the genomic DNA may occur by any method known in the art. For example, fragmentation may comprise mechanical shearing. Alternatively, fragmentation may comprise digestion of the genomic DNA with one or more restriction nuclease. As shown in Step 2 of FIG. 21, the DNA fragments (2120) can be stochastically labeled with a plurality of oligonucleotide tags (2140) to produce a stochastically labeled molecule (2170). The oligonucleotide tag (2140) may comprise an adapter sequence (2150) and a unique identifier region (2160). The adapter sequence (2150) may enable attachment of the oligonucleotide tag (2140) to the DNA fragments. The adapter sequence (2150) may comprise one or more nucleotides that can anneal to the DNA fragments. Each stochastically labeled molecule (2170) may comprise one or more oligonucleotide tags (2150). The method may further comprise amplifying the stochastically labeled molecules (2170) to produce one or more stochastically labeled amplicons. The method may further comprise removing one or more DNA fragments prior to amplification. Removing the one or more DNA fragments may comprise digesting the DNA fragments with one or more restriction enzymes prior to amplification to prevent the replication of certain fragments. The method may further comprise detecting the stochastically labeled molecules. Detection may comprise hybridization to digital arrays detects the number of distinct unique identifier regions ligated to each DNA fragment.

Further disclosed herein are methods, kits and systems for analyzing one or more RNA molecules. The RNA molecules may be a small RNA molecule. The small RNA molecule may be a microRNA. FIG. 22 depicts a general method for analyzing a small RNA molecule. As shown in Step 1 of FIG. 22, one or more miRNA molecules (2210) are stochastically labeled with a first plurality of oligonucleotide tags (2230). The oligonucleotide tags (2230) may comprise an adapter sequence (2240) and a unique identifier region (2250). The adapter sequence (2240) may enable attachment of the oligonucleotide tag (2230) to the miRNA molecule (2220) to produce a 3'-stochastically labeled miRNA (2260). As shown in Step 2 of FIG. 22, the method may further comprise stochastically labeling the 3'-stochastically labeled microRNA (2260) with a second plurality of oligonucleotide tags (2270). The second plurality of oligonucleotide tags (2270) may comprise an adapter sequence (2290) and a unique identifier region (2280). The adapter sequence (2290) may enable attachment of the oligonucleotide tag (2270) to the 3'-stochastically labeled miRNA molecule (2260) to produce a 5' and 3'-stochastically labeled miRNA (2295). The method may further comprise reverse transcribing the stochastically labeled miRNA, amplifying the stochastically labeled miRNA, detecting the stochastically labeled miRNA, quantifying the miRNA by detecting the stochastically labeled miRNA, hybridizing the stochastically labeled miRNA to an array, or a combination thereof. The array may be a digital array. The miRNA molecule may comprise any of the miRNA sequences. For example, the miRNA molecule may comprise a sequence disclosed in miRBase 18 http://www.mirbase.org/, which was released November 2011 and lists 1921 unique mature human miRNAs. An array of 2 million features can adequately detect 1000 labels ligated to the 1921 miRNAs.

Figure 23A:
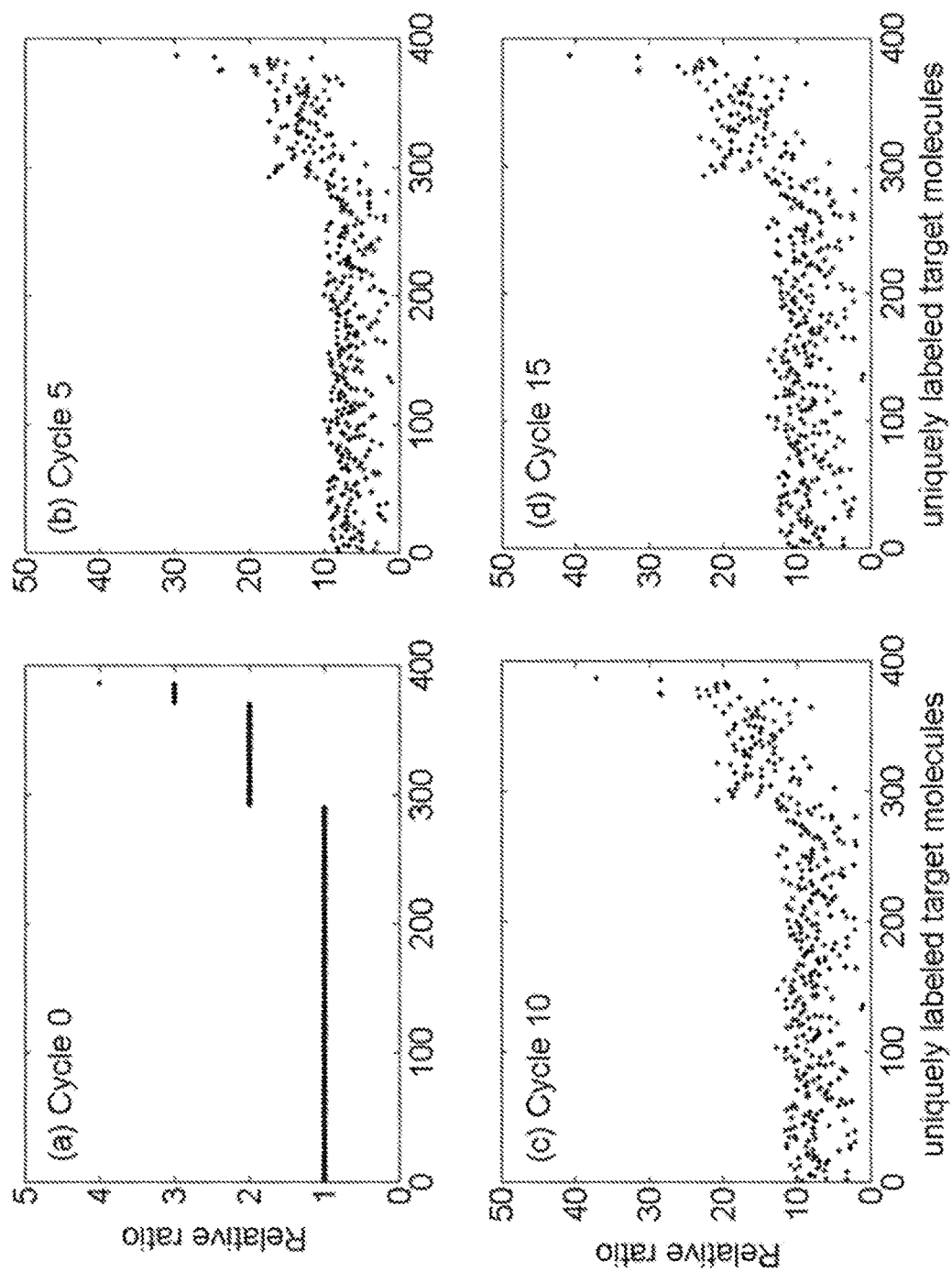
FIG. 23B shows a schematic of a method for single cell pre-implantation genetic diagnosis (PGD)
Figure 23B:
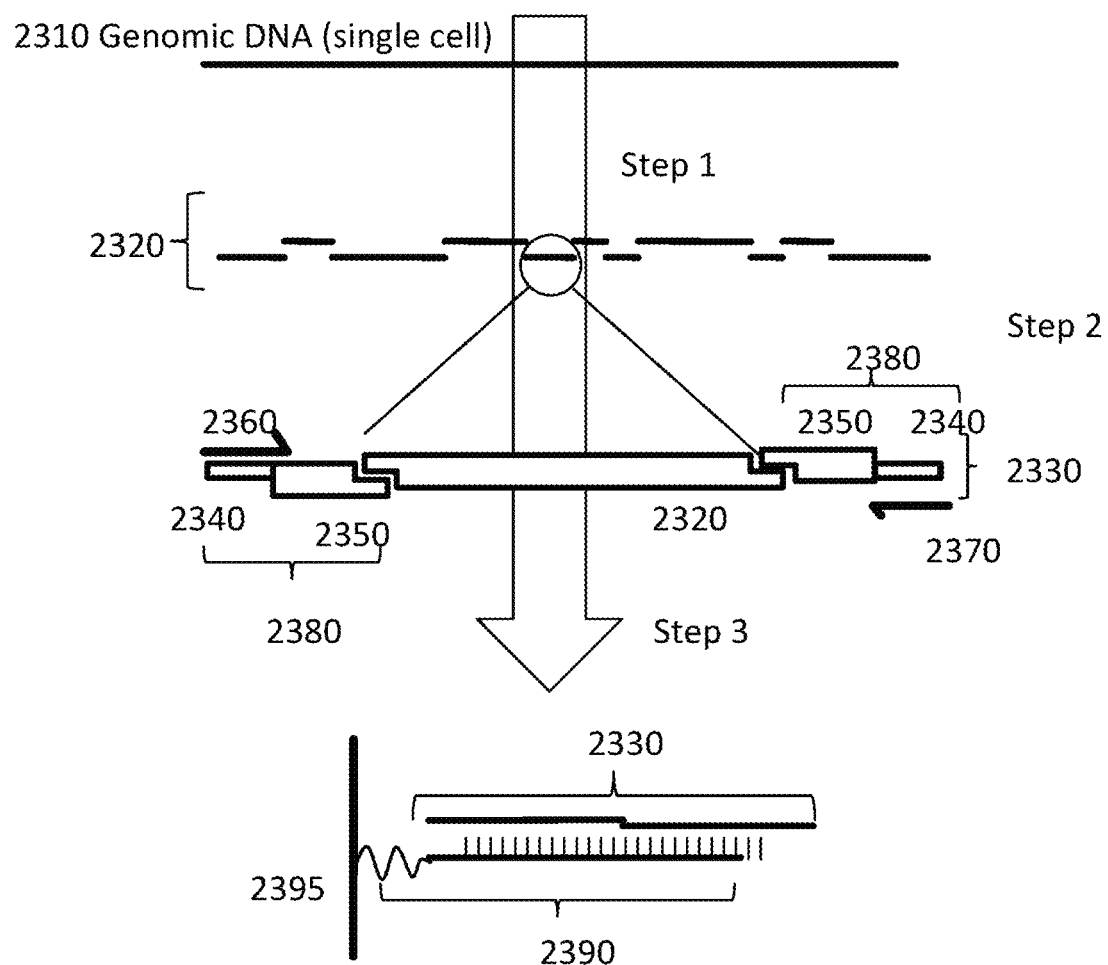

The methods, kits and systems disclosed herein can be used for genetical diagnosis. For example, the methods, kits and systems disclosed herein can be used for single cell pre-implantation genetic diagnosis (PGD). Primary challenges with single-cell genomic DNA amplification assays can be from allele dropout and replication bias. As shown in the computation modeling analysis depicted in FIG. 23A where every molecule has a 0.8 probability of replication, molecules of 1:1 initial copy ratios can easily be distorted to 1:10 or greater just after a few replication cycles. However, when labels are first attached prior to amplification, counting labels to determine copy number is unaffected by replication bias, so long as replication occurs. Aneuploidy determination and large regions of deletion or amplification can be easily and accurately determined by the stochastic labeling method disclosed herein. FIG. 23B depicts a schematic of the general method. As shown in Step 1 of FIG. 23B, the method may comprise fragmenting a genomic DNA (gDNA, 2310) to produce one or more fragmented molecules (2320). Fragmentation of the gDNA (2310) may comprise any method known in the art. For example, fragementation may comprise conducting a restriction digest reaction. As shown in Step 2 of FIG. 23B, the fragmented DNA (2320) can be stochastically labeled with a plurality of oligonucleotide tags (2380) to produce one or more stochastically labeled molecules (2330). The stochastically labeled molecule (2330) may comprise one or more oligonucleotide tags (2380). The oligonucleotide tags (2380) may comprise unique identifier sequence (2350) and a universal primer binding site (2340). The stochastically labeled molecule (2380) may be amplified using one or more primers (2360, 2370) that can hybridize to the universal primer binding site (2340) to produce one or more stochastically labeled amplicons. As shown in Step 3 of FIG. 23B, the stochastically labeled molecules (2330) can be detected by a GeneChip detector (2395). The stochastically labeled molecule (2330) can hybridize to a probe (2390) on the GeneChip detector (2395).

The methods, kits, and systems disclosed herein can be used in fetal diagnostics. The method may comprise (a) fragmenting a nucleic acid molecule in a sample to produce one or more nucleic acid fragments; (b) stochastically labeling the one or more nucleic acid fragments with a plurality of oligonucleotide tags comprising a unique identifier region to produce one or more stochastically labeled molecules; and (c) detecting the stochastically labeled molecules by counting the number of unique identifier regions. The method may further comprise diagnosing a fetal genetic disorder based on the detection of the stochastically labeled molecules.

Figure 24:
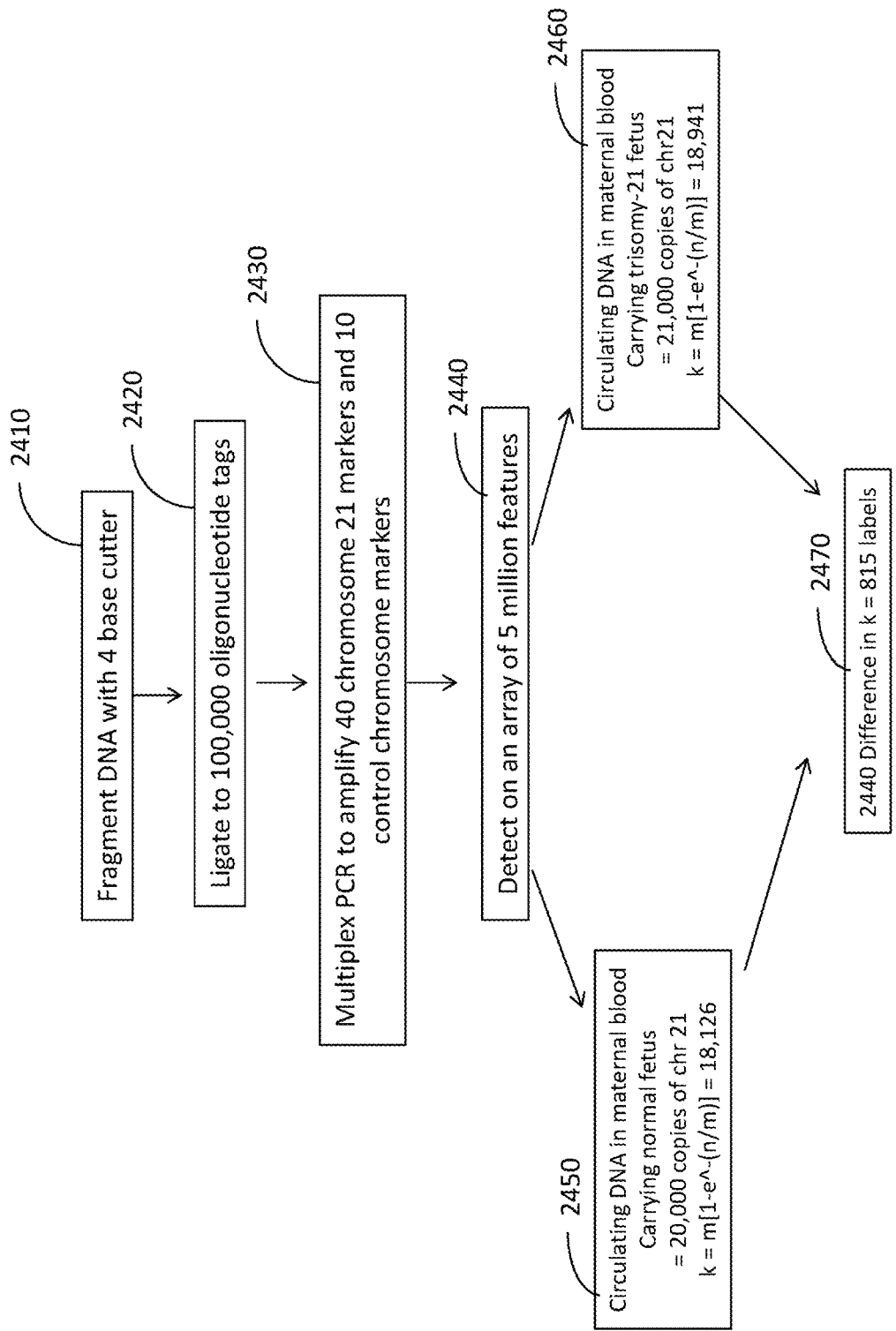
FIG. 24 Digital microarray for measuring fetal aneuploidy in maternal circulating nucleic acids—e.g., Trisomy 21

FIG. 24 depicts a general schematic for using the stochastic labeling method in fetal diagnostics. In 100 nanograms of circulating DNA there may be about 10,000 genome equivalents. the first trimester of maternal plasma, the total concentration of the fetal DNA can be about 10% of the total DNA in the maternal plasma sample. The method, as depicted in FIG. 24, may comprise fragmenting the DNA molecules (2410). Fragmentation may comprise the use of a 4-base restriction enzyme cutter. The fragmented DNA molecules may be stochastically labeled with a plurality of oligonucleotide tags (2420). Stochastic labeling may comprise ligating one or more oligonucleotide tags to the fragmented DNA molecules to produce one or more stochastically labeled molecules. The stochastically labeled molecules may be amplified in a multiplex reaction (2430) to produce one or more stochastically labeled amplicons. The stochastically labeled amplicons may be detected on an array (2440). The array may comprise 5 million features. Diagnosis of a fetal genetic disorder (e.g., trisomy 21) can be based on the detection of the stochastically labeled amplicons (2450, 2460). The 100,000 oligonucleotide tags may be synthesized as described in: Methods for screening factorial chemical libraries, Stephen P. A. Fodor et al, U.S. Pat. No. 5,541,061, issued Jul. 30, 1996.

FIG. 26 depicts a schematic for stochastic labeling of one or more molecules with an inert primer. The method may comprise (a) reverse transcribing an mRNA molecule (2610) with a primer (2620) comprising an oligodU sequence to produce a cDNA copy of the mRNA molecule (2630), wherein the cDNA copy comprises a 3' polyA tail and a 5' oligodT sequence; and (b) stochastically labeling the cDNA copy (2620) with an oligonucleotide tag (2640) comprising a universal primer binding site (2650), unique identifier region (2660) and an oligodU sequence (2670) to produce stochastically labeled cDNA molecule (2680). The method may further comprise a second stochastic labeling step to produce a stochastically labeled cDNA molecule, wherein both ends of the cDNA molecule are stochastically labeled with an oligonucleotide tag. The method may further comprise treating the sample with uracil DNA glycosylase (UDG) to remove the oligodU primer (2620) and the oligonucleotide tags comprising the oligodU sequence. The method may further comprise amplifying the stochastically labeled cDNA molecule to produce one or more stochastically labeled amplicons.

FIG. 27 depicts a schematic for analyzing one or more molecules. The method may comprise (a) reverse transcribing an mRNA molecule (2710) with an oligonucleotide tag (2720) comprising an oligodU sequence (2730), unique identifier region (2740), and a universal primer binding site (2750) to produce a cDNA copy (2760) of the mRNA molecule, wherein the cDNA copy (2760) comprises the unique identifier region (2740) and the universal primer binding site (2750); and (b) amplifying the cDNA copy with a first primer (2790) comprising an oligodU sequence and a second primer (2780) comprising the universal primer sequence to produce stochastically labeled amplicons. The method may comprise treating the molecules with one or more restriction enzymes. The method may further comprise conducting an emulsion PCR reaction on the stochastically labeled molecules.

The methods depicted in FIG. 26-27 may rely on homopolymer tailing. FIG. 28 depicts a method that does not rely on homopolymer tailing. As depicted in FIG. 28, the method may comprise reverse transcribing an mRNA molecule to produce a cDNA copy. Reverse transcription of the mRNA molecule may be carried out on a bead surface. The method may comprise RNAse H digestion of the mRNA molecule. The method may comprise stochastically labeling the cDNA copy with a plurality of oligonucleotide tags to produce one or more stochastically labeled cDNA molecules. The oligonucleotide tag may comprise a secondary structure. The secondary structure may be a hairpin. The oligonucleotide tag may comprise a universal primer binding site, unique identifier region, restriction enzyme recognition site, target specific region, or any combination thereof. The loop portion of the hairpin oligonucleotide tag may comprise a universal primer binding sequence. The loop portion of the hairpin oligonucleotide tag may comprise a unique identifier region. The loop portion of the hairpin oligonucleotide tag may further comprise a restriction enzyme recognition site. The oligonucleotide tag may be single stranded. The oligonucleotide tag may be double stranded. The method may further comprise amplifying the stochastically labeled cDNA molecule to produce one or more stochastically labeled amplicons. The method may further comprise digesting the stochastically labeled amplicons with a restriction nuclease to produce a digested stochastically labeled amplicon. The method may further comprise ligating one or more primers to the digested stochastically labeled amplicon to produce a primer-stochastically labeled amplicon. The primer may be a sequencing primer. The method may further comprise sequencing the primer-stochastically labeled amplicon. This method may reduce or prevent un-intended incorporation of oligonucleotide tags during PCR amplification. This method may improve sequencing of the stochastically labeled molecules compared to the sequencing of the stochastically labeled molecules from a reaction based on homopolymer tails. This method may reduce or prevent sequencing errors. The oligonucleotide tag may comprise a 3' phosphate. The 3' phosphate can prevent extension of the 3' end during a PCR reaction, thereby reducing or preventing non-specific amplification.

Figure 29:
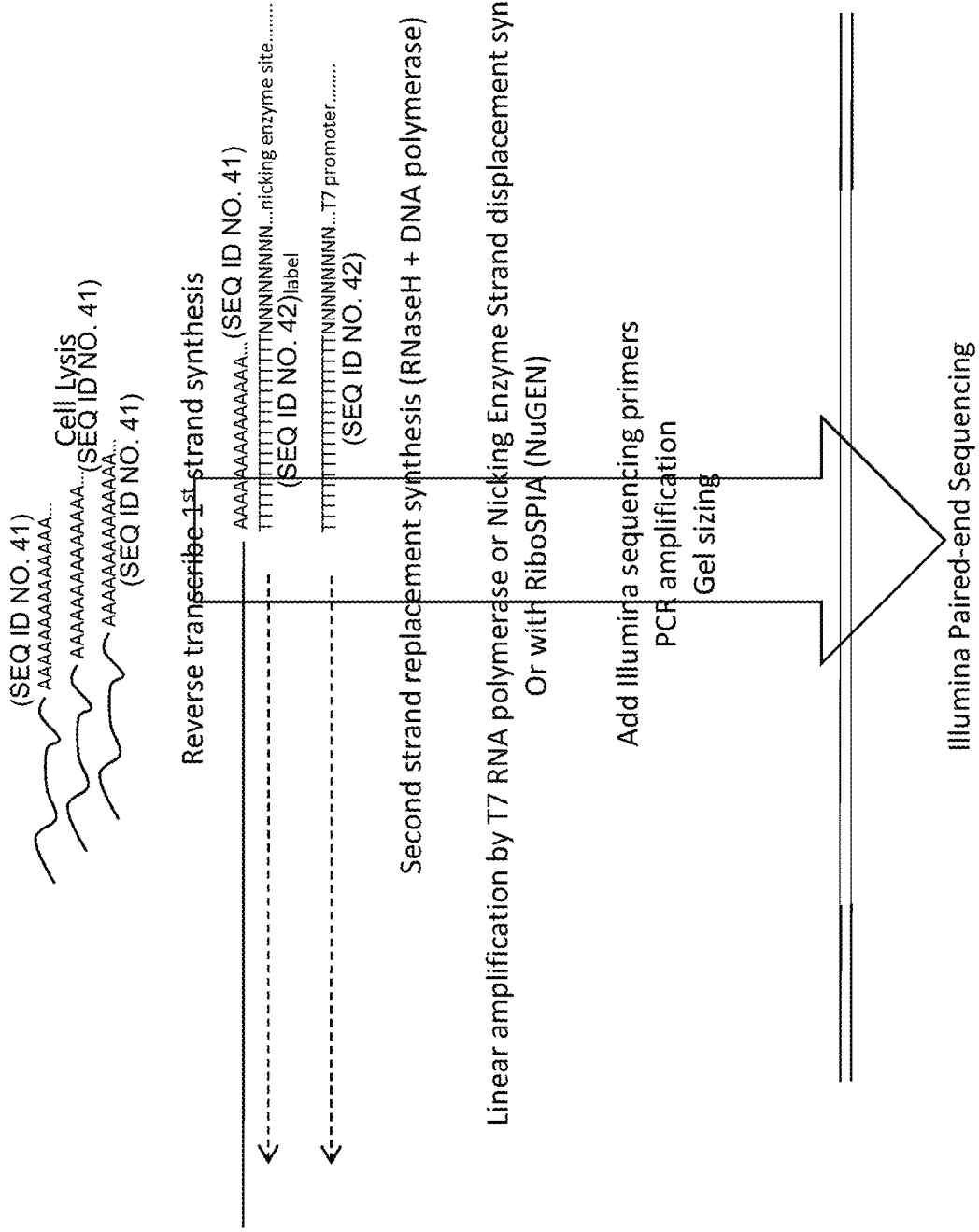

FIG. 29 depicts a linear amplification method. The method may comprise reverse transcribing one or more mRNA molecules by stochastically labeling the one or more RNA molecules with a plurality of oligonucleotide tags to produce one or more cDNA copies of the mRNA molecules, wherein the cDNA copies comprise the oligonucleotide tag. The oligonucleotide tag may comprise a universal primer binding site, unique identifier region and an oligodT sequence. The method may further comprise synthesizing a DNA copy of the mRNA molecule by second strand synthesis. The method may comprise linear amplification of the stochastically labeled cDNA molecule. Linear amplification may comprise amplifying the stochastically labeled cDNA molecule by T7 RNA polymerase, nicking enzyme strand displacement synthesis or RiboSPIA (NuGEN). The method may further comprise attaching one or more sequencing primes to the stochastically labeled molecule. The method may further comprise amplifying the stochastically labeled molecule to produce one or more stochastically labeled amplicons. The method may further comprise sequencing the stochastically labeled amplicons. This method may comprise a low level of initial amplification followed by exponential PCR. This method may be independent of ligation. This method may reduce or prevent artifacts generated by PCR.

Figure 30:
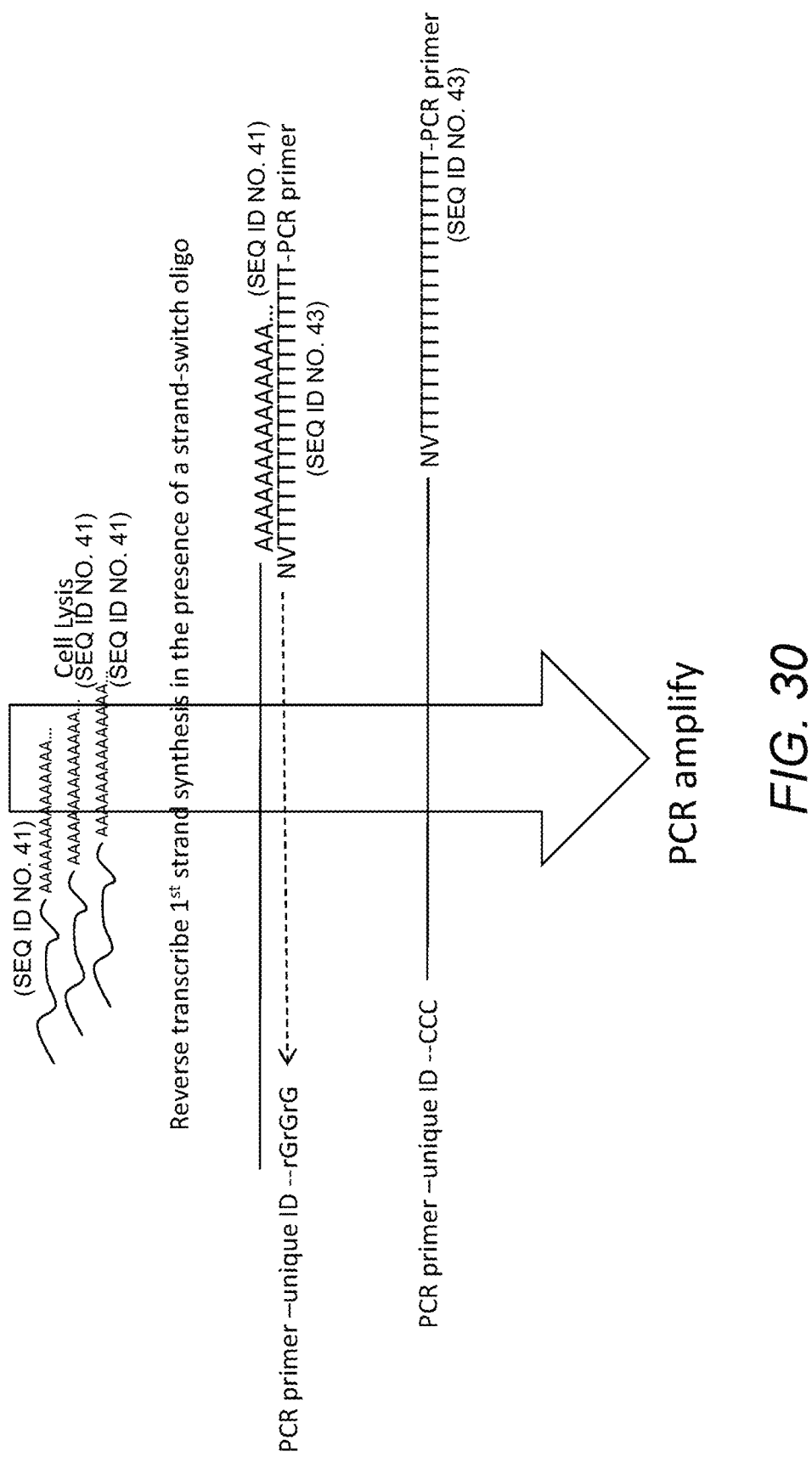

FIG. 30 depicts a method of stochastically labeling one or more molecules by strand switching. The method may comprise reverse transcribing a first strand synthesis in the presence of a strand-switch oligonucleotide to produce a stochastically labeled cDNA molecule. The method may further comprise amplifying the stochastically labeled cDNA molecule.

Figure 31:
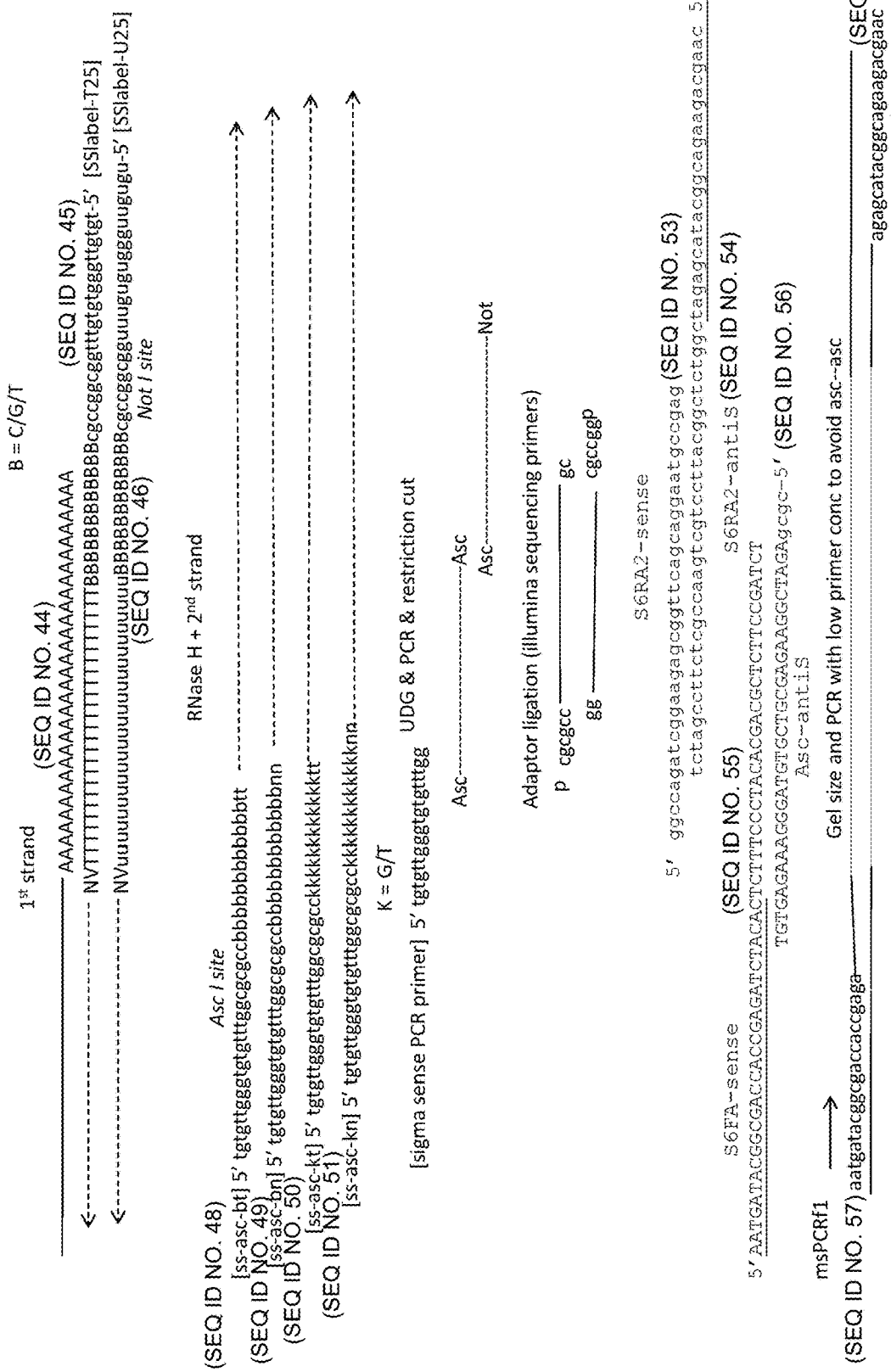

FIG. 31 depicts a method of stochastically labeling one or more molecules by random priming. The method may comprise reverse transcribing an mRNA molecule to produce a stochastically labeled cDNA copy. Reverse transcribing may comprise stochastically labeling one or more molecules with a plurality of oligonucleotide tags, wherein the oligonucleotide tag comprises an oligodU sequence, a unique identifier sequence and a universal primer sequence. The oligonucleotide tag may further comprise a restriction enzyme recognition site. The method may further comprise removing the mRNA molecules with RNAse H. The method may further comprise conducting a second strand synthesis reaction with a second set of oligonucleotide tags. The second set of oligonucletotide tags may comprise a universal primer binding site, a restriction enzyme recognition site, and a unique identifier region. The method may further comprise treating the sample with UDG to remove oligonucleotide tags comprising one or more uracils. The method may further comprise amplifying the stochastically labeled molecules. The method may further comprise attaching one or more adapters to the stochastically labeled molecules. The oligonucleotide tag may comprise any three nucleotides (e.g., C, G, T—no A; C, G, A—no T). The oligonucleotide tag may comprise any two nucleotides (e.g., G, T—no A, C; A, C—no G, T). As shown in FIG. 31, the method may comprise first strand cDNA synthesis with an-oligo dT (or dU for subsequent removal with UDG) oligonucleotide tag bearing 12 variable label nucleotides (C/G/T—A was excluded to prevent spurious self-priming to the T/U string). However, instead of TdT tailing to generate the second PCR priming site, an oligonucleotide tag containing a quasi-random string and a PCR sequence is used.

Figure 43:
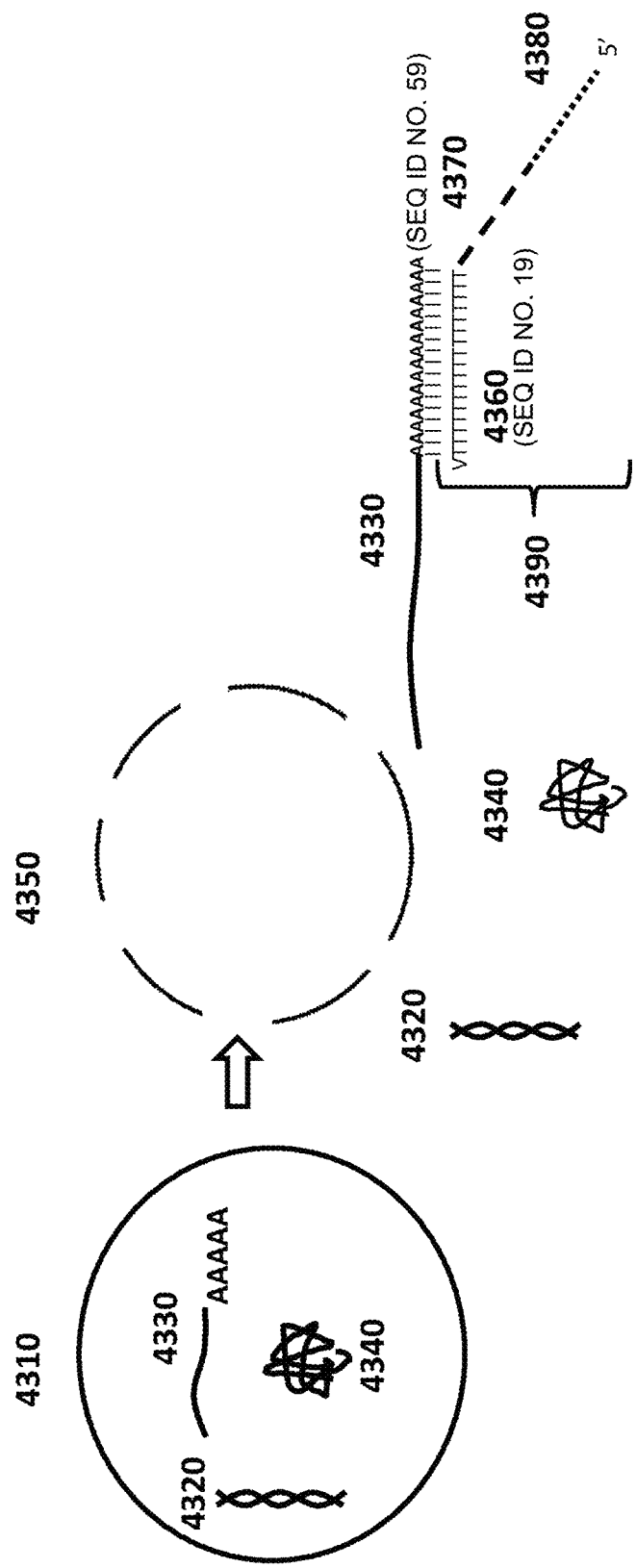

FIG. 43 depicts a schematic of a method for absolute quantitation of one or more molecules directly from one or more cell lysates. As shown in FIG. 43, an intact cell (4310) comprising one or more DNA molecules (4320), RNA molecules (4330), proteins (4340), or a combination thereof is lysed to produce a lysed cell (4350). The one or more DNA molecules (4320), RNA molecules (4330) and/or proteins (4340) can be released from the cell. The quantity of one or more mRNA molecules (4330) can be determined by stochastically labeling the mRNA molecules with a plurality of oligonucleotide tags (4390). The oligonucleotide tag may comprise a target specific region (4360), unique identifier region (4370) and a universal primer binding site (4380).

In some instances, the target molecule is a DNA molecule. Alternatively, the target molecule is an RNA molecule. In some instances, the methods disclosed herein further comprise reverse transcribing the RNA molecule. The labeled gene-specific oligo can comprise one or more nucleotides. The one or more nucleotides can be a deoxynucleotide. Alternatively, or additionally, the one or more nucleotides are a deoxyribonucleotide. The one or more nucleotides can be a synthetic nucleotide. The labeled gene-specific oligo can comprise at least about 5 nucleotides. Alternatively, the labeled gene-specific oligo comprises at least about 10 nucleotides. Alternatively, the labeled gene-specific oligo comprises at least about 12 nucleotides. The labeled gene-specific oligo can comprise at least about 15 nucleotides. The labeled gene-specific oligo can comprise at least about 17 nucleotides. The labeled gene-specific oligo can comprise at least about 20 nucleotides. In some instances, the labeled gene-specific oligo comprises at least about 25, 30, 35, 40, 45, 50, 55, 60, 65, 70, 75, 80, 85, 90, 95, or 100 nucleotides.

The labeled gene-specific oligo can comprise a target specific region. The target specific region of the labeled gene-specific oligo can be at least partially complementary to at least a portion of the target molecule. In some instances, the target specific region comprises at least about 5 nucleotides that are complementary to at least a portion of the target molecule. Alternatively, the target specific region comprises at least about 10 nucleotides that are complementary to at least a portion of the target molecule. In other instances, the target specific region comprises at least about 12 nucleotides that are complementary to at least a portion of the target molecule. The target specific region can comprise at least about 15 nucleotides that are complementary to at least a portion of the target molecule. The target specific region can comprise at least about 17 nucleotides that are complementary to at least a portion of the target molecule. The target specific region can comprise at least about 20 nucleotides that are complementary to at least a portion of the target molecule. The target specific region can comprise at least about 25, 30, 35, 40, 45, 50, 55, 60, 65, 70, 75, 80, 85, 90, 96, or 100 nucleotides that are complementary to at least a portion of the target molecule. The target specific region can comprise a sequence that is at least about 60% complementary to at least a portion of the target molecule. Alternatively, the target specific region comprises a sequence that is at least about 70% complementary to at least a portion of the target molecule. The target specific region can comprise a sequence that is at least about 80% complementary to at least a portion of the target molecule. The target specific region can comprise a sequence that is at least about 85% complementary to at least a portion of the target molecule. The target specific region can comprise a sequence that is at least about 90% complementary to at least a portion of the target molecule. The target specific region can comprise a sequence that is at least about 95% complementary to at least a portion of the target molecule. The target specific region can comprise a sequence that is at least about 97% complementary to at least a portion of the target molecule. The target specific region can comprise a sequence that is at least about 98% complementary to at least a portion of the target molecule.

The labeled gene-specific oligo can comprise any label disclosed herein. In some instances, the label is a fluorophore. Alternatively, the label is a cyanine dye (e.g., Cy3, Cy5).

The solid support can be any solid support disclosed herein. In some instances, the solid support is a detector array. The detector array can comprise a plurality of probes. The target molecule can be hybridized to one or more probes of the plurality of probes on the detector array.

The method can further comprise amplifying the target molecule prior to hybridization to the solid support. The methods disclosed herein can further comprise sequencing the target molecules hybridized to the solid support. The methods disclosed herein can be used to prevent false-positive detection of PCR amplified DNAs that do not contain the gene of interest.

The method can further comprise detecting the labeled-target molecules. Methods to detect the labeled-target molecule can comprise any of the detection methods and instruments disclosed herein. In some instances, detecting the labeled-target molecule comprises detecting the label. Detecting the labeled-target molecule can comprise a fluorometer. Alternatively, detecting the labeled-target molecule comprises a luminometer. In other instances, detecting the labeled-target molecule comprises a plate reader.

Further disclosed herein are methods, kits, and systems for capturing and/or enriching a population of target molecules. FIG. 8 shows a schematic of the method. Generally, the method comprises: a) stochastically labeling one or more nucleic acid molecules in a sample to produce a stochastically labeled molecule; and b) capturing one or more stochastically labeled molecules to produce a captured molecule, wherein the captured molecule comprise a target molecule.

Capturing the stochastically labeled molecule can comprise the use of one or more gene-specific oligos. The gene-specific oligos can attach to a specific stochastically labeled molecule to produce an oligo linked molecule. In some instances, the methods disclosed herein further comprise isolating the oligo linked molecule from the sample. The gene-specific oligo can comprise a label or tag. The label or tag can enable isolation of the oligo linked molecule.

Alternatively, capturing the stochastically labeled molecule can comprise contacting the sample comprising the stochastically labeled molecules with a solid support. In some instances, the stochastically labeled molecule comprising the target molecule hybridizes to the solid support, thereby capturing the stochastically labeled molecule. Alternatively, the stochastically labeled molecule hybridized to the solid support does not comprise the target molecule and capturing the stochastically labeled molecule comprises collecting any unbound stochastically labeled molecules (e.g., stochastically labeled molecules that are not hybridized to the solid support). The solid support can be any of the solid supports disclosed herein. In some instances, the solid support is an array. In other instances, the solid support is a bead. The bead can be a magnetic bead. In some instances, capturing the stochastically labeled molecule comprises the use of a magnet.

The method can further comprise amplification of the stochastically labeled molecule and/or captured molecule. Amplification of the stochastically labeled molecule and/or captured molecule can comprise any of the amplification methods disclosed herein. In some instances, amplification of the stochastically labeled molecule and/or captured molecule comprises PCR.

The methods disclosed herein can further comprise sequencing of the captured molecule. Sequencing can comprise any of the sequencing methods disclosed herein. In some instances, the captured molecules are directly sequenced on the solid support.

Further disclosed herein are methods, kits, and systems for digital detection and/or quantification of a nucleic acid molecule. Generally, the methods, kits, and systems comprise (a) stochastically labeling a nucleic acid molecule with a plurality of oligonucleotide tags to produce a stochastically labeled-nucleic acid molecule; and (b) detecting and/or quantifying the stochastically labeled-nucleic acid molecule. The nucleic acid molecule can be a DNA molecule. The nucleic acid molecule can be from a cell. Alternatively, the nucleic acid molecule is a cell-free molecule. The nucleic acid molecule can be derived from a subject. Alternatively, the nucleic acid molecule can be derived from a foreign subject. The foreign subject can be a pathogen (e.g., virus, bacteria, fungus).

The method can further comprise amplifying the stochastically labeled-nucleic acid molecules to produce stochastically-labeled nucleic acid molecule amplicons. The stochastically labeled-nucleic acid molecules or any products thereof (e.g., stochastically-labeled nucleic acid molecule amplicons) can be repeatedly amplified.

In some instances, the method further comprises attaching one or more detectable labels to the stochastically labeled-nucleic acid molecules or products thereof. In some instances, at least one detectable label is attached to the stochastically labeled-nucleic acid molecules or products thereof. Alternatively, at least two detectable labels are attached to the stochastically labeled-nucleic acid molecules or products thereof. The detectable label can be biotin. Alternatively, the detectable label is a fluorescent dye. The fluorescent dye can be a Cy™ dye or a TYE 563 dye. The Cy™ dye can be Cy3.

The method can further comprise hybridization of the stochastically labeled-nucleic acid molecules or any products thereof to a solid support. The solid support can be a bead. Alternatively, the solid support is an array.

The method can further comprise conducting a sequencing reaction to determine the sequence of at least a portion of the stochastically labeled-nucleic acid molecule or product thereof. In some instances, at least a portion of the oligonucleotide tag of the stochastically labeled-nucleic acid molecule or product thereof is sequences. For example, at least a portion of the unique identifier region of the oligonucleotide tag is sequenced. In another example, at least a portion of the target specific region of the oligonucleotide tag is sequenced. Alternatively, or additionally, at least a portion of the nucleic acid molecule of the stochastically labeled-nucleic acid molecule is sequenced.

Detection and/or quantification of the stochastically labeled-nucleic acid molecules can comprise detection and/or quantification of the stochastically-labeled cDNA copies and/or the stochastically-labeled nucleic acid molecule amplicons. Detection and/or quantification of the stochastically labeled-nucleic acid molecules can further comprise detection of one or more detectable labels attached to the stochastically labeled-nucleic acid molecules or products thereof. Detection and/or quantification of the stochastically labeled-nucleic acid molecules or products thereof can comprise any of the detection and/or quantification methods disclosed herein. For example, a fluorescence reader can be used to detect and/or quantify the stochastically labeled-nucleic acid molecules or products thereof. Alternatively, a microarray reader can be used to detect and/or quantify the stochastically labeled-nucleic acid molecules or products thereof.

Further disclosed herein are methods, kits, and systems for digital detection and/or digital quantification of viral molecules. Generally, the methods, kits, and systems comprise (a) stochastically labeling one or more viral molecules with a plurality of oligonucleotide tags to produce a stochastically labeled-viral molecule; and (b) detecting and/or quantifying the stochastically labeled-viral molecule. In some instances, the viral molecules are nucleic acid molecules. The nucleic acid molecules can be DNA or RNA.

The method can further comprise conducting a reverse transcription reaction to produce a stochastically-labeled cDNA copy of the stochastically-labeled viral molecule (e.g., stochastically-labeled viral RNA molecule). The stochastically-labeled viral molecule can be repeatedly reverse transcribed to produce multiple stochastically-labeled cDNA copies of the stochastically-labeled viral molecule. The methods can further comprise amplifying the stochastically labeled-viral molecules or any products thereof (e.g., stochastically-labeled cDNA copy) to produce stochastically-labeled viral amplicons. The stochastically labeled-viral molecules can be repeatedly amplified. Alternatively, the products of the stochastically-labeled viral molecules can be repeatedly amplified. In some instances, the products of the stochastically-labeled viral molecules are the stochastically-labeled cDNA copies of the stochastically-labeled viral molecule. Alternatively, the products of the stochastically-labeled viral molecules are the stochastically-labeled viral amplicons.

In some instances, the method further comprises attaching one or more detectable labels to the stochastically labeled-viral molecules or products thereof. In some instances, at least one detectable label is attached to the stochastically labeled-viral molecules or products thereof. Alternatively, at least two detectable labels are attached to the stochastically labeled-viral molecules or products thereof. The detectable label can be biotin. Alternatively, the detectable label is a fluorescent dye. The fluorescent dye can be a Cy™ dye or a TYE 563 dye. The Cy™ dye can be Cy3.

The method can further comprise hybridization of the stochastically labeled-viral molecules or any products thereof to a solid support. The solid support can be a bead. Alternatively, the solid support is an array.

The method can further comprise conducting a sequencing reaction to determine the sequence of at least a portion of the stochastically labeled-viral molecule or product thereof. In some instances, at least a portion of the oligonucleotide tag of the stochastically labeled-viral molecule or product thereof is sequences. For example, at least a portion of the unique identifier region of the oligonucleotide tag is sequenced. In another example, at least a portion of the target specific region of the oligonucleotide tag is sequenced. Alternatively, or additionally, at least a portion of the viral molecule of the stochastically labeled-viral molecule is sequenced.

Detection and/or quantification of the stochastically labeled-viral molecules can comprise detection and/or quantification of the stochastically-labeled cDNA copies and/or the stochastically-labeled viral amplicons. Detection and/or quantification of the stochastically labeled-viral molecules can further comprise detection of one or more detectable labels attached to the stochastically labeled-viral molecules or products thereof. Detection and/or quantification of the stochastically labeled-viral molecules or products thereof can comprise any of the detection and/or quantification methods disclosed herein. For example, a fluorescence reader can be used to detect and/or quantify the stochastically labeled-viral molecules or products thereof. Alternatively, a microarray reader can be used to detect and/or quantify the stochastically labeled-viral molecules or products thereof.

In some instances, digital detection and/or digital quantification of the viral molecules can be used to determine the viral load in a subject suffering from a viral infection. Alternatively, digital detection and/or digital quantification of the viral molecules can be used in the diagnosis and/or prognosis of a viral infection. In some instances, digital detection and/or digital quantification of the viral molecules can be used in monitoring an antiviral therapeutic regimen.

Further disclosed herein are methods, kits, and systems for digital detection and/or quantification of a biomarker. The methods, kits, and systems can be used to quantify a biomarker. Generally, the methods, kits, and systems comprise (a) stochastically labeling a biomarker with a plurality of oligonucleotide tags to produce a stochastically labeled-biomarker;

and (b) detecting and/or quantifying the stochastically labeled-biomarker. The biomarker can be a cancer biomarker. The biomarker can be a nucleic acid molecule or a protein. The nucleic acid molecule can be a DNA molecule. Alternatively, the nucleic acid molecule can be a RNA molecule. The biomarker can be derived from a subject. Alternatively, the biomarker can be derived from a foreign subject. The foreign subject can be a pathogen (e.g., virus, bacteria, fungus).

The method can further comprise conducting a reverse transcription reaction to produce a stochastically-labeled cDNA copy of the stochastically-labeled biomarker (e.g., stochastically-labeled biomarker RNA molecule). The stochastically-labeled biomarker can be repeatedly reverse transcribed to produce multiple stochastically-labeled cDNA copies of the stochastically-labeled biomarker. The methods can further comprise amplifying the stochastically labeled-biomarkers or any products thereof (e.g., stochastically-labeled cDNA copy) to produce stochastically-labeled biomarker amplicons. The stochastically labeled-biomarkers can be repeatedly amplified. Alternatively, the products of the stochastically-labeled biomarkers can be repeatedly amplified. In some instances, the products of the stochastically-labeled biomarkers are the stochastically-labeled cDNA copies of the stochastically-labeled biomarker. Alternatively, the products of the stochastically-labeled biomarkers are the stochastically-labeled biomarker amplicons.

In some instances, the method further comprises attaching one or more detectable labels to the stochastically labeled-biomarkers or products thereof. In some instances, at least one detectable label is attached to the stochastically labeled-biomarkers or products thereof. Alternatively, at least two detectable labels are attached to the stochastically labeled-biomarkers or products thereof. The detectable label can be biotin. Alternatively, the detectable label is a fluorescent dye. The fluorescent dye can be a Cy™ dye or a TYE 563 dye. The Cy™ dye can be Cy3.

The method can further comprise hybridization of the stochastically labeled-biomarkers or any products thereof to a solid support. The solid support can be a bead. Alternatively, the solid support is an array.

The method can further comprise conducting a sequencing reaction to determine the sequence of at least a portion of the stochastically labeled-biomarker or product thereof. In some instances, at least a portion of the oligonucleotide tag of the stochastically labeled-biomarker or product thereof is sequences. For example, at least a portion of the unique identifier region of the oligonucleotide tag is sequenced. In another example, at least a portion of the target specific region of the oligonucleotide tag is sequenced. Alternatively, or additionally, at least a portion of the biomarker of the stochastically labeled-biomarker is sequenced.

Detection and/or quantification of the stochastically labeled-biomarkers can comprise detection and/or quantification of the stochastically-labeled cDNA copies and/or the stochastically-labeled biomarker amplicons. Detection and/or quantification of the stochastically labeled-biomarkers can further comprise detection of one or more detectable labels attached to the stochastically labeled-biomarkers or products thereof. Detection and/or quantification of the stochastically labeled-biomarkers or products thereof can comprise any of the detection and/or quantification methods disclosed herein. For example, a fluorescence reader can be used to detect and/or quantify the stochastically labeled-biomarkers or products thereof. Alternatively, a microarray reader can be used to detect and/or quantify the stochastically labeled-biomarkers or products thereof.

In some instances, digital detection and/or digital quantification of the biomarkers can be used to diagnose or prognose a condition in a subject in need thereof. In some instances, digital detection and/or digital quantification of the biomarkers can be used to monitor a therapeutic regimen.

The condition can be a cancer. The cancer can be a sarcoma, carcinoma, leukemia, or lymphoma.

Alternatively, the condition is a pathogenic infection. The pathogenic infection can be a bacterial or viral infection.

Further disclosed herein are methods, kits and systems for counting or determining a number of nucleic acid molecules in a sample. The method may comprise: (a) providing a plurality of oligonucleotide tags wherein a oligonucleotide tag comprises a unique identifier sequence, a target sequence, and an optional PCR primer sequence; (b) combining a sample comprising nucleic acid molecules with the plurality of labeled primers to form a labeled nucleic acid molecule, wherein each target nucleic acid molecule is capable of attaching to a oligonucleotide tag with a unique identifier sequence; and (c) detecting (i) the nucleic acid molecule, a complement of the nucleic acid molecule, a reverse complement of the nucleic acid molecule, or a portion thereof, and (ii) the oligonucleotide tag, a complement of the oligonucleotide tag, a reverse complement of the oligonucleotide tag, or a portion thereof to determine the count or number of different labeled nucleic acid molecules, thereby counting or determining a number of nucleic acid molecules in the sample. The method may comprise counting or determining a number of 10 or more different nucleic acid molecules. The method may comprise counting or determining a number of 20 or more different nucleic acid molecules. The different nucleic acid molecules may differ by 1 or more nucleotides or base pairs. The different nucleic acids may be counted simultaneously. Alternatively, the different nucleic acid molecules may be counted sequentially.

The method of counting or determining a number of nucleic acid molecules in a sample may comprise: (a) providing a plurality of oligonucleotide tags wherein a oligonucleotide tag comprises a unique identifier sequence, a target sequence, and an optional PCR primer sequence; (b) combining a sample comprising nucleic acid molecules with the plurality of labeled primers to form a labeled nucleic acid molecule, wherein the attachment of the nucleic acid molecule to the oligonucleotide tag forms a unique molecule-tag junction; and (c) detecting the unique molecule-tag junction, a complement of the unique molecule-tag junction, a reverse complement of the unique molecule-tag junction, or a portion thereof to determine the count or number of different labeled nucleic acid molecules, thereby counting or determining a number of nucleic acid molecules in the sample. The method may comprise counting or determining a number of 10 or more different nucleic acid molecules. The method may comprise counting or determining a number of 20 or more different nucleic acid molecules. The different nucleic acid molecules may differ by 1 or more nucleotides or base pairs. The different nucleic acids may be counted simultaneously. Alternatively, the different nucleic acid molecules may be counted sequentially.

The method of counting or determining a number of nucleic acid molecules in a sample may comprise: (a) providing a plurality of oligonucleotide tags, wherein the oligonucleotide tag comprises a target-specific sequence, a unique identifier sequence comprising a ribonucleic acid, and an optional PCR primer sequence; (b) combining a sample comprising nucleic acid molecules with the plurality of oligonucleotide tags to form a labeled nucleic acid molecule, wherein a target nucleic acid molecule is capable of attaching to oligonucleotide tags with different unique identifier sequences; (c) synthesizing a copy of the labeled nucleic acid molecule, wherein the copy of the labeled nucleic acid molecule comprises a copy of the nucleic acid molecule and a copy of the oligonucleotide tag and the ribonucleic acid of the unique identifier sequence comprises replaced with a deoxyribonucleic acid; and (d) detecting the copy of the labeled nucleic acid molecule, a complement of the copy of the labeled nucleic acid molecule, a reverse complement of the copy of the labeled nucleic acid molecule, or a portion thereof to determine a count of the copy of the labeled nucleic acid molecule, thereby counting or determining a number of nucleic acid molecules in the sample. The method may comprise counting or determining a number of 10 or more different nucleic acid molecules. The method may comprise counting or determining a number of 20 or more different nucleic acid molecules. The different nucleic acid molecules may differ by 1 or more nucleotides or base pairs. The different nucleic acids may be counted simultaneously. Alternatively, the different nucleic acid molecules may be counted sequentially.

The method of counting or determining a number of RNA molecules in a sample may comprise: (a) combining a sample comprising RNA molecules with a plurality of oligonucleotide tags, wherein the oligonucleotide tag comprises an RNA-specific sequence, a unique identifier sequence, and an optional PCR primer sequence; (b) synthesizing a copy of an RNA molecule by attaching a oligonucleotide tag to the RNA molecule to form a labeled DNA molecule, wherein each RNA molecule is capable of attaching to oligonucleotide tags with different unique identifier sequences and each labeled DNA molecule comprises a copy of the RNA molecule and a copy of the oligonucleotide tag; and (c) detecting the labeled DNA molecule, a complement of the labeled DNA molecule, a reverse complement of the labeled DNA molecule, or a portion thereof to determine a count of the labeled DNA molecule, thereby counting or determining a number of RNA molecules in the sample.

The method of counting or determining a number of RNA molecules in a sample may comprise: (a) providing a plurality of oligonucleotide tags, wherein the oligonucleotide tag comprises an RNA-specific sequence, a unique identifier sequence comprising a ribonucleic acid, and an optional PCR primer sequence; (b) combining a sample comprising RNA molecules with the plurality of oligonucleotide tags to form a labeled RNA molecule, wherein a target RNA molecule is capable of attaching to oligonucleotide tags with different unique identifier sequences; (c) synthesizing a copy of the labeled RNA molecule to form a labeled DNA molecule, wherein the labeled DNA molecule comprises a copy of the RNA molecule and a copy of the oligonucleotide tag and the ribonucleic acid of the unique identifier sequence comprises replaced with a deoxyribonucleic acid; and (d) detecting the labeled DNA molecule, a complement of the labeled DNA molecule, a reverse complement of the labeled DNA molecule, or a portion thereof to determine a count of the labeled DNA molecule, thereby counting or determining a number of RNA molecules in the sample.

The method of counting or determining a number of RNA molecules in a sample may comprise: (a) combining a sample comprising RNA molecules with a plurality of oligonucleotide tags to form a labeled RNA molecule, wherein each target RNA molecule is capable of attaching to a different label; (b) optionally attaching a second oligonucleotide tag to the labeled RNA molecule to form a dual-labeled RNA molecule; (c) synthesizing a copy of the labeled RNA molecule or dual-labeled RNA molecule to form a labeled DNA molecule or dual-labeled DNA molecule, wherein the labeled DNA molecule and the dual-labeled DNA molecule comprise a copy of the oligonucleotide tag and a copy of the RNA molecule; and (d) detecting the labeled DNA molecule, a complement of the labeled DNA molecule, a reverse complement of the labeled-DNA molecule, the dual-labeled DNA molecule, a complement of the dual-labeled DNA molecule, a reverse complement of the dual-labeled DNA molecule, or a portion thereof to count or determine the number of different labeled DNA molecules or different dual-labeled DNA molecules, thereby counting or determining a number of RNA molecules in the sample.

The method of counting or determining a number of RNA molecules in a sample may comprise: (a) combining a sample comprising RNA molecules with a plurality of labels to form a labeled RNA molecule, wherein each target RNA molecule is capable of attaching to a different label; (b) optionally attaching a second label to the labeled RNA molecule to form a dual-labeled RNA molecule; and (c) detecting the labeled RNA molecule, a complement of the labeled RNA molecule, a reverse complement of the labeled-RNA molecule, the dual-labeled RNA molecule, a complement of the dual-labeled RNA molecule, a reverse complement of the dual-labeled RNA molecule, or a portion thereof to count or determine the number of different labeled RNA molecules or different dual-labeled RNA molecules, thereby counting or determining a number of RNA molecules in the sample.

The method of counting or determining a number of mRNA molecules in a sample may comprise: (a) providing a plurality of oligonucleotide tags, wherein the oligonucleotide tag comprises a target-specific sequence, a unique identifier sequence, and an optional PCR primer sequence; (b) combining a sample comprising mRNA molecules with the plurality of oligonucleotide tags to form a labeled mRNA molecule, wherein each target mRNA molecule is capable of attaching to a different oligonucleotide tag; (b) synthesizing a copy of the labeled mRNA molecule to form a labeled DNA molecule, wherein the labeled DNA molecule comprises a copy of the mRNA molecule and a oligonucleotide tag or a copy of the oligonucleotide tag; and (c) detecting the labeled DNA molecule, a complement of the labeled DNA molecule, a reverse complement of the labeled DNA molecule, or a portion thereof to determine a count of different labeled DNA molecules, thereby counting or determining a number of mRNA molecules in the sample.

In one aspect, polyadenylated RNA from a single cell is analyzed by the methods disclosed herein. After cell lysis the polyA RNA may be enriched by capture on a solid support, such as a bead, having oligo dT attached or the amplification can be performed on the lysate. A labeled-cDNA copy of the RNA is made by hybridizing a primer that has an oligo dT region and a label-tag region. The label-tag region being 5' of the oligo dT region. Preferably there is an amplification sequence that is 5' of the label-tag region so that the label-tag region, which is variable between primers, is between a 5' common amplification primer sequence and a 3' oligo dT region. Second strand cDNA is then synthesized using standard methods, for example use of RNaseH and DNA polymerase. The resulting dsDNA can then be linearly amplified depending on the amplification primer sequence. For example, if the amplification primer sequence is a T7 RNA polymerase promoter sequence, antisense RNA can be generated by IVT using T7 RNA pol. If the amplification prime sequence includes a site for s nicking enzyme (e.g. Nt. BspQl), nicking enzyme strand displacement can be used to generate DNA copies of the RNA targets. The copies can then be modified to include sequencing primers at one or both ends and the products can be sequenced. Sequence information is collected for the tag and enough of the adjacent sequence to provide an identification of the target.

In some instances, the oligonucleotide tag comprises a ribonucleic acid. The oligonucleotide tag may comprise a ribonucleic acid that is uracil. The oligonucleotide tag may comprise a ribonucleic acid that is cytosine. The oligonucleotide tag may comprise a ribonucleic acid that is adenine. The oligonucleotide tag may comprise a ribonucleic acid that is guanosine.

The unique identifier sequence may comprise a predetermined sequence. The unique identifier sequence may comprise a random sequence.

The target-specific sequence of the oligonucleotide tag may be specific for a plurality of targets. In some aspects, the target-specific sequence of the oligonucleotide tag comprises an oligo dT sequence. In some aspects, the target-specific sequence of the oligonucleotide tag may comprise an oligo dU sequence. In some instances, the target-specific sequence does not comprise an oligo dT nor oligo dU sequence.

The copy of the labeled DNA molecule may be synthesized by a reverse transcriptase enzyme. The reverse transcriptase enzyme may be selected from a retroviral reverse transcriptase, a phage DNA polymerase, or a DNA polymerase.

The method may further comprise synthesizing a copy of the labeled nucleic acid molecule to replace a ribonucleic acid with a deoxyribonucleic acid.

In some aspects, the detecting step comprises detecting the copy of the labeled nucleic acid molecule, a complement of the copy of the labeled nucleic acid molecule, a reverse complement of the copy of the labeled nucleic acid molecule, or a portion thereof. In some aspects, the detection step may comprise hybridization of the nucleic acid molecule portion of the labeled nucleic acid molecule, a complement of the nucleic acid molecule portion of the labeled nucleic acid molecule, a reverse complement of the nucleic acid molecule portion of the labeled nucleic acid molecule, the oligonucleotide tag of the labeled nucleic acid molecule, a complement of the oligonucleotide tag of the labeled nucleic acid molecule, a reverse complement of the oligonucleotide tag of the labeled nucleic acid molecule, a portion thereof, or any combination thereof to a solid support. In some aspects, the detection step may comprise hybridization of the nucleic acid molecule portion of the copy of the labeled nucleic acid molecule, the oligonucleotide tag portion of the copy of the labeled nucleic acid molecule, a complement thereof, a reverse complement thereof, a portion thereof, or any combination thereof to a solid support.

In some aspects, the detecting step comprises detecting the copy of the oligonucleotide tag, a complement of the copy of the oligonucleotide tag, a reverse complement of the copy of the oligonucleotide tag, or a portion thereof.

The detection step may comprise hybridization of the unique molecule-tag junction, a complement of the unique molecule-tag junction, a reverse complement of the unique molecule-tag junction, or a portion thereof to a solid support. The detection step may comprise hybridization of a copy of the unique molecule-tag junction, a complement of the copy of the unique molecule-tag junction, a reverse complement of the copy of the unique molecule-tag junction, or a portion thereof to a solid support.

In some aspects, the solid support comprises an array. The array may comprise probes attached to the surface. The array may further comprise a probe feature for each possible labeled nucleic acid molecule combination. In another aspect, the solid support may comprise a bead.

In some aspects, the detection step comprises sequencing of (i) the nucleic acid molecule portion of the labeled nucleic acid molecule, a complement thereof, a reverse complement thereof, or a portion thereof, and (ii) the oligonucleotide tag portion of the labeled nucleic acid molecule, a complement thereof, a reverse complement thereof, or a portion thereof. In some aspects, the detection step comprises sequencing of (i) the nucleic acid molecule portion of the copy of the labeled nucleic acid molecule, a complement thereof, a reverse complement thereof, or a portion thereof, and (ii) the oligonucleotide tag portion of the copy of the labeled nucleic acid molecule, a complement thereof, a reverse complement thereof, or a portion thereof.

In some aspects, the detection step may comprise sequencing the unique oligonucleotide tag-DNA junction, a complement of the unique oligonucleotide tag-DNA junction, a reverse complement of the unique oligonucleotide tag-DNA junction, or a portion thereof. In some aspects, the detection step may comprise sequencing the copy of the unique oligonucleotide tag-DNA junction, a complement of the copy of the unique oligonucleotide tag-DNA junction, a reverse complement of the copy of the unique oligonucleotide tag-DNA junction, or a portion thereof.

In another aspect, the labeled nucleic acid molecule is amplified. In another aspect, the copy of the labeled nucleic acid sequence is amplified. The amplification of the labeled nucleic acid molecule or the copy of the labeled nucleic acid molecule may comprise a PCR-based method. The PCR-based method may comprise qPCR. The PCR-based method may comprise RT-PCR. The PCR-based method may comprise emulsion PCR. The amplification of the nucleic acid molecule-labeled conjugate may comprise a non-PCR-based method. The non-PCR-based method may comprise multiple displacement amplification. The non-PCR-based method may comprise random priming by a strand displacement polymerase.

In another aspect, the sample is from at least one single cell. Alternatively, the sample is from a plurality of cells. The sample may be from less than about 100 cells.

In some aspects, the nucleic acid molecule is a DNA molecule. In another aspect, the nucleic acid molecule is an RNA molecule. The nucleic acid molecule may be an mRNA molecule. The nucleic acid molecule may a noncoding RNA molecule. The noncoding RNA molecule may be a small noncoding RNA molecule. The noncoding RNA molecule may be a long noncoding RNA molecule. The noncoding RNA molecule may be a microRNA molecule. In some aspects, the oligonucleotide tag is attached to the nucleic acid molecule by ligation. In another aspect, the oligonucleotide tag is attached to the nucleic acid molecule by hybridization.

In another aspect is a method of counting or determining a number of DNA molecules in a sample comprising: (a) providing a plurality of oligonucleotide tags wherein a oligonucleotide tag comprises a unique identifier sequence, a target sequence, and an optional PCR primer sequence; (b) combining a sample comprising DNA molecules with the plurality of labeled primers to form a labeled DNA molecule, wherein the labeled DNA molecule comprises a DNA molecule and a oligonucleotide tag and each target DNA molecule is capable of attaching to a different oligonucleotide tag; and (c) detecting (i) the DNA molecule, a complement of the DNA molecule, a reverse complement of the DNA molecule, or a portion thereof, and (ii) the oligonucleotide tag, a complement of the oligonucleotide tag, a reverse complement of the oligonucleotide tag, or a portion thereof to determine the count or number of different labeled DNA molecules, thereby counting or determining a number of DNA molecules in the sample.

In another aspect is a method of counting or determining a number of DNA molecules in a sample comprising: (a) providing a plurality of oligonucleotide tags wherein a oligonucleotide tag comprises a unique identifier sequence, a target sequence, and an optional PCR primer sequence; (b) combining a sample comprising DNA molecules with the plurality of labeled primers to form a labeled DNA molecule, wherein the attachment of the DNA molecule to the oligonucleotide tag forms a unique molecule-tag junction; and (c) detecting the unique molecule-tag junction, a complement of the unique molecule-tag junction, a reverse complement of the unique molecule-tag junction, or a portion thereof to determine the count or number of different labeled DNA molecules, thereby counting or determining a number of DNA molecules in the sample.

In another aspect is a method for determining a copy number of a target DNA in a sample comprising: (a) providing a plurality of adaptors, wherein the adaptors comprise a unique identifier sequence and each adaptor is capable of attaching to a plurality of different DNA molecules; (b) fragmenting a sample comprising genomic DNA to produce a sample comprising DNA fragments; (c) combining a plurality of adaptors with the sample comprising DNA fragments to form an adaptor-DNA fragment conjugate, wherein substantially all of the DNA fragments are randomly attached to an adaptor with a unique identifier sequence; and (d) detecting the adaptor, a complement of the adaptor, a reverse complement of the adaptor or a portion thereof to determine the number of different adaptor-DNA fragment conjugates, thereby determining a copy number of a target DNA.

In another aspect is a method determining a copy number of a target DNA molecule in a sample comprising: (a) providing a plurality of adaptors, wherein the adaptors comprise a unique identifier sequence and the adaptors are capable of attaching to a plurality of different DNA molecules; (b) fragmenting a sample comprising genomic DNA to produce a sample comprising DNA fragments; (c) attaching adaptors to the DNA fragments, wherein substantially all of the DNA fragments capable of being randomly attached to an adaptor with a unique identifier sequence and the attachment of the adaptor to the DNA fragment forms a unique adaptor-DNA junction; and (d) detecting the unique adaptor-DNA junction, a complement of the unique adaptor-DNA junction, a reverse complement of the unique adaptor-DNA junction, or a portion thereof to determine the count or number of different unique adaptor-DNA junctions, thereby determining a copy number of a target DNA.

In some aspects, the adaptor comprises a ribonucleic acid. In some aspects, the ribonucleic acid is uracil. In some aspects, the ribonucleic acid is cytosine. In some aspects, the ribonucleic acid is adenine. In some aspects, the ribonucleic acid is guanine.

In some aspects, the method further comprises synthesizing a copy of the adaptor-DNA fragment conjugate to replace a ribonucleic acid sequence in the adaptor with a deoxyribonucleic acid sequence.

In some aspects, the detecting step comprises detecting the copy of the unique adaptor-DNA junction, a complement of the copy of the unique adaptor-DNA junction, a reverse complement of the copy of the unique adaptor-DNA junction, or a portion thereof. In some aspects, the detecting step comprises detecting the copy of the adaptor, a complement of the copy of the adaptor, a reverse complement of the copy of the adaptor, or a portion thereof.

In some aspects, the detection step comprises hybridization of the unique adaptor-DNA junction, a complement of the unique adaptor-DNA junction, a reverse complement of the unique adaptor-DNA junction, or a portion thereof to a solid support. In another aspect, the detection step comprises hybridization of the copy of the unique adaptor-DNA junction, a complement of the copy of the unique adaptor-DNA junction, a reverse complement of the copy of the unique adaptor-DNA junction, or a portion thereof to a solid support.

In some aspects, solid support comprises an array. In some aspects, the array comprises probes attached to the surface. In some aspects, the array comprises a probe feature for each unique-adaptor DNA junction. In some aspects, the array comprises a probe feature for each copy of the unique-adaptor DNA junction. In another aspect, the solid support comprises a bead. In some aspects, the detection step comprises sequencing the unique adaptor-DNA junction, a complement of the unique adaptor-DNA junction, a reverse complement of the unique adaptor-DNA junction, or a portion thereof. In some aspects, the detection step comprises sequencing the copy of the unique adaptor-DNA junction, a complement of the copy of the unique adaptor-DNA junction, a reverse complement of the copy of the unique adaptor-DNA junction, or a portion thereof.

In some aspects, the detection step comprises sequencing the copy of the adaptor, a complement of the copy of the adaptor, a reverse complement of the copy of the adaptor, or a portion thereof. In some aspects, the adaptor-DNA fragment conjugate is amplified.

In some aspects is a method of determining the presence or absence of genetic abnormalities comprising: (a) providing a plurality of oligonucleotide tags wherein a oligonucleotide tag comprises a unique identifier sequence, a target sequence, and an optional PCR primer sequence; (b) combining a sample comprising genomic DNA with the plurality of labeled primers to form a genomic DNA-oligonucleotide tag conjugate, wherein each genomic DNA is capable of attaching to a oligonucleotide tag with a unique identifier sequence; and (c) detecting the genomic DNA-oligonucleotide tag conjugate, a complement of genomic DNA-oligonucleotide tag conjugate, a reverse complement of the genomic DNA-oligonucleotide tag conjugate, or a portion thereof to count or determine a number of different genomic DNA-oligonucleotide tag conjugates, thereby determining the presence or absence of genetic abnormalities.

In some aspects, the detecting step comprises detecting the genomic DNA, a complement of the genomic DNA, a reverse complement of the genomic DNA, or a portion thereof. In some aspects, the detecting step comprises detecting the oligonucleotide tag, a complement of the oligonucleotide tag, a reverse complement of the oligonucleotide tag, or a portion thereof.

In some aspects, the genetic abnormality comprises an aneupoloidy. The aneuploidy may be monosomy. The monosomy may be monosomy of the sex chromosome. The aneupoloidy may be trisomy. The trisomy may be trisomy 21. The trisomy may be trisomy 18. The trisomy may be trisomy 13. The aneuploidy may be tetrasomy. The aneuploidy may be pentasomy. In some aspects, the method further comprises diagnosing a genetic abnormality. In some aspects, the method may further comprise diagnosing Turner syndrome. In some aspects, the method may further comprise diagnosing Down syndrome. In some aspects, the method may further comprise diagnosing Edwards syndrome. In some aspects, the method may further comprise diagnosing Patau syndrome. In some aspects, the genetic abnormality comprises a deletion in the genomic DNA. In some aspects, the genetic abnormality comprises a polymorphism. In some aspects, the genetic abnormality comprises a single gene disorders. In some aspects, the genetic abnormality comprises a chromosome translocation.

In some aspects, the sample is from an embryo. In some aspects, the sample comprises at least one cell from the embryo.

In some aspects, the method further comprises determining an implantation status of the embryo based on the detecting step. In some aspects, the genomic DNA is fragmented prior to attachment of the oligonucleotide tags.

In some aspects, the genomic DNA is fragmented by a restriction enzyme. In some aspects, the genomic DNA is fragmented by an allele-specific restriction enzyme.

In some aspects, the oligonucleotide tag comprises a ribonucleic acid. In some aspects, the ribonucleic acid is uracil. In some aspects, the ribonucleic acid is cytosine. In some aspects, the ribonucleic acid is adenine. In some aspects, the ribonucleic acid is guanine. In some aspects, the method further comprises synthesizing a copy of the genomic DNA-oligonucleotide tag conjugate to replace a ribonucleic acid sequence in the oligonucleotide tag with a deoxyribonucleic acid sequence.

In some aspects, the detecting step comprises detecting the copy of the genomic DNA-oligonucleotide tag conjugate, a complement of the copy of the genomic DNA-oligonucleotide tag conjugate, a reverse complement of the copy of the genomic DNA-oligonucleotide tag conjugate, or a portion thereof.

In some aspects, the copy of the genomic DNA-oligonucleotide tag conjugate is synthesized by a reverse transcriptase enzyme.

In some aspects, the detection step comprises hybridization of the genomic DNA-oligonucleotide tag conjugate, a complement of the genomic DNA-oligonucleotide tag conjugate, a reverse complement of the genomic DNA-oligonucleotide tag conjugate, or a portion thereof to a solid support. In some aspects, the detection step comprises hybridization of the genomic DNA, a complement of the genomic DNA, a reverse complement of the genomic DNA, or a portion thereof to a solid support. In some aspects, the detection step comprises hybridization of the oligonucleotide tag, a complement of the oligonucleotide tag, a reverse complement of the oligonucleotide tag, or a portion thereof to a solid support. In some aspects, the detection step comprises hybridization of the copy of the genomic DNA-oligonucleotide tag conjugate, a complement of the copy of the genomic DNA-oligonucleotide tag conjugate, a reverse complement of the copy of the genomic DNA-oligonucleotide tag conjugate, or a portion thereof to a solid support. In some aspects, the detection step comprises hybridization of the copy of the genomic DNA, a complement of the copy of the genomic DNA, a reverse complement of the copy of the genomic DNA, or a portion thereof to a solid support. In some aspects, the detection step comprises hybridization of the copy of the oligonucleotide tag, a complement of the copy of the oligonucleotide tag, a reverse complement of the copy of the oligonucleotide tag, or a portion thereof to a solid support.

In some aspects, the detection step comprises sequencing of the genomic DNA-oligonucleotide tag conjugate, a complement of the genomic DNA-oligonucleotide tag conjugate, a reverse complement of the genomic DNA-oligonucleotide tag conjugate, or a portion thereof. In some aspects, the detection step comprises sequencing of the genomic DNA, a complement of the genomic DNA, a reverse complement of the genomic DNA, or a portion thereof. In some aspects, the detection step comprises sequencing of the oligonucleotide tag, a complement of the oligonucleotide tag, a reverse complement of the oligonucleotide tag, or a portion thereof. In some aspects, the detection step comprises sequencing of the copy of the genomic DNA-oligonucleotide tag conjugate, a complement of the copy of the genomic DNA-oligonucleotide tag conjugate, a reverse complement of the copy of the genomic DNA-oligonucleotide tag conjugate, or a portion thereof. In some aspects, the detection step comprises sequencing of the copy of the genomic DNA, a complement of the copy of the genomic DNA, a reverse complement of the copy of the genomic DNA, or a portion thereof. In some aspects, the detection step comprises sequencing of the copy of the oligonucleotide tag, a complement of the copy of the oligonucleotide tag, a reverse complement of the copy of the oligonucleotide tag, or a portion thereof.

In some aspects, the genomic DNA-oligonucleotide tag conjugate is amplified. In some aspects, the copy of the genomic DNA-oligonucleotide tag conjugate is amplified.

Further disclosed herein are kits and compositions for stochastically labeling a molecule (e.g., nucleic acids such as DNA and RNA molecules, or polypeptides such as proteins and enzymes). In some instances, the kits and compositions are used for stochastically labeling a polyadenylated molecule. The polyadenylated molecule can be a polyadenylated RNA molecule. Alternatively, the kits and compositions are used for stochastically labeling a DNA molecule.

In some instances, the kits comprise a stochastic label primer, universal PCR primer, dye-labeled primer, reverse transcriptase, UDG enzyme, polymerase, buffers, dNTP, array, gene specific primers, target specific primers, control oligo, or any combination thereof. Alternatively, the kits comprise a) a universal PCR primer; b) a Cy3 labeled universal PCR primer; c) a Cy3 TrueTag Grid; and d) an array. The array can be a 2×8 array. The kits disclosed herein can further comprise a stochastic label primer, carrier, control oligo, reverse transcriptase, UDG enzyme, polymerase, gene specific primers, target specific primers, dNTP, or any combination thereof.

The stochastic label primer can comprise a primer attached to an oligonucleotide tag, wherein the oligonucleotide tag comprises an oligo dT sequence, a unique identifier region, and a universal primer binding site, and wherein the universal primer binding site can enable annealing of the universal PCR primer of the kit to the stochastic label primer. In some instances, a stochastic label oligo dT primer is an oligonucleotide tag attached to an oligo dT primer.

The dye-labeled primer can comprise a primer labeled with a dye. The primer can be a universal PCR primer. Alternatively, the primer is a target-specific primer. The dye can be a fluorescent dye. In some instances, the dye is a Cy™ dye. In some instances, the Cy™ dye is a Cy3 dye.

The kits and compositions disclosed herein can further comprise a plurality of probes. In some instances, the plurality of probes is hybridized to the array. The plurality of probes can allow hybridization of the labeled-molecule to the array. The plurality of probes can comprise a sequence that is complementary to the stochastic label oligo dT. Alternatively, or additionally, the plurality of probes comprises a sequence that is complementary to the molecule.

The kits and compositions disclosed herein can further comprise one or more reagents to remove non-labeled molecules, excess primers, or excess oligonucleotide tags (or stochastic label primers) from the sample comprising labeled-molecules.

In some instances, the kits and compositions comprise a reverse transcriptase enzyme. The reverse transcriptase can be MMLV reverse transcriptase.

The kits and compositions can comprise a polymerase enzyme. The polymerase can be a Taq polymerase. For example, the Taq polymerase is a Titatium Taq polymerase.

In some instances, the kits and compositions comprise an enzyme. The enzyme can be an RNase enzyme. Alternatively, the enzyme is UDG. In other instances, the enzyme is a restriction enzyme. The enzyme can be a protease. In some instances, the enzyme is a DNase enzyme. Alternatively, the enzyme is a ligase. The kits and compositions can comprise one or more reagents that can deactivate an enzyme disclosed herein.

In some instances, the kit further comprises a carrier substance. The carrier substance can increase the efficiency of a reaction (e.g., amplification, reverse transcription, ligation, hybridization). The carrier substance can be a nucleic acid molecule. The nucleic acid molecule can be an RNA molecule. The RNA molecule can be a polyadenylated RNA or phage RNA. The phage RNA can be RNA from a MS2 phage. Alternatively, the nucleic acid molecule is a plasmid.

The kit can further comprise a solid support. The solid support can be a bead. The bead can hybridize to the labeled-molecule. The bead can enable detection of the labeled molecule. The bead can be a streptavidin bead or biotin-labeled bead.

The kit can further comprise an algorithm for detecting and/or quantifying the labeled-molecule. Alternatively, or additionally, the kit comprises a software program for detecting/and or quantifying the labeled-molecule. In some instances, the kits further comprise a thermal cycler. The kits can further comprise one or more components for sequencing the labeled-molecule. The one or more components for sequencing can comprise a sequencer, one or more primers for sequencing, beads for sequencing, or any combination thereof. The kit can further comprise one or more components for detecting and/or quantifying the labeled-molecule. The one or more components for detecting and/or quantifying the labeled-molecule can comprise an array detector, array reader, bead detector, scanner, fluorometer, or any of the instruments or components disclosed herein.

EXAMPLES

Example 1. Absolute Counting Protocol

Part 1. Reverse Transcription and Stochastic Labeling

In this step, the stochastic labels are annealed to the poly A RNA. To increase the overall efficiency of the subsequent reverse transcription reaction, a large amount of carrier RNA is also added to the sample.

In some instances, tips with low nucleic acid binding properties are used when pipetting extremely low concentrations of RNA. These special tips can be used for pipetting the RNA sample into the annealing master mix. If a dilution of the RNA is needed, low binding tubes can be used as well. Once the RNA has been added to the annealing master mix, regular tubes/tips can be used.

Make a master mix by combining the reagents listed below:

| Water | 7.8 μl |
| K562 Total RNA (1 μg/μl) | 1 μl |
| 10 mM dNTP | 1 μl |

-continued

| Gene Specific dUTP Primer (10 μM) | 0.4 μl |
| Stochastic Labels (10 μM)* | 0.4 μl |
| Total | 10.6 μl |

Add 2 μl of the RNA sample to be analyzed.
Mix well by pipetting and spin briefly
Incubate at 65° for 5 minutes (Program 1), and then place the tubes on ice for at least 1 minute.

In this step, double stranded cDNA is created for the specific gene of interest. Each cDNA molecule will now contain a primer site for the subsequent PCR step. Combine the following to make a master mix for reverse transcription:

| 5X First Strand Buffer | 4 μl |
| 0.1M DTT | 1 μl |
| SuperRNaseIn (20 U/μl) | 1 μl |
| MMLV RT | 1 μl |
| NEB Taq Polymerase | 0.4 μl |

The Use MMLV RT and NEB Taq Polymerase Instead of Superscript III and Titanium Taq can Alternatively be Used Add 7.4 μl of master mix to each tube and mix by pipetting gently. Spin briefly.

Run the following program (Program 2) on the thermal cycler:
37° for 60 minutes
3 cycles of:
94° for 2 minutes
55° for 2 minutes
68° for 2 minutes
Then 4° forever After the PCR reaction, it is necessary to digest the sample with Uracil DNA Glycosylase (UDG) to prevent the unincorporated primer from being amplified in the gene specific PCR.

To each reaction, add 0.5 μl of UDG. Mix very well by pipetting. Transfer all liquid to a new PCR tube to ensure that there is no carryover of unmixed sample.

Incubate at 37° for 30 minutes, then 4°.

Part 2. Initial Gene Specific PCR

Combine the following reagents to make a master mix for PCR:

| Nuclease-free water | 10.9 μl |
| 10X NEB Taq Buffer | 1.5 μl |
| 10 mM dNTP | 0.3 μl |
| Gene Specific Primer (1 μM) | 1 μl |
| Universal PCR primer (1 μM)* | 1 μl |
| NEB Taq Polymerase | 0.3 μl |
| Total | 15 μl |

Final concentration of 0.05 uM primer increases specificity of products

Add 5 μl of labeled product from the previous step to a new PCR tube. Add 15 μl PCR master mix to each sample.
Mix well by pipetting and spin briefly.
Run the following program (Program 4) on the thermal cycler:
94° for 2 minutes
30 cycles of:
94° for 2 minutes
55° for 2 minutes
68° for 2 minutes Then 68° for 4 minutes
4° forever
Part 3. Second, Nested PCR
Prepare the master mix for the second, nested, PCR in the pre-PCR area.

| Nuclease-free water | 39.5 µl |
|---|---|
| 10X NEB Taq Buffer | 5 µl |
| 10 mM dNTP | 1 µl |
| Gene Specific Nested Primer (10 µM) | 1 µl |
| 5Tye563 Labeled Universal PCR primer (10 µM)* | 1 µl |
| NEB Taq Polymerase | 0.5 µl |
| Total | 48 µl |

Aliquot 48 µl of master mix to a new PCR tube.

Add 2 µl from the first PCR reaction to the tube in a separate room designated for post amplification processing to avoid contamination of the pre-PCR area. Perform all subsequent steps in this area.

Mix well by pipetting and spin briefly.

Run the following program (Program 4) on the thermal cycler:
94° for 2 minutes
30 cycles of:
94° for 2 minutes
55° for 2 minutes
68° for 2 minutes
Then 68° for 4 minutes
4° forever Optional Step: Run 4 ul of PCR product on a polyacrylamide 4-20% gradient TBE gel to assess size and purity Part 4. Target Hybridization Turn hyb oven on at 37°.

Prepare samples for hybridization to an Applied Microarray Inc. array slide. Add the following in a 0.2 mL PCR tube:

| Wash A (6X SSPE + 0.01% Triton X-100) | 55 µl |
|---|---|
| Cy3 Control Oligo (760 pM)* | 1 µl |
| PCR product | 20 µl |
| Total | 76 µl |

Mix by pipetting and spin briefly.

Incubate tubes at 95° to denature and then place on ice.

Remove adhesive seal from AMI array slide. Pipet each hybridization cocktail into a well of the AMI array slide. Make a note of the order in which the targets are added. Cover slide with second strip of adhesive (included)

Place sealed array slide into humidity chamber and put into hybridization oven.

Incubate at 37° overnight.

Part 5. Array Wash and Scan

After the overnight hybridization, take the array slide out of the hybridization oven and remove adhesive cover. Pipet out remaining hybridization cocktail and save at −20° if desired.

Dispense 150 µl Wash A to each used well. Aspirate liquid and dispense 150 µl Wash B (0.6×SSPE+0.01% Triton X-100) to each well. Aspirate liquid and bring array slide to scanner as the arrays will be scanned dry.

Turn on the Sensovation FLAIR instrument. Wait 10 minutes for the machine to warm up.

Open the software and click, "Tray Open". Place the array slide into the 4-slide holder. Be sure to seat the slide properly. In the software, click "Tray Close".

Click the "Scan" Icon. A window appears with information about the scan to be performed. Modify the name of the scan if desired and select the appropriate wells to be scanned by clicking the " . . . " icon in the "scan positions" field. Click each well that is to be scanned. The software will circle each selected well in yellow. Click "ok".

The Plate Overview window will appear showing the progress of the scan. Once a well is scanned, the color on the screen will turn from grey to green if the reference pattern has been detected and the grid has been positioned. If the reference pattern has not been detected, the well will be colored red. If any of the scans do not detect the reference, the grid may be manually aligned by clicking the "reanalyze" button at the top of the screen. This will display the grid, which can be positioned properly. Click the green "accept analysis" button at the top of the screen.

Once all of the grids have been aligned, the data can be exported. To obtain windows functionality, press the "windows" key on the keyboard and "D" simultaneously. Locate the scan results in the "my documents" folder under ArrayReader/sensovation/arrayreader.scanresults. Open the appropriate scan folder and copy the TIFF images and the result .csv files to a flash drive or transfer through the network.

Proceed to data analysis either manually or with a computer software package.

Example 2. Four Experiments where 120 RNA Molecules were Added to a Sample of Background Total RNA 240 copies of a polyadenylated nucleic acid fragment was added to a 10 µL reaction containing 1× titanium Taq DNA polymerase buffer, 0.2 µM dNTPs, 0.2 µM of a pool of 960 oligo (dT) stochastic labels, 0.2 µM of a second strand cDNA primer and 0.2 µL of Taq DNA polymerase. In some reactions, an additional number of polyadenylated DNA fragments with sequences unrelated to the 240 copies of test nucleic acid fragment were also added. In reaction A, $1\times10^{10}$ background polyadenylated DNA molecules were added to the reaction. In reaction B, $1\times10^{9}$ background polyadenylated DNA molecules were added to the reaction. In reaction C, $1\times10^{6}$ background polyadenylated DNA molecules were added to the reaction. And, in reaction D, no background polyadenylated DNA molecules were added to the reaction. 10 ng, 1 ng or 1 pg of randomly fragmented and polyadenylated human genomic DNA was tested. After 3 cycles of incubation at 94° C. for 2 min, 45° C. for 2 min and 65° C. for 5 min, 1 unit of Uracil DNA glycosylase is added and the reaction is incubated for 30 min at 37° C. Half of the reaction is then added into a 20 µL PCR reaction consisting of 1× Titanium buffer, 0.2 µM dNTP, 0.2 µM gene-specific forward primer, 0.2 µM universal reverse primer and 0.3 µL Titanium Taq polymerase. PCR conditions were 94° C. for 2 min followed by 30 cycles of 94° C. for 20 sec, 58° C. for 20 sec and 68° C. for 20 sec. A final incubation at 68° C. for 4 min was performed. A nested PCR is performed following the same conditions as the first PCR, except that a nested Forward primer was used. 2 µL of a 1:25 dilution of the initial PCR was used as template for the nested PCR. PCR products were randomly fragmented with DNase, biotin-labeled with Terminal transferase enzyme and then hybridized to a detector array for 12 hours at 37° C. Signals from hybridized DNAs were detected via staining with Streptavidin conjugated Phycoerytherin and imaging on a microarray scanner. FIG. 2A-D shows the signals from hybridized DNAs for reactions A-D, respectively. The number of labels present in the hybridized DNA is counted and used to determine the number of original copies of nucleic acid fragments.

| Reaction | # of labels | # of original copies |
|----------|-------------|----------------------|
| A | 122 | 130 |
| B | 116 | 124 |
| C | 109 | 114 |
| D | 115 | 122 |

Example 3. Comparison with Digital PCR

Figure 3:
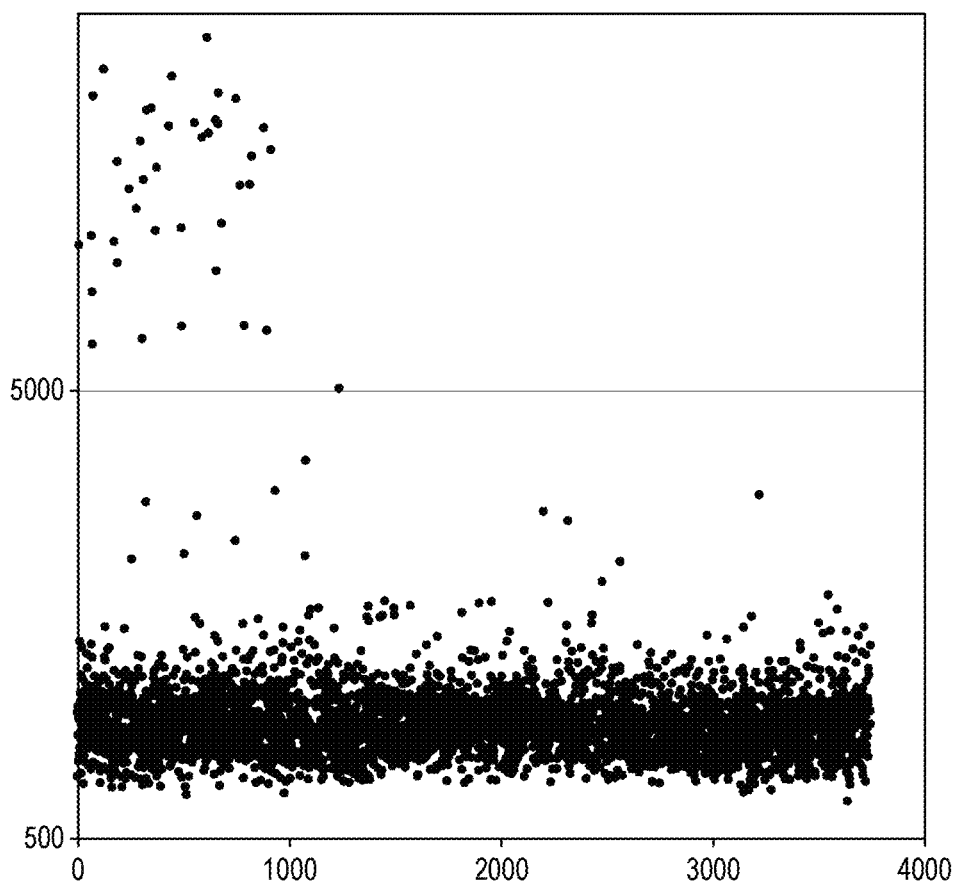
FIG. 3 shows signals for the detection of labels in hybridized molecules
Figure 4B:
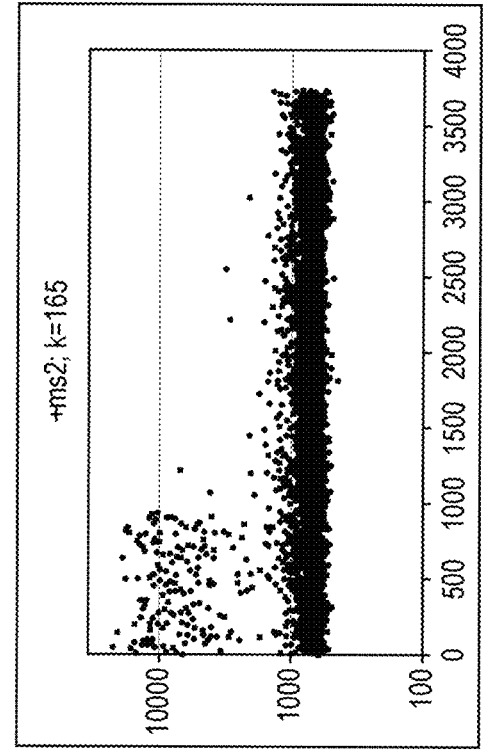
FIG. 4A-FIG. 4D show signals for the detection of labels in hybridized molecules
Figure 4D:
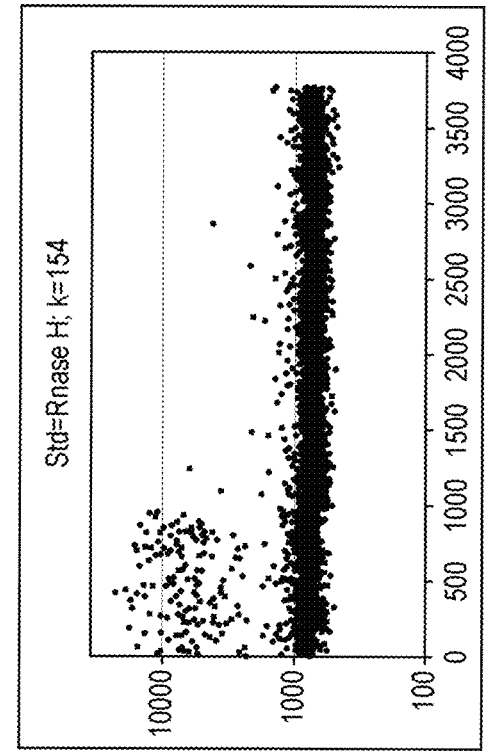
Figure 4A:
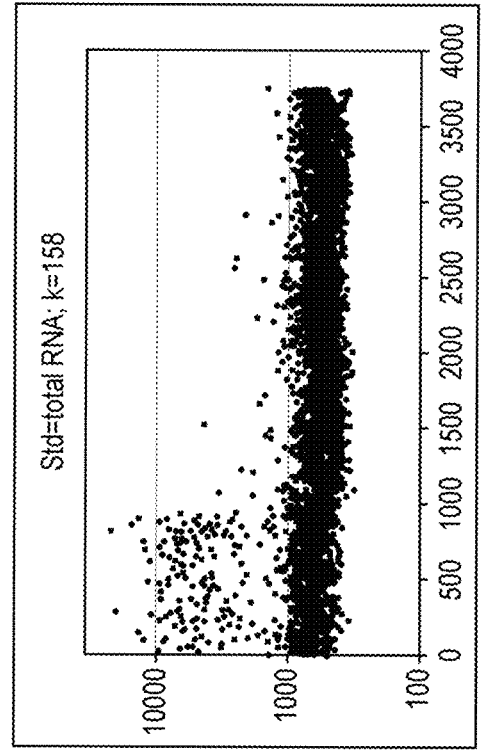
Figure 4C:
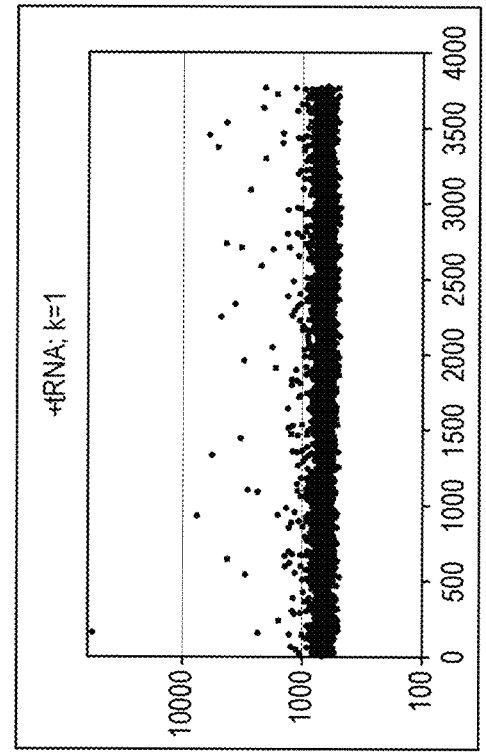

The concentration of an in vitro transcribed RNA was determined using an Agilent bioanalyzer instrument. 0.5 μg of the RNA was mixed with 2 μg of a K562 cell line total RNA which was used as a carrier. The RNA mixture in 3 μL was added to 1 μL of a 10 mM dNTP solution and 2 μL of a 10 μM pool of 960 oligo (dT) labels and 7 μL of water. This mixture was incubated at 65° C. for 5 min and immediately chilled on ice. 4 μL of a first strand reaction buffer (250 mM Tris-HCl (pH 8.3 at 25° C.), 375 mM KCl), 1 μL of 0.1 M DTT, 1 μL of RNase inhibitor (20 units) and 1 μL of superscript II reverse transcriptase (200 units) was added and the reaction was incubated at 50° C. for 60 min and then at 70° C. for 15 min. 1 μL of RNase H (2 units) was added and the reaction was incubated at 37° C. for 20 min. Digital PCR was used to quantitate the number of copies of cDNA synthesized from the in vitro transcribed RNA. The sample was also test by stochastic labeling PCR. 90 copies of the cDNA (as determined by digital PCR) was added to a 10 μL reaction containing 1× titanium PCR buffer, 0.2 μM dNTPs and 0.2 μL of titanium taq polymerase. The reaction was incubated for 3 cycles at 94° C. for 2 min, 55° C. for 2 min and 68° C. for 2 min. 1 unit of uracil DNA glycosylase was added and the reaction was incubated at 37° C. for 30 min. First and nested PCRs, fragmentation, biotin-labeling and array detection were performed as described in Example 2. FIG. 3 shows the signals from the labels in the hybridized DNA. The number of labels present in the hybridized DNA is counted and used to determine the number of original copies of nucleic acid fragments. 40 labels were present in the hybridized DNA and 41 copies were determined by stochastic labeling, as compared to 43 copies as determined by digital PCR. These results demonstrate that stochastic labeling is an effective method for determining the count of a molecule and its accuracy is comparable to digital PCR.

Example 4. RT Yield Increased with Reaction Carriers

To test the effectiveness of carrier RNAs on improving the reverse transcription yield and as a means to reduce non-specific RNA or cDNA losses during reactions, copies of an in vitro transcribed polyadenylated RNA was tested with stochastic labeling following the protocol described in example 2. Additionally, total RNA isolated from mammalian cells, yeast, or E. coli, short polyadenylated synthetic ribonucleotide, yeast tRNA, or MS2 phage RNA were added to the reaction mixture. Each reaction used anywhere between 0.5 μg to 2 μg of carrier RNA. The number of RNA molecules reverse transcribed to cDNA was determined by the number of observed labels detected on the array, and in each case, the effectiveness of each carrier RNA tested could be easily determined. FIG. 4A-D shows the observed labels for reactions A-D, respectively.

| Reaction | # of Input molecules | Carrier RNA | RNase H | # of labels |
|----------|----------------------|-------------|---------|-------------|
| A | 188 | Total RNA from X | — | 158 |
| B | 188 | MS2 phage RNA | — | 165 |
| C | 188 | Yeast tRNA | — | 1 |
| D | 188 | — | RNase H | 154 |

Example 5. Comparison of MMLV and RNase H Minus MMLV Reverse Transcriptase

Figure 5B:
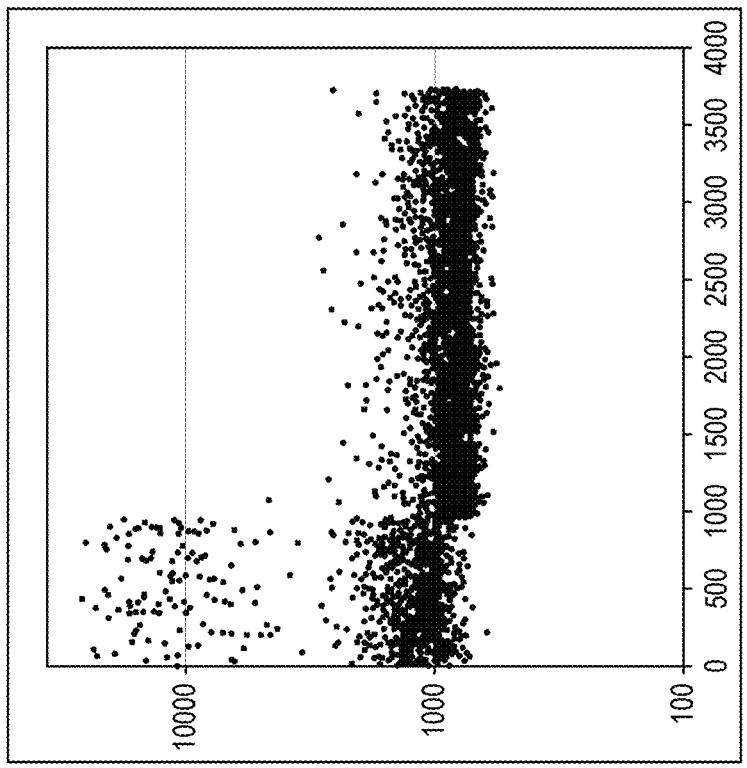
FIG. 5A-FIG. 5B show signals for the detection of labels in hybridized molecules
Figure 5A:
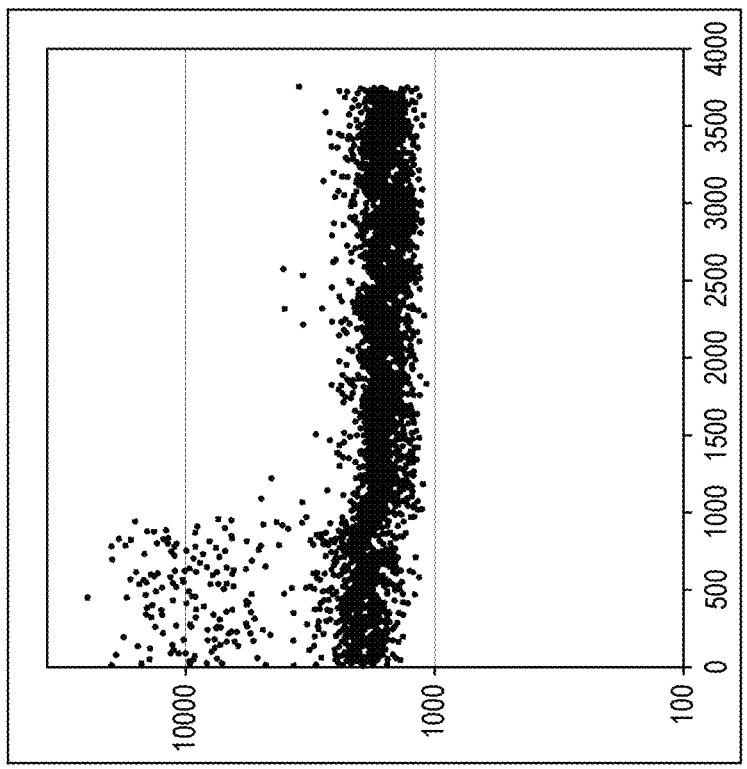
Figure 6B:
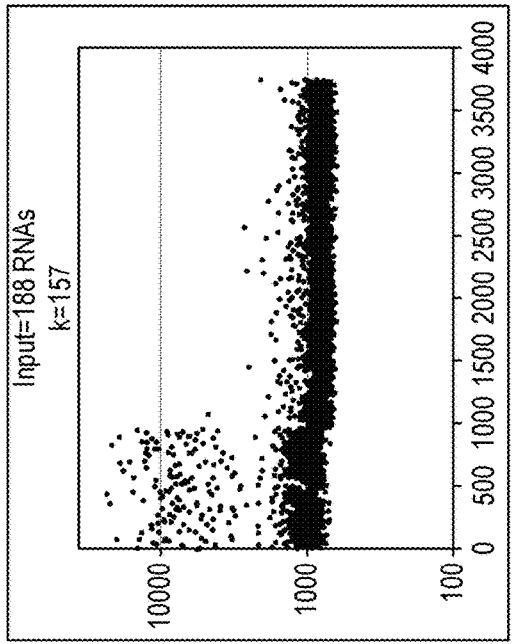
FIG. 6A-FIG. 6D show signals for the detection of labels in hybridized molecules
Figure 6D:
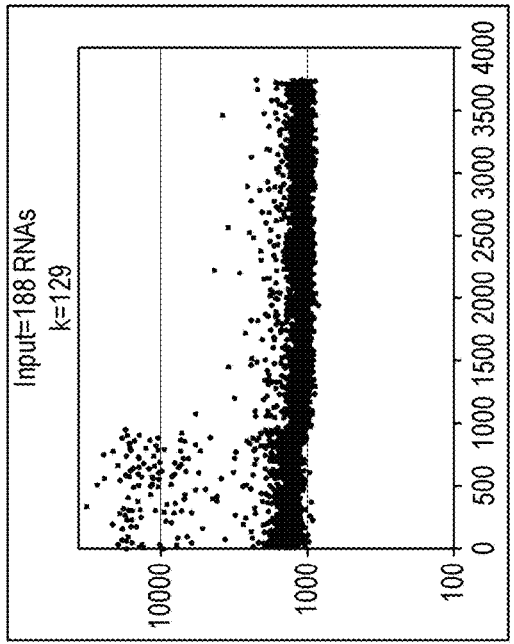
Figure 6A:
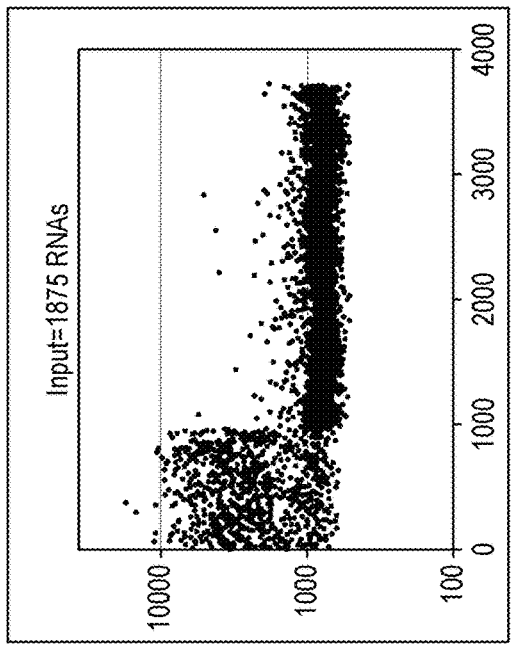
Figure 6C:
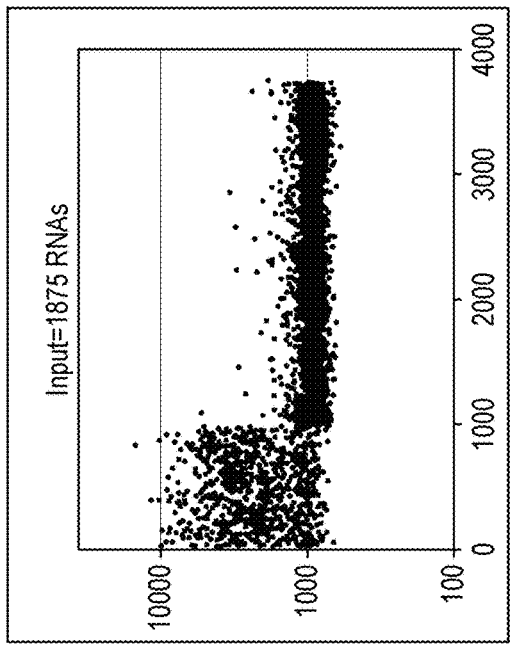

The performance of the wild type MMLV reverse transcriptase was compared with the RNase H minus mutant version (Superscript III) of the enzyme. 375 copies of an in vitro transcribed polyadenylated RNA was added to a carrier of 1 μg of a K562 cell line total RNA. The RNAs were added into a 12.6 μL reaction containing 1 μL of a 10 mM dNTP solution, 0.4 μL of a 10 μM second strand primer, 0.4 μL of a 10 μM pool of 960 oligo(dT) labels. The reaction was incubated at 65° C. for 5 min to denature the RNA, and then quickly chilled on ice. 4 μL of a 5× first strand buffer, 1 μL of a 0.1M DTT, 1 μL of superase RNase inhibitor (20 units) and 0.4 μL of Taq DNA polymerase (2 units) was added. Additionally, in reaction A, 1 μL (200 units) of the RNase H minus mutant (Superscript III) was added. And, in reaction B, 1 μL (200 units) of the wild type MMLV reverse transcriptase was added. The reactions were incubated at 42° C. for 60 min, followed by 3 cycles of 94° C. for 2 min, 55° C. for 2 min and 68° C. for 2 min. 1 unit of uracil DNA glycosylase was added and the reaction was mixed and moved to a new tube and incubated at 37° C. for 30 min. 5 μL of the reaction was then added to a 20 μL PCR reaction consisting of 1× Titanium buffer, 0.2 μM dNTP, 0.2 uM gene-specific forward primer, 0.2 μM universal reverse primer and 0.3 μL Titanium Taq polymerase. PCR conditions were 94° C. for 2 min followed by 30 cycles of 94° C. for 20 sec, 58° C. for 20 sec and 68° C. for 20 sec. A final incubation at 68° C. for 4 min was performed. A nested PCR is performed following the same conditions as the first PCR, except that a nested Forward primer was used. 2 μL of a 1:25 dilution of the initial PCR was used as template for the nested PCR. PCR products were randomly fragmented with DNase, biotin-labeled with Terminal transferase enzyme and then hybridized to a detector array for 12 hours at 37° C. Signals from hybridized DNAs were detected via staining with Streptavidin conjugated Phycoerytherin and imaging on a microarray scanner. FIG. 5A-B show the labels present in the hybridized DNA in reactions A and B, respectively. The number of labels present in the hybridized DNA is counted and used to determine the number of original copies of nucleic acid fragments.

| Reaction | # Input RNA molecules | Reverse Transcriptase | # of labels |
|----------|-----------------------|-----------------------|-------------|
| A | 188 | Superscript III | 159 |
| B | 188 | MMLV | 124 |

Example 6. Comparison of Polymerases for Second Strand Synthesis

The performance of Taq polymerase was compared to Titanium Taq polymerase. 1875 copies of an in vitro transcribed polyadenylated RNA was added to reaction A. 188 copies of an in vitro transcribed polyadenylated RNA was added to reaction B. 1875 copies of an in vitro transcribed polyadenylated RNA was added to reaction C. And, 188 copies of an in vitro transcribed polyadenylated RNA was added to reaction D. 1 µg of carrier RNA from a K562 cell line was added to each of the reaction mixtures. The RNAs were added into a 12.6 µL reaction containing 1 µL of a 10 mM dNTP solution, 0.4 µL of a 10 µM second strand primer, 0.4 µL of a 10 µM pool of 960 oligo(dT) labels. The reactions were incubated at 65° C. for 5 min to denature the RNA, and then quickly chilled on ice. 4 µL of a 5× first strand buffer, 1 µL of a 0.1M DTT, 1 µL of superase RNase inhibitor (20 units), reverse transcriptase, and 0.4 µL of Taq DNA polymerase (2 units) were added to each reaction. The reactions were incubated at 42° C. for 60 min, followed by 3 cycles of 94° C. for 2 min, 55° C. for 2 min and 68° C. for 2 min. 1 unit of uracil DNA glycosylase was added and the reaction was mixed and moved to a new tube and incubated at 37° C. for 30 min. 5 µL of reactions A and B were mixed with a 20 µL PCR reaction consisting of 1× Taq buffer, 0.2 µM dNTP, 0.2 uM gene-specific forward primer, 0.2 µM universal reverse primer and 0.3 µL Taq polymerase. 5 µL of reactions C and D were mixed with a 20 µL PCR reaction consisting of 1× Titanium buffer, 0.2 µM dNTP, 0.2 uM gene-specific forward primer, 0.2 µM universal reverse primer and 0.3 µL Titanium Taq polymerase. PCR conditions were 94° C. for 2 min followed by 30 cycles of 94° C. for 20 sec, 58° C. for 20 sec and 68° C. for 20 sec. A final incubation at 68° C. for 4 min was performed. A nested PCR is performed following the same conditions as the first PCR, except that a nested Forward primer was used. 2 µL of a 1:25 dilution of the initial PCR was used as template for the nested PCR. PCR products were randomly fragmented with DNase, biotin-labeled with Terminal transferase enzyme and then hybridized to a detector array for 12 hours at 37° C. Signals from hybridized DNAs were detected via staining with Streptavidin conjugated Phycoerytherin and imaging on a microarray scanner. FIG. 6A-D shows the labels present in the hybridized DNA in reactions A-D, respectively. The number of labels present in the hybridized DNA is counted and used to determine the number of original copies of nucleic acid fragments.

| Reaction | # Input RNA molecules | Polymerase | # of labels |
|---|---|---|---|
| A | 1875 | Taq | — |
| B | 188 | Taq | 157 |
| C | 1875 | Titanium Taq | — |
| D | 188 | Titanium Taq | 129 |

Example 7. Absolute Quantitation of mRNA by Counting Individual DNA Molecules mRNA molecules can be quantitated by the addition of labels prior to amplification of cDNA molecules (FIG. 19). Labeled cDNA molecules are formed by cDNA synthesis of an mRNA molecule by the addition of a deoxy-oligonucleotide primer with (1) an oligo dT sequence to anneal to the poly-A RNA tail; (2) a collection of predetermined or random sequence label tags; and (3) a common or universal PCR primer sequence. The labeled cDNA molecules are amplified using gene-specific primers and a common or universal PCR primer. After amplification, the number of labels of different sequence composition can be readily detected by hybridization, sequencing or other detection methods. The difficult task of counting the number of individual mRNA molecules in solution is transformed into the simple task of determining the number of types of different labels, each being present at high concentrations following amplification, provided that the initial label sequence diversity is sufficiently greater than the number of molecules present. Any other suitable method can also be used to incorporate labels into the RNA or cDNA molecules before or during amplification. Any other PCR or non-PCR based methods can also be used to amplify the RNA or cDNA molecules. Although helpful in these examples, amplification of the labeled molecules may not be required for detection.

Example 8. Digital Microarray for RNA Expression

The mRNA is reverse transcribed using a pool of n oligo-dT label primers (random primers with labels may also be used) (FIG. 20). The cDNA can be optionally amplified with methods such as PCR and T7 amplification. The labels are amplified along with each cDNA molecule. cDNAs are hybridized to digital arrays to determine the number of distinct labels for each gene of interest. Hybridization requires both presence of the gene sequence, most likely a segment on the 3'exon of the gene, and one of the label sequences. An array with 7 million features is sufficient to detect a collection of 350 labels applied to a sample with 20,000 different mRNA sequences to determine the number of copies of each mRNA present in the sample. A subset of the 350 label primers may be applied at a lower concentration to increase the effective dynamic range of measurement. This method is particularly advantageous for sampling limiting amounts of starting material, such as in single cells.

Example 9. Digital Microarray for DNA Copy Number

Genomic DNA is digested into small fragments in one or more reactions using one or more restriction enzymes. Adaptors with label sequences are ligated to the DNA fragments (FIG. 21). The ligated fragments are optionally amplified. Ligated fragments may optionally be digested with one or more restriction enzymes prior to amplification to prevent the replication of certain fragments, which is useful in the selective amplification of only fragments of interest. Hybridization to digital arrays detects the number of distinct labels ligated to each restricted fragment. Using 350 label sequences, an array of 7 million features can assay 20,000 fragments in the genome, which represents average intervals of 150 kb in humans. Additionally, some allele specific fragments may be assayed by choosing restriction enzymes (e.g., 4 base cutters) specific for an allele of interest.

Example 10. Digital Microarray for microRNAs

Labels are attached to the 3' and 5' ends of microRNA by ligation or other means (FIG. 22). The label-microRNA complex is reverse transcribed to generate label-DNA products. The label-DNA products are optionally amplified. The label-DNA products are hybridized on digital array to detect the number of labels per microRNA. miRBase 18 (http://www.mirbase.org/) was released in November 2011 and lists 1921 unique mature human miRNAs. An array of 2 million features can adequately detect 1000 labels ligated to the 1921 miRNAs.

Example 11. Digital Microarray for Single Cell Pre-Implantation Genetic Diagnosis (PGD)

Primary challenge with single-cell genomic DNA amplification assays is from allele dropout and replication bias. As shown in the computation modeling analysis in FIG. 43 where every molecule has a 0.8 probability of replication, molecules of 1:1 initial copy ratios can easily be distorted to 1:10 or greater just after a few replication cycles.

However, when labels are first attached prior to amplification, counting labels to determine copy number is unaffected by replication bias, so long as replication occurs. Although, this does not solve the problem of allele dropouts, aneuploidy determination and large regions of deletion or amplification can be easily and accurately determined. This is particularly useful for PGD applications.

Example 12. Digital Microarray for Measuring Fetal Aneuploidy in Maternal Circulating Nucleic Acids Digital microarray can be used to measure fetal aneuploidy in maternal circulating nucleic acids. A sample comprising maternal circulating nucleic acids is provided. The DNA is fragmented using a 4 base cutter. Labels are attached to the fragmented DNA. Circulate and multiplex PCR to amplify 40 chromosome 21 markers and 10 control chromosome markers. Detect amplified label-DNA products on an array of 5 million features. The number of copies of chromosome 21 can be used to determine the occurrence of fetal aneuploidy (FIG. 24).

Example 13. Absolute Quantitation of mRNA by Counting Individual DNA Molecules mRNA molecules can be quantitated by the incorporation of labels during first-strand cDNA synthesis (FIG. 25). Labeled cDNA molecules are formed by cDNA synthesis of an mRNA molecule by the addition of a deoxy-oligonucleotide primer with (1) an oligo dT sequence to anneal to the poly-A RNA tail; (2) a collection of predetermined or random sequence label tags; and (3) a common or universal PCR primer sequence. After first-strand cDNA synthesis, the number of labels of different sequence composition can be readily detected by hybridization, sequencing or other detection methods. The difficult task of counting the number of individual mRNA molecules in solution is transformed into the simple task of determining the number of types of different labels, each being present at high concentrations following amplification, provided that the initial label sequence diversity is sufficiently greater than the number of molecules present. Any other suitable method can also be used to incorporate labels into the RNA or cDNA molecules before or during first-strand cDNA synthesis.

Example 14: Titration Experiment with Serial Dilutions of Kanamycin RNA

Figure 35:
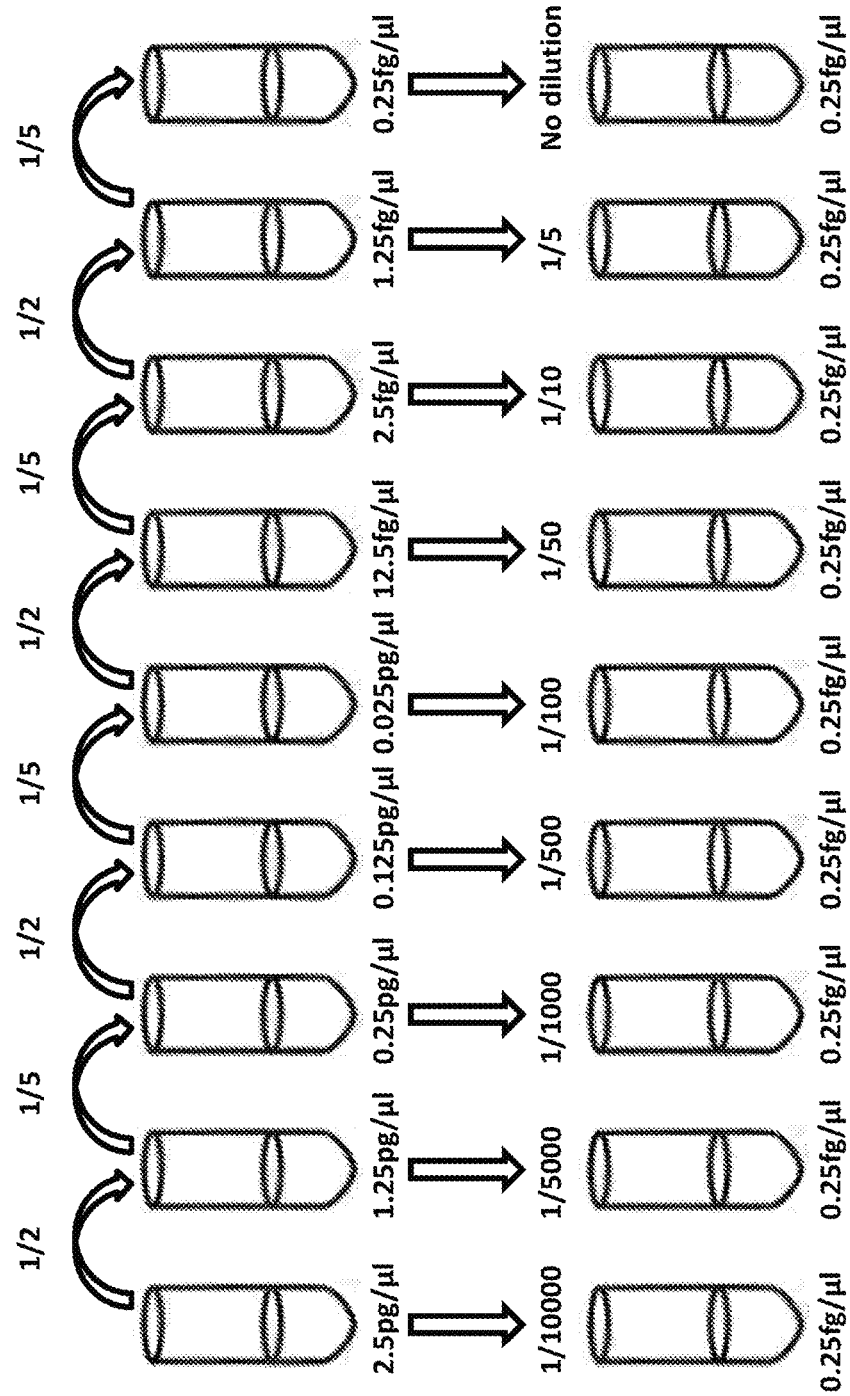
Figure 36A:
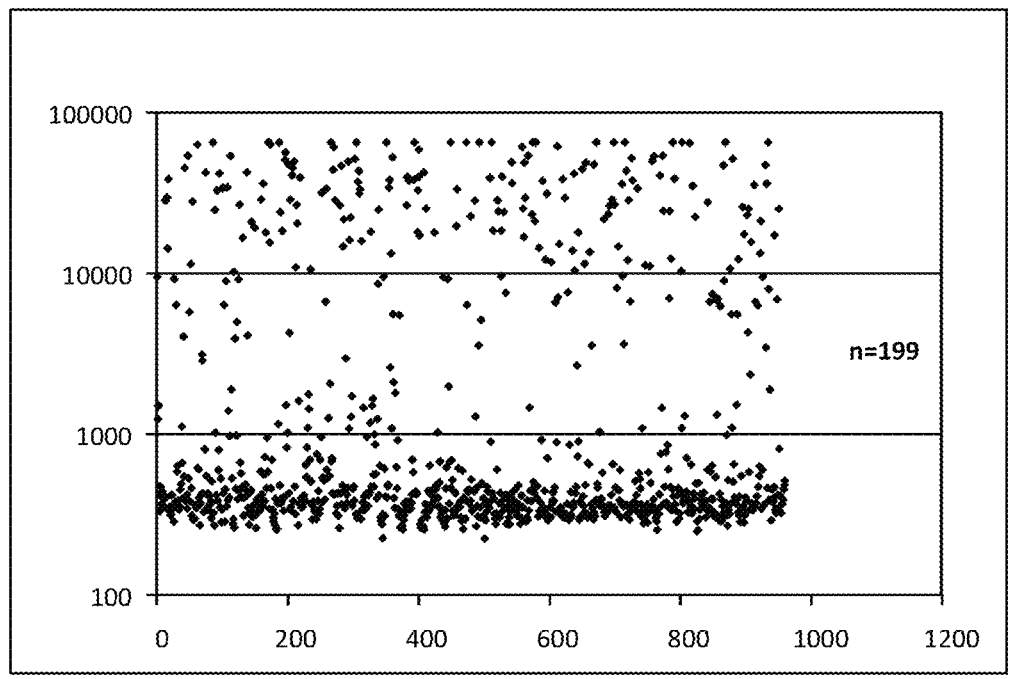
FIG. 36A-FIG. 36H show the scatter plots of results for the titration experiment with serial dilutions of kanamycin RNA
Figure 36B:
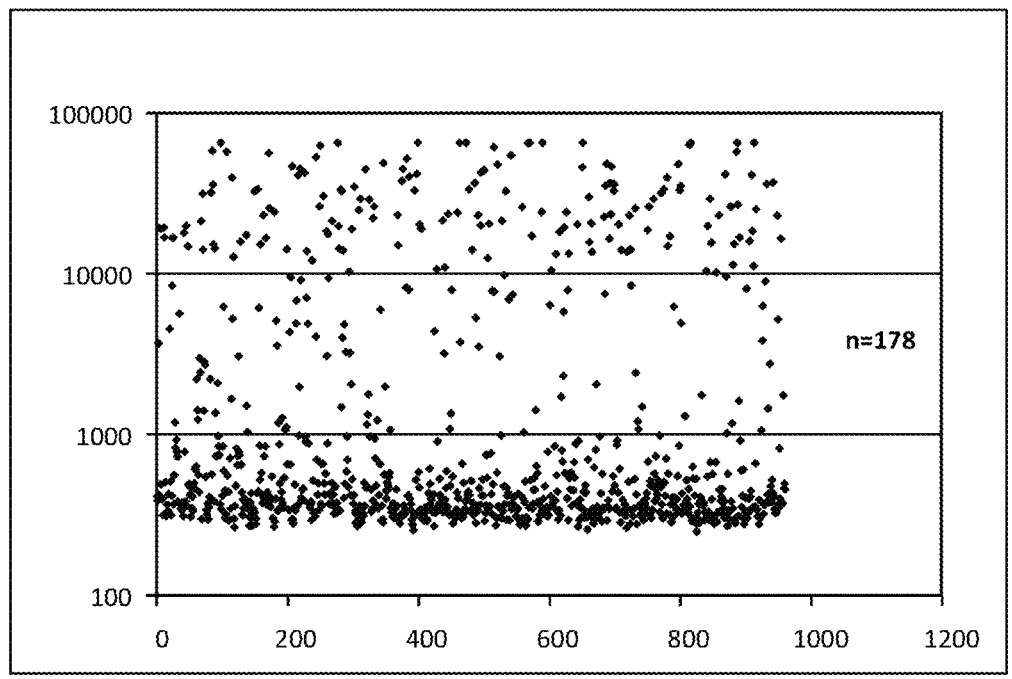
Figure 36C:
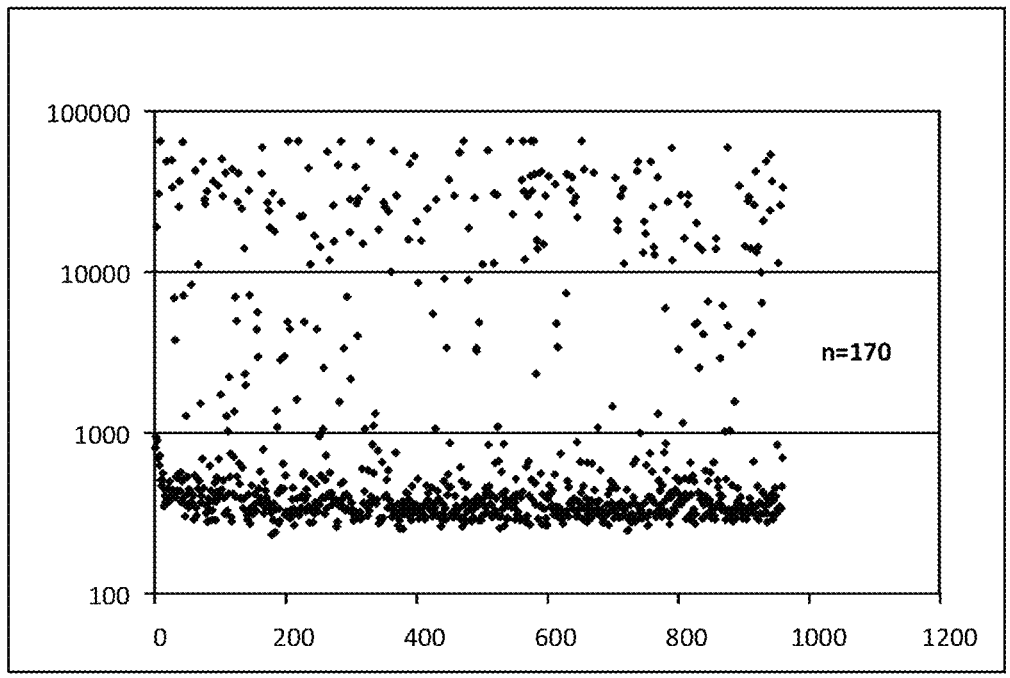
Figure 36D:
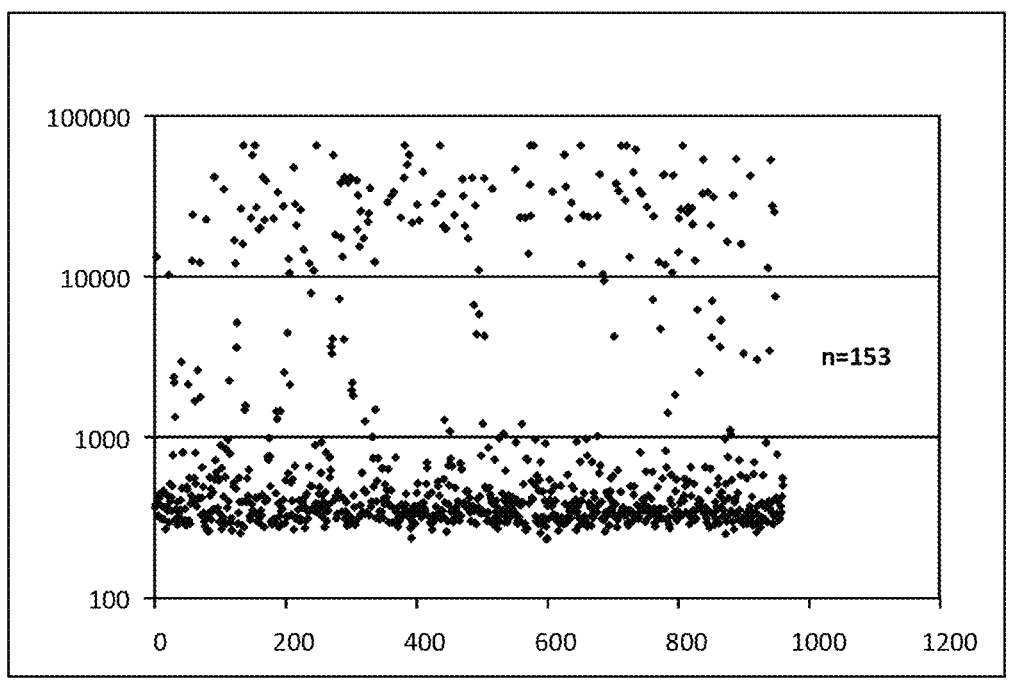
Figure 36E:
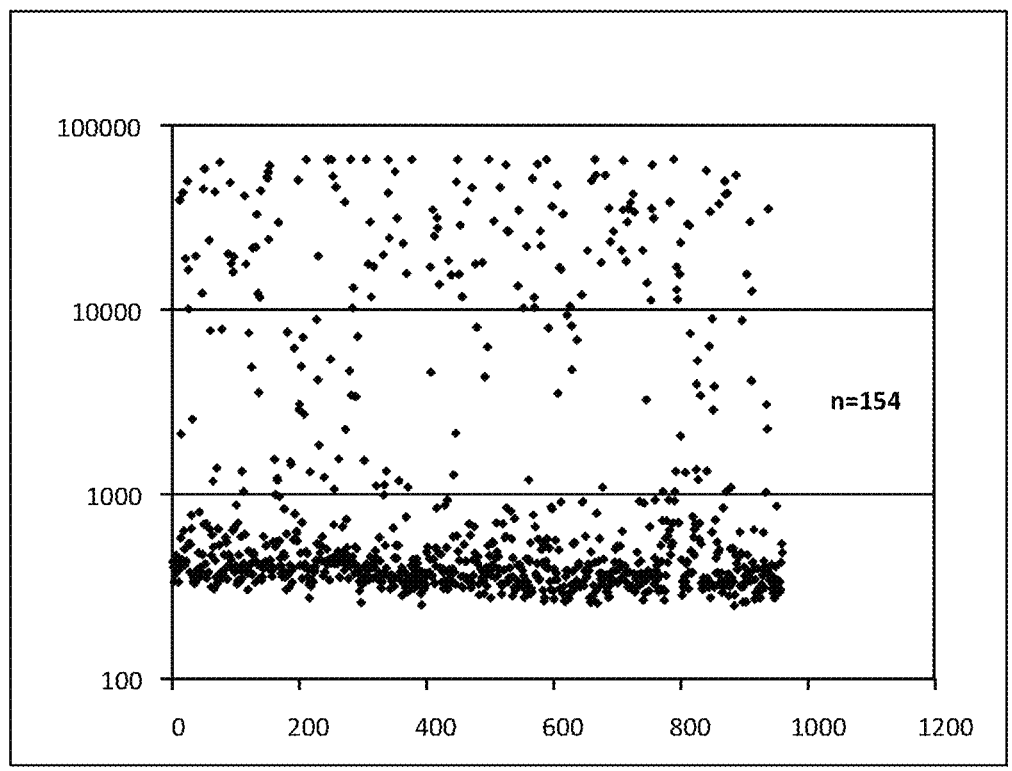
Figure 36F:
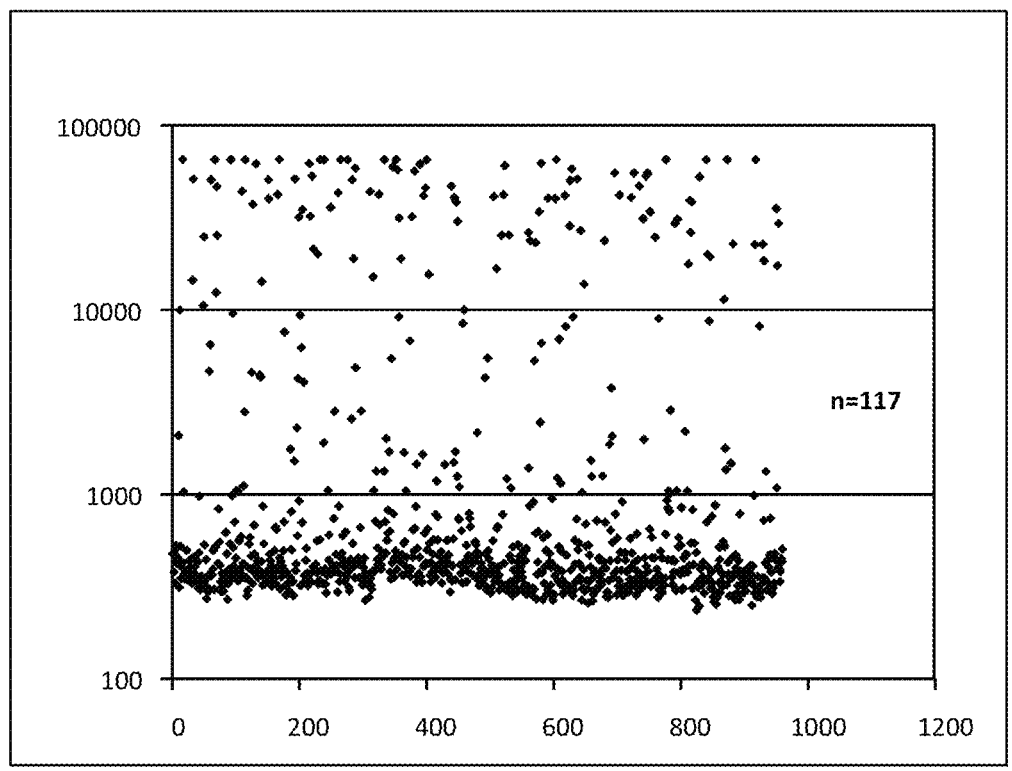
Figure 36G:
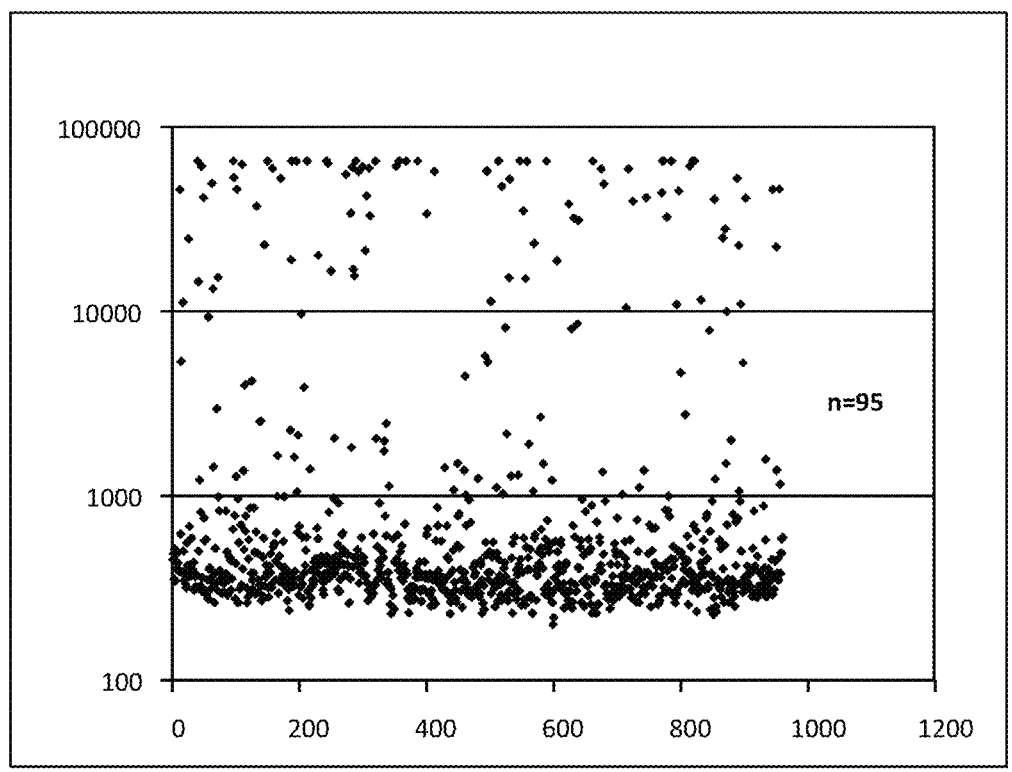
Figure 36H:
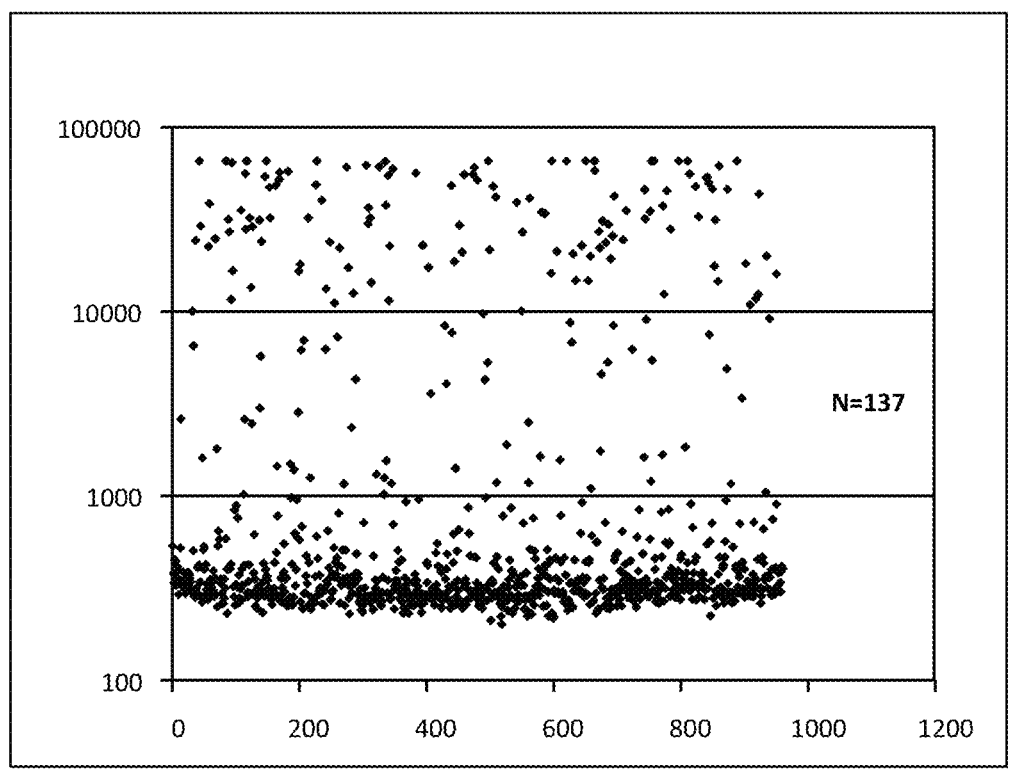
Figure 37:
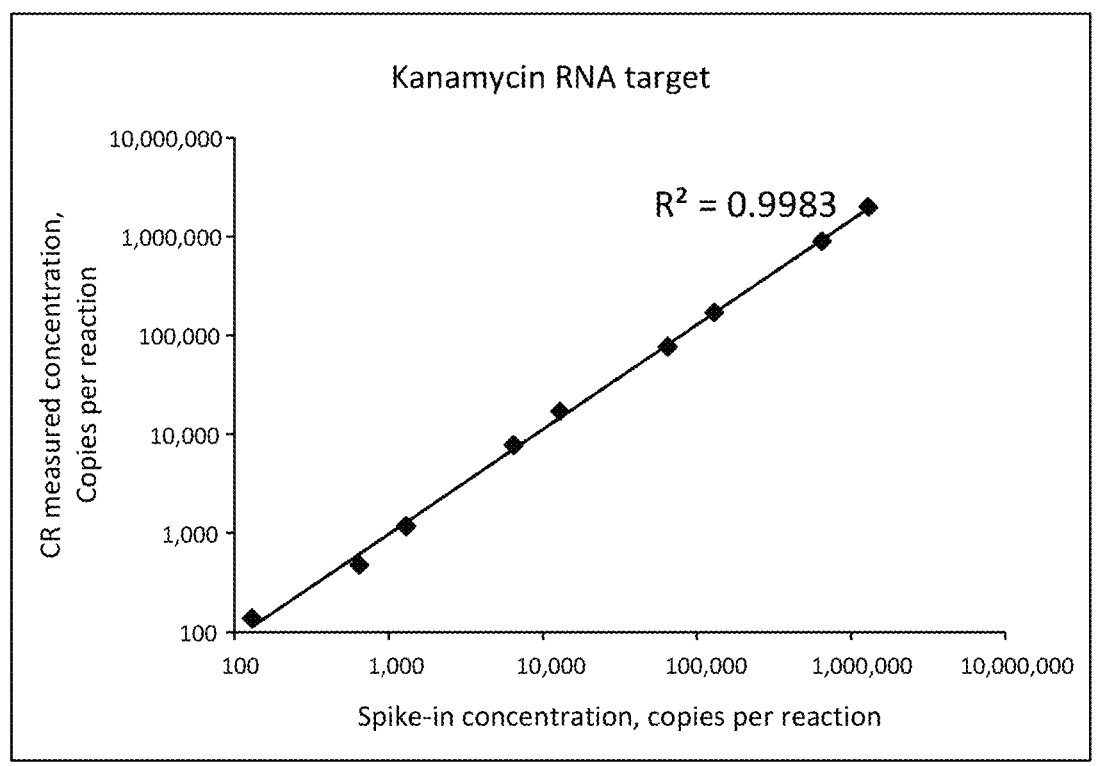
FIG. 37 shows the Correlation graph for the titration experiment with serial dilutions of kanamycin RNA FIG. 38 Schematic of the serial dilution scheme for the titration experiment with serial dilutions of human liver RNA to measure GAPDH expression

A titration curve was generated by performing serial dilutions of kanamycin RNA to illustrate the broad dynamic range of the absolute counting protocol. Each of 9 serial dilutions was normalized to a concentration of 0.25 fg/µl from 2.5 pg/µl, 1.25 pg/µl, 0.25 pg/µl, 0.125 pg/µl, 0.025 pg/µl, 12.5 fg/µl, 2.5 fg/µl, 1.25 fg/µl and 0.25 fg/µl. All of the dilutions were made using a dilution solution of 1 ng/µl E. Coli total RNA in tubes pre-rinsed with a solution of 10 ng/µl yeast RNA to hinder the sticking of the sample RNA to the walls of the tube. The samples were added to a 12.6 µl reaction containing 1 µg E. Coli total RNA, 1 µl of a 10 mM solution of dNTP's, 0.4 µl of a 10 uM dU primer specific for kanamycin and 0.4 µl of a 10 µM pool of 960 dT oligo labels. The reaction was incubated at 65° C. for 5 min to denature the RNA, and then quickly chilled on ice. 4 µL of a 5× first strand buffer, 1 µL of a 0.1M DTT, 1 µL of superase RNase inhibitor (20 units), 1 µL (200 units) of the wild type MMLV reverse transcriptase and 0.4 µL of Taq DNA polymerase (2 units) were added. The reactions were incubated at 37° C. for 60 min, followed by 3 cycles of 94° C. for 2 min, 55° C. for 2 min and 72° C. for 2 min. 1 unit of uracil DNA glycosylase was added and the reaction was mixed and moved to a new tube and incubated at 37° C. for 30 min. 5 µL of the reaction was then added to a 20 µL PCR reaction consisting of 1× Taq Reaction buffer, 0.2 µM dNTP, 0.05 uM gene-specific forward primer, 0.05 µM universal reverse primer and 0.3 µL Taq polymerase. PCR conditions were 94° C. for 2 min followed by 30 cycles of 94° C. for 20 sec, 58° C. for 20 sec and 72° C. for 20 sec. A final incubation at 72° C. for 4 min was performed. A nested PCR was performed using a nested forward primer and the universal reverse primer with a Cy3 label attached. 0.5 µl of the initial PCR was used as template for the nested PCR. PCR conditions were the same as for the first PCR except that the 58° C. step was performed at 55° C. The samples were hybridized to a detector array at 37° C. overnight and scanned the following day using a fluorescence reader to detect which positions on the array contained the Cy3 label. The number of positive spots was used to determine the initial concentration of sample. FIG. 35 shows the dilution scheme. FIG. 36A-H shows the scatter plots of results and Table 1 shows the results. FIG. 37 shows the correlation graph.

TABLE 1

| FIG | Initial Concentration | Dilution Factor | Expected Count | Actual Count |
|---|---|---|---|---|
| 36A | 2.5 pg/µL | 10000 | 130 | 199 |
| 36B | 1.25 pg/µL | 5000 | 130 | 178 |
| 36C | 0.25 pg/µL | 1000 | 130 | 170 |
| 36D | 0.125 pg/µL | 500 | 130 | 153 |
| 36E | 1.025 pg/µL | 50 | 130 | 154 |
| 36F | 12.5 fg/µL | 10 | 130 | 117 |
| 36G | 2.5 fg/µL | 5 | 130 | 95 |
| 36H | 1.25 fg/µL | 1 | 130 | 137 |

Figure 38:
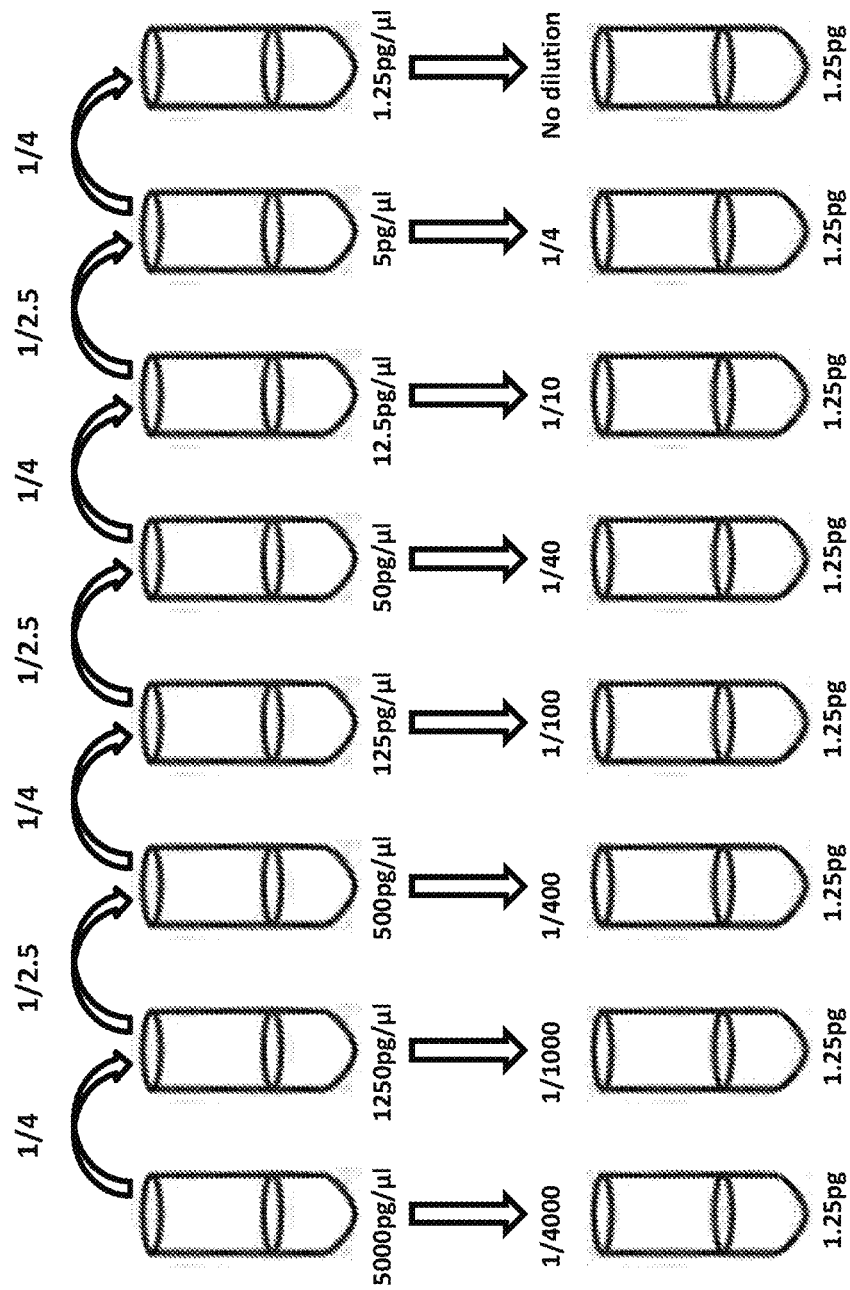
Figure 39A:
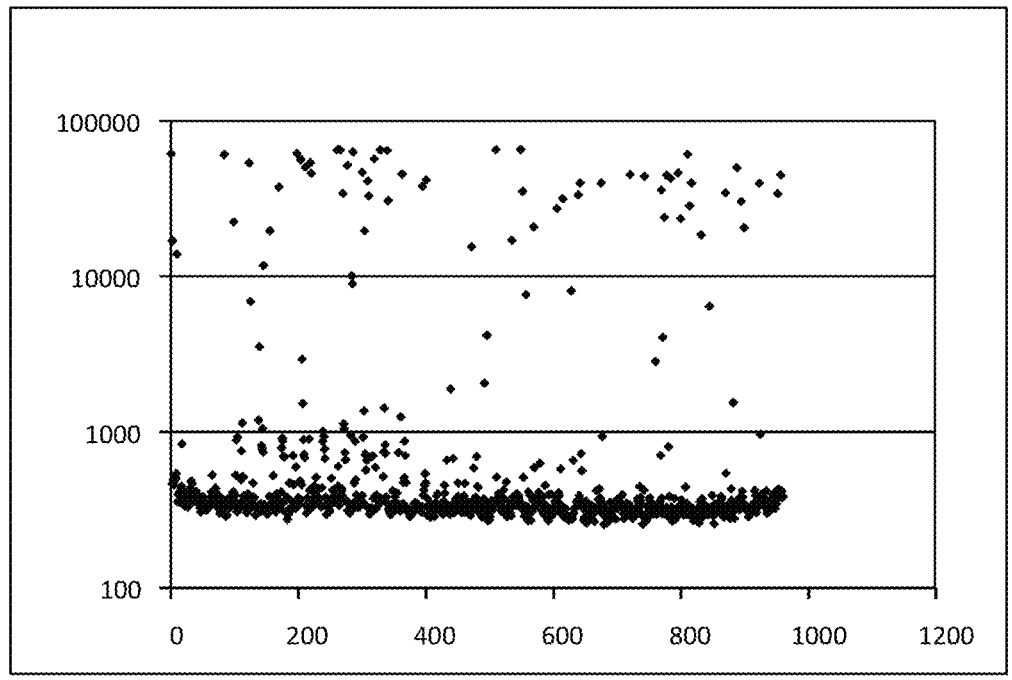
FIG. 39A-FIG. 39H show the scatter plots of results for the titration experiment with serial dilutions of human liver RNA to measure GAPDH expression
Figure 39B:
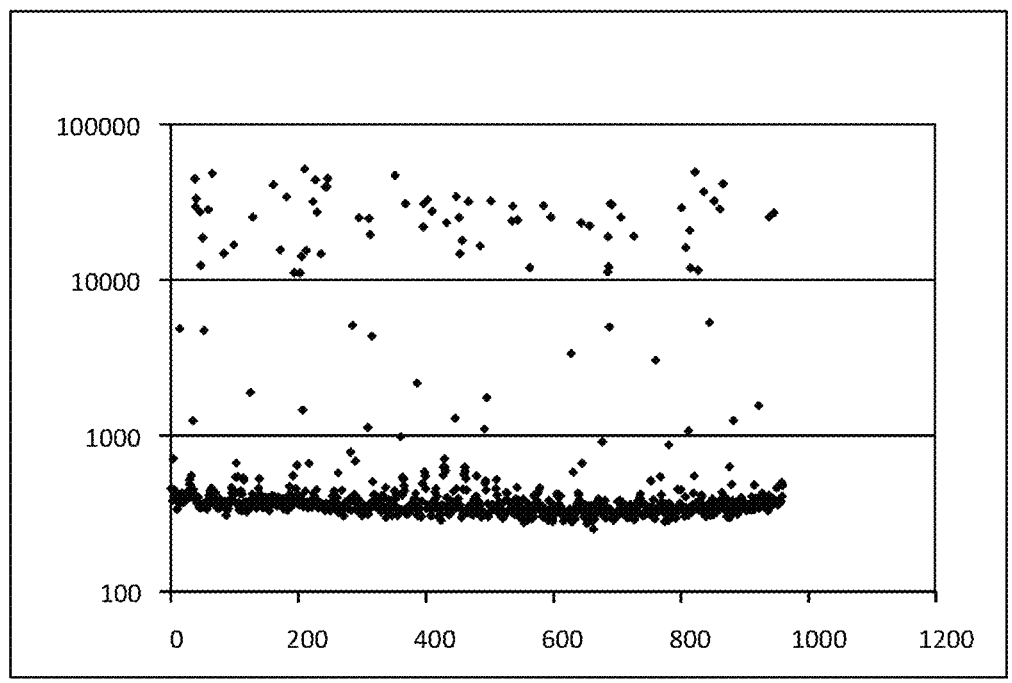
Figure 39C:
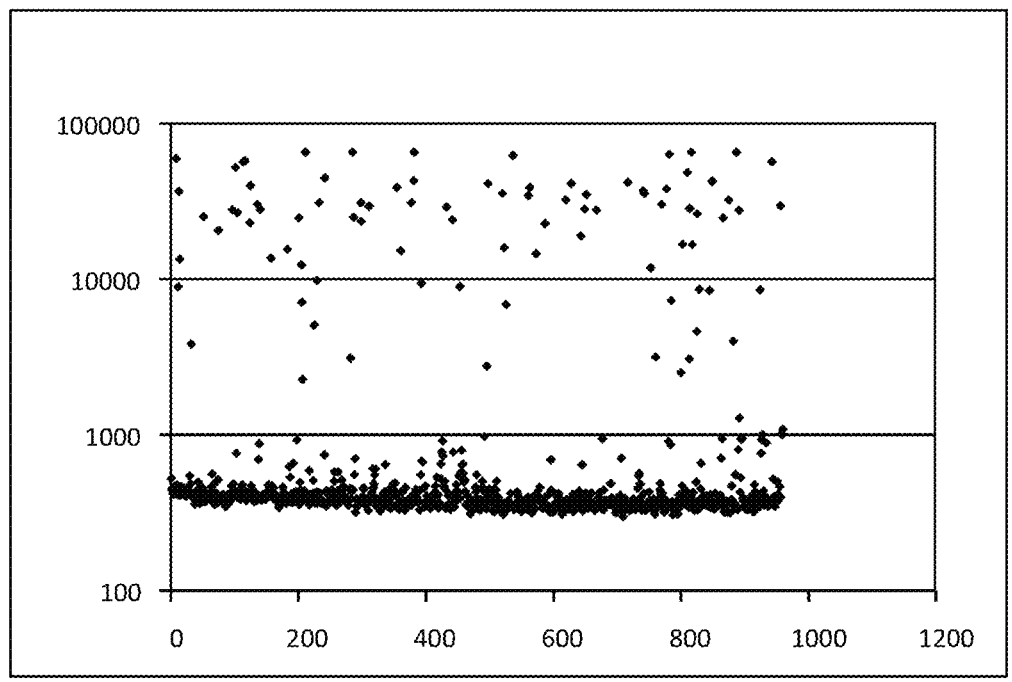
Figure 39D:
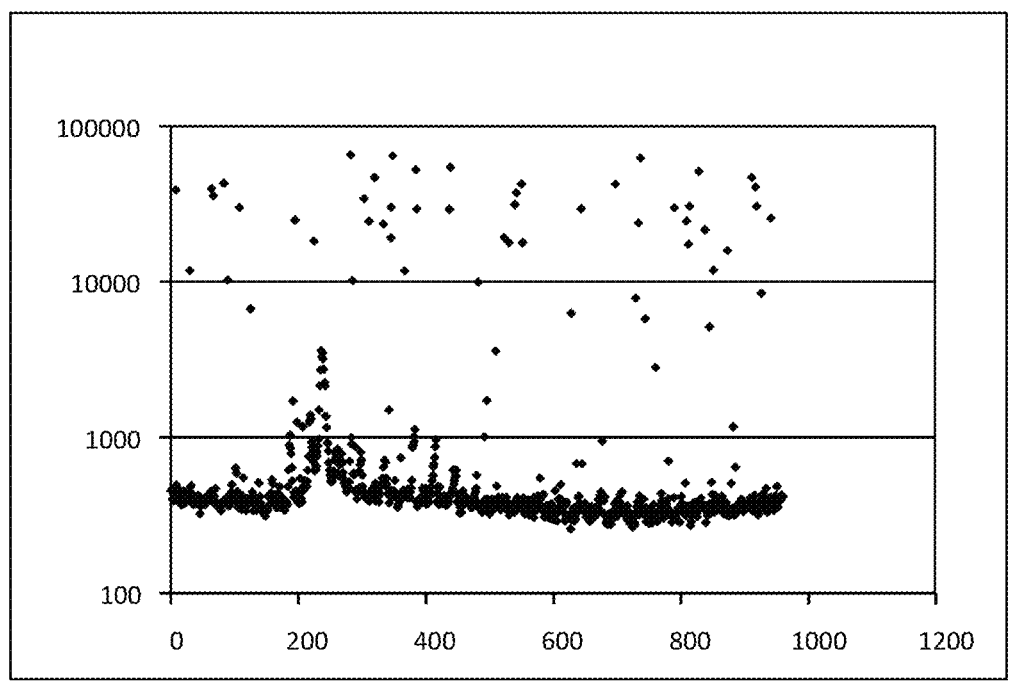
Figure 39E:
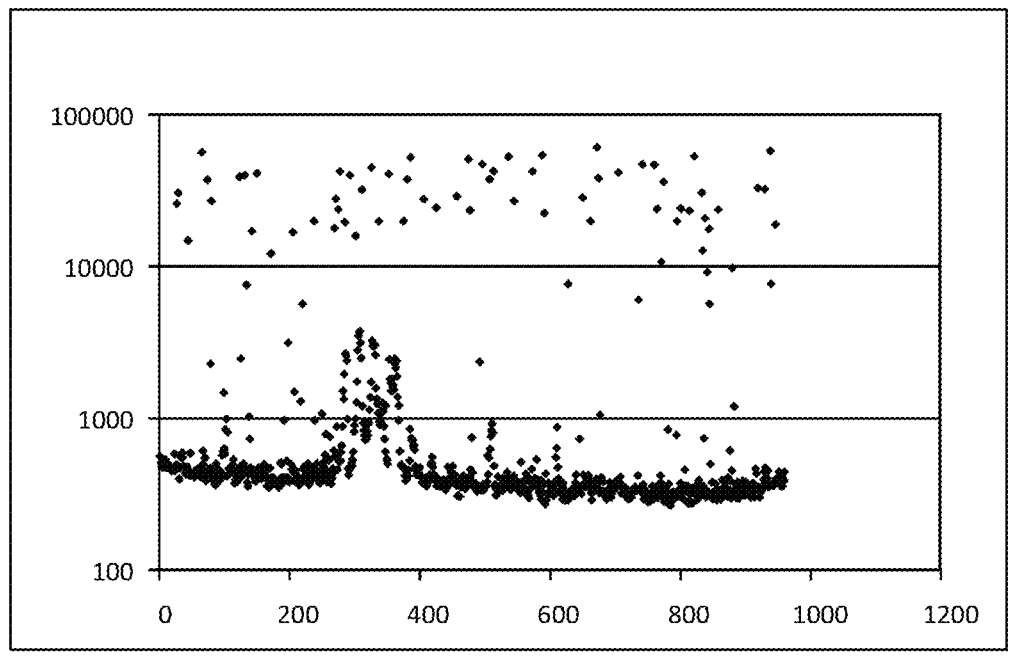
Figure 39F:
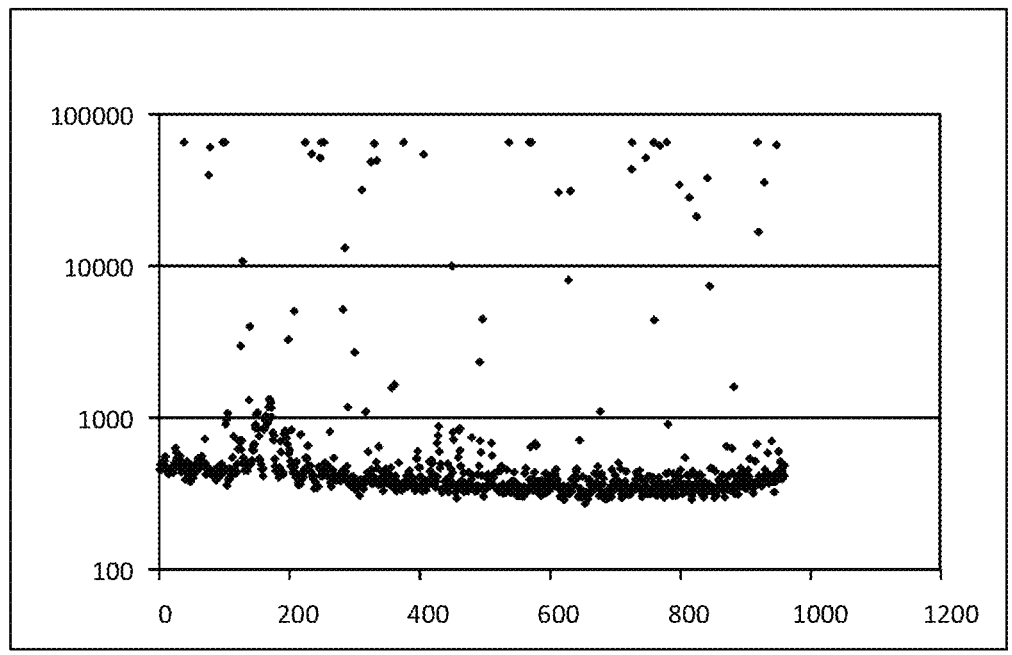
Figure 39G:
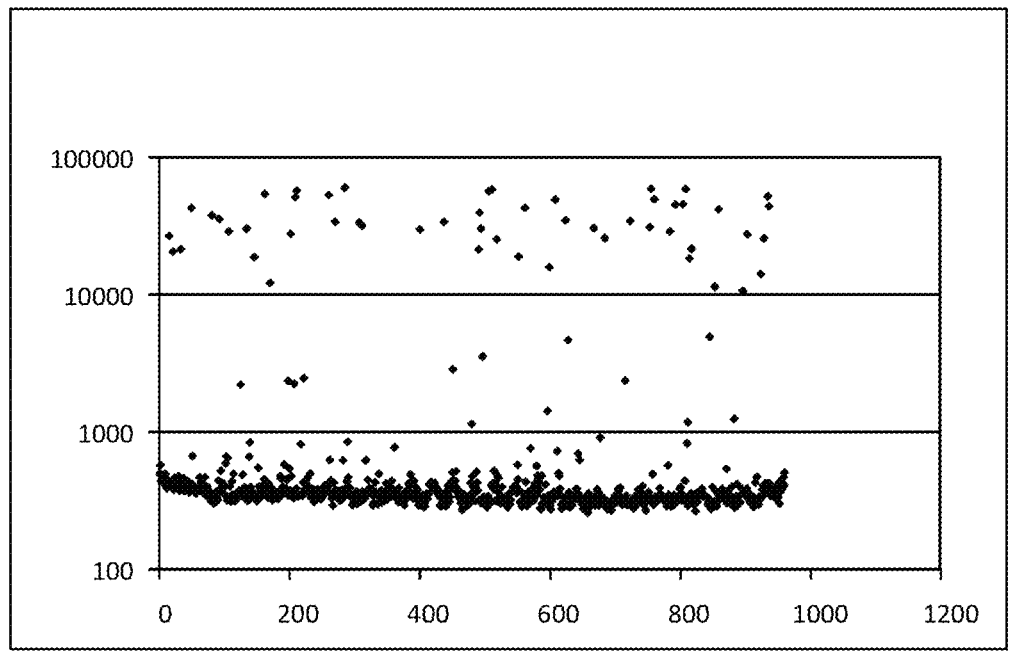
Figure 39H:
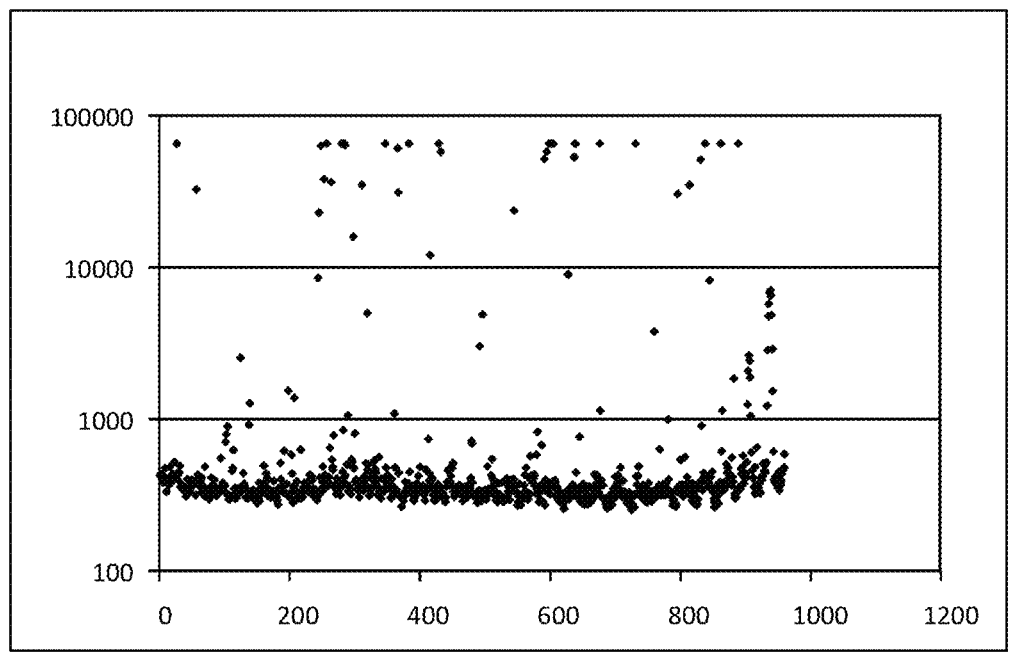
Figure 40:
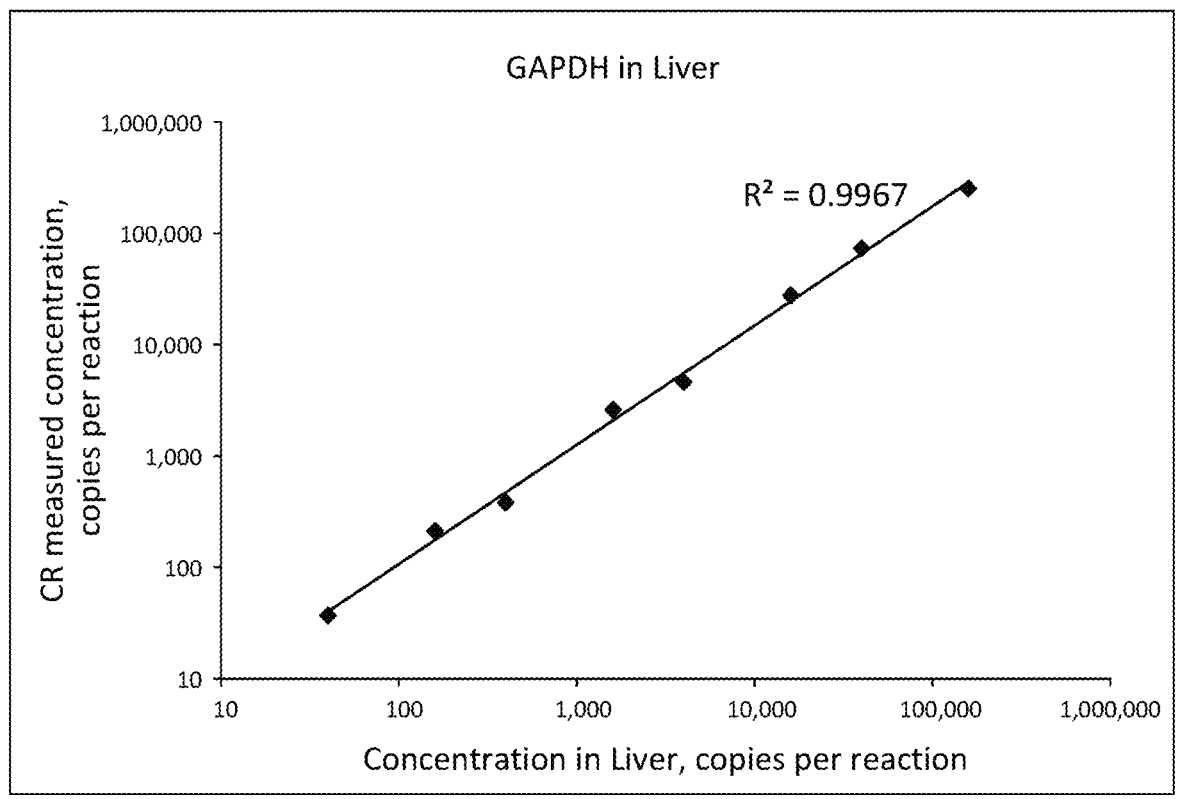
FIG. 40 shows the correlation graph for the titration experiment with serial dilutions of human liver RNA to measure GAPDH expression
Figure 41A:
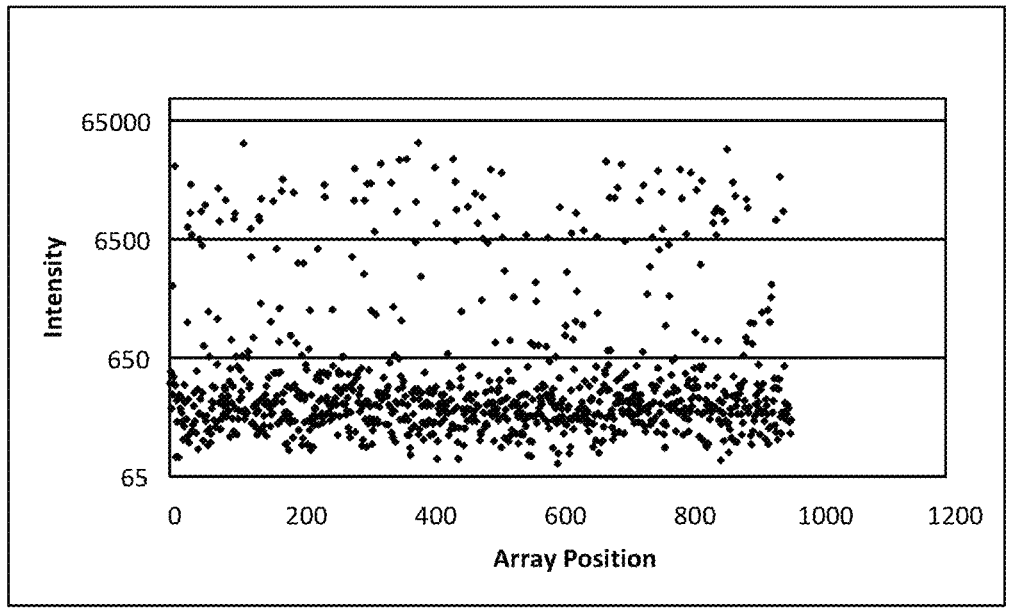
FIG. 41A-FIG. 41D show the scatter plots of results for the accurate measurements of control bacterial genes
Figure 41B:
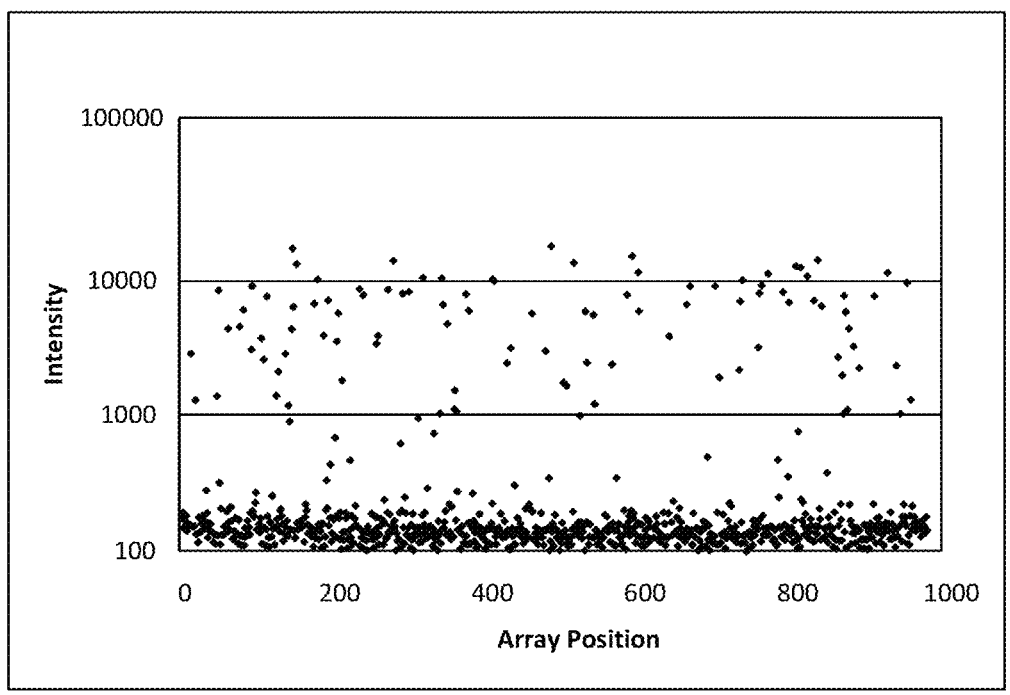
Figure 41C:
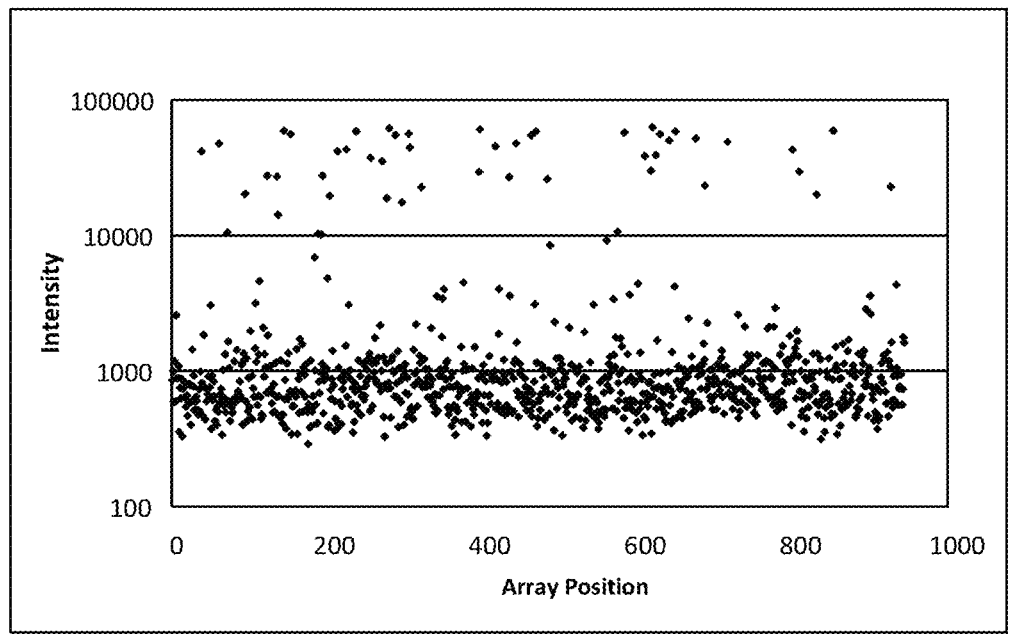
Figure 41D:
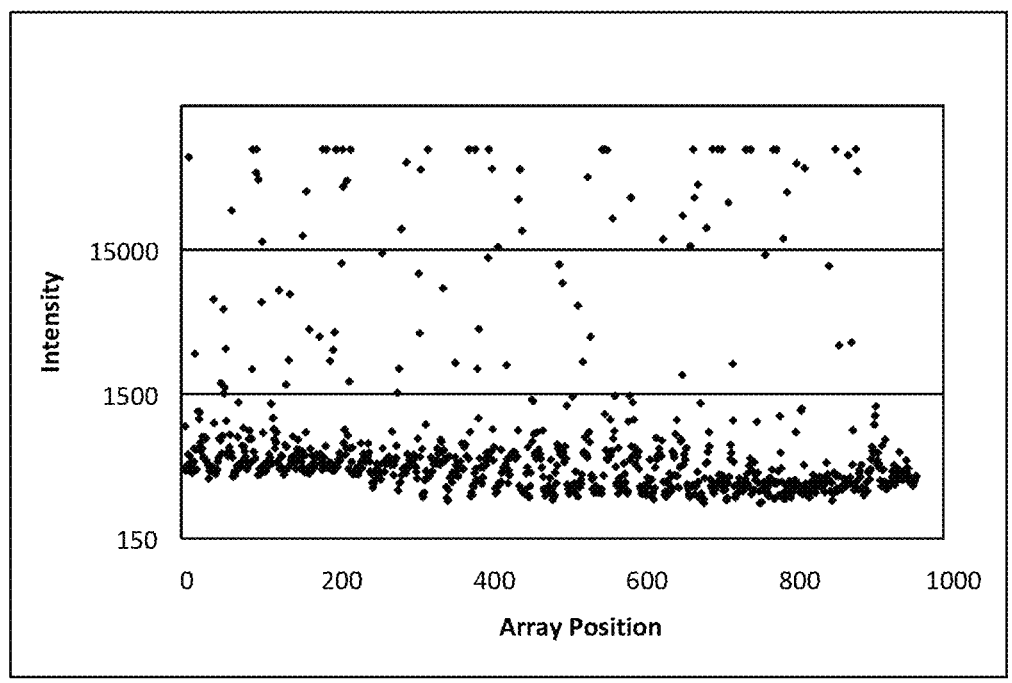

Example 15: Titration Experiment with Serial Dilutions of Human Liver RNA to Measure GAPDH Expression A titration curve was generated by performing serial dilutions of human liver total RNA to illustrate the ability of the stochastic labeling protocol to detect levels of gene expression. Each of 8 serial dilutions was normalized to a concentration of 1.25 pg/µl from 5000 pg/µl, 1250 pg/µl, 500 pg/µl, 125 pg/µl, 50 pg/µl, 12.5 pg/µl, 5 pg/µl and 1.25 pg/µl. All of the dilutions were made using a dilution solution of 1 ng/µl E. Coli total RNA in tubes pre-rinsed with a solution of 10 ng/µl yeast RNA to hinder the sticking of the sample RNA to the walls of the tube. The samples were added to a 12.6 µl reaction containing 1 µg E. Coli total RNA, 1 µl of a 10 mM solution of dNTP's, 0.4 µl of a 10 uM dU primer specific for GAPDH and 0.4 µl of a 10 µM pool of 960 dT oligo labels. The reaction was incubated at 65° C. for 5 min to denature the RNA, and then quickly chilled on ice. 4 µL of a 5× first strand buffer, 1 µL of a 0.1 M DTT, 1 µL of superase RNase inhibitor (20 units), 1 µL (200 units) of the wild type MMLV reverse transcriptase and 0.4 µL of Taq DNA polymerase (2 units) was added. The reactions were incubated at 37° C. for 60 min, followed by 3 cycles of 94° C. for 2 min, 55° C. for 2 min and 72° C. for 2 min. 1 unit of uracil DNA glycosylase was added and the reaction was mixed and moved to a new tube and incubated at 37° C. for 30 min. 5 µL of the reaction was then added to a 20 µL PCR reaction consisting of 1× Taq Reaction buffer, 0.2 µM dNTP, 0.05 uM gene-specific forward primer, 0.05 µM universal reverse primer and 0.3 µL Taq polymerase. PCR conditions were 94° C. for 2 min followed by 30 cycles of 94° C. for 20 sec, 58° C. for 20 sec and 72° C. for 20 sec. A final incubation at 72° C. for 4 min was performed. A nested PCR was performed using a nested forward primer and the universal reverse primer with a Cy3 label attached. 0.5 µl of the initial PCR was used as template for the nested PCR. PCR conditions were the same as for the first PCR except that the 58° C. step was performed at 55° C. The samples were hybridized to a detector array at 37° C. overnight and scanned the following day using a fluorescence reader to detect which positions on the array contained the Cy3 label. The number of positive spots was used to determine the initial concentration of sample. FIG. 38 shows the dilution scheme. FIG. 39 shows the scatter plots of results and Table 2 shows the results. FIG. 40 shows and correlation graph.

TABLE 2

| FIG | Initial Concentration | Dilution Factor | Actual Count |
|---|---|---|---|
| 39A | 5000 pg/µL | 4000 | 73 |
| 39B | 1250 pg/µL | 1000 | 63 |
| 39C | 500 pg/µL | 400 | 69 |
| 39D | 125 pg/µL | 100 | 46 |
| 39E | 50 pg/µL | 40 | 65 |
| 39F | 12.5 pg/µL | 10 | 38 |
| 39G | 5 pg/µL | 4 | 53 |
| 39H | 1.25 pg/µL | 1 | 37 |

Example 16: Measurements of Control Bacterial Genes

The protocol was validated using Poly A bacterial control RNAs (Lys, Thr, Dap and Phe), as well as RNA from the Kanamycin resistance gene. 4 different dilutions of each control were used to validate the accuracy of the counts. The samples were added to a 12.6 µl reaction containing 1 µg E. Coli total RNA, 1 µl of a 10 mM solution of dNTP's, 0.4 µl of a 10 uM gene specific dU primer and 0.4 µl of a 10 µM pool of 960 dT oligo labels. The reaction was incubated at 65° C. for 5 min to denature the RNA, and then quickly chilled on ice. 4 µL of a 5× first strand buffer, 1 µL of a 0.1 M DTT, 1 µL of superase RNase inhibitor (20 units), 1 µL (200 units) of the wild type MMLV reverse transcriptase and 0.4 µL of Taq DNA polymerase (2 units) was added. The reactions were incubated at 37° C. for 60 min, followed by 3 cycles of 94° C. for 2 min, 55° C. for 2 min and 72° C. for 2 min. 1 unit of uracil DNA glycosylase was added and the reaction was mixed and moved to a new tube and incubated at 37° C. for 30 min. 5 µL of the reaction was then added to a 20 µL PCR reaction consisting of 1× Taq Reaction buffer, 0.2 µM dNTP, 0.05 uM gene-specific forward primer, 0.05 µM universal reverse primer and 0.3 µL Taq polymerase. PCR conditions were 94° C. for 2 min followed by 30 cycles of 94° C. for 20 sec, 58° C. for 20 sec and 72° C. for 20 sec. A final incubation at 72° C. for 4 min was performed. A nested PCR was performed using a nested forward primer and the universal reverse primer with a Cy3 label attached. 0.5 µl of the initial PCR was used as template for the nested PCR. PCR conditions were the same as for the first PCR except that the 58° C. step was performed at 55° C. The samples were hybridized to a detector array at 37° C. overnight and scanned the following day using a fluorescence reader to detect which positions on the array contained the Cy3 label. The number of positive spots was used to determine the initial concentration of sample. FIG. 41 shows scatter plots of the results from the lowest concentration dilutions and Table 3 displays a summary table of the results.

TABLE 3

| FIG. | Gene | Copies in reaction (manufacturer) | Copies measured (CR) | Copies measured (digital PCR) |
|---|---|---|---|---|
| 41A | Lys (B. subtilis) | 190 | 195 | |
| 41B | Dap (B. subtilis) | 137 | 119 | |
| 41C | Phe (B. subtilis) | 162 | 116 | |
| 41D | Thr (B. subtilis) | 189 | 108 | |
| 42 | Kanamycin resistance gene (plasmid) | 750 | 608 | 520 |

Figure 42:
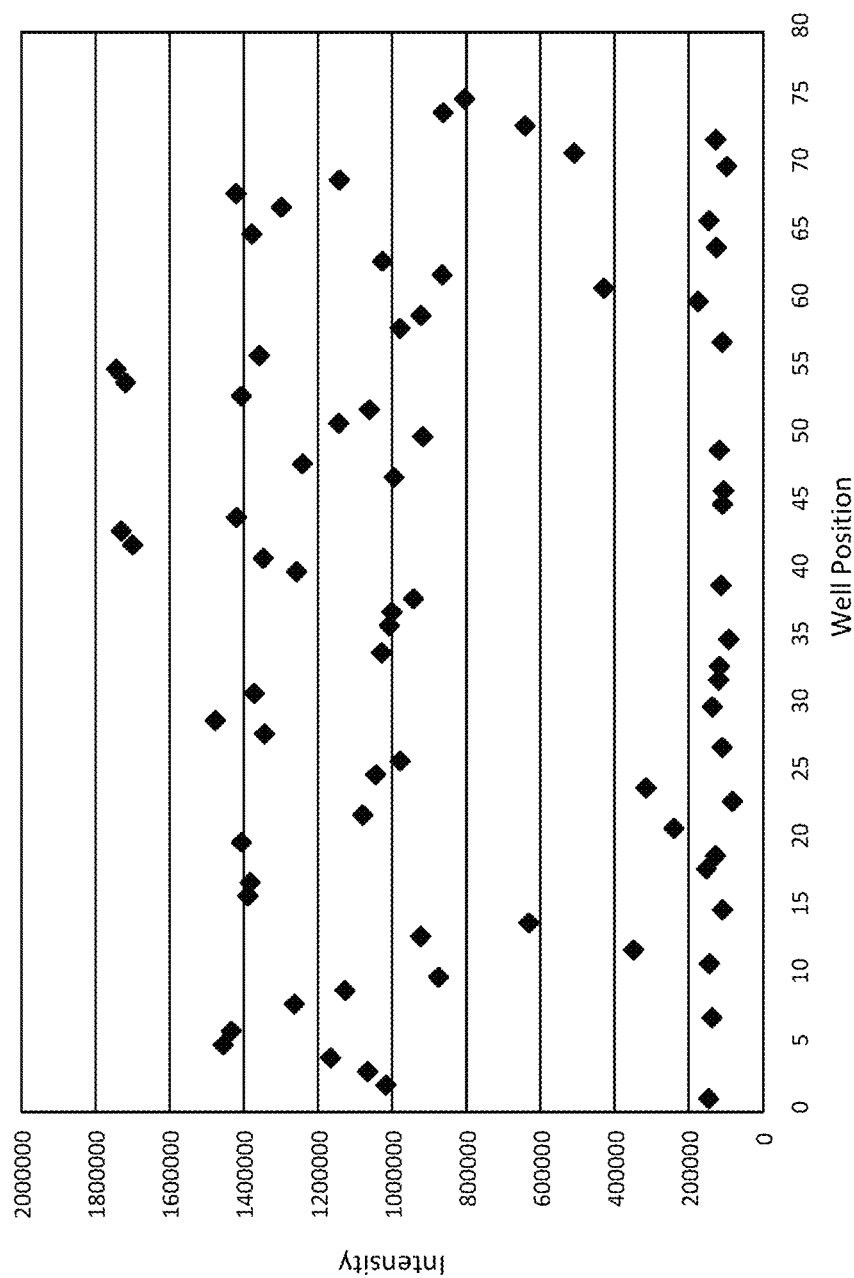
FIG. 42 shows the scatter plot for the validation of kanamycin counts by digital PCR experiment FIG. 43 Schematic of the method for absolute quantitation of mRNA molecules directly from cell lysates

Example 17: Comparison of Quantification of Kanamycin RNA by Stochastic Labeling and Digital PCR The counts of kanamycin RNA generated by stochastic labeling were compared to the counts obtained from digital PCR as another example of validation. 5 µg of kanamycin RNA was added to a 13 µl reaction containing 2 µg of E. Coli total RNA, 1 µl of a 10 mM solution of dNTP's and 2 µl of a 10 uM solution of 960 dT oligo labels. The sample was heated to 65° C. for 5 minutes, then chilled on ice. 4 µL of a 5× first strand buffer, 1 µL of a 0.1M DTT, 1 µL of superase RNase inhibitor (20 units), 1 µL (200 units) of Superscript III reverse transcriptase was added to the reaction. The sample was incubated at 50° C. for 60 minutes, then heated to 70° C. for 15 minutes, then cooled to 4° C. 2 units of RNase H were added and the sample was incubated at 37° C. for 20 minutes. 29 µl of TE was added after the final incubation. A 50 million-fold serial dilution was performed and 1 ul was used in seventy-five 15 ul digital PCR reactions. Each of these reactions contained 7.5 µl of a 2× SYBR PCR master mix, 0.13 µl of a 10 uM kanamycin forward primer and 0.13 µl of a 10 uM kanamycin reverse primer. PCR conditions included an initial incubation at 95° C. for 30 seconds followed by 45 cycles of 95° C. for 15 seconds and 58° C. for 60 seconds. A melting curve program followed the PCR for the purpose of validating the results. FIG. 42 shows the scatter plot of results and Table 3 shows the summary of the counts for kanamycin. FIG. 42 shows the dPCR results of 0.0002 pg Kanamycin RNA using SYBR green qPCR reagents. As shown in FIG. 42, 50 positive wells were observed out of 75 reactions, n=104 molecules present in 0.0002 pg (520 molecules present in 0.001 pg).

Example 18: Gene Expression Measurements in Liver RNA

The gene expression values of targets of varying abundance were measured using stochastic labeling. Based on previous assumptions of transcript abundance, differing concentrations of human liver total RNA were used to test each of 9 genes; GAPDH, B2M, RPL19, SDHA, GUSB, TUBB, ABCF1, G6PD, and TBP. The RNA quantities used in each reaction were designed to target the ideal counting range of 1-300 molecules and they were 0.625 pg, 1.25 pg, 1.25 pg, 125 pg, 12.5 pg, 12.5 pg, 2500 pg, 650 µg and 650 pg, respectively. The samples were added to a 12.6 µl reaction containing 1 µg E. Coli total RNA, 1 µl of a 10 mM solution of dNTP's, 0.4 µl of a 10 uM gene specific dU primer and 0.4 µl of a 10 µM pool of 960 dT oligo labels. The reaction was incubated at 65° C. for 5 min to denature the RNA, and then quickly chilled on ice. 4 µL of a 5× first strand buffer, 1 µL of a 0.1 M DTT, 1 µL of superase RNase inhibitor (20 units), 1 µL (200 units) of the wild type MMLV reverse transcriptase and 0.4 µL of Taq DNA polymerase (2 units) was added. The reactions were incubated at 37° C. for 60 min, followed by 3 cycles of 94° C. for 2 min, 55° C. for 2 min and 72° C. for 2 min. 1 unit of uracil DNA glycosylase was added and the reaction was mixed and moved to a new tube and incubated at 37° C. for 30 min. 5 µL of the reaction was then added to a 20 µL PCR reaction consisting of 1× Taq Reaction buffer, 0.2 µM dNTP, 0.05 uM gene-specific forward primer, 0.05 µM universal reverse primer and 0.3 µL Taq polymerase. PCR conditions were 94° C. for 2 min followed by 30 cycles of 94° C. for 20 sec, 58° C. for 20 sec and 72° C. for 20 sec. A final incubation at 72° C. for 4 min was performed. A nested PCR was performed using a nested forward primer and the universal reverse primer with a Cy3 label attached. 0.5 µl of the initial PCR was used as template for the nested PCR. PCR conditions were the same as for the first PCR except that the 58° C. step was performed at 55° C. The samples were hybridized to a detector array at 37° C. overnight and scanned the following day using a fluorescence reader to detect which positions on the array contained the Cy3 label. The number of positive spots was used to determine the initial concentration of sample. Table 4 shows a summary of the counts for all 9 genes.

TABLE 4

| Liver RNA | Gene | Copies measured by CR |
|---|---|---|
| 10 picograms (~1 cell) | B2M | 304 |
| | RPL19 | 200 |
| | GAPDH | 376 |
| 10 picograms (~1 cell) | SDHA | 82 |
| | GUSB | 19 |
| | TUBB | 34 |
| 100 picograms (~10 cells) | GP6D | 30 |
| | ABCF1 | 3 |
| | TBP | 15 |

Example 19: Absolute Quantitation of mRNA Molecules Directly from Cell Lysates

This example describes a method to generate transcript counts directly from cell lysates. A range of 40-100 cells from the Ramos (RA1) cell line washed in PBS were placed in a PCR tube with the following reagents: 1 µl Triton X-100 5%, 1 µg E. Coli total RNA, 1 µl of a 10 mM solution of dNTP's, 0.4 µl of a gene specific dU primer and 0.4 µl of a 10 uM pool of 960 dT Oligos. The samples were heated to 70° C. for 10 minutes and chilled on ice to lyse the cells and allow the primers to anneal. 4 µL of a 5× first strand buffer, 1 µL of a 0.1M DTT, 1 µL of superase RNase inhibitor (20 units), 1 µL (200 units) of the wild type MMLV reverse transcriptase and 0.4 µL of Taq DNA polymerase (2 units) was added. Control samples were also performed for the same cell numbers without the reverse transcriptase. The reactions were incubated at 37° C. for 60 min, followed by 3 cycles of 94° C. for 2 min, 55° C. for 2 min and 72° C. for 2 min. 1 unit of uracil DNA glycosylase was added and the reaction was mixed and moved to a new tube and incubated at 37° C. for 30 min. 5 µL of the reaction was then added to a 20 µL PCR reaction consisting of 1× Taq Reaction buffer, 0.2 µM dNTP, 0.05 uM gene-specific forward primer, 0.05 µM universal reverse primer and 0.3 µL Taq polymerase. PCR conditions were 94° C. for 2 min followed by 30 cycles of 94° C. for 20 sec, 58° C. for 20 sec and 72° C. for 20 sec. A final incubation at 72° C. for 4 min was performed. A nested PCR was performed using a nested forward primer and the universal reverse primer with a Cy3 label attached. 0.5 µl of the initial PCR was used as template for the nested PCR. PCR conditions were the same as for the first PCR except that the 58° C. step was performed at 55° C. The samples were hybridized to a detector array at 37 C overnight and scanned the following day using a fluorescence reader to detect which positions on the array contained the Cy3 label. The number of positive spots was used to determine the initial concentration of the RPL19 transcript in the cells. FIG. 43 shows a diagram summarizing the adaptation of the stochastic labeling protocol directly to cells.

Example 20. Optimization of cDNA Synthesis

Three cDNA synthesis reactions were conducted. The composition of the three reactions are described below.

Reaction 1: Std=control RNA+10 nM dT24+Reverse Transcriptase

Figure 32A:
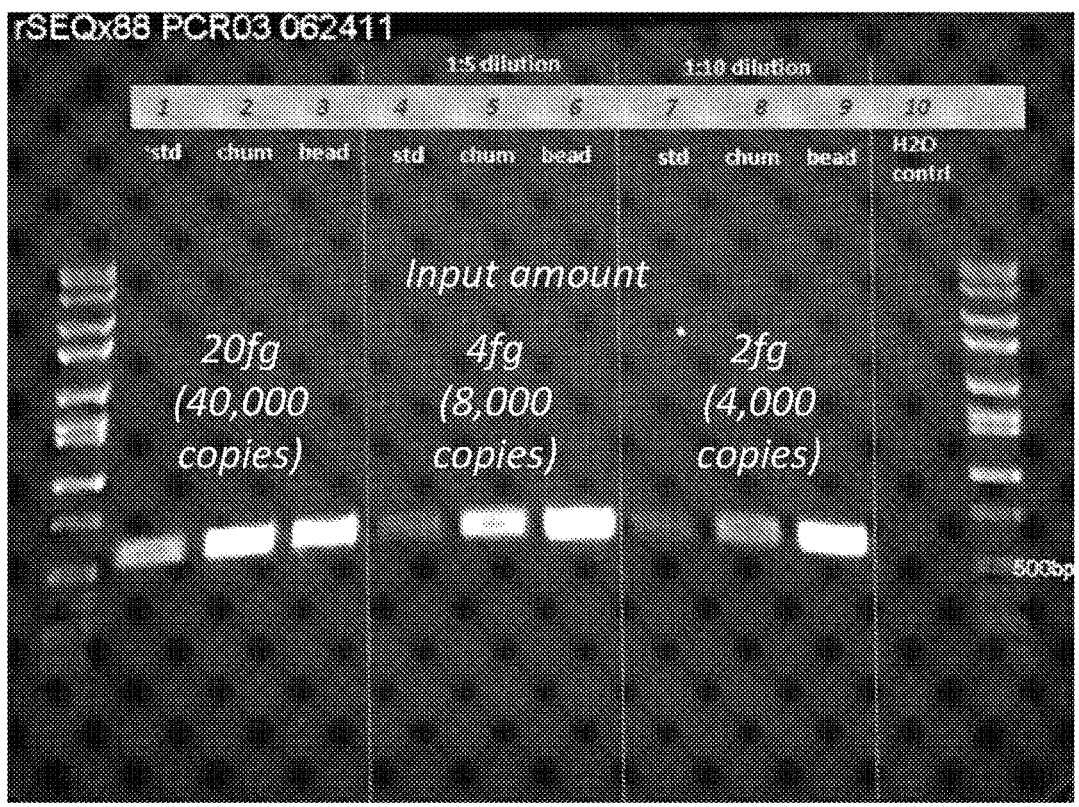
FIG. 32A-FIG. 32B show the results for the optimization of cDNA synthesis FIG. 33 Schematic of stochastic labeling followed by HCR detection of nucleic acid molecules FIG. 34 Schematic of stochastic labeling of hairping HCR oligonucleotides FIG. 35 Schematic of the serial dilution scheme for the titration experiment with serial dilutions of kanamycin RNA
Figure 32B:

Reaction 2: Chum=control RNA+10 ng poly A carrier RNA+10 nM dT24+Reverse Transcriptase Reaction 3: Bead=control RNA+1×10^6 dT40 beads+Reverse Transcriptase The reactions were incubated for 1 hour at 42° C., then diluted to the indicated number of input RNA copies for 35 cycles of PCR. The PCR products for each reaction are shown in FIG. 32. As shown in FIG. 32A, the RNA conversion to cDNA is higher on beads than in-solution

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification arc indicative of the level of skill of those skilled in the art to which this invention pertains, and arc herein incorporated by reference to the same extent as if each individual publication, patent or patent application was specifically and individually indicated to be incorporated by reference.

What is claimed is:

1. A method for the absolute quantification of copies of mRNA molecules in a sample, comprising:
   (a) stochastically labeling mRNA copies of a gene of interest in a sample with a plurality of oligonucleotide tags to produce a plurality of labelled-mRNA copies, wherein:
       (i) the number of mRNA copies of the gene of interest is at least one;
       (ii) the plurality of oligonucleotide tags each comprises an oligodT sequence, a universal primer binding site, and an identifier region;
       (iii) the plurality of oligonucleotide tags comprises at least 100 oligonucleotide tags having identifier regions of different sequences for determining the number of mRNA copies of the gene of interest; and
       (iv) a number of oligonucleotide tags having identifier regions of different sequences in the plurality of oligonucleotide tags is at least 5 times greater than the number of mRNA copies of any of the two or more genes of interest;
   (b) conducting a first strand synthesis reaction by contacting the plurality of labelled-mRNA copies with a reverse transcriptase enzyme to produce a plurality of single-stranded labelled-cDNA molecules;
   (c) amplifying the plurality of single-stranded labelled-cDNA molecules to produce a plurality of double-stranded labelled-cDNA molecules;
   (d) conducting a nested PCR reaction on the plurality of double-stranded labelled-cDNA molecules to produce a plurality of nested PCR labelled-amplicons; and
   (e) detecting at least a portion of amplicons of the nested PCR labelled-amplicons to count the number of different identifier regions associated with the labeled mRNA copies, thereby counting the absolute number of mRNA copies of the gene of interest in the sample.

2. The method of claim 1, wherein amplifying the plurality of single-stranded labelled-cDNA molecules to produce a plurality of double-stranded labelled-cDNA molecules comprises annealing a first universal primer to the universal primer binding site of the single-stranded labelled-cDNA molecules and annealing a first target-specific primer to the single-stranded labelled-cDNA molecules.

3. The method of claim 1, wherein conducting a nested PCR reaction on the plurality of double-stranded labelled-cDNA molecules to produce a plurality of nested PCR labelled-amplicons comprises annealing a second universal primer to the universal primer binding site of the double-stranded labelled-cDNA molecules and annealing a second target-specific primer to the double-stranded labelled-cDNA molecules, wherein the second target-specific primer anneals downstream of the first target-specific primer.

4. The method of claim 1, wherein the sample is from a single cell.

5. The method of claim 4, wherein the single cell is a cancerous cell, a diseased cell, a healthy cell, or an infected cell.

6. The method of claim 4, wherein the single cell is a cell from a subject suffering from a disease or a condition.

7. The method of claim 4, wherein the sample is cell lysate.

8. The method of claim 1, wherein the sample is from less than 50 cells.

9. The method of claim 1, wherein said step (a) is not performed on a bead surface.

10. The method of claim 1, wherein said detecting comprises determining the sequence of at least a portion of at least one of the nested PCR labelled-amplicons, a complement thereof, a reverse complement thereof, or any combination thereof.

11. The method of claim 1, wherein said detecting comprises using an array detector, fluorescent reader, non-fluorescent detector, CR reader, sequencer, or scanner.

12. The method of claim 1, wherein said detecting comprises hybridizing said nested PCR labelled-amplicons to a solid support.

13. The method of claim 12, further comprising determining the sequence of at least a portion of at least one of said nested PCR labelled-amplicons.

14. The method of claim 1, wherein the number of oligonucleotide tags having identifier regions of different sequences in the plurality of oligonucleotide tags is at least 1000.

15. The method of claim 1, wherein the number of oligonucleotide tags having identifier regions of different sequences in the plurality of oligonucleotide tags is at least 10,000.

16. The method of claim 1, wherein said detecting comprises hybridization chain reaction (HCR).

17. The method of claim 1, wherein the first strand synthesis reaction of (b) is not performed on a solid surface.

18. The method of claim 1, wherein the first strand synthesis reaction of (b) is not performed on a bead surface.

19. The method of claim 1, wherein the identifier region is at least four nucleotides in length.

20. The method of claim 1, wherein the oligonucleotide tag is at least ten nucleotides in length.

* * * * *